(12) United States Patent
Combette et al.

(10) Patent No.: US 10,596,223 B2
(45) Date of Patent: Mar. 24, 2020

(54) JNK INHIBITOR MOLECULES FOR TREATMENT OF VARIOUS DISEASES

(71) Applicant: Xigen Inflammation Ltd., Limassol (CY)

(72) Inventors: Jean-Marc Combette, Saint Cergues (FR); Catherine Deloche, Geneva (CH)

(73) Assignee: Xigen Inflammation Ltd., Limassol (CY)

( * ) Notice: Subject to any disclaimer, the term of this patent is extended or adjusted under 35 U.S.C. 154(b) by 0 days.

(21) Appl. No.: 15/217,326

(22) Filed: Jul. 22, 2016

(65) Prior Publication Data

US 2017/0056466 A1  Mar. 2, 2017

Related U.S. Application Data

(62) Division of application No. 14/367,706, filed as application No. PCT/EP2012/005362 on Dec. 21, 2012, now abandoned.

(30) Foreign Application Priority Data

Dec. 21, 2011  (WO) ................. PCT/EP2011/006481

(51) Int. Cl.
| | |
|---|---|
| A61K 38/10 | (2006.01) |
| A61K 38/08 | (2019.01) |
| C07K 7/06 | (2006.01) |
| C07K 7/08 | (2006.01) |
| C07K 14/00 | (2006.01) |
| A61K 38/00 | (2006.01) |
| A61K 38/16 | (2006.01) |
| C12N 7/00 | (2006.01) |

(52) U.S. Cl.
CPC ............ *A61K 38/08* (2013.01); *A61K 38/005* (2013.01); *A61K 38/10* (2013.01); *A61K 38/162* (2013.01); *C07K 7/06* (2013.01); *C07K 7/08* (2013.01); *C07K 14/001* (2013.01); *C12N 7/00* (2013.01); *A61K 38/00* (2013.01); *C12N 2740/16322* (2013.01); *C12N 2740/16334* (2013.01)

(58) Field of Classification Search
None
See application file for complete search history.

(56) References Cited

U.S. PATENT DOCUMENTS

| | | |
|---|---|---|
| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,595,756 A | 1/1997 | Bally et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,620,914 B1 | 9/2003 | Waeber et al. |
| 6,630,351 B1 | 10/2003 | Monahan et al. |
| 6,653,443 B2 | 11/2003 | Zhang et al. |
| 6,673,908 B1 | 1/2004 | Stanton |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,033,597 B2 | 4/2006 | Bonny |
| 7,034,109 B2 | 4/2006 | Bonny |
| 7,148,215 B2 | 12/2006 | Ratcliffe et al. |

(Continued)

FOREIGN PATENT DOCUMENTS

| | | |
|---|---|---|
| CA | 2738951 A1 | 7/2010 |
| CN | 1738901 B | 5/2010 |

(Continued)

OTHER PUBLICATIONS

Conti et al., "Atherosclerosis: a chronic inflammatory disease mediated by mast cells", Central European Journal of Immunology, 2015, pp. 380-386 (Year: 2015).*
Rovina et al., "Inflammation and Immune Response in COPD: Where Do We Stand?", Mediators of Inflammation, 2013, pp. 1-9 (Year: 2013).*
Murdoch et al., "Chronic inflammation and asthma", Mutation Research, 2010, pp. 24-39 (Year: 2010).*
Donath et al., "Type 2 diabetes as an inflammatory disease", Nature Reviews-Immunology, 2011, pp. 98-107 (Year: 2011).*
Todd et al., "GeneticProtection from the Inflammatory Disease Type 1 Diabetes in Humans and Animal Models", Immunity, 2011, pp. 387-395 (Year: 2011).*

(Continued)

*Primary Examiner* — Lianko G Garyu
(74) *Attorney, Agent, or Firm* — Harness Dickey & Pierce P.L.C.

(57) ABSTRACT

The present invention relates to the use of novel JNK inhibitor molecules and their use in a method of treatment of the human or animal body by therapy.

5 Claims, 45 Drawing Sheets
Specification includes a Sequence Listing.

(56) References Cited

U.S. PATENT DOCUMENTS

| | | |
|---|---|---|
| 7,166,692 B2 | 1/2007 | Karas |
| 7,538,091 B2 | 5/2009 | Bonny |
| 7,635,681 B2 | 12/2009 | Bonny |
| 7,803,749 B2 | 9/2010 | Bonny |
| 7,943,574 B2 | 5/2011 | Bonny |
| 8,063,012 B2 | 11/2011 | Watt et al. |
| 8,080,517 B2 | 12/2011 | Bonny |
| 8,183,339 B1 | 5/2012 | Bonny |
| 8,236,924 B2 | 8/2012 | Bonny |
| 8,278,413 B2 | 10/2012 | Bonny |
| 8,569,447 B2 | 10/2013 | Bonny |
| 8,748,395 B2* | 6/2014 | Bonny ............... C07K 14/4703 514/1.1 |
| 8,981,052 B2 | 3/2015 | Bonny |
| 9,006,185 B2* | 4/2015 | Bonny ............... A61K 38/28 424/192.1 |
| 9,150,618 B2 | 10/2015 | Combette et al. |
| 9,180,159 B2 | 11/2015 | Bonny |
| 9,290,538 B2 | 3/2016 | Bonny |
| 9,610,330 B2 | 4/2017 | Bonny |
| 9,624,267 B2 | 4/2017 | Bonny |
| 2002/0042423 A1 | 4/2002 | Richert |
| 2002/0090696 A1 | 7/2002 | Miller et al. |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0148395 A1 | 8/2003 | Liu et al. |
| 2003/0220480 A1 | 11/2003 | Bonny |
| 2004/0058875 A1 | 3/2004 | Gamache |
| 2004/0082509 A1* | 4/2004 | Bonny ............... A61K 38/1709 514/15.1 |
| 2004/0265879 A1 | 12/2004 | Iversen et al. |
| 2005/0019366 A1* | 1/2005 | Zeldis ............... A61K 31/415 424/423 |
| 2005/0043241 A1 | 2/2005 | Bonny |
| 2005/0059597 A1 | 3/2005 | Tymianski |
| 2005/0106695 A1 | 5/2005 | Bonny |
| 2006/0094753 A1 | 5/2006 | Pang et al. |
| 2006/0166881 A1 | 7/2006 | Hotchkiss et al. |
| 2006/0178310 A1 | 8/2006 | Bonny |
| 2006/0223807 A1 | 10/2006 | Davis et al. |
| 2006/0258706 A1 | 11/2006 | Saindane |
| 2006/0270646 A1 | 11/2006 | Graczyk et al. |
| 2007/0003531 A1 | 1/2007 | Mukherji et al. |
| 2007/0015779 A1 | 1/2007 | Griffin et al. |
| 2007/0060514 A1 | 3/2007 | Bonny |
| 2008/0008749 A1 | 1/2008 | Pearlman et al. |
| 2008/0051410 A1 | 2/2008 | Watterson et al. |
| 2008/0274956 A1 | 11/2008 | Bonny et al. |
| 2009/0281036 A1 | 11/2009 | Meyer |
| 2009/0305968 A1* | 12/2009 | Bonny ............... C07K 14/4703 514/1.1 |
| 2010/0098635 A1 | 4/2010 | Lamping et al. |
| 2010/0216716 A1 | 8/2010 | Bonny |
| 2010/0256041 A1 | 10/2010 | Bonny et al. |
| 2010/0331335 A1 | 12/2010 | Sham et al. |
| 2011/0052566 A1 | 3/2011 | Rosenblum et al. |
| 2011/0183888 A1 | 7/2011 | Bonny |
| 2012/0058137 A1 | 3/2012 | Bonny |
| 2012/0071483 A1 | 3/2012 | Cohen et al. |
| 2012/0101046 A1 | 4/2012 | Hirai et al. |
| 2012/0142584 A1 | 6/2012 | Bonny |
| 2012/0148590 A1 | 6/2012 | Bonny |
| 2012/0258982 A1 | 10/2012 | Cheung et al. |
| 2012/0328609 A1 | 12/2012 | Lewcock et al. |
| 2014/0057834 A1 | 2/2014 | Bonny |
| 2014/0309400 A1 | 10/2014 | Combette et al. |
| 2015/0133393 A1 | 5/2015 | Combette et al. |
| 2016/0089413 A1 | 3/2016 | Combette et al. |
| 2016/0115200 A1 | 4/2016 | Combette et al. |
| 2016/0199444 A1 | 7/2016 | Combette et al. |
| 2016/0264630 A1 | 9/2016 | Bonny |
| 2017/0056466 A1 | 3/2017 | Combette et al. |
| 2017/0128516 A1 | 5/2017 | Combette et al. |
| 2017/0137481 A1 | 5/2017 | Combette et al. |
| 2017/0290877 A1 | 10/2017 | Combette et al. |
| 2017/0320917 A1 | 11/2017 | Bonny |
| 2018/0170983 A1 | 6/2018 | Combette et al. |
| 2019/0060392 A1 | 2/2019 | Combette et al. |

FOREIGN PATENT DOCUMENTS

| | | |
|---|---|---|
| EP | 0375040 | 12/1989 |
| EP | 0 679 716 A1 | 11/1995 |
| EP | 0 897 002 A2 | 2/1999 |
| EP | 1 364 949 A1 | 11/2003 |
| EP | 1676574 A2 | 7/2006 |
| EP | 2627346 A1 | 8/2013 |
| JP | 58-146538 | 9/1983 |
| JP | 02-221294 | 4/1990 |
| JP | 2003-531871 A | 10/2003 |
| JP | 2004-516811 A | 6/2004 |
| JP | 2005-525096 A | 8/2005 |
| JP | 2006-501165 A | 1/2006 |
| JP | 2006-502719 A | 1/2006 |
| JP | 2006-512143 A | 4/2006 |
| JP | 2008-519785 A | 6/2008 |
| JP | 2011-524861 A | 9/2011 |
| JP | 2012-513427 | 6/2012 |
| JP | 5711666 B2 | 5/2015 |
| JP | 2015/197193 A | 11/2015 |
| WO | 1992-018138 A1 | 10/1992 |
| WO | 1993-018759 A1 | 9/1993 |
| WO | 1994-004562 A1 | 3/1994 |
| WO | 1994-004686 | 3/1994 |
| WO | 1994-005311 A1 | 3/1994 |
| WO | 1994-023751 A1 | 10/1994 |
| WO | 1995-034295 | 12/1995 |
| WO | 96/34093 | 10/1996 |
| WO | 1997-005265 | 2/1997 |
| WO | 1997-010836 | 3/1997 |
| WO | 1998-011907 | 3/1998 |
| WO | 1998-023781 A1 | 6/1998 |
| WO | 1998-044106 A1 | 10/1998 |
| WO | 1998-047913 A1 | 10/1998 |
| WO | 1998-049188 | 11/1998 |
| WO | 1998-051325 A2 | 11/1998 |
| WO | 1998-051825 A1 | 11/1998 |
| WO | 1998-052614 | 11/1998 |
| WO | 1999-007728 A2 | 2/1999 |
| WO | 1999-016787 A1 | 4/1999 |
| WO | 1999020624 A1 | 4/1999 |
| WO | 1999-049879 | 10/1999 |
| WO | 1999-050282 A2 | 10/1999 |
| WO | 1999-058561 A1 | 11/1999 |
| WO | 1999-067284 A2 | 12/1999 |
| WO | 2000-012587 A2 | 3/2000 |
| WO | 2000-041719 A1 | 7/2000 |
| WO | 2001-010888 A1 | 2/2001 |
| WO | 2001-013957 A2 | 3/2001 |
| WO | 2001-015511 A2 | 3/2001 |
| WO | 2001-027268 | 4/2001 |
| WO | 01/39784 | 6/2001 |
| WO | 2001/043774 A1 | 6/2001 |
| WO | 01/82975 | 11/2001 |
| WO | 2001/098324 A1 | 12/2001 |
| WO | 02/32437 | 4/2002 |
| WO | 2002-031109 A2 | 4/2002 |
| WO | 2002-061105 A2 | 8/2002 |
| WO | 2002-062396 A2 | 8/2002 |
| WO | 2002-065986 A2 | 8/2002 |
| WO | 2002-069930 A1 | 9/2002 |
| WO | 2002-081504 A2 | 10/2002 |
| WO | 2002-081505 A2 | 10/2002 |
| WO | 2003008553 A2 | 1/2003 |
| WO | 03/057725 | 7/2003 |
| WO | 2003-075917 A1 | 9/2003 |
| WO | 2003-103698 A1 | 12/2003 |
| WO | 2003-103718 A2 | 12/2003 |
| WO | 2003106491 A2 | 12/2003 |
| WO | 2004-022580 A2 | 3/2004 |

(56) References Cited

FOREIGN PATENT DOCUMENTS

| WO | 2004-035793 A1 | 4/2004 | |
|---|---|---|---|
| WO | 2004026406 A1 | 4/2004 | |
| WO | 2004/037196 | 5/2004 | |
| WO | 2004-045535 A2 | 6/2004 | |
| WO | 2004-054501 A2 | 7/2004 | |
| WO | 2004060318 A2 | 7/2004 | |
| WO | 2004-070052 A2 | 8/2004 | |
| WO | 2004-092339 A2 | 10/2004 | |
| WO | 2005-084158 A2 | 9/2005 | |
| WO | 2005-097116 A1 | 10/2005 | |
| WO | 200601582 A1 | 1/2006 | |
| WO | 2006021458 A2 | 3/2006 | |
| WO | 2006/050930 | 5/2006 | |
| WO | 2007-031098 A1 | 3/2007 | |
| WO | 2007/031280 | 3/2007 | |
| WO | 2008-028860 A1 | 3/2008 | |
| WO | 2008095943 A1 | 8/2008 | |
| WO | 2008094208 A3 | 10/2008 | |
| WO | 2009/137602 | 11/2009 | |
| WO | 2009-143864 A1 | 12/2009 | |
| WO | 2009-143865 A1 | 12/2009 | |
| WO | 2009/144038 | 12/2009 | |
| WO | 2009144037 A1 | 12/2009 | |
| WO | 2010/065850 | 6/2010 | |
| WO | 2010091310 A1 | 8/2010 | |
| WO | 2010113753 A1 | 10/2010 | |
| WO | 2011/082328 A1 | 7/2011 | |
| WO | 2011/160653 A1 | 12/2011 | |
| WO | 2011/160827 A2 | 12/2011 | |
| WO | WO-2011160827 A2 * | 12/2011 | ............... C07K 7/06 |
| WO | 2012/048721 A1 | 4/2012 | |
| WO | 2012/048893 A1 | 4/2012 | |
| WO | 2013/091670 | 6/2013 | |
| WO | 2013/091896 | 6/2013 | |
| WO | 2014206426 A1 | 12/2014 | |
| WO | 2014206564 A1 | 12/2014 | |
| WO | 2015197193 A3 | 2/2016 | |

OTHER PUBLICATIONS

Dugan et al., "Role of c-Jun N-terminal Kinase (JNK) activation in micturition reflexes in cyclophosphamide (CYP)-induced cystitis in female rats", Society for Neuroscience Abstract Viewer and Itinerary Planner,2011,41st Ann. Meeting of the Society-for-Neuroscience Washington, DC, USA. Nov. 12-16, 2011.*
Juszczak et al., "Animal models of overactive bladder: Cyclophosphamide (CYP)-induced cystitis in rats", N46, EAU 3rd North Eastern European Meeting (NEEM)/ European Urology Supplements 8 (2009) 583-584 (Year: 2009).*
Witkowski et al.—Conversion of a β-Ketoacyl Synthase to a Malonyl Decarboxylase by Replacement of the Active-Site Cysteine with Glutamine—Biochemistry—Aug. 18, 1999—pp. 11643-11650—vol. 38—American Chemical Society—USA.
Wyszko et al., "Interaction of Native RNAs with Tat Peptides," RNA Biochemistry and Biotechnology, NATO Science Series, 70:277-290 (1999); Chemical Abstracts Database Accession No. 133:204452.
Yamamoto et al.—Molecular Design of Bioconjugated Cell Adhesian Peptide with a Water-Soluble Polymeric Modifer for Enhancement of Antimetastatic Effect—Current Drug Targets—2002—pp. 123-130—vol. 3—Bentham Science Publishers Ltd.—USA.
Yang et al.—Differential Targeting of MAP Kinases to the ETS-Domain Transcription Factor Elk-1—The EMBO Journal—1998—pp. 1740-1749—vol. 17—No. 6—European Molecular Biology Organisation—Oxford University Press—United Kingdom.
Yasuda et al.—The JIP Group of Mitogen-Activated Protein Kinase Scaffold Proteins—Molecular and Cellular Biology—Oct. 1999—pp. 7245-7254—vol. 19—No. 10—American Society for Microbiology—USA.
Zhang et al.—Preparation of Functionally Active Cell-Permeable Peptides by Single-Step Ligation of Two Peptide Modules—Proceedings of National Academy of Sciences—Biochemistry—Aug. 1998—pp. 9184-9189—vol. 95—National Academy of Sciences—USA.
Zoukhri et al.—c-Jun NH2-Terminal Kinase Mediates Interleukin-1 β-Induced Inhibition of Lacrimal Gland Secretion—Journal of Neurochemistry—2006—pp. 126-135—vol. 96—International Society for Neurochemistry—USA.
NCBI Sequence Viewer—Accession No. AAD20443—Reports—Islet-Brain 1 (*Homo sapiens*)—Two References—Mooser et al.—Mar. 17, 1999—2 pages—USA.
NCBI Sequence Viewer—Accession No. AAD22543—Reports—Islet-Brain 1 (Rattus Norvegicus)—Three References—Bonny et al.—Mar. 1, 2006—2 pages—USA.
Westwick et al., "Activatin of Jun kinase is an early event in hepatic regeneration," The Journal of the Clinical Investigation, 95(2): 803-810 (1995).
NCBI Sequence Viewer—Accession No. AF074091—Reports—*Homo sapiens* Islet-Brain 1 mRNA—Complete Cds.—Two References—Mooser et al.—Mar. 17, 1999—2 pages—USA.
NCBI Sequence Viewer—Accession No. AF108959—Reports—Rattus Norvegicus Islet-Brain 1 (IB1) mRNA—Complete Cds.—Three References—Bonny et al.—Mar. 1, 2006—2 pages—USA.
NCBI Sequence Viewer—Accession No. AF218778—Reports—*Homo sapiens* Islet-Brain 2 mRNA—Complete Cds—Three References—Kristensen et al.—Mar. 2, 2006—2 pages—USA.
NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.
Ahmed et al., "Basal cancer cell survival involves JNK2 suppression of a novel JNK1/c-Jun/Bcl-3 apoptotic network," PLoS ONE, 4(10):e7305 (2009).
Bowie et al., "Deciphering the message in protein sequences: tolerance to amino acid substitutions," Science, 247(4948): 1306-1310 (1990).
Database WPI, Thompson Scientific, Accession No. 2010-M79716, 2010, 3 pages; XP002643212.
Ferrandi et al., "Inhibition of c-Jun N-terminal kinase decreases cardiomyocyte apoptosis and infarct size after myocardial ischemia and reperfusion in anaesthetized rats," British Journal of Pharmacology, 142(6): 953-960 (2004).
Hirt et al., "D-JNKI1, a cell-penetrating c-Jun-N-terminal kinase inhibitor, protects against cell death in severe cerebral ischemia," Stroke, 35(7): 1738-1743 (2004).
Kugler et al., "MAP kinase pathways involved in glioblastoma response to erucylphosphocholine," International Journal of Oncology, 25(6):1721-1727 (2004).
Stedman's Online Dictionary Definition of "inflammation", Obtained from www.pdrel.com, last viewed on Dec. 18, 2010, 2 pages.
Wang et al., "A single amino acid determines lysophospholipid specificity of the S1P1 (EDG1) and LPA1 (EDG2) phospholipid growth factor receptors," Journal of Biological Chemistry, 276(52): 49213-49220 (2001).
Wells, "Additivity of mutational effects in proteins," Biochemistry, 29(37): 8509-8517 (1990).
Tan et al., "Selective inhibition of ErbB2-overexpressing breast cancer in vivo by a novel TAT-based ErbB2-targeting signal transducers and activators of transcription 3-blocking peptide," Cancer Res. 66:3764-3772, 2008.
De Paiva et al., "Essential role for c-Jun N-terminal kinase 2 in corneal epithelial response to desiccating stress," Arch Ophthalmol., 127(12): 1625-1631, 2009.
Hommes et al., "Inhibition of stress-activated MAP kinases induces clinical improvement in moderate to severe Crohn's disease," Gastroenterology, 122(1):7-14 (2002).
Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).

(56) References Cited

OTHER PUBLICATIONS

Bost et al., "The Jun kinase 2 isoform is preferentially required for epidermal growth factor-induced transformation of human A549 lung carcinoma cells," Molecular and Cellular Biology, 19(3): 1938-1949 (1999).
Chang Lufen et al., "JNK1 is required for maintenance of neuronal microtubules and controls phosphorylation of microtubule-associated proteins, Developmental Cell, 4(4): 521-533 (2003).
Hunot Stephan et al., "JNK-mediated induction of cyclooxygenase 2 is required for neurodegeneration in a mouse model of Parkinson's disease," Proceedings of the National Academy of Sciences of the United States of America,101(2): 665-670 (2004).
Jaeschke et al., "Disruption of the Jnk2 (Mapk9) gene reduces destructive insulitis and diabetes in a mouse model of type I diabetes," Proceedings of the National Academy of Sciences of the United States of America, 102(19): 6931-6935.
Kaneto et al., "Possible novel therapy for diabetes with cell-permeable JNK-inhibitory peptide," Nature Medicine, 10(10):1128-1132 (2004).
Kuan et al., "A critical role of neural-specific JNK3 for ischemic apoptosis," Proceedings of the National Academy of Sciences of the United States of America, 100(25): 15184-15189 (2003).
Polyakov et al., "Novel Tat-peptide chelates for direct transduction of technetium-99m and rhenium into human cells for imaging and radiotherapy" Bioconjugate Chem., 11: 762-771 (2000).
Saar et al., "Cell-penetrating peptides: a comparative membrane toxicity study," Analytical Biochemistry, 345(1):55-65 (2005).
Sabapathy, "Role of the JNK pathway in human diseases," Progress in Molecular Biology and Translational Science, 106:145-169 (2012).
Salh, "c-Jun N-terminal kinases as potential therapeutic targets," Expert Opin Ther Targets, 11(10):1339-1353 (2007).
Seki et al., "A liver full of JNK: signaling in regulation of cell function and disease pathogenesis, and clinical approaches," Gastroenterology, 143(2):307-320 (2012).
Sumara et al. "Jnking atherosclerosis," Cellular and Molecular Life Sciences, Birkhäuser Verlag, 62(21): 2487-2494 (2005).
Tachibana et al., "JNK1 is required to preserve cardiac function in the early response to pressure overload, Biochemical and Biophysical Research Communications," 343(4): 1060-1066 (2006).
Du H. et al., "JNK inhibition reduces apoptosis and neovascularization in a murine model of age-related macular degeneration," Proc Natl Acad Sci USA. Feb. 5, 2013;110(6):2377-82. Epub Jan. 22, 2013.
Iyer S. et al., "RDP58, a rationally designed peptide, inhibits multiple forms of pathogenic inflammation through the inhibition of p38MAPK and JNK," Biopolymers, vol. 71, No. 3, 061, p. 298, Jan. 2013.
Noguchi H. et al., "Cell Permeable Peptide of JNK Inhibitor Prevents Islet Apoptosis Immediately After Isolation and Improves Islet Graft Function," American Journal of Transplantation, vol. 5, No. 8, pp. 1848-1855, Aug. 2005.
Noguchi H. et al., "Effect of JNK Inhibitor During Islet Isolation and Transplantation," Transplantation proceedings, vol. 40, No. 2, pp. 379-381, Mar. 2008.
Sakane T. et al., "Current Concepts: Behcet's disease," The New England Journal of Medicine, vol. 341, No. 17, pp. 1284-1291, Oct. 21, 1999.
Bogoyevitch et al., "Taking the cell by stealth or storm? Protein transduction domains (PTDs) as versatile vectors for delivery," DNA Cell Biol., 21(12):879-894 (2002).
Chemical Abstracts Accession No. 2004:27781 and CAS Registry File CN 647864-97-9.
InVivoGen, Inc., SP600125: MAP Kinase Inhibitor—Autophagy Inhibitor—JNK inhibitor, Downloaded Jun. 9, 2014.
Kelekar et al., "Bcl-2-family proteins: the role of the BH3 domain in apoptosis," Trends Cell Biol., 8(8):324-330 (1998).
Killick et al, "Clusterin regulates ß-amyloid toxicity via Dickkopf-1-driven induction of the wnt-PCP-JNK pathway," Mol Psychiatry., 19(1):88-98 (2014).

Aarts et al., "Treatment of ischemic brain damage by perturbing NMDA receptor-PSD-95 protein interactions," Science, 298(5594):846-850 (2002).
Abaza et al., "Effects of amino acid substitutions outside an antigenic site on protein binding to monoclonal antibodies of predetermined specificity obtained by peptide immunization: demonstration with region 94-100 (antigenic site 3) of myoglobin," Journal of Protein Chemistry, 11(5):433-444 (1992).
Patel et al. "Getting into the brain—approaches to enhance brain drug delivery," CNS Drugs, 23(1): 35-58 (2009).
Aldrian-Herrada et al., "A peptide nucleic acid (PNA) is more rapidly internalized in cultured neurons when coupled to a retro-inverso delivery peptide. The antisense activity depresses the target mRNA and protein in magnocellular oxytocin neurons," Nucleic Acids Research, 26(21):4910-4916 (1998).
Assi et al., "The specific JNK inhibitor SP600125 targets tumour necrosis factor-alpha production and epithelial cell apoptosis in acute murine colitis," Immunology, 118(1):112-121 (2006).
Barr et al., "Identification of the critical features of a small peptide inhibitor of JNK activity," The Journal of Biological Chemistry, 277(13):10987-10997 (2002).
Berendsen, "A Glimpse of the Holy Grail?," Science, 282(5389):642-643 (1998).
Bessalle et al., "All-D-magainin: chirality, antimicrobial activity and proteolytic resistance," FEBS Letters, 274(1-2):151-155 (1990).
Bonny et al.,"Cell-permeable peptide inhibitors of JNK: novel blockers of beta-cell death," Diabetes, 50(1):77-82 (2001).
Bonny et al.,"IB1, a JIP-1-related nuclear protein present in insulin-secreting cells," Journal of Biological Chemistry, 273(4):1843-1846 (1998).
Bonny et al.,"Pancreatic-specific expression of the glucose transporter type 2 gene: identification of cis-elements and islet-specific trans-acting factors," Molecular Endrocrinology, 9(10):1413-1426 (1995).
Bonny et al.,"Targeting the JNK pathway as a therapeutic protective strategy for nervous system diseases," Reviews in the Neurosciences, 16(1):57-67 (2005).
Borsello et al., "A peptide inhibitor of c-Jun N-terminal kinase protects against excitotoxicity and cerebral ischemia," Nature Medicine, 9(9):1180-1186 (2003).
Borsello et al., "Use of cell-permeable peptides to prevent neuronal degeneration," TRENDS in Molecular Medicine, 10(5):239-244 (2004).
Bradley et al., "Limits of cooperativity in a structurally modular protein: response of the Notch ankyrin domain to analogous alanine substitutions in each repeat," Journal of Molecular Biology, 324(2):373-386 (2002).
Branden et al., "A peptide nucleic acid-nuclear localization signal fusion that mediates nuclear transport of DNA," Nature Biotechnology, 17(8):784-787 (1999).
Branden et al., Introduction to Protein Structure, Second Edition, Garland Publishing, Inc., USA, p. 382 (1999).
Branden et al., Introduction to Protein Structure, Garland Publishing, Inc., USA, p. 247 (1991).
Cardozo et al., "Cell-permeable peptides induce dose- and length-dependent cytotoxic effects," Biochimica et Biophysica Acta, 1768(9):2222-2234 (2007).
Chaloin et al., "Design of carrier peptide-oligonucleotide conjugates with rapid membrane translocation and nuclear localization properties," Biochemical and Biophysical Research Communications, 243(2):601-608 (1998).
Creighton (Editor), Janin, "Protein-Protein Interactions," Encyclopedia of Molecular Biology, pp. 2027-2033, vol. 1, A Wiley-Interscience Publication, John Wiley & Sons, Inc., USA (1999).
Derossi et al., "Cell internalization of the third helix of the Antennapedia homeodomain is receptor-independent," The Journal of Biological Chemistry, 271(30):18188-181893 (1996).
Designing Custom Peptides, Sigma Genosys, Technical Bulletin, 2 pages, (Dec. 16, 2004), Retrieved from <http://www.sigma-genosys.com/peptide_design.asp>.
Dickens et al., Database—UNIPROT—Retrieved from EBI—Database Accession No. Q9WVI9—Abstracts—Feb. 28, 2003—Document No. XP-002366175—USA.

(56) References Cited

OTHER PUBLICATIONS

Dickens et al., "A cytoplasmic inhibitor of the JNK signal transduction pathway," Science, 277(5326):693-696 (1997).
Dietz et al., "Delivery of bioactive molecules into the cell: the Trojan horse approach," Molecular and Cellular Neuroscience, 27(2):85-131 (2004).
Domínguez-Bendala et al., "TAT-mediated neurogenin 3 protein transduction stimulates pancreatic endocrine differentiation in vitro," Diabetes, 54(3):720-726 (2005).
Fawell et al., "Tat-mediated delivery of heterologous proteins into cells," Proceedings of the National Academy of Sciences USA, 91(2):664-668 (1994).
Fornoni et al.The I-isoform but not d-isoforms of a JNK inhibitory peptide protects pancreatic beta-cells, Biochemical and Biophysical Research Communications, 354(1):227-233 (2007).
Frankel et al., "Cellular uptake of the tat protein from human immunodeficiency virus," Cell, 55(6):1189-1193 (1988).
Parenteau et al., "Free uptake of cell-penetrating peptides by fission yeast," FEBS Letters, 579: 4873-4878 (2005).
Futaki et al., "Arginine-rich peptides. An abundant source of membrane-permeable peptides having potential as carriers for intracellular protein delivery," The Journal of Biological Chemistry, 276(8):5836-5840 (2001).
Gammon et al., "Quantitative analysis of permeation peptide complexes labeled with Technetium-99m: chiral and sequence-specific effects on net cell uptake," Bioconjugate Chemistry, 14(2):368-376 (2003).
Gotthardt et al., "Interactions of the low density lipoprotein receptor gene family with cytosolic adaptor and scaffold proteins suggest diverse biological functions in cellular communication and signal transduction," The Journal of Biological Chemistry, 275(33):25616-25624 (2000).
Guichard et al., "Antigenic mimicry of natural L-peptides with retro-inverso-peptidomimetics," Proceedings of the National Academy of Sciences USA, 91(21): 9765-9769 (1994).
Gunaseelan et al., "Synthesis of poly(ethylene glycol)-based saquinavir prodrug conjugates and assessment of release and anti-HIV-1 bioactivity using a novel protease inhibition assay," Bioconjugate Chemistry,15(6):1322-1333 (2004).
Gura, Systems for identifying new drugs are often faulty, Science, 278(5340):1041-1042 (1997).
Hawiger, "Noninvasive intracellular delivery of functional peptides and proteins," Current Opinion in Chemical Biology, 3(1):89-94 (1999).
Hayashi et al., "Development of oligoarginine-drug conjugates linked to new peptidic self-cleavable spacers toward effective intestinal absorption," Bioorganic and Medicinal Chemistry Letters, 17(18):5129-5132 (2007).
Heemskerk et al., "From chemical to drug: neurodegeneration drug screening and the ethics of clinical trials," Nature Neuroscience, Supplement: 1027-1029 (2002).
Herve et al., "On the immunogenic properties of retro-inverso peptides. Total retro-inversion of T-cell epitopes causes a loss of binding to MHC II molecules," Molecular Immunology, 34(2):157-163 (1997).
EMBL Sequence Database—R85141, Hillier et al., *Homo sapiens*,The WashU-Merck EST Project, p. 1, XP-002076858, USA (Aug. 17, 1995).
Ho et al., "Synthetic protein transduction domains: enhanced transduction potential in vitro and in vivo," Cancer Research, 61(2):474-477 (2001).
Holinger et al., "Bak BH3 peptides antagonize Bcl-xL function and induce apoptosis through cytochrome c-independent activation of caspases," The Journal of Biological Chemistry, 274(19):13298-13304 (1999).
Holzberg et al., "Disruption of the c-JUN-JNK complex by a cell-permeable peptide containing the c-JUN delta domain induces apoptosis and affects a distinct set of interleukin-1-induced inflammatory genes," The Journal of Biological Chemistry, 278(41):40213-40223 (2003).
Houghten, "General method for the rapid solid-phase synthesis of large numbers of peptides: specificity of antigen-antibody interaction at the level of individual amino acids," Proceedings of the National Academy of Sciences USA, 82(15):5131-5135 (1985).
Huq et al., "Specific recognition of HIV-1 TAR RNA by a D-Tat peptide," Nature Structural Biology, 4(11):881-882 (1997).
Johnson et al., "The c-jun Kinase/Stress-Activated Pathway: Regulation, Function and Role in Human Disease," Biochim Biophys Acta., 1773(8): 1341-1348 (2007).
Pinilla et al., "Chapter 5. The Versatility of Nonsupport-Bound Combinatorial Libraries," in Combinatorial Peptide and Nonpeptide Libraries: A Handbook (ed G. Jung), Wiley-VCH Verlag GmbH, Weinheim, Germany, pp. 139-171 (1997).
Spatola et al., "Chapter 11. Cyclic Peptide Libraries: Recent Developments," in Combinatorial Peptide and Nonpeptide Libraries: A Handbook (ed G. Jung), Wiley-VCH Verlag GmbH, Weinheim, Germany, pp. 327-347 (1997).
Nori, Aparna and Kopecek, Jindrich—Intracellular Targeting of Polymer-Bound Drugs for Cancer Chemotherapy—Advanced Drug Delivery Reviews—Dec. 24, 2004—pp. 609-636—vol. 57—ScienceDirect—Elsevier B.V.—The Netherlands.
Okitsu et al.—Protein Transduction Domains Enable Isolated Islets to Efficiently Internalize the Target Protein—Transplantation Proceedings—Feb. 2003—p. 479—vol. 35—Elsevier Science inc.—USA.
Pan et al.—Small Peptide Inhibitor of JNKs Protects Against MPTP-Induced Nigral Dopaminergic Injury via Inhibiting the JNK-Signaling Pathway—Laboratory Investigation—Feb. 2010—pp. 156-167—vol. 90—USCAP, Inc.—USA.
Parkinson's Disease: Challenges, Progress, and Promise—Publication—National Institute of Neurological Disorders and Stroke—National Institutes of Health—2004—22 pages—No. 05-5595—<http://www.ninds.nih.gov/disorders/parkinsons_disease/parkinsons_research_pr.htm.
Penco et al., "Identification of an Import Signal for, and the Nuclear Localization of, Human Lactoferrin," Biotechnology and Applied Biochemistry, 34:151-159 (2001).
Hruby et al., "Chapter 11. Design of novel synthetic peptides including cyclic conformationally and topographically constrained analogs," Methods in Molecular Biology, vol. 35 Peptide Synthesis Protocols, Humana Press Inc., NJ, USA, pp. 201-239 (1994).
Pennington et al., "Chapter 12. Solid-Phase Synthesis of Peptides Containing the CH2NH Reduced Bond Surrogate," Methods in Molecular Biology, vol. 35 Peptide Synthesis Protocols, Humana Press Inc., NJ, USA, pages—pp. 241-247 (1994).
Pirvola et al.—Rescue of Hearing, Auditory Hair Cells, and Neurons by CEP-1347/KT7515, an Inhibitor of c-Jun N-Terminal Kinase Activation—The Journal of Neuroscience—01-01-200—pp. 43-50—vol. 20—No. 1—Society of Neuroscience—USA.
Pratner et al.—Synthesis and Characterization of a Gd-DOTA-D-Permeation Peptide for Magnetic Resonance Relaxation Enhancement of Intracellular Targets—Research Article—Massachusetts Institute of Technology—Molecular Imaging—Oct. 2003—pp. 333-341—vol. 2—No. 4—The Society of Molecular Imaging—USA.
Guichard et al., Chapters 165 and 166; Gur'Yanov et al., Chapter 167; In R. Ramage and R. Epton (eds.), Peptides 1996 : Proceedings of the Twenty-Fourth European Peptide Symposium (Sep. 8-13, 1996, Edinburgh, Scotland), European Peptide Society, Mayflower Scientific Ltd., United Kingdom), pp. 447-451 (1998).
Horvath et al., Chapter 183; Hruby et al., Chapter 184; In R. Ramage and R. Epton (eds.), Peptides 1996 : Proceedings of the Twenty-Fourth European Peptide Symposium (Sep. 8-13, 1996, Edinburgh, Scotland), European Peptide Society, Mayflower Scientific Ltd., United Kingdom), pp. 483-486 (1998).
Ramanathan et al.—Targeting the Sodium-Dpendent Multivitamin Transporter (SMVT) for Improving the Oral Absorption Properties of a Retro-Inverso Tat Nonapeptide—Pharmaceutical Research—Jul. 2001—pp. 950-956—vol. 18—No. 7—USA.
Ribeiro et al.—Heme Oxygenase-1 Fused to a TAT Peptide Transduces and Protects Pancreatic β-Cells—BBRC—Biochemical and Biophysical Research Communications—Apr. 4, 2003—pp. 876-881—vol. 305—ScvienceDirect—Academic Press—Elesevier Science (USA)—USA.

(56) References Cited

OTHER PUBLICATIONS

Mitsuyama et al., "Pro-inflammatory signaling by Jun-N-terminal kinase in inflammatory bowel disease," Int J Mol Med., 17(3):449-55 (2006).
Robinson et al.—Properties and Structure-Activity Studies of Cyclic β-hairpin Peptidomimetics Based on the Cationic Antimicrobial Peptide Protegrin I—Bioorganic & Medicinal Chemistry—Jan. 7, 2005—pp. 2055-2064—vol. 13—ScienceDirect—Elsevier Ltd.—USA.
Roduit, Raphaël and Schorderet, Daniel F.—Map Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.
Rojas et al.—Controlling Epidermal Growth Factor (EGF)-Stimulated Ras Activation in Intact Cells by a Cell-Permeable Peptide Mimicking Phosphorylated EGF Receptor—Journal of Biological Chemistry—Nov. 1, 1996—pp. 27456-27461—vol. 271—No. 44—The American Society for Biochemistry and Molecular Biology, Inc.—USA.
Roy et al.—Role of the JNK Signal Transduction Pathway in Inflammatory Bowel Disease—World Journal of Gastroenterol—Jan. 14, 2008—pp. 200-202—vol. 14—No. 2—www.wjgnet.com—USA.
Ruben et al.—Structural and Functional Characterization of Human Immunodeficiency Virus tat Protein—Journal of Virology—Jan. 1989—pp. 1-8—vol. 63—No. 1—American Society for Microbiology—USA.
Rudikoff et al.—Single Amino Acid Substitution Altering Antigen-Binding Specificity—Immunology—Proceedings of the National Academy of Science—Mar. 1982—pp. 1979-1983—vol. 79—National Academy of Science—USA.
Rudinger, J.—Characteristics of the Amino Acids as Components of a Peptide Hormone Sequence—Peptide Hormones—1976—pp. 1-7—University Park Press, Baltimore—USA.
Saito, Naoyuki G. and Paterson, Yvonne—Contribution of Peptide Backbone Atoms to Binding of an Antigenic Peptide to Class 1 Major Histocompatibility Complex Module—Molecular Immunology—Nov. 13, 1997—pp. 1133-1145—vol. 34—Nos. 16-17—Pergamon—Elsevier Science Ltd.—United Kingdom.
Schimmer et al—The BH3 Domain of BAD Fused to the Antennapedia Peptide Induces Apoptosis via its Alpha Helical Structure and Independent of Bcl-2—Cell Death and Differentiation—Feb. 18, 2001 pp. 725-733—vol. 8—No. 7—Canada.
Schinzel, R. and Druecks, P.—The Phosphate Recognition Site of *Escherichia coli* Maltodextrin Phosphorylase—FEBS Letters—Jul. 29, 1991—pp. 125-128—vol. 286—Nos. 1 and 2—Federation of European Biochemical Societies—Elsevier Science Publishers B.V.—The Netherlands.
Schwarze et al.—In Vivo Protein Transduction: Delivery of a Biologically Active Protein into the Mouse—Science—Sep. 3, 1999—pp. 1569-1572—vol. 285—Science Magazine—USA.
Sebestyen et al.—DNA Vector Chemistry: The Covalent Attachment of Signal Peptides to Plasmid DNA—Research—Nature Biotechnology—Jan. 16, 1998—pp. 80-85—vol. 16—USA.
Oehlke et al., "Rapid Translocation of Amphipathic α-Helical and β-Sheet-Forming Peptides through Plasma Membranes of Endothelian Cells," Peptide Science—Present and Future (Shimonishi eds.), Kluwer Academic Publisher, United Kingdom, pp. 782-783 (1999).
Van Regenmortel et al., "Peptide Analogues as Vaccines and Immunomodulators," Peptide Science—Present and suture (Shimonishi eds.), Kluwer Academic Publisher, United Kingdom, pp. 784-787 (1999).
Smilek et al.—A Single Amino Acid Change in a Myelin Basic Protein Peptide Confers the Capacity to Prevent Rather than Induce Experimental Autoimmune Encephalomyelitis—Immunology—Proceedings of the National Academy of Science—Nov. 1, 1991—pp. 9633-9637—vol. 88—No. 21—The National Academy of Science—USA.
Stevens et al.—Efficient Generation of Major Histocompatibility Complex Class I-Peptide Complexes Using Synthetic Peptide Libraries—The Journal of Biological Chemistry—Jan. 3, 1998—pp. 2874-2884—vol. 273—No. 5—The American Society for Biochemistry and Molecular Biology, Inc.—USA.
Stevens et al.—Peptide Length Preferences for Rat and Mouse MHC Class I Molecules Using Random Peptide Libraries—European Journal of Immunology—April—pp. 1272-1279—vol. 28—No. 4—Wiley-VCH Verlag GmbH—Germany.
Saito et al., "Contribution of Peptide Backbone Atoms to Binding of an Antigenic Peptide to Class I Major Histocompatibility Complex Molecule," Peptide Science—Present and Future (Shimonishi eds.), Kluwer Academic Publisher, United Kingdom, pp. 805-807 (1999).
Qin et al., "TAT Protein Transduction Domains : New Promise for Protein Therapy," Chinese Journal of Biochemistry and Molecular Biology, 23(7): 519-524 (2007) (Abstract Translated).
Torchilin et al.—Fluorescence Microscopy to Follow the Targeting of Liposomes and Micelles to Cells and their Intracellular Fate—Advanced Drug Delivery Reviews—Jan. 2005—pp. 95-109—vol. 57—ScienceDirect Elsevier B.V.—The Netherlands.
Torgerson et al.—Regulation of NF-kappa B, AP-1, NFAT, and STAT1 Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.
Touchard et al.—A Peptide Inhibitor of c-Jun N-Terminal Kinase for the Treatment of Endotoxin-Induced Uveitis—Immunology and Microbiology—Investigative Ophthalmology & Visual Science—Sep. 2010—pp. 4683-4693—vol. 51—No. 9—Association for Research in Vision and Ophthalmology—USA.
Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.
Van Regenmortel et al.—D-Peptides as Immunogens and Diagnostic Reagents—Protein Engineering—Current Opinion of Biotechnology—1998—pp. 377-382—vol. 8—Current Biology Publications—France.
Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.
Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.
Vocero-Akbani et al.—Killing HIV-Infected Cells by Transduction with an HIV Protease-Activated Caspase-3 Protein—Nature Medicine—Jan. 1999—pp. 29-33—vol. 5—No. 1—Nature America Inc.—USA.
Voet, Donald and Voet, Judith G.—Abnormal Hemoglobins—1995—pp. 235-241—Biochemistry Second Edition—John Wiley & Sons, Inc.—USA.
Wadia et al.—Delivery of Novel Anti-Cancer Peptides by Protein Transduction Domains—Peptides—May 2004—pp. 65-69—American Pharmaceutical Review—USA.
Waldmeier et al.—Recent Clinical Failures in Parkinson's Disease with Apoptosis Inhibitors Underline the Need for a Paradigm Shift in Drug Discovery for Neurodegenerative Diseases—Biochemical Pharmacology—Nov. 15, 2006—pp. 1197-1206—vol. 72—No. 10—ScienceDirect—Elsevier Inc.—USA.
Walsh et al.—Erythrocyte Survival is Promoted by Plasma and Suppressed by a Bak-Derived BH3 Peptide that Interacts with Membrane-Associated Bcl-XL—Red Cells—Blood—May 1, 2002 pp. 3439-3448—vol. 99—No. 9—The American Society of Hematology—USA.
Wender et al.—The Design, Synthesis, and Evaluation of Molecules that Enable or Enhance Cellular Uptake: Peptoid Molecular Transporters—Proceedings of the National Academy of Science—Nov. 21, 2000—pp. 13003-13008—vol. 97—No. 24—The National Academy of Science—USA.

(56) References Cited

OTHER PUBLICATIONS

Whitmarsh et al.—A Mammalian Scaffold Complex that Selectively Mediates MAP Kinase Activation—Science—Sep. 11, 1998—pp. 1671-1674—vol. 281—5383—www.sciencemag.org—USA.
Whitmarsh, A.J. and Davis, R.J.—Transcription Factor AP-1 Regulation by Mitogen-Activated Protein Kinase Signal Transduction Pathways—Review—Journal of Molecular Medicine Oct. 7, 1996—pp. 589-607—vol. 74—No. 10—Springer-Verlag—USA.
Wilson, David—Preventing Nerve Cell Death in ALS—Internet document—<http://www.als.caJ_news/57.aspx>—Dec. 5, 2001—2 pages—USA.
Wishart et al.—A Single Mutation Converts a Novel Phosphotyrosine Binding Domain into a Dual-specificity Phosphatase—Communication—The Journal of Biological Chemistry—Nov. 10, 1995—pp. 26782-26785—vol. 270—No. 45—The American Society for Biochemistry and Molecular Biology, Inc.—USA.
Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.
Adler, et al.—Regulation of JNK Signaling by GSTp—The EMBO Journal—Mar. 1, 1999—pp. 1321-1334—vol. 18—No. 5—European Molecular Biology Organization—USA.
Brady, Leo and Dodson, Guy—Reflections on a Peptide—Nature—News and Views—Drug Design—Apr. 21, 1994—pp. 692-693—vol. 368 (6473)—Nature Publishing Group—USA.
Briand et al—A Retro-Inverso Peptide Corresponding to the GH Loop of Foot-and-Mouth Disease Virus Elicits High Levels of Long-Lasting Protective Neutralizing Antibodies—Proceedings of National Academy of Sciences—Immunology—Nov. 1997—pp. 12545-12550—vol. 94—National Academy of Sciences—USA.
Brugidou et al.—The Retro-Inverso Form of a Homeobox-Derived Short Peptide is Rapidly Internalized by Cultured Neurons: A New Basis for an Efficient Intracellular Delivery System—Biochemical and Biophysical Research Communications—Sep. 14, 1995—pp. 685-693—vol. 214—No. 2—Academic Press, Inc.—USA.
Chie et al.—Identification of the Site of Inhibition of Oncogenic ras-p21-Induced Signal Transduction by a Peptide from a Ras Effector Domain—Journal of Protein Chemistry—Nov. 4, 1999—pp. 881-884—vol. 18—No. 8—USA.
Chorev et al.—A Dozen Years of Retro-Inverso Peptidomimetics—Accounts of Chemical Research—1993—pp. 266-273—vol. 26—American Chemical Society—USA.
Chorev et al.—Recent Developments in Retro Peptides and Proteins—An Ongoing Topochemical Exploration—Oct. 1995—pp. 438-445—vol. 13—No. 10—TIBTECH (Trends in Biotechnology) Elsevier Science Ltd.—USA.
Dang et al.—Nuclear and Nucleolar Targeting Sequences of c-erb-A, c-myb, N-myc, p53, HSP70, and HIV tat Proteins—Journal of Biological Chemistry—Oct. 25, 1989—pp. 18019-18023—vol. 264—No. 30—The American Society for Biochemistry and Molecular Biology, Inc.—USA.
Ausubel et al., "Using Synthetic Oligonucleotides as Probes," Current Protocols in Molecular Biology, Supplement 2, John Wiley & Sons, New York, pp. 6.4.1-6.4.10 (Apr. 1998).
Elliott et al.—Intercellular Trafficking and Protein Delivery by a Herpesvirus Structural Protein—Cell—Jan. 24, 1997—pp. 223-233—vol. 88—No. 2—Cell Press—United Kingdom.
Frankel et al.—Activity of Synthetic Peptides from the Tat Protein of Human Immunodeficiency Virus Type 1—Proceedings of National Academy of Sciences—Biochemistry—Oct. 1989—pp. 7397-7401—vol. 86—National Academy of Sciences—USA.
Giorello et al—Inhibition of Cancer Cell Growth and c-Myc Transcriptional Activity by a c-Myc Helix 1-Type Peptide Fused to an Internalization Sequence—Cancer Research—Aug. 15, 1998—pp. 3654-3659—vol. 58—USA.
Guichard et al.—Partially Modified Retro-Inverso Pseudopeptides as Non-Natural Ligands for the Human Class I Histocompatibility Molecule HLA-A2—Journal of Medicinal Chemistry—1996—pp. 2030-2039—vol. 39—American Chemical Society—USA.

Hauber et al.—Mutational Analysis of the Conserved Basic Domain of Human Immunodeficiency Virus tat Protein—Journal of Virology—Mar. 1989—pp. 1181-1187—vol. 63—No. 3—American Society of Microbiology—USA.
Inhibit.Dictionary.com—The American Heritage® Stedman's Medical Dictionary—Houghton Mifflin Company—One Page—Internet document: http://dictionary.reference.com/browse/inhibit—Accessed on Oct. 10, 2007—USA.
Jackson et al.—Heat Shock Induces the Release of Fibroblast Growth Factor 1 from NIH 3T3 Cells—Proceedings of National Academy of Sciences—Cell Biology—Nov. 1992—pp. 10691-10695—vol. 89—National Academy of Sciences—USA.
Jameson et al.—A Rationally Designed CD4 Analogue Inhibits Experimental Allergic Encephalomyelitis—Nature—Letters to Nature—Apr. 21, 1994—pp. 744-746—vol. 368 Nature Publishing Group—USA.
Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.
Kida et al.—Design and Synthesis of a Tat-related Gene Transporter: A Tool for Carrying the Adenovirus Vector into Cells—Bioorganic and Medicinal Chemistry Letters—Dec. 6, 2005—pp. 743-745—vol. 16—ScienceDirect—Elsevier Ltd—USA.
Kieber-Emmons et al.—Therapeutic Peptides and Peptidomimetics—Current Opinion in Biotechnology—1997—pp. 435-441—vol. 8—Current Biology Ltd.—USA.
Nori et al.—Tat-Conjugated Synthetic Macromolecules Facilitate Cytoplasmic Drug Delivery to Human Ovarian Carcinoma Cells—Bioconjugate Chemistry—Nov. 16, 2002—pp. 44-50—vol. 14—No. 1—American Chemical Society—USA.
Kisselev, Lev—Polypeptide Release Factors in Prokaryotes and Eukaryotes: Same Function, Different Structure—Jan. 2002—pp. 8-9—vol. 10—Structure—Elsevier Science Ltd—USA.
Lebleu, Bernard—Delivering Information-Rich Drugs—Prospects and Challenges—Meeting Report—Apr. 1996—pp. 109-110—vol. 14—No. 4—Tibtech (Trends in Biotechnology) Elsevier Science Ltd.—USA.
Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.
Lewis et al.—Lymphoma Cell Uptake of Radiometal- and Fluorescent-Labelled BCL-2 Antisense PNA Conjugates is Mediated by a Retro-Inverso Delivery Peptide—Abstracts—Journal of Label Compounds and Radiopharmaceuticals—2003—p. S13—vol. 46—SI-S403—XP-002347557—USA.
Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.
Lim et al.—Penetration Enhancement in Mouse Skin and Lipolysis in Adipocytes by TAT-GKH, A New Cosmetic Ingredient—Journal of Cosmetic Science—Sep./Oct. 2003—pp. 483-491—vol. 54—USA.
Lin et al.—Inhibition of Nuclear Translocation of Transcription Factor NF-kappa B by a Synthetic Peptide Containing a Cell Membrane-Permeable Motif and Nuclear Localization Sequence—Journal of Biological Chemistry—Jun. 16, 1995—pp. 14255-14258—vol. 270—No. 24—The American Society for Biochemistry and Molecular Biology, Inc.—USA.
Lloyd-Williams et al.—Chapter 5—Chemical Approaches to the Synthesis of Peptides and Proteins—1997—Formation of Disulfide Bridges—pp. 209-236—CRC Press LLC—USA.
Lloyd-Williams et al.—Chapter 6—Chemical Approaches to the Synthesis of Peptides and Proteins—1997—Peptide Libraries—pp. 237 and 264-267—CRC Press LLC—USA.
Mann, David A. and Frankel, Alan D.—Endocytosis and Targeting of Exogenous HIV-1 Tat Protein—The EMBO Journal—1991—pp. 1733-1739—vol. 10—No. 7—Oxford University Press—United Kingdom.
Marino et al.—Inhibition of Experimental Autoimmune Encephalomyelitis in SJL Mice by Oral Administration of Retro-Inverso

(56) References Cited

OTHER PUBLICATIONS

Derivative of Encephalitogenic Epitope P87-99—European Journal of Immunology—1999—pp. 2560-2566—vol. 29—Wiley-VCH Verlag GmbH—Weinheim—Germany.
Marks et al.—Protein Targeting by Tyrosine- and Di-leucine-based Signals: Evidence for Distinct Saturable Components—The Journal of Cell Biology—Oct. 1, 1996—pp. 341-354—vol. 135—No. 2—The Rockefeller University Press—USA.
Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd—USA.
Mazur, Dan J. and Perrino, Fred W.—Identification and Expression of the TREX1 and TREX2 cDNA Sequences Encoding Mammalian 3'→5' Exonucleases—The Journal of Biological Chemistry—Jul. 9, 1999—pp. 19655-19660—vol. 274—No. 28—The American Society for Biochemistry and Molecular Biology, Inc.—USA.
Melikov, K. and Chernomordik, L.V.—Review—Arginine-rich Cell Penetrating Peptides: From Endosomal Uptake to Nuclear Delivery—Cellular and Molecular Life Sciences—Oct. 18, 2005—pp. 2739-2749—vol. 62—Birkhauser Verlag—Switzerland.
Messer, Jr., Dr. William S.—MBC 3320 Posterier Pituitary Hormones—Vasopression and Oxytocin—Apr. 3, 2000—pp. 1-5—,http://www.neurosci.pharm.utoledo.edu/MBC3320/vasopressin.htm>—USA.
Mi et al.—Characterization of a Class of Cationic Peptides able to Facilitate Efficient Protein Transduction in Vitro and in Vivo—Article—Molecular Therapy—Oct. 2000—pp. 339-347—vol. 2—No. 4—The American Society of Gene Therapy—USA.
Milano et al.—A Peptide Inhibitor of c-Jun NM2-terminal Kinase Reduces Myocardial Ischemia-reperfusion Injury and Infarct Size in Vivo—American Journal of Physiology—Heart Circulation Physiology—Apr. 2007—pp. H1828-H1835—vol. 292—www.ajpheart.org—The American Physiological Society—USA.
Mooi et al.—Regulation and Structure of an *Escherichia coli* Gene Coding for an Outer Membrane Protein involved in Export of K88ab Fimbrial Subunits—Nucleic Acids Research—1996—pp. 2443-2457—vol. 14—No. 6—IRL Press Limited—United Kingdom.
Moon et al. Bcl-2 Overexpression Attenuates SP600125-induced Apoptosis in Human Leukemia U937 Cells—Cancer Letters—Feb. 3, 2008—pp. 316-325—vol. 264—ScienceDirect—Elsevier Ireland Ltd—Ireland.
Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.
Nagahara et al.—Transduction of Full-Length TAT Fusion Proteins into Mammalian Cells: TAT-p27Kip1 Induces Cell Migration—Nature Medicine—Dec. 1998—pp. 1449-1452—vol. 4—No. 12—Nature America Inc.—USA.
Negri at al.—Design of a Novel Peptide Inhibitor of the JNK Signaling Pathway—1217-P—Journal—Diabetes—Abstract Book—61st Scientific Session—Jun. 2001—p. A294—vol. 50—Supplement No. 2—American Diabetes Association—USA.
Neundorf et al.—Detailed Analysis Concerning the Biodistribution and Metabolism of Human Calcitonin-Derived Cell-Penetrating Peptides—Bioconjugate Chemistry—Jul. 24, 2008—pp. 1596-1603—vol. 19—No. 8—American Chemical Society—USA.
Ngo et al.—Computational Complexity, Protein Structure Prediction, and the Levinthal Paradox—The Protein Folding Problem and Tertiary Structure Prediction—Merz et al. (Editors)—1994—pp. 433, 492-495—Birkhauser Boston—USA.
Noguchi et al.—Regulation of c-Myc through Phosphorylation at Ser-62 and Ser-71 by c-Jun N-Terminal Kinase—Journal of Biological Chemistry—Nov. 12, 1999—pp. 32580-32587—vol. 274—No. 46—The American Society for Biochemistry and Molecular Biology, Inc.—USA.
Office Action dated Jun. 14, 2018 issued in U.S. Appl. No. 14/891,067, 15 pages.
Office Action dated Mar. 22, 2019 issued in U.S. Appl. No. 14/891,067, 17 pages.
Office Action dated Sep. 27, 2019 issued in U.S. Appl. No. 14/891,067, 10 pages.
Office Action dated Aug. 16, 2018 issued in U.S. Appl. No. 15/321,893, 8 pages.
Office Action dated Dec. 4, 2018 issued in U.S. Appl. No. 15/321,904, 14 pages.
Office Action dated Nov. 29, 2018 issued in U.S. Appl. No. 15/737,480, 16 pages.
Office Action dated Jan. 30, 2019 issued in U.S. Appl. No. 15/628,771, 17 pages.
Office Action dated Aug. 24, 2017 issued in U.S. Appl. No. 15/516,943, 14 pages.
Office Action dated Jun. 15, 2018 issued in U.S. Appl. No. 15/516,943, 9 pages.
Office Action dated Jan. 10, 2019 issued in U.S. Appl. No. 15/516,943, 10 pages.
Office Action dated Aug. 8, 2019 issued in U.S. Appl. No. 15/516,943, 11 pages.
Office Action dated Dec. 11, 2013 issued in U.S. Appl. No. 14/035,450, 9 pages.
Office Action dated Sep. 24, 2014 issued in U.S. Appl. No. 14/035,450, 7 pages.
Office Action dated Apr. 27, 2015 issued in U.S. Appl. No. 14/035,450, 10 pages.
Office Action dated Aug. 31, 2015 issued in U.S. Appl. No. 14/035,450, 10 pages.
Office Action dated May 2, 2016 issued in U.S. Appl. No. 14/035,450, 10 pages.
Office Action dated Jan. 26, 2017 in U.S. Appl. No. 14/849,374, 19 pages.
Office Action dated Sep. 26, 2017 in U.S. Appl. No. 14/849,374, 16 pages.
Office Action dated Mar. 29, 2017 in U.S. Appl. No. 15/045,058, 43 pages.
Office Action dated Jul. 22, 2015 in U.S. Appl. No. 14/144,938, 12 pages.
Office Action dated Dec. 28, 2010 in U.S. Appl. No. 12/066,657, 27 pages.
Office Action dated Jun. 28, 2010 in U.S. Appl. No. 12/066,657, 9 pages.
Office Action dated Jul. 19, 2012 in U.S. Appl. No. 12/066,657, 13 pages.
Office Action dated Jul. 8, 2011 in U.S. Appl. No. 12/101,911, 14 pages.
Office Action dated Aug. 29, 2006 in U.S. Appl. No. 10/457,614, 21 pages.
Office Action dated Oct. 12, 2007 in U.S. Appl. No. 10/457,614, 17 pages.
www.healthline.com—"What is Cystitis?", obtained Sep. 21, 2019; pp. 1-14 (Year: 2019).
TgCRND8 Research Model, Alzforum, www.alzforum.org /research -models /tgcmd8, retrieved Nov. 25, 2018. (Year: 2018).
XG-102 C-Terminal acid, Compound Summary for CID 72941992, PubChem, pubchem.ncbi.nlm.nih.gov /compound /72941992#section= Top, retrieved Nov. 24, 2018. (Year: 2018).
Sclip A et al. c-Jun N-terminal kinase has a key role in Alzheimer disease synaptic dysfunction in vivo. Cell Death and Disease, 5, e1019. Published online Jan. 23, 2014. (Year: 2014).
Sharma N et al. SP600125, a competitive inhibitor of JNK attenuates streptozotocin induced neurocognitive deficit and oxidative stress in rats. Pharmacology, Biochemistry and Behavior, 96, 386-394. (Year: 2010).
Office Action dated Feb. 1, 2016 issued in U.S. Appl. No. 14/367,706, 24 pages.
Office Action dated Apr. 8, 2019 issued in U.S. Appl. No. 15/934,735, 8 pages.
Office Action dated Mar. 21, 2014 issued in U.S. Appl. No. 13/141,314, 21 pages.
Office Action dated Jul. 31, 2014 issued in U.S. Appl. No. 13/141,314, 17 pages.

(56) References Cited

OTHER PUBLICATIONS

Office Action dated Aug. 27, 2015 issued in U.S. Appl. No. 13/141,314, 9 pages.
Office Action dated Mar. 23, 2017 issued in U.S. Appl. No. 14/891,067, 14 pages.
Office Action dated Nov. 20, 2017 issued in U.S. Appl. No. 14/891,067, 12 pages.
133:204452, Interaction of native RNAs with Tat peptides. Chemical Abstracts Database Sep. 29, 2000:1-3.
Chen et al., "The Role of c-Jun N-terminal Kinase (JNK) in Apoptosis Induced by Ultraviolet C and gamma Radiation," J. of Bio, Chem., 271(50):31929-31936 (1996).
Branden and Tooze, Prediction, Engineering and Design of Protein Structures, Introduction to Protein Structure, 1991:247.
GenBank Database Accession No. AAD20443. islet-brain 1 [Homo sapiens]. GenBank Mar. 17, 1999: 1-2.
GenBank Database Accession No. AAD22543, islet-brain 1 (*Rattus norvegicus*]. GenBank Mar. 1, 2006: 1-2.
GenBank Database Accession No. AF074091. Homo sapiens islet-brain 1 mRNA, complete cds. GenBank Mar. 17, 1999: 1-2.
GenBank Database Accession No. AF108959. *Rattus norvegicus* islet-brain 1 (IBI) mRNA, complete cds. GenBank Mar. 1, 2006: 1-3.
GenBank Database Accession No. AF218778. Homo sapiens islet-brain 2 mRNA, complete cds. GenBank Mar. 2, 2006: 1-2.
Copy of International Search Report and Written Opinion dated Apr. 27, 2010 issued in PCT/EP2009/009229.
Copy of international Search Report and Written Opinion dated Jun. 2, 2010 issued in PCT/EP2009/009228.
Q9WVI9, JIPI_MOUSE Standard; PRT; 707 AA. Database UniProt 2003.
Inflammation. Stedman's Medical Dictionary 28th Edition, PDR® Electronic Library(TM): Stedman Definitions, (www.pdrel.com), Dec. 18, 2010:1-2.
Manheimer, PH0878; 1g kappa chain V region. NCB I Sequence Viewer v2., GenBank May 30, 1997.
Selective Dimerisation of Cysteines to form Heterodimers. NJE Feb. 3, 1997.
Fujita et al.—Prophylactic or Therapeutic Agent for Retinal Diseases and Method for Preventing or Treating Retinal Diseases, Each Comprising JNK (C-JUN N-Terminal Kinase)-Inhibiting Peptide, and Use of the Peptide- International Application No. PCT/JP2010/55208 - Santen Pharmaceutical Co., Lid.—Database WPI—Thompson Scientific—pp. 1-4—USA.
Hanyu et al., "Pioglitazone improved cognition in a pilot study on patients with Alzheimer's disease and mild cognitive impairmenl with diabetes mellitus," Journal of the American Geriatrics Society, 57(1):177-179 (2009).
Herve et al., "On the Immunogenic Properties of Retro -Inverso Peptides, Total Retro- Inversion of T -Cell Epitopes Causes a Loss of Binding to MHC II Molecules, Molecular Immunology, 34: 157 -163 (1997).
Horvath et at., "Somatostatin Octa- and Heptapeptides, Structural and Biological Characteristics," Peptides (Ramage et al, ed) 483 -484 (1996).
Hruby et al., "Design of Potent and Specific Melanotropin Agonists and Antagonists: Investigating Ligands for New Receptors," Peptides (Ramage et al, ed) 485-486 (1996).
Janin, "Protein- Protein Interactions" Encyclopedia of Molecular Biology (Creighton, ed.) 2027 -2033 (1999).
Manning et al., "Targeting JNK for therapeutic benefit: from junk to gold?" Nature Reviews Drug Discovery, 2: 554-565 (2003).
Nakamura et al., "Expression of mitogen activated protein kinases in labial salivary glands of patients with Sjogren's syndrome," Annals of the Rheumatic Diseases, 58(6):382-385 (1999).
Tsuyoshi et al., Behcet's disease. NE J Med. 1999:1284-1291.
Cui et al., JNK pathway: diseases and therapeutic potential. Acta Pharmacol Sin. May 26, 2007(5):601 -608.

Josephson et al., High -Efficiency Intracellular Magnetic Labeling with Novel Superparamagnetic-Tat Peptide Conjugates. Bioconjug Chem. Mar.-Apr. 1999;10(2):186 -191.
Moschos et al., Lung Delivery Studies Using siRNA Conjugated to TAT(48-60) and Penetratin Reveal Peptide Induced Reduction in Gene Expression and Induction of Innate Immunity. Bioconjug Chem. Sep.-Oct. 2007:18 (5):1450 -1459.
Moulin et al. "Islet-brain (IB)/JNK-interacting proteins (JIPs): future targets for the treatment of neurodegenerative diseases?" Current Neurovascular Research, 1(2):111-127 (2004).
Rickels et al., "Phage display selection of ligand residues important for Src homology 3 domain binding specificity," Proc Natl Acad Sci USA., 92(24):10909-10913 (1995).
Chemical Abstracts Database, Accession No. 133:204452 CA, (Sep. 29, 2000), 3 pages.
Cerbone et al., "AS601245, an anti -inflammatory JNK inhibitor, and clofibrate have a synergistic effect in inducing cell responses and in affecting the gene expression profile in CaCo -2 colon cancer cells," PPAR Research, 2012: 269751, 1 -16 (2012).
Budur et al., "A pharmacogenetics supported clinical trial to delay onset of mild cognitive impairment due to Alzheimer's disease using low dose pioglitazone: the tomorrow study," Neuropsychopharmacology, 39: S342 (2014).
Bloch et al., "Increased ERK and JNK activation and decreased ERK/JNK ratio are associated with long-term organ damage in patients with systemic lupus erythematosus," Rheumatology 53: 1034 -1042 (2014).
Barichello et al., "Dexamethasone treatment reverses cognitive impairment but increases brain oxidative stress in rats submitted to pneumococcal meningitis," Oxidative Medicine and Cellular Longevity, 1 -7 (2011).
Aisen et al., "A randomized controlled trial of prednisone in Alzheimer's disease," Neurology, 54: 588 -593 (2000).
Melino et al., "The effect of the JNK inhibitor, JIP peptide, on human T lymphocyte proliferation and cytokine production," 181(10): 7300-7306 (2008).
Wang et al., "JNK inhibition as a potential strategy in treating Parkinson's disease," Drug News Perspect., 17 (10):646-654 (2004).
Weston et al., "The JNK signal transduction pathway," Curr. Opin. Cell Biol., 19(2):142-149, (2007).
Soejima et al., "Activation of MKK4 (SEK1), JNK, and C-Jun in Labial Salivary Infiltrating T Cells in Patients With Sjogren's Syndrome," Rheumatology International, 27(4): 329-333 (2006).
Shimazawa et al., "Inhibitor of double stranded RNA-dependent protein kinase protects against cell damage induced by ER stress," Neurosci Lett., 409(3):192-195 (2006).
Kishan, KV. Radha and Agrawal, Vishal—SH3—like Fold Proteins are Structurally Conserved and Functionally Divergent—Current Protein and Peptide Science—1995—pp. 143-150—vol. 6—Nentharn Science Publishers Ltd.—USA.
Duby et al. (Contributors)—Using Synthetic Oligonucleotides as Probes —Current Protocols in Molecular Biology—Supplement 2—Apr. 1988—pp. 6.4.1-6.4.10—John Wiley & Sons—USA.
NCBI Sequence Viewer—Accession No. AAF32323—Reports—Islet—Brain 2 (Homo Sapiens)—Two References—Negri et al.—Feb. 9, 2000—2 pages—USA.
Neidle, S. ed., "Cancer Drug Design and Discovery," Elsevier/Academic Press, 427-431 (2008).
Auerbach et al., "Angiogenesis assays: Problems and pitfalls," Cancer and Metastasis Reviews, 19: 167-172 (2000).
Jain, R., "Barriers to Drug Delivery in Solid Tumors," Scientific American, 58-65 (1994).
Sporn et al., "Chemoprevention of cancer," Carcinogenesis; 21: 525-530 (2000).
Thoren et al,—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.
Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.

(56) References Cited

OTHER PUBLICATIONS

Pennington, Michael W. and Dunn, Ben M. {Editors}—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc.—USA.

Branden et al., Introduction to Protein Structure, Garland Publishing Inc., New York, p. 2471(1999).

Database UniProt, Retrieved from EBI, Database Accession No. Q9WVI9, Abstract (Feb. 28, 2003).

Guichard et al.; Horvath et al.; Hruby et al., Peptides 1996: Proceedings of the twenty-fourth European Peptide Symposium, Sep. 8-13, 1996, Edinburgh, Scotland; Ramage /Epton (Eds.), The European Peptide Society, Mayflower Scientific Ltd., Kingswinford, pp. 447-450 and 483-486 (1996).

Ohelke et al., Van Regenmortel et al., Saito et al., Peptide Science-Present and Future, Edited by Y. Shimonishi, Kluwer Academic Publishers, Dordrecht, The Netherlands, pp. 782-787 and 805-807 (1999).

Chung et al., "Endogenous Nerve Growth Factor Regulates Collagen Expression and Bladder Hypertrophy Through AKT and MAPK Pathways During Cystitis," Journal of Biological Chemistry, 265: 4206-4212 (2010).

Guichard et al., "Mimicry of an Immunodominant Epitope of Foot and Mouth Disease Virus with Retro-inverson Isomers: A New Approach in the Design of Peptide Based Vaccines," Peptides (Ramage et al. ed) 447-448 (1996).

Guichard et al., "Partially Modified Retro -inverson Psudopeptides as Non- natural Ligands for the Human Class I Histocompatibility Molecule, HLA -A2," Peptides (Ramage et al. ed) 449-450 (1996).

Multifocal choroiditis, "National Center of Advancing Translational Science," https://rarediseases.info.nih.gov/diseases/9824/multifocal-choroiditis; 5 pages (2017).

Theoretical pI /Mw average of the amino acid sequence DQSRPVQPFLNLTTPRKPRPPRRRQRRKKRG; http://web.expasy.org/cgi-bin/compute_pi/pi_tool; obtained Sep. 20, 2017; p. 1 (2017).

Sclip A et al. c-Jun N-terminal kinase regulates soluble Abeta oligomers and cognitive impairment in AD mouse model, J. Biol. Chem. 286(51), 43871-43880. (Year: 2011).

Office Action dated Oct. 31, 2019 issued in U.S. Appl. No. 15/934,735, 9 pages.

NIH, "Panuveitis", https://rarediseases.info.nih.gov/diseases/8577/panuveitis; 2016, pp. 1-7 (2016).

Garg, "Successful Management of Uveitis in a Patient with Unilateral Multifocal Choroiditis", Insert to Retina Today, pp. 1-8 (2019).

\* cited by examiner

| SEQ ID NO. | | Sequence | | | | hJNK1 | | | hJNK2 | | | hJNK3 | | |
|---|---|---|---|---|---|---|---|---|---|---|---|---|---|---|
| | | | | | | IC50 | SEM | n | IC50 | SEM | n | IC50 | SEM | n |
| 193 | NH2 | R P K R P T T L N L F | CONH2 | | | 39,52 | 0,57 | 2 | 183,85 | 50,45 | 2 | 67,68 | 13,92 | 2 |
| 2 | NH2 | r P K R P T T L N L F | CONH2 | | | 65,55 | 26,03 | 3 | 423,53 | 241,45 | 3 | 103,32 | 36,53 | 3 |
| 3 | NH2 | R P K R P T T L N L F | CONH2 | | | 311,63 | 99,86 | 4 | 1213,53 | 437,87 | 4 | 359,47 | 161,02 | 4 |
| 5 | NH2 | R P K R P T T L n L F | CONH2 | | | 347,55 | 174,17 | 4 | 1501,88 | 701,33 | 4 | 387,15 | 179,51 | 4 |
| 6 | NH2 | R P K R P T T L r L F | CONH2 | | | 90,50 | 29,63 | 4 | 358,75 | 105,28 | 4 | 119,50 | 39,82 | 4 |
| 7 | NH2 | R P K R P T T L N L f | CONH2 | | | 69,53 | 21,75 | 4 | 278,18 | 51,43 | 4 | 88,97 | 26,72 | 4 |

Fig. 2

| SEQ ID NO: | | Sequence | | hJNK1 | | | hJNK2 | | | hJNK3 | | |
|---|---|---|---|---|---|---|---|---|---|---|---|---|
| | | | | IC50 | SEM | n | IC50 | SEM | n | IC50 | SEM | n |
| 196 | NH2 | G R K K R R Q R R R P P K R P T T L N L F P Q V P R S Q D | CONH2 | 42,20 | 8,17 | 8 | 8,43 | 2,01 | 6 | 5,22 | 0,71 | 6 |
| 197 | CONH2 | G r k k r r q r r r p p k r p t t l n l f p q v p r s q d | NH2 | 24358,50 | 10019,91 | 8 | 801,77 | 114,86 | 11 | 1294,24 | 255,51 | 11 |
| 194 | NH2 | G R K K R R Q R R R P P K R P T T L N L F P Q V P R S Q D | CONH2 | 13,99 | 0,06 | 2 | 2,70 | 0,48 | 2 | 2,59 | 0,08 | 2 |
| 195 | NH2 | G R K K R R Q R R R P P K R P T T L N L F P Q V P R S Q D | CONH2 | 10,77 | 1,83 | 2 | 11,26 | 0,56 | 2 | 4,92 | 0,27 | 2 |
| 172 | NH2 | r K K R r Q R R r R P K r R P a T L N L f | CONH2 | 722,49 | 124,58 | 7 | 54,66 | 13,04 | 7 | 102,32 | 47,81 | 7 |
| 200 | NH2 | r K K R r Q R R r R P K r R P K A A a A A N A f | CONH2 | NA | NA | 6 | 3324,00 | 2469,99 | 6 | 3820,81 | 3190,08 | 6 |
| 46 | NH2 | r K K R r Q R R r | CONH2 | NA | NA | 3 | 5340,33 | 1803,08 | 3 | 8130,86 | 5323,73 | 3 |
| 173 | NH2 | r K K R r Q R R r R P T T L r L f | CONH2 | 86,36 | 4,02 | 3 | 33,03 | 0,16 | 2 | 16,76 | 2,03 | 3 |
| 174 | NH2 | r K K R r Q R R r R P T T L N L f | CONH2 | 333,73 | 36,46 | 3 | 123,13 | 4,53 | 3 | 63,12 | 6,04 | 3 |
| 175 | NH2 | r K K R r Q R R r R P T T L N L f | CONH2 | 185,30 | 18,10 | 3 | 82,30 | 9,26 | 3 | 60,60 | 6,01 | 3 |
| 176 | NH2 | r K K R r Q R R r R P T T T L N L w | CONH2 | 131,17 | 12,28 | 3 | 40,33 | 4,60 | 3 | 22,36 | 1,60 | 3 |
| 177 | NH2 | r K K R r Q R R r R P T D L N L f | CONH2 | 355,10 | 34,02 | 3 | 67,20 | 7,12 | 3 | 45,38 | 6,70 | 3 |
| 178 | NH2 | r K K R r Q R R r R P T T L r L w | CONH2 | 329,33 | 12,26 | 3 | 106,60 | 42,64 | 3 | 30,41 | 5,81 | 3 |
| 179 | NH2 | r K K R r Q R R r R P T T L r L w | CONH2 | 249,47 | 22,35 | 3 | 122,11 | 20,73 | 3 | 45,66 | 3,79 | 3 |
| 180 | NH2 | r K K R r Q R R r R P T D L r L w | CONH2 | 265,20 | 34,65 | 3 | 117,65 | 10,58 | 3 | 46,99 | 8,21 | 3 |
| 181 | NH2 | r K K R r Q R R r R P T D L r L w | CONH2 | 293,70 | 9,79 | 2 | 160,22 | 40,13 | 2 | 47,56 | 5,77 | 2 |
| 182 | NH2 | r K K R r Q R R r R P a T L N L f | CONH2 | 1677,50 | 34,50 | 2 | 168,40 | 20,80 | 2 | 59,36 | 2,35 | 2 |
| 183 | NH2 | r K K R r Q R R r R P a T L N L f | CONH2 | 2588,00 | 494,00 | 2 | 427,30 | 25,00 | 2 | 199,20 | 3,90 | 2 |
| 184 | NH2 | r K K R r Q R r K R P a T L N L f | CONH2 | 2426,00 | 129,00 | 2 | 205,95 | 8,25 | 2 | 129,45 | 9,65 | 2 |
| 185 | NH2 | r K K R r Q R R r R P K R P s T L N L f | CONH2 | 765,65 | 78,15 | 2 | 72,09 | 2,85 | 2 | 35,52 | 6,34 | 2 |
| 186 | NH2 | r K K R r Q R R r R P K R P g T L N L f | CONH2 | 1021,30 | 100,70 | 2 | 52,59 | 2,73 | 2 | 44,24 | 4,80 | 2 |
| 187 | NH2 | r K K R r Q R R r R P K R P K T L N L f | CONH2 | 594,45 | 40,45 | 2 | 37,88 | 5,47 | 2 | 25,41 | 8,95 | 2 |
| 188 | NH2 | r K K R r Q R R r G K R K A L K L f | CONH2 | 1421,00 | 98,00 | 2 | 98,14 | 27,26 | 2 | 36,12 | 2,46 | 2 |
| 189 | NH2 | r K K R r Q R R r G K R K A L r L f | CONH2 | 22270,00 | 5090,00 | 2 | 175,60 | 1,30 | 2 | 127,72 | 31,88 | 2 |
| 190 | NH2 | r K K R r Q R R r R K A L r L f | CONH2 | 8969,50 | 2070,50 | 2 | 148,20 | 9,70 | 2 | 159,35 | 13,45 | 2 |

Fig. 4

SEQUENCE LISTING

```
<160> NUMBER OF SEQ ID NOS: 200

<210> SEQ ID NO 1
<211> LENGTH: 11
<212> TYPE: PRT
<213> ORGANISM: Artificial
<220> FEATURE:
<223> OTHER INFORMATION: Consensus new JNK inhibitors
<220> FEATURE:
<221> NAME/KEY: Variant
<222> LOCATION: (1)..(1)
<223> OTHER INFORMATION: X1 may be R, P, Q or D-enantiomeric r
<220> FEATURE:
<221> NAME/KEY: Variant
<222> LOCATION: (2)..(2)
<223> OTHER INFORMATION: X2 may be R, P, G or D-enantiomeric r
<220> FEATURE:
<221> NAME/KEY: Variant
<222> LOCATION: (3)..(3)
<223> OTHER INFORMATION: X3 may be K, R or D-enantionmeric k or r
<220> FEATURE:
<221> NAME/KEY: Variant
<222> LOCATION: (5)..(5)
<223> OTHER INFORMATION: X4 may be P or K
<220> FEATURE:
<221> NAME/KEY: Variant
<222> LOCATION: (6)..(6)
<223> OTHER INFORMATION: X5 may be T, or D-enantiomeric a, s, q, k or
     absent
<220> FEATURE:
<221> NAME/KEY: Variant
<222> LOCATION: (7)..(7)
<223> OTHER INFORMATION: X6 may be T, D or A
<220> FEATURE:
<221> NAME/KEY: Variant
<222> LOCATION: (9)..(9)
<223> OTHER INFORMATION: X7 may be N, K or D-enantiomeric n or r
<220> FEATURE:
<221> NAME/KEY: Variant
<222> LOCATION: (11)..(11)
<223> OTHER INFORMATION: X8 may be F or D-enantiomeric f or w

<400> SEQUENCE: 1

Xaa Xaa Xaa Arg Xaa Xaa Xaa Leu Xaa Leu Xaa
1               5                   10

<210> SEQ ID NO 2
<211> LENGTH: 11
<212> TYPE: PRT
<213> ORGANISM: Artificial
<220> FEATURE:
<223> OTHER INFORMATION: rPKRPTTLNLF JNK inhibitor
<220> FEATURE:
<221> NAME/KEY: Variant
<222> LOCATION: (1)..(1)
<223> OTHER INFORMATION: Arg is D-enantiomeric Arg

<400> SEQUENCE: 2
```

```
Arg Pro Lys Arg Pro Thr Thr Leu Asn Leu Phe
1               5                   10

<210> SEQ ID NO 3
<211> LENGTH: 11
<212> TYPE: PRT
<213> ORGANISM: Artificial
<220> FEATURE:
<223> OTHER INFORMATION: RPkRPTTLNLF JNK inhibitor
<220> FEATURE:
<221> NAME/KEY: Variant
<222> LOCATION: (3)..(3)
<223> OTHER INFORMATION: Lys is D-enantiomeric Lys

<400> SEQUENCE: 3

Arg Pro Lys Arg Pro Thr Thr Leu Asn Leu Phe
1               5                   10

<210> SEQ ID NO 4
<211> LENGTH: 11
<212> TYPE: PRT
<213> ORGANISM: Artificial
<220> FEATURE:
<223> OTHER INFORMATION: RPKRPaTLNLF JNK inhibitor
<220> FEATURE:
<221> NAME/KEY: Variant
<222> LOCATION: (6)..(6)
<223> OTHER INFORMATION: Ala is D-enantiomeric Ala

<400> SEQUENCE: 4

Arg Pro Lys Arg Pro Ala Thr Leu Asn Leu Phe
1               5                   10

<210> SEQ ID NO 5
<211> LENGTH: 11
<212> TYPE: PRT
<213> ORGANISM: Artificial
<220> FEATURE:
<223> OTHER INFORMATION: RPKRPTTLnLF JNK inhibitor
<220> FEATURE:
<221> NAME/KEY: Variant
<222> LOCATION: (9)..(9)
<223> OTHER INFORMATION: Asn is D-enantiomeric Asn

<400> SEQUENCE: 5

Arg Pro Lys Arg Pro Thr Thr Leu Asn Leu Phe
1               5                   10

<210> SEQ ID NO 6
<211> LENGTH: 11
<212> TYPE: PRT
<213> ORGANISM: Artificial
<220> FEATURE:
<223> OTHER INFORMATION: RPKRPTTLrLF JNK inhibitor
<220> FEATURE:
<221> NAME/KEY: Variant
<222> LOCATION: (9)..(9)
<223> OTHER INFORMATION: Arg is D-enantiomeric Arg

<400> SEQUENCE: 6

Arg Pro Lys Arg Pro Thr Thr Leu Arg Leu Phe
1               5                   10

<210> SEQ ID NO 7
<211> LENGTH: 11
<212> TYPE: PRT
<213> ORGANISM: Artificial
<220> FEATURE:
<223> OTHER INFORMATION: RPKRPTTLNLf JNK inhibitor
```

```
<220> FEATURE:
<221> NAME/KEY: Variant
<222> LOCATION: (11)..(11)
<223> OTHER INFORMATION: Phe is D-enantiomeric Phe

<400> SEQUENCE: 7

Arg Pro Lys Arg Pro Thr Thr Leu Asn Leu Phe
1               5                   10

<210> SEQ ID NO 8
<211> LENGTH: 11
<212> TYPE: PRT
<213> ORGANISM: Artificial
<220> FEATURE:
<223> OTHER INFORMATION: RPkRPaTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 8

Arg Pro Lys Arg Pro Ala Thr Leu Asn Leu Phe
1               5                   10

<210> SEQ ID NO 9
<211> LENGTH: 11
<212> TYPE: PRT
<213> ORGANISM: Artificial
<220> FEATURE:
<223> OTHER INFORMATION: RPkRPTTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 9

Arg Pro Lys Arg Pro Thr Thr Leu Asn Leu Phe
1               5                   10

<210> SEQ ID NO 10
<211> LENGTH: 11
<212> TYPE: PRT
<213> ORGANISM: Artificial
<220> FEATURE:
<223> OTHER INFORMATION: RPkRPTTLrLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 10

Arg Pro Lys Arg Pro Thr Thr Leu Arg Leu Phe
```

```
1               5                   10

<210> SEQ ID NO 11
<211> LENGTH: 11
<212> TYPE: PRT
<213> ORGANISM: Artificial
<220> FEATURE:
<223> OTHER INFORMATION: RRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 11

Arg Arg Arg Arg Pro Thr Thr Leu Asn Leu Phe
1               5                   10

<210> SEQ ID NO 12
<211> LENGTH: 11
<212> TYPE: PRT
<213> ORGANISM: Artificial
<220> FEATURE:
<223> OTHER INFORMATION: QRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 12

Gln Arg Arg Arg Pro Thr Thr Leu Asn Leu Phe
1               5                   10

<210> SEQ ID NO 13
<211> LENGTH: 11
<212> TYPE: PRT
<213> ORGANISM: Artificial
<220> FEATURE:
<223> OTHER INFORMATION: RPkRPTTLNLw JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Trp is D-enantiomeric Trp

<400> SEQUENCE: 13

Arg Pro Lys Arg Pro Thr Thr Leu Asn Leu Trp
1               5                   10

<210> SEQ ID NO 14
<211> LENGTH: 11
<212> TYPE: PRT
<213> ORGANISM: Artificial
<220> FEATURE:
<223> OTHER INFORMATION: RPkRPTDLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
```

```
<223> OTHER INFORMATION: Phe is D-enantiomeric Phe

<400> SEQUENCE: 14

Arg Pro Lys Arg Pro Thr Asp Leu Asn Leu Phe
1               5                   10

<210> SEQ ID NO 15
<211> LENGTH: 11
<212> TYPE: PRT
<213> ORGANISM: Artificial
<220> FEATURE:
<223> OTHER INFORMATION: RRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 15

Arg Arg Arg Arg Pro Thr Thr Leu Arg Leu Trp
1               5                   10

<210> SEQ ID NO 16
<211> LENGTH: 11
<212> TYPE: PRT
<213> ORGANISM: Artificial
<220> FEATURE:
<223> OTHER INFORMATION: QRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 16

Gln Arg Arg Arg Pro Thr Thr Leu Arg Leu Trp
1               5                   10

<210> SEQ ID NO 17
<211> LENGTH: 11
<212> TYPE: PRT
<213> ORGANISM: Artificial
<220> FEATURE:
<223> OTHER INFORMATION: RRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 17
```

Arg Arg Arg Arg Pro Thr Asp Leu Arg Leu Trp
1               5                   10

<210> SEQ ID NO 18
<211> LENGTH: 11
<212> TYPE: PRT
<213> ORGANISM: Artificial
<220> FEATURE:
<223> OTHER INFORMATION: QRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 18

Gln Arg Arg Arg Pro Thr Asp Leu Arg Leu Trp
1               5                   10

<210> SEQ ID NO 19
<211> LENGTH: 11
<212> TYPE: PRT
<213> ORGANISM: Artificial
<220> FEATURE:
<223> OTHER INFORMATION: RRrRPaTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 19

Arg Arg Arg Arg Pro Ala Thr Leu Asn Leu Phe
1               5                   10

<210> SEQ ID NO 20
<211> LENGTH: 11
<212> TYPE: PRT
<213> ORGANISM: Artificial
<220> FEATURE:
<223> OTHER INFORMATION: QRrRPaTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 20

Gln Arg Arg Arg Pro Ala Thr Leu Asn Leu Phe
1               5                   10

```
<210> SEQ ID NO 21
<211> LENGTH: 11
<212> TYPE: PRT
<213> ORGANISM: Artificial
<220> FEATURE:
<223> OTHER INFORMATION: RrKRPaTLNLf JNK inhibitor
<220> FEATURE:
<221> NAME/KEY: Variant
<222> LOCATION: (2)..(2)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 21

Arg Arg Lys Arg Pro Ala Thr Leu Asn Leu Phe
 1               5                  10

<210> SEQ ID NO 22
<211> LENGTH: 11
<212> TYPE: PRT
<213> ORGANISM: Artificial
<220> FEATURE:
<223> OTHER INFORMATION: RPkRPsTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ser is D-enantiomeric Ser
<220> FEATURE:
<221> NAME/KEY: Variant
<222> LOCATION: (11)..(11)
<223> OTHER INFORMATION: Phe is D-enantiomeric Phe

<400> SEQUENCE: 22

Arg Pro Lys Arg Pro Ser Thr Leu Asn Leu Phe
 1               5                  10

<210> SEQ ID NO 23
<211> LENGTH: 11
<212> TYPE: PRT
<213> ORGANISM: Artificial
<220> FEATURE:
<223> OTHER INFORMATION: RPkRPqTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Gln is D-enantiomeric Gln
<220> FEATURE:
<221> NAME/KEY: Variant
<222> LOCATION: (11)..(11)
<223> OTHER INFORMATION: Phe is D-enantiomeric Phe

<400> SEQUENCE: 23

Arg Pro Lys Arg Pro Gln Thr Leu Asn Leu Phe
 1               5                  10

<210> SEQ ID NO 24
<211> LENGTH: 11
<212> TYPE: PRT
<213> ORGANISM: Artificial
```

```
<220> FEATURE:
<223> OTHER INFORMATION: RPkRPkTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 24

Arg Pro Lys Arg Pro Lys Thr Leu Asn Leu Phe
1               5                   10

<210> SEQ ID NO 25
<211> LENGTH: 10
<212> TYPE: PRT
<213> ORGANISM: Artificial
<220> FEATURE:
<223> OTHER INFORMATION: rGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe  is D-enantiomeric Phe

<400> SEQUENCE: 25

Arg Gly Lys Arg Lys Ala Leu Lys Leu Phe
1               5                   10

<210> SEQ ID NO 26
<211> LENGTH: 10
<212> TYPE: PRT
<213> ORGANISM: Artificial
<220> FEATURE:
<223> OTHER INFORMATION: rGKRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe

<400> SEQUENCE: 26

Arg Gly Lys Arg Lys Ala Leu Arg Leu Phe
1               5                   10

<210> SEQ ID NO 27
<211> LENGTH: 10
<212> TYPE: PRT
<213> ORGANISM: Artificial
<220> FEATURE:
<223> OTHER INFORMATION: RRrRKALrLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
```

```
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe

<400> SEQUENCE: 27

Arg Arg Arg Arg Lys Ala Leu Arg Leu Phe
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of artificial sequence: generic
      subformula (Ib) DlLLLxDmLLLyDn
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid""
<220> FEATURE:
<221> NAME/KEY: REPEAT
<222> LOCATION: (1)..(1)
<223> OTHER INFORMATION: number of repeats is 1 or 2
<220> FEATURE:
<221> NAME/KEY: REPEAT
<222> LOCATION: (4)..(4)
<223> OTHER INFORMATION: number of repeats is 0, 1 or 2
<220> FEATURE:
<221> NAME/KEY: VARIANT
<222> LOCATION: (5)..(5)
<223> OTHER INFORMATION: /replace="D-amino acid""
<220> FEATURE:
<221> NAME/KEY: REPEAT
<222> LOCATION: (5)..(5)
<223> OTHER INFORMATION: number of repeats is 1 or 2
<220> FEATURE:
<221> NAME/KEY: REPEAT
<222> LOCATION: (8)..(8)
<223> OTHER INFORMATION: number of repeats is 0, 1 or 2
<220> FEATURE:
<221> NAME/KEY: VARIANT
<222> LOCATION: (9)..(9)
<223> OTHER INFORMATION: /replace="D-amino acid""
<220> FEATURE:
<221> NAME/KEY: REPEAT
<222> LOCATION: (9)..(9)
<223> OTHER INFORMATION: number of repeats is 1 or 2

<400> SEQUENCE: 28

Xaa Xaa Xaa Xaa Xaa Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Description of artificial sequence: generic
      subformula (Ie) DLLLD(LLLD)a
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
<220> FEATURE:
```

```
<221> NAME/KEY: VARIANT
<222> LOCATION: (5)..(5)
<223> OTHER INFORMATION: /replace="D-amino acid"
<220> FEATURE:
<221> NAME/KEY: REPEAT
<222> LOCATION: (6)..(9)
<223> OTHER INFORMATION: number of repeats is 0, 1, 2 or 3
<220> FEATURE:
<221> NAME/KEY: VARIANT
<222> LOCATION: (9)..(9)
<223> OTHER INFORMATION: /replace="D-amino acid"

<400> SEQUENCE: 29

Xaa Xaa Xaa Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Description of artificial sequence: generic
      subformula (If) DLLLDLLLD
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 30

Xaa Xaa Xaa Xaa Xaa Xaa Xaa Xaa Xaa
1               5

<210> SEQ ID NO 31
<211> LENGTH: 9
<212> TYPE: PRT
<213> ORGANISM: Artificial
<220> FEATURE:
<223> OTHER INFORMATION: Description of sequence: consensus sequence
      rXXXrXXXr
<220> FEATURE:
<221> NAME/KEY: misc_feature
<222> LOCATION: (1)..(1)
<223> OTHER INFORMATION: Arg is D-enantiomeric Arg
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Arg is D-enantiomeric Arg
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Arg is D-enantiomeric Arg

<400> SEQUENCE: 31

Arg Xaa Xaa Xaa Arg Xaa Xaa Xaa Arg
```

-continued

```
<210> SEQ ID NO 32
<211> LENGTH: 9
<212> TYPE: PRT
<213> ORGANISM: Artificial
<220> FEATURE:
<223> OTHER INFORMATION: r3 (generic; right half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(8)
<223> OTHER INFORMATION: Xaa can be any naturally occurring amino acid
<220> FEATURE:
<221> NAME/KEY: Variant
<222> LOCATION: (9)..(9)
<223> OTHER INFORMATION: Arg is D-enantiomeric Arg

<400> SEQUENCE: 32

Arg Lys Lys Arg Arg Xaa Xaa Xaa Arg
1               5

<210> SEQ ID NO 33
<211> LENGTH: 9
<212> TYPE: PRT
<213> ORGANISM: Artificial
<220> FEATURE:
<223> OTHER INFORMATION: r3 (generic; left half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(4)
<223> OTHER INFORMATION: Xaa can be any naturally occurring amino acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 33

Arg Xaa Xaa Xaa Arg Gln Arg Arg Arg
1               5

<210> SEQ ID NO 34
<211> LENGTH: 9
<212> TYPE: PRT
<213> ORGANISM: Artificial
<220> FEATURE:
<223> OTHER INFORMATION: r3 (generic; individual)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(2)
<223> OTHER INFORMATION: Xaa is K or any other naturally occuring amino
      acid
<220> FEATURE:
<221> NAME/KEY: Variant
<222> LOCATION: (3)..(3)
```

```
<223> OTHER INFORMATION: Xaa is K or any other naturally occuring amino
      acid
<220> FEATURE:
<221> NAME/KEY: Variant
<222> LOCATION: (4)..(4)
<223> OTHER INFORMATION: Xaa is R or any other naturally occuring amino
      acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(6)
<223> OTHER INFORMATION: Xaa is Q or any other naturally occuring amino
      acid
<220> FEATURE:
<221> NAME/KEY: Variant
<222> LOCATION: (7)..(7)
<223> OTHER INFORMATION: Xaa is R or any other naturally occuring amino
      acid
<220> FEATURE:
<221> NAME/KEY: Variant
<222> LOCATION: (8)..(8)
<223> OTHER INFORMATION: Xaa is R or any other naturally occuring amino
      acid
<220> FEATURE:
<221> NAME/KEY: Variant
<222> LOCATION: (9)..(9)
<223> OTHER INFORMATION: Arg is D-enantiomeric Arg

<400> SEQUENCE: 34

Arg Xaa Xaa Xaa Arg Xaa Xaa Xaa Arg
1               5

<210> SEQ ID NO 35
<211> LENGTH: 86
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 1-86)

<400> SEQUENCE: 35

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 36
<211> LENGTH: 36
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 37-72)

<400> SEQUENCE: 36

Cys Phe Ile Thr Lys Ala Leu Gly Ile Ser Tyr Gly Arg Lys Lys Arg
```

```
                1               5                   10                  15
Arg Gln Arg Arg Arg Pro Pro Gln Gly Ser Gln Thr His Gln Val Ser
                    20                  25                  30
Leu Ser Lys Gln
            35

<210> SEQ ID NO 37
<211> LENGTH: 22
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 37-58)

<400> SEQUENCE: 37

Cys Phe Ile Thr Lys Ala Leu Gly Ile Ser Tyr Gly Arg Lys Lys Arg
1               5                   10                  15

Arg Gln Arg Arg Arg Pro
            20

<210> SEQ ID NO 38
<211> LENGTH: 24
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 38-58) including an additional N-terminal GCC

<400> SEQUENCE: 38

Phe Ile Thr Lys Ala Leu Gly Ile Ser Tyr Gly Arg Lys Lys Arg Arg
1               5                   10                  15

Gln Arg Arg Arg Pro Gly Gly Cys
            20

<210> SEQ ID NO 39
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 47-58) including an additional C-terminal GCC

<400> SEQUENCE: 39

Cys Gly Gly Tyr Gly Arg Lys Lys Arg Arg Gln Arg Arg Arg Pro
1               5                   10                  15

<210> SEQ ID NO 40
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 47-58) including an additional N-terminal GCC

<400> SEQUENCE: 40

Tyr Gly Arg Lys Lys Arg Arg Gln Arg Arg Arg Pro Gly Gly Cys
1               5                   10                  15

<210> SEQ ID NO 41
<211> LENGTH: 56
<212> TYPE: PRT
<213> ORGANISM: Human immunodeficiency virus type 1
```

```
<220> FEATURE:
<221> NAME/KEY: misc_feature
<223> OTHER INFORMATION: Description of sequence:  HIV-1 TAT sequence
      (aa 1-72) including a mutated Cys to Ala residue at position 37

<400> SEQUENCE: 41

Met Glu Pro Val Asp Pro Arg Leu Glu Pro Trp Lys His Pro Gly Ser
1               5                   10                  15

Gln Pro Lys Thr Ala Phe Ile Thr Lys Ala Leu Gly Ile Ser Tyr Gly
            20                  25                  30

Arg Lys Lys Arg Arg Gln Arg Arg Pro Pro Gln Gly Ser Gln Thr
        35                  40                  45

His Gln Val Ser Leu Ser Lys Gln
    50                  55

<210> SEQ ID NO 42
<211> LENGTH: 10
<212> TYPE: PRT
<213> ORGANISM: Artificial
<220> FEATURE:
<223> OTHER INFORMATION: Description of sequence:  trafficking sequence
      L-TAT (s1a)

<400> SEQUENCE: 42

Gly Arg Lys Lys Arg Arg Gln Arg Arg Arg
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of sequence:  trafficking sequence
      L-TAT (s1b)

<400> SEQUENCE: 43

Arg Lys Lys Arg Arg Gln Arg Arg Arg
1               5

<210> SEQ ID NO 44
<211> LENGTH: 11
<212> TYPE: PRT
<213> ORGANISM: Artificial Sequence
<220> FEATURE:
<223> OTHER INFORMATION: Description of sequence:  trafficking sequence
      L-TAT (s1c)

<400> SEQUENCE: 44

Tyr Asp Arg Lys Lys Arg Arg Gln Arg Arg Arg
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of artificial sequence: D-TAT
<220> FEATURE:
<221> NAME/KEY: VARIANT
<222> LOCATION: (1)..(9)
<223> OTHER INFORMATION: all amino acids are D-enantiomeric amino acids

<400> SEQUENCE: 45

Arg Arg Arg Gln Arg Arg Lys Lys Arg
1               5
```

```
<210> SEQ ID NO 46
<211> LENGTH: 9
<212> TYPE: PRT
<213> ORGANISM: Artificial Sequence
<220> FEATURE:
<223> OTHER INFORMATION: trafficking sequence r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 46

Arg Lys Lys Arg Arg Gln Arg Arg Arg
1               5

<210> SEQ ID NO 47
<211> LENGTH: 9
<212> TYPE: PRT
<213> ORGANISM: Artificial Sequence
<220> FEATURE:
<223> OTHER INFORMATION: trafficking sequence r3-L-TATi
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 47

Arg Arg Arg Gln Arg Arg Lys Lys Arg
1               5

<210> SEQ ID NO 48
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 48

Arg Lys Lys Arg Arg Gln Arg Arg Arg
1               5
```

```
<210> SEQ ID NO 49
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 49

Arg Arg Arg Gln Arg Arg Lys Lys Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Description of sequence:  trafficking sequence
      FITC-betaA-r3-L-TAT
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 50

Arg Lys Lys Arg Arg Gln Arg Arg Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Description of sequence:  trafficking sequence
      FITC-betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant
<222> LOCATION: (5)..(5)
```

```
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 51

Arg Arg Arg Gln Arg Arg Lys Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-1)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 52

Arg Ala Lys Arg Arg Gln Arg Arg Arg
1               5

<210> SEQ ID NO 53
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-2)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 53

Arg Lys Ala Arg Arg Gln Arg Arg Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-3)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
```

```
<220> FEATURE:
<221> NAME/KEY: Variant
<222> LOCATION: (9)..(9)
<223> OTHER INFORMATION: Arg is D-enantiomeric Arg

<400> SEQUENCE: 54

Arg Lys Lys Ala Arg Gln Arg Arg Arg
1               5

<210> SEQ ID NO 55
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-4)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 55

Arg Lys Lys Arg Arg Ala Arg Arg Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-5)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 56

Arg Lys Lys Arg Arg Gln Ala Arg Arg
1               5

<210> SEQ ID NO 57
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-6))
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
```

```
<221> NAME/KEY: Variant
<222> LOCATION: (9)..(9)
<223> OTHER INFORMATION: Arg is D-enantiomeric Arg

<400> SEQUENCE: 57

Arg Lys Lys Arg Arg Gln Arg Ala Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-7)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 58

Arg Asp Lys Arg Arg Gln Arg Arg Arg
1               5

<210> SEQ ID NO 59
<211> LENGTH: 9
<212> TYPE: PRT
<213> ORGANISM: Artificial Sequence
<220> FEATURE:
<223> OTHER INFORMATION: trafficking sequence TAT(s2-8)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 59

Arg Lys Asp Arg Arg Gln Arg Arg Arg
1               5

<210> SEQ ID NO 60
<211> LENGTH: 9
<212> TYPE: PRT
<213> ORGANISM: Artificial Sequence
<220> FEATURE:
<223> OTHER INFORMATION: trafficking sequence TAT(s2-9)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

<400> SEQUENCE: 60

Arg Lys Lys Asp Arg Gln Arg Arg Arg
1               5

<210> SEQ ID NO 61
<211> LENGTH: 9
<212> TYPE: PRT
<213> ORGANISM: Artificial Sequence
<220> FEATURE:
<223> OTHER INFORMATION: trafficking sequence TAT(s2-10)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 61

Arg Lys Lys Arg Arg Asp Arg Arg Arg
1               5

<210> SEQ ID NO 62
<211> LENGTH: 9
<212> TYPE: PRT
<213> ORGANISM: Artificial Sequence
<220> FEATURE:
<223> OTHER INFORMATION: trafficking sequence TAT(s2-11)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 62

Arg Lys Lys Arg Arg Gln Asp Arg Arg
1               5

<210> SEQ ID NO 63
<211> LENGTH: 9
<212> TYPE: PRT
<213> ORGANISM: Artificial Sequence
<220> FEATURE:
<223> OTHER INFORMATION: trafficking sequence TAT(s2-12)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 63

Arg Lys Lys Arg Arg Gln Arg Asp Arg

<210> SEQ ID NO 64
<211> LENGTH: 9
<212> TYPE: PRT
<213> ORGANISM: Artificial Sequence
<220> FEATURE:
<223> OTHER INFORMATION: trafficking sequence TAT(s2-13)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 64

Arg Glu Lys Arg Arg Gln Arg Arg Arg
1               5

<210> SEQ ID NO 65
<211> LENGTH: 9
<212> TYPE: PRT
<213> ORGANISM: Artificial Sequence
<220> FEATURE:
<223> OTHER INFORMATION: trafficking sequence TAT(s2-14)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 65

Arg Lys Glu Arg Arg Gln Arg Arg Arg
1               5

<210> SEQ ID NO 66
<211> LENGTH: 9
<212> TYPE: PRT
<213> ORGANISM: Artificial Sequence
<220> FEATURE:
<223> OTHER INFORMATION: trafficking sequence TAT(s2-15)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 66

Arg Lys Lys Glu Arg Gln Arg Arg Arg
1               5

<210> SEQ ID NO 67

```
-continued

<211> LENGTH: 9
<212> TYPE: PRT
<213> ORGANISM: Artificial Sequence
<220> FEATURE:
<223> OTHER INFORMATION: trafficking sequence TAT(s2-16)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 67

Arg Lys Lys Arg Arg Glu Arg Arg Arg
1               5

<210> SEQ ID NO 68
<211> LENGTH: 9
<212> TYPE: PRT
<213> ORGANISM: Artificial Sequence
<220> FEATURE:
<223> OTHER INFORMATION: trafficking sequence TAT(s2-17)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 68

Arg Lys Lys Arg Arg Gln Glu Arg Arg
1               5

<210> SEQ ID NO 69
<211> LENGTH: 9
<212> TYPE: PRT
<213> ORGANISM: Artificial Sequence
<220> FEATURE:
<223> OTHER INFORMATION: trafficking sequence TAT(s2-18)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 69

Arg Lys Lys Arg Arg Gln Arg Glu Arg
1               5

<210> SEQ ID NO 70
<211> LENGTH: 9
<212> TYPE: PRT
<213> ORGANISM: Artificial Sequence
<220> FEATURE:
```

```
<223> OTHER INFORMATION: trafficking sequence TAT(s2-19)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 70

Arg Phe Lys Arg Arg Gln Arg Arg Arg
1               5

<210> SEQ ID NO 71
<211> LENGTH: 9
<212> TYPE: PRT
<213> ORGANISM: Artificial Sequence
<220> FEATURE:
<223> OTHER INFORMATION: trafficking sequence TAT(s2-20)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 71

Arg Lys Phe Arg Arg Gln Arg Arg Arg
1               5

<210> SEQ ID NO 72
<211> LENGTH: 9
<212> TYPE: PRT
<213> ORGANISM: Artificial Sequence
<220> FEATURE:
<223> OTHER INFORMATION: trafficking sequence TAT(s2-21)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 72

Arg Lys Lys Phe Arg Gln Arg Arg Arg
1               5

<210> SEQ ID NO 73
<211> LENGTH: 9
<212> TYPE: PRT
<213> ORGANISM: Artificial Sequence
<220> FEATURE:
<223> OTHER INFORMATION: trafficking sequence TAT(s2-22)
<220> FEATURE:
<221> NAME/KEY: Variant
<222> LOCATION: (1)..(1)
```

```
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 73

Arg Lys Lys Arg Arg Phe Arg Arg Arg
1               5

<210> SEQ ID NO 74
<211> LENGTH: 9
<212> TYPE: PRT
<213> ORGANISM: Artificial Sequence
<220> FEATURE:
<223> OTHER INFORMATION: trafficking sequence TAT(s2-23)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 74

Arg Lys Lys Arg Arg Gln Phe Arg Arg
1               5

<210> SEQ ID NO 75
<211> LENGTH: 9
<212> TYPE: PRT
<213> ORGANISM: Artificial Sequence
<220> FEATURE:
<223> OTHER INFORMATION: trafficking sequence TAT(s2-24)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 75

Arg Lys Lys Arg Arg Gln Arg Phe Arg
1               5

<210> SEQ ID NO 76
<211> LENGTH: 9
<212> TYPE: PRT
<213> ORGANISM: Artificial Sequence
<220> FEATURE:
<223> OTHER INFORMATION: trafficking sequence TAT(s2-25)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
```

```
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 76

Arg Arg Lys Arg Arg Gln Arg Arg Arg
1               5

<210> SEQ ID NO 77
<211> LENGTH: 9
<212> TYPE: PRT
<213> ORGANISM: Artificial Sequence
<220> FEATURE:
<223> OTHER INFORMATION: trafficking sequence TAT(s2-26)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 77

Arg Lys Arg Arg Arg Gln Arg Arg Arg
1               5

<210> SEQ ID NO 78
<211> LENGTH: 9
<212> TYPE: PRT
<213> ORGANISM: Artificial Sequence
<220> FEATURE:
<223> OTHER INFORMATION: trafficking sequence TAT(s2-27)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 78

Arg Lys Lys Lys Arg Gln Arg Arg Arg
1               5

<210> SEQ ID NO 79
<211> LENGTH: 9
<212> TYPE: PRT
<213> ORGANISM: Artificial Sequence
<220> FEATURE:
<223> OTHER INFORMATION: trafficking sequence TAT(s2-28)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
```

<223> OTHER INFORMATION: Arg is D-enantiomeric Arg

<400> SEQUENCE: 79

Arg Lys Lys Arg Arg Arg Arg Arg Arg
1               5

<210> SEQ ID NO 80
<211> LENGTH: 9
<212> TYPE: PRT
<213> ORGANISM: Artificial Sequence
<220> FEATURE:
<223> OTHER INFORMATION: trafficking sequence TAT(s2-29)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 80

Arg Lys Lys Arg Arg Gln Lys Arg Arg
1               5

<210> SEQ ID NO 81
<211> LENGTH: 9
<212> TYPE: PRT
<213> ORGANISM: Artificial Sequence
<220> FEATURE:
<223> OTHER INFORMATION: trafficking sequence TAT(s2-30)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 81

Arg Lys Lys Arg Arg Gln Arg Lys Arg
1               5

<210> SEQ ID NO 82
<211> LENGTH: 9
<212> TYPE: PRT
<213> ORGANISM: Artificial Sequence
<220> FEATURE:
<223> OTHER INFORMATION: trafficking sequence TAT(s2-31)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 82

```
Arg His Lys Arg Arg Gln Arg Arg Arg
1               5

<210> SEQ ID NO 83
<211> LENGTH: 9
<212> TYPE: PRT
<213> ORGANISM: Artificial Sequence
<220> FEATURE:
<223> OTHER INFORMATION: trafficking sequence TAT(s2-32)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 83

Arg Lys His Arg Arg Gln Arg Arg Arg
1               5

<210> SEQ ID NO 84
<211> LENGTH: 9
<212> TYPE: PRT
<213> ORGANISM: Artificial Sequence
<220> FEATURE:
<223> OTHER INFORMATION: trafficking sequence TAT(s2-33)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 84

Arg Lys Lys His Arg Gln Arg Arg Arg
1               5

<210> SEQ ID NO 85
<211> LENGTH: 9
<212> TYPE: PRT
<213> ORGANISM: Artificial Sequence
<220> FEATURE:
<223> OTHER INFORMATION: trafficking sequence TAT(s2-34)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 85

Arg Lys Lys Arg Arg His Arg Arg Arg
1               5
```

```
<210> SEQ ID NO 86
<211> LENGTH: 9
<212> TYPE: PRT
<213> ORGANISM: Artificial Sequence
<220> FEATURE:
<223> OTHER INFORMATION: trafficking sequence TAT(s2-35)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 86

Arg Lys Lys Arg Arg Gln His Arg Arg
1               5

<210> SEQ ID NO 87
<211> LENGTH: 9
<212> TYPE: PRT
<213> ORGANISM: Artificial Sequence
<220> FEATURE:
<223> OTHER INFORMATION: trafficking sequence TAT(s2-36)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 87

Arg Lys Lys Arg Arg Gln Arg His Arg
1               5

<210> SEQ ID NO 88
<211> LENGTH: 9
<212> TYPE: PRT
<213> ORGANISM: Artificial Sequence
<220> FEATURE:
<223> OTHER INFORMATION: trafficking sequence TAT(s2-37)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 88

Arg Ile Lys Arg Arg Gln Arg Arg Arg
1               5

<210> SEQ ID NO 89
<211> LENGTH: 9
<212> TYPE: PRT
<213> ORGANISM: Artificial Sequence
```

```
<220> FEATURE:
<223> OTHER INFORMATION: trafficking sequence TAT(s2-38)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 89

Arg Lys Ile Arg Arg Gln Arg Arg Arg
1               5

<210> SEQ ID NO 90
<211> LENGTH: 9
<212> TYPE: PRT
<213> ORGANISM: Artificial Sequence
<220> FEATURE:
<223> OTHER INFORMATION: trafficking sequence TAT(s2-39)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 90

Arg Lys Lys Ile Arg Gln Arg Arg Arg
1               5

<210> SEQ ID NO 91
<211> LENGTH: 9
<212> TYPE: PRT
<213> ORGANISM: Artificial Sequence
<220> FEATURE:
<223> OTHER INFORMATION: trafficking sequence TAT(s2-40)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 91

Arg Lys Lys Arg Arg Ile Arg Arg Arg
1               5

<210> SEQ ID NO 92
<211> LENGTH: 9
<212> TYPE: PRT
<213> ORGANISM: Artificial Sequence
<220> FEATURE:
<223> OTHER INFORMATION: trafficking sequence TAT(s2-41)
<220> FEATURE:
<221> NAME/KEY: Variant
```

```
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 92

Arg Lys Lys Arg Arg Gln Ile Arg Arg
1               5

<210> SEQ ID NO 93
<211> LENGTH: 9
<212> TYPE: PRT
<213> ORGANISM: Artificial Sequence
<220> FEATURE:
<223> OTHER INFORMATION: trafficking sequence TAT(s2-42)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 93

Arg Lys Lys Arg Arg Gln Arg Ile Arg
1               5

<210> SEQ ID NO 94
<211> LENGTH: 9
<212> TYPE: PRT
<213> ORGANISM: Artificial Sequence
<220> FEATURE:
<223> OTHER INFORMATION: trafficking sequence TAT(s2-43)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 94

Arg Leu Lys Arg Arg Gln Arg Arg Arg
1               5

<210> SEQ ID NO 95
<211> LENGTH: 9
<212> TYPE: PRT
<213> ORGANISM: Artificial Sequence
<220> FEATURE:
<223> OTHER INFORMATION: trafficking sequence TAT(s2-44)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
```

```
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 95

Arg Lys Leu Arg Arg Gln Arg Arg Arg
1               5

<210> SEQ ID NO 96
<211> LENGTH: 9
<212> TYPE: PRT
<213> ORGANISM: Artificial Sequence
<220> FEATURE:
<223> OTHER INFORMATION: trafficking sequence TAT(s2-45)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 96

Arg Lys Lys Leu Arg Gln Arg Arg Arg
1               5

<210> SEQ ID NO 97
<211> LENGTH: 9
<212> TYPE: PRT
<213> ORGANISM: Artificial Sequence
<220> FEATURE:
<223> OTHER INFORMATION: trafficking sequence TAT(s2-46)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 97

Arg Lys Lys Arg Arg Leu Arg Arg Arg
1               5

<210> SEQ ID NO 98
<211> LENGTH: 9
<212> TYPE: PRT
<213> ORGANISM: Artificial Sequence
<220> FEATURE:
<223> OTHER INFORMATION: trafficking sequence TAT(s2-47)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
```

```
<222> LOCATION: (9)..(9)
<223> OTHER INFORMATION: Arg is D-enantiomeric Arg

<400> SEQUENCE: 98

Arg Lys Lys Arg Arg Gln Leu Arg Arg
1               5

<210> SEQ ID NO 99
<211> LENGTH: 9
<212> TYPE: PRT
<213> ORGANISM: Artificial Sequence
<220> FEATURE:
<223> OTHER INFORMATION: trafficking sequence TAT(s2-48)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 99

Arg Lys Lys Arg Arg Gln Arg Leu Arg
1               5

<210> SEQ ID NO 100
<211> LENGTH: 9
<212> TYPE: PRT
<213> ORGANISM: Artificial Sequence
<220> FEATURE:
<223> OTHER INFORMATION: trafficking sequence TAT(s2-49)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 100

Arg Met Lys Arg Arg Gln Arg Arg Arg
1               5

<210> SEQ ID NO 101
<211> LENGTH: 9
<212> TYPE: PRT
<213> ORGANISM: Artificial Sequence
<220> FEATURE:
<223> OTHER INFORMATION: trafficking sequence TAT(s2-50)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 101
```

Arg Lys Met Arg Arg Gln Arg Arg Arg
1               5

<210> SEQ ID NO 102
<211> LENGTH: 9
<212> TYPE: PRT
<213> ORGANISM: Artificial Sequence
<220> FEATURE:
<223> OTHER INFORMATION: trafficking sequence TAT(s2-51)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 102

Arg Lys Lys Met Arg Gln Arg Arg Arg
1               5

<210> SEQ ID NO 103
<211> LENGTH: 9
<212> TYPE: PRT
<213> ORGANISM: Artificial Sequence
<220> FEATURE:
<223> OTHER INFORMATION: trafficking sequence TAT(s2-52)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 103

Arg Lys Lys Arg Arg Met Arg Arg Arg
1               5

<210> SEQ ID NO 104
<211> LENGTH: 9
<212> TYPE: PRT
<213> ORGANISM: Artificial Sequence
<220> FEATURE:
<223> OTHER INFORMATION: trafficking sequence TAT(s2-53)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 104

Arg Lys Lys Arg Arg Gln Met Arg Arg
1               5

```
<210> SEQ ID NO 105
<211> LENGTH: 9
<212> TYPE: PRT
<213> ORGANISM: Artificial Sequence
<220> FEATURE:
<223> OTHER INFORMATION: trafficking sequence TAT(s2-54)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 105

Arg Lys Lys Arg Arg Gln Arg Met Arg
1               5

<210> SEQ ID NO 106
<211> LENGTH: 9
<212> TYPE: PRT
<213> ORGANISM: Artificial Sequence
<220> FEATURE:
<223> OTHER INFORMATION: trafficking sequence TAT(s2-55)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 106

Arg Asn Lys Arg Arg Gln Arg Arg Arg
1               5

<210> SEQ ID NO 107
<211> LENGTH: 9
<212> TYPE: PRT
<213> ORGANISM: Artificial Sequence
<220> FEATURE:
<223> OTHER INFORMATION: trafficking sequence TAT(s2-56)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 107

Arg Lys Asn Arg Arg Gln Arg Arg Arg
1               5

<210> SEQ ID NO 108
<211> LENGTH: 9
<212> TYPE: PRT
```

```
<213> ORGANISM: Artificial Sequence
<220> FEATURE:
<223> OTHER INFORMATION: trafficking sequence TAT(s2-57)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 108

Arg Lys Lys Asn Arg Gln Arg Arg Arg
1               5

<210> SEQ ID NO 109
<211> LENGTH: 9
<212> TYPE: PRT
<213> ORGANISM: Artificial Sequence
<220> FEATURE:
<223> OTHER INFORMATION: trafficking sequence TAT(s2-58)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 109

Arg Lys Lys Arg Arg Asn Arg Arg Arg
1               5

<210> SEQ ID NO 110
<211> LENGTH: 9
<212> TYPE: PRT
<213> ORGANISM: Artificial Sequence
<220> FEATURE:
<223> OTHER INFORMATION: trafficking sequence TAT(s2-59)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 110

Arg Lys Lys Arg Arg Gln Asn Arg Arg
1               5

<210> SEQ ID NO 111
<211> LENGTH: 9
<212> TYPE: PRT
<213> ORGANISM: Artificial Sequence
<220> FEATURE:
<223> OTHER INFORMATION: trafficking sequence TAT(s2-60)
<220> FEATURE:
```

```
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 111

Arg Lys Lys Arg Arg Gln Arg Asn Arg
1               5

<210> SEQ ID NO 112
<211> LENGTH: 9
<212> TYPE: PRT
<213> ORGANISM: Artificial Sequence
<220> FEATURE:
<223> OTHER INFORMATION: trafficking sequence TAT(s2-61)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 112

Arg Gln Lys Arg Arg Gln Arg Arg Arg
1               5

<210> SEQ ID NO 113
<211> LENGTH: 9
<212> TYPE: PRT
<213> ORGANISM: Artificial Sequence
<220> FEATURE:
<223> OTHER INFORMATION: trafficking sequence TAT(s2-62)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 113

Arg Lys Gln Arg Arg Gln Arg Arg Arg
1               5

<210> SEQ ID NO 114
<211> LENGTH: 9
<212> TYPE: PRT
<213> ORGANISM: Artificial Sequence
<220> FEATURE:
<223> OTHER INFORMATION: trafficking sequence TAT(s2-63)
<220> FEATURE:
<221> NAME/KEY: Variant
<222> LOCATION: (1)..(1)
<223> OTHER INFORMATION: Arg is D-enantiomeric Arg
<220> FEATURE:
```

```
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 114

Arg Lys Lys Gln Arg Gln Arg Arg
1               5

<210> SEQ ID NO 115
<211> LENGTH: 9
<212> TYPE: PRT
<213> ORGANISM: Artificial Sequence
<220> FEATURE:
<223> OTHER INFORMATION: trafficking sequence TAT(s2-64)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 115

Arg Lys Lys Arg Arg Lys Arg Arg Arg
1               5

<210> SEQ ID NO 116
<211> LENGTH: 9
<212> TYPE: PRT
<213> ORGANISM: Artificial Sequence
<220> FEATURE:
<223> OTHER INFORMATION: trafficking sequence TAT(s2-65)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 116

Arg Lys Lys Arg Arg Gln Gln Arg Arg
1               5

<210> SEQ ID NO 117
<211> LENGTH: 9
<212> TYPE: PRT
<213> ORGANISM: Artificial Sequence
<220> FEATURE:
<223> OTHER INFORMATION: trafficking sequence TAT(s2-66)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
```

```
<221> NAME/KEY: Variant
<222> LOCATION: (9)..(9)
<223> OTHER INFORMATION: Arg is D-enantiomeric Arg

<400> SEQUENCE: 117

Arg Lys Lys Arg Arg Gln Arg Gln Arg
1               5

<210> SEQ ID NO 118
<211> LENGTH: 9
<212> TYPE: PRT
<213> ORGANISM: Artificial Sequence
<220> FEATURE:
<223> OTHER INFORMATION: trafficking sequence TAT(s2-67)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 118

Arg Ser Lys Arg Arg Gln Arg Arg Arg
1               5

<210> SEQ ID NO 119
<211> LENGTH: 9
<212> TYPE: PRT
<213> ORGANISM: Artificial Sequence
<220> FEATURE:
<223> OTHER INFORMATION: trafficking sequence TAT(s2-68)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 119

Arg Lys Ser Arg Arg Gln Arg Arg Arg
1               5

<210> SEQ ID NO 120
<211> LENGTH: 9
<212> TYPE: PRT
<213> ORGANISM: Artificial Sequence
<220> FEATURE:
<223> OTHER INFORMATION: trafficking sequence TAT(s2-69)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

```
<400> SEQUENCE: 120

Arg Lys Lys Ser Arg Gln Arg Arg
1               5

<210> SEQ ID NO 121
<211> LENGTH: 9
<212> TYPE: PRT
<213> ORGANISM: Artificial Sequence
<220> FEATURE:
<223> OTHER INFORMATION: trafficking sequence TAT(s2-70)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 121

Arg Lys Lys Arg Arg Ser Arg Arg Arg
1               5

<210> SEQ ID NO 122
<211> LENGTH: 9
<212> TYPE: PRT
<213> ORGANISM: Artificial Sequence
<220> FEATURE:
<223> OTHER INFORMATION: trafficking sequence TAT(s2-71)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 122

Arg Lys Lys Arg Arg Gln Ser Arg Arg
1               5

<210> SEQ ID NO 123
<211> LENGTH: 9
<212> TYPE: PRT
<213> ORGANISM: Artificial Sequence
<220> FEATURE:
<223> OTHER INFORMATION: trafficking sequence TAT(s2-72)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 123

Arg Lys Lys Arg Arg Gln Arg Ser Arg
1               5
```

<210> SEQ ID NO 124
<211> LENGTH: 9
<212> TYPE: PRT
<213> ORGANISM: Artificial Sequence
<220> FEATURE:
<223> OTHER INFORMATION: trafficking sequence TAT(s2-73)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 124

Arg Thr Lys Arg Arg Gln Arg Arg Arg
1               5

<210> SEQ ID NO 125
<211> LENGTH: 9
<212> TYPE: PRT
<213> ORGANISM: Artificial Sequence
<220> FEATURE:
<223> OTHER INFORMATION: trafficking sequence TAT(s2-74)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 125

Arg Lys Thr Arg Arg Gln Arg Arg Arg
1               5

<210> SEQ ID NO 126
<211> LENGTH: 9
<212> TYPE: PRT
<213> ORGANISM: Artificial Sequence
<220> FEATURE:
<223> OTHER INFORMATION: trafficking sequence TAT(s2-75)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 126

Arg Lys Lys Thr Arg Gln Arg Arg Arg
1               5

<210> SEQ ID NO 127
<211> LENGTH: 9

```
<212> TYPE: PRT
<213> ORGANISM: Artificial Sequence
<220> FEATURE:
<223> OTHER INFORMATION: trafficking sequence TAT(s2-76)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 127

Arg Lys Lys Arg Arg Thr Arg Arg Arg
1               5

<210> SEQ ID NO 128
<211> LENGTH: 9
<212> TYPE: PRT
<213> ORGANISM: Artificial Sequence
<220> FEATURE:
<223> OTHER INFORMATION: trafficking sequence TAT(s2-77)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 128

Arg Lys Lys Arg Arg Gln Thr Arg Arg
1               5

<210> SEQ ID NO 129
<211> LENGTH: 9
<212> TYPE: PRT
<213> ORGANISM: Artificial Sequence
<220> FEATURE:
<223> OTHER INFORMATION: trafficking sequence TAT(s2-78)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 129

Arg Lys Lys Arg Arg Gln Arg Thr Arg
1               5

<210> SEQ ID NO 130
<211> LENGTH: 9
<212> TYPE: PRT
<213> ORGANISM: Artificial Sequence
<220> FEATURE:
<223> OTHER INFORMATION: trafficking sequence TAT(s2-79)
```

```
-continued

<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 130

Arg Val Lys Arg Arg Gln Arg Arg Arg
1               5

<210> SEQ ID NO 131
<211> LENGTH: 9
<212> TYPE: PRT
<213> ORGANISM: Artificial Sequence
<220> FEATURE:
<223> OTHER INFORMATION: trafficking sequence TAT(s2-80)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 131

Arg Lys Val Arg Arg Gln Arg Arg Arg
1               5

<210> SEQ ID NO 132
<211> LENGTH: 9
<212> TYPE: PRT
<213> ORGANISM: Artificial Sequence
<220> FEATURE:
<223> OTHER INFORMATION: trafficking sequence TAT(s2-81)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 132

Arg Lys Lys Val Arg Gln Arg Arg Arg
1               5

<210> SEQ ID NO 133
<211> LENGTH: 9
<212> TYPE: PRT
<213> ORGANISM: Artificial Sequence
<220> FEATURE:
<223> OTHER INFORMATION: trafficking sequence TAT(s2-82)
<220> FEATURE:
<221> NAME/KEY: Variant
<222> LOCATION: (1)..(1)
<223> OTHER INFORMATION: Arg is D-enantiomeric Arg
```

```
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 133

Arg Lys Lys Arg Arg Val Arg Arg Arg
1               5

<210> SEQ ID NO 134
<211> LENGTH: 9
<212> TYPE: PRT
<213> ORGANISM: Artificial Sequence
<220> FEATURE:
<223> OTHER INFORMATION: trafficking sequence TAT(s2-83)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 134

Arg Lys Lys Arg Arg Gln Val Arg Arg
1               5

<210> SEQ ID NO 135
<211> LENGTH: 9
<212> TYPE: PRT
<213> ORGANISM: Artificial Sequence
<220> FEATURE:
<223> OTHER INFORMATION: trafficking sequence TAT(s2-84)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 135

Arg Lys Lys Arg Arg Gln Arg Val Arg
1               5

<210> SEQ ID NO 136
<211> LENGTH: 9
<212> TYPE: PRT
<213> ORGANISM: Artificial Sequence
<220> FEATURE:
<223> OTHER INFORMATION: trafficking sequence TAT(s2-85)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
```

```
<220> FEATURE:
<221> NAME/KEY: Variant
<222> LOCATION: (9)..(9)
<223> OTHER INFORMATION: Arg is D-enantiomeric Arg

<400> SEQUENCE: 136

Arg Trp Lys Arg Arg Gln Arg Arg Arg
1               5

<210> SEQ ID NO 137
<211> LENGTH: 9
<212> TYPE: PRT
<213> ORGANISM: Artificial Sequence
<220> FEATURE:
<223> OTHER INFORMATION: trafficking sequence TAT(s2-86)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 137

Arg Lys Trp Arg Arg Gln Arg Arg Arg
1               5

<210> SEQ ID NO 138
<211> LENGTH: 9
<212> TYPE: PRT
<213> ORGANISM: Artificial Sequence
<220> FEATURE:
<223> OTHER INFORMATION: trafficking sequence TAT(s2-87)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 138

Arg Lys Lys Trp Arg Gln Arg Arg Arg
1               5

<210> SEQ ID NO 139
<211> LENGTH: 9
<212> TYPE: PRT
<213> ORGANISM: Artificial Sequence
<220> FEATURE:
<223> OTHER INFORMATION: trafficking sequence TAT(s2-88)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

-continued

```
<400> SEQUENCE: 139

Arg Lys Lys Arg Arg Trp Arg Arg Arg
1               5

<210> SEQ ID NO 140
<211> LENGTH: 9
<212> TYPE: PRT
<213> ORGANISM: Artificial Sequence
<220> FEATURE:
<223> OTHER INFORMATION: trafficking sequence TAT(s2-89)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 140

Arg Lys Lys Arg Arg Gln Trp Arg Arg
1               5

<210> SEQ ID NO 141
<211> LENGTH: 9
<212> TYPE: PRT
<213> ORGANISM: Artificial Sequence
<220> FEATURE:
<223> OTHER INFORMATION: trafficking sequence TAT(s2-90)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 141

Arg Lys Lys Arg Arg Gln Arg Trp Arg
1               5

<210> SEQ ID NO 142
<211> LENGTH: 9
<212> TYPE: PRT
<213> ORGANISM: Artificial Sequence
<220> FEATURE:
<223> OTHER INFORMATION: trafficking sequence TAT(s2-91)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 142

Arg Tyr Lys Arg Arg Gln Arg Arg Arg
```

<210> SEQ ID NO 143
<211> LENGTH: 9
<212> TYPE: PRT
<213> ORGANISM: Artificial Sequence
<220> FEATURE:
<223> OTHER INFORMATION: trafficking sequence TAT(s2-92)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 143

Arg Lys Tyr Arg Arg Gln Arg Arg Arg
1               5

<210> SEQ ID NO 144
<211> LENGTH: 9
<212> TYPE: PRT
<213> ORGANISM: Artificial Sequence
<220> FEATURE:
<223> OTHER INFORMATION: trafficking sequence TAT(s2-93)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 144

Arg Lys Lys Tyr Arg Gln Arg Arg Arg
1               5

<210> SEQ ID NO 145
<211> LENGTH: 9
<212> TYPE: PRT
<213> ORGANISM: Artificial Sequence
<220> FEATURE:
<223> OTHER INFORMATION: trafficking sequence TAT(s2-94)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 145

Arg Lys Lys Arg Arg Tyr Arg Arg Arg
1               5

<210> SEQ ID NO 146

```
<211> LENGTH: 9
<212> TYPE: PRT
<213> ORGANISM: Artificial Sequence
<220> FEATURE:
<223> OTHER INFORMATION: trafficking sequence TAT(s2-95)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 146

Arg Lys Lys Arg Arg Gln Tyr Arg Arg
1               5

<210> SEQ ID NO 147
<211> LENGTH: 9
<212> TYPE: PRT
<213> ORGANISM: Artificial Sequence
<220> FEATURE:
<223> OTHER INFORMATION: Trafficking sequence TAT(s2-96)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 147

Arg Lys Lys Arg Arg Gln Arg Tyr Arg
1               5

<210> SEQ ID NO 148
<211> LENGTH: 8
<212> TYPE: PRT
<213> ORGANISM: Artificial
<220> FEATURE:
<223> OTHER INFORMATION: Trafficking sequence TAT(s2-97)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 148

Arg Lys Lys Arg Arg Gln Arg Arg
1               5

<210> SEQ ID NO 149
<211> LENGTH: 9
<212> TYPE: PRT
<213> ORGANISM: Artificial
<220> FEATURE:
```

```
<223> OTHER INFORMATION: Trafficking sequence TAT(s2-98)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 149

Arg Lys Lys Arg Arg Gln Arg Arg Lys
1               5

<210> SEQ ID NO 150
<211> LENGTH: 9
<212> TYPE: PRT
<213> ORGANISM: Artificial
<220> FEATURE:
<223> OTHER INFORMATION: Trafficking sequence TAT(s2-99)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 150

Arg Lys Lys Arg Arg Gln Arg Arg Arg
1               5

<210> SEQ ID NO 151
<211> LENGTH: 9
<212> TYPE: PRT
<213> ORGANISM: Artificial Sequence
<220> FEATURE:
<223> OTHER INFORMATION: trafficking sequence r3R6
<220> FEATURE:
<221> NAME/KEY: VARIANT
<222> LOCATION: (1)..(1)
<223> OTHER INFORMATION: /replace="D-enatiomeric amino acid arginine"
<220> FEATURE:
<221> NAME/KEY: VARIANT
<222> LOCATION: (5)..(5)
<223> OTHER INFORMATION: /replace="D-enatiomeric amino acid arginine"
<220> FEATURE:
<221> NAME/KEY: VARIANT
<222> LOCATION: (9)..(9)
<223> OTHER INFORMATION: /replace="D-enatiomeric amino acid arginine"

<400> SEQUENCE: 151

Arg Arg Arg Arg Arg Arg Arg Arg Arg
1               5

<210> SEQ ID NO 152
<211> LENGTH: 9
<212> TYPE: PRT
<213> ORGANISM: Artificial Sequence
<220> FEATURE:
<223> OTHER INFORMATION: trafficking sequence L-R9

<400> SEQUENCE: 152
```

```
Arg Arg Arg Arg Arg Arg Arg Arg Arg
1               5

<210> SEQ ID NO 153
<211> LENGTH: 8
<212> TYPE: PRT
<213> ORGANISM: Artificial Sequence
<220> FEATURE:
<223> OTHER INFORMATION: trafficking sequence L-R8

<400> SEQUENCE: 153

Arg Arg Arg Arg Arg Arg Arg Arg
1               5

<210> SEQ ID NO 154
<211> LENGTH: 7
<212> TYPE: PRT
<213> ORGANISM: Artificial Sequence
<220> FEATURE:
<223> OTHER INFORMATION: trafficking sequence L-R7

<400> SEQUENCE: 154

Arg Arg Arg Arg Arg Arg Arg
1               5

<210> SEQ ID NO 155
<211> LENGTH: 6
<212> TYPE: PRT
<213> ORGANISM: Artificial Sequence
<220> FEATURE:
<223> OTHER INFORMATION: trafficking sequence L-R6

<400> SEQUENCE: 155

Arg Arg Arg Arg Arg Arg
1               5

<210> SEQ ID NO 156
<211> LENGTH: 5
<212> TYPE: PRT
<213> ORGANISM: Artificial Sequence
<220> FEATURE:
<223> OTHER INFORMATION: trafficking sequence L-R5

<400> SEQUENCE: 156

Arg Arg Arg Arg Arg
1               5

<210> SEQ ID NO 157
<211> LENGTH: 9
<212> TYPE: PRT
<213> ORGANISM: Artificial
<220> FEATURE:
<223> OTHER INFORMATION: all D transporter construct (all amino acid
      residues are D-amino acids)
<220> FEATURE:
<221> NAME/KEY: Variant
<222> LOCATION: (1)..(9)
<223> OTHER INFORMATION: Arg is D-enantiomeric Arg

<400> SEQUENCE: 157

Arg Arg Arg Arg Arg Arg Arg Arg Arg
1               5

<210> SEQ ID NO 158
<211> LENGTH: 9
<212> TYPE: PRT
<213> ORGANISM: Artificial
<220> FEATURE:
```

```
<223> OTHER INFORMATION: Description of sequence: D/L transporter
      construct (D and L amino acid residues alternate, beginning wit D
      amino acids)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (7)..(7)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 158

Arg Arg Arg Arg Arg Arg Arg Arg Arg
1               5

<210> SEQ ID NO 159
<211> LENGTH: 9
<212> TYPE: PRT
<213> ORGANISM: Artificial
<220> FEATURE:
<223> OTHER INFORMATION: Description of sequence: DD/LL transporter
      construct
<220> FEATURE:
<221> NAME/KEY: Variant
<222> LOCATION: (1)..(2)
<223> OTHER INFORMATION: Arg is D-enantiomeric Arg
<220> FEATURE:
<221> NAME/KEY: Variant
<222> LOCATION: (5)..(6)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 159

Arg Arg Arg Arg Arg Arg Arg Arg Arg
1               5

<210> SEQ ID NO 160
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 160

Tyr Ala Arg Ala Ala Ala Arg Gln Ala Arg Ala
1               5                   10

<210> SEQ ID NO 161
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 161

Trp Ala Arg Ala Ala Ala Arg Gln Ala Arg Ala
```

```
1               5                   10
```

<210> SEQ ID NO 162
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 162

```
Trp Ala Arg Ala Gln Arg Ala Ala Ala Arg Ala
1               5                   10
```

<210> SEQ ID NO 163
<211> LENGTH: 16
<212> TYPE: PRT
<213> ORGANISM: Artificial Sequence
<220> FEATURE:
<223> OTHER INFORMATION: trafficking sequence L-P1 (Penetratin)

<400> SEQUENCE: 163

```
Arg Gln Val Lys Val Trp Phe Gln Asn Arg Arg Met Lys Trp Lys Lys
1               5                   10                  15
```

<210> SEQ ID NO 164
<211> LENGTH: 16
<212> TYPE: PRT
<213> ORGANISM: Artificial Sequence
<220> FEATURE:
<223> OTHER INFORMATION: trafficking sequence D-P1 (Penetratin)

<400> SEQUENCE: 164

```
Lys Lys Trp Lys Met Arg Arg Asn Gln Phe Trp Val Lys Val Gln Arg
1               5                   10                  15
```

<210> SEQ ID NO 165
<211> LENGTH: 17
<212> TYPE: PRT
<213> ORGANISM: Artificial Sequence
<220> FEATURE:
<223> OTHER INFORMATION: trafficking sequence JNK1, bestfit

<400> SEQUENCE: 165

```
Trp Lys Arg Ala Ala Ala Arg Lys Ala Arg Ala Met Ser Leu Asn Leu
1               5                   10                  15

Phe
```

<210> SEQ ID NO 166
<211> LENGTH: 17
<212> TYPE: PRT
<213> ORGANISM: Artificial Sequence
<220> FEATURE:
<223> OTHER INFORMATION: trafficking sequence JNK1, bestfit (variant 1)

<400> SEQUENCE: 166

```
Trp Lys Arg Ala Ala Ala Arg Ala Ala Arg Ala Met Ser Leu Asn Leu
1               5                   10                  15

Phe
```

<210> SEQ ID NO 167
<211> LENGTH: 9
<212> TYPE: PRT
<213> ORGANISM: Artificial Sequence
<220> FEATURE:
<223> OTHER INFORMATION: trafficking sequence MDCK transcytose sequence

```
<400> SEQUENCE: 167

Arg Tyr Arg Gly Asp Leu Gly Arg Arg
1               5

<210> SEQ ID NO 168
<211> LENGTH: 4
<212> TYPE: PRT
<213> ORGANISM: Artificial Sequence
<220> FEATURE:
<223> OTHER INFORMATION: trafficking sequence YKGL

<400> SEQUENCE: 168

Tyr Lys Gly Leu
1

<210> SEQ ID NO 169
<211> LENGTH: 4
<212> TYPE: PRT
<213> ORGANISM: Artificial
<220> FEATURE:
<223> OTHER INFORMATION: trafficking sequence RRTK

<400> SEQUENCE: 169

Arg Arg Thr Lys
1

<210> SEQ ID NO 170
<211> LENGTH: 4
<212> TYPE: PRT
<213> ORGANISM: Artificial
<220> FEATURE:
<223> OTHER INFORMATION: trafficking sequence RRPK

<400> SEQUENCE: 170

Arg Arg Pro Lys
1

<210> SEQ ID NO 171
<211> LENGTH: 20
<212> TYPE: PRT
<213> ORGANISM: Artificial
<220> FEATURE:
<223> OTHER INFORMATION: rKKRrQRRrRPkRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 171

Arg Lys Lys Arg Arg Gln Arg Arg Arg Pro Lys Arg Pro Thr Thr
1               5                   10                  15

Leu Asn Leu Phe
            20
```

```
<210> SEQ ID NO 172
<211> LENGTH: 20
<212> TYPE: PRT
<213> ORGANISM: Artificial
<220> FEATURE:
<223> OTHER INFORMATION: rKKrQRRrRPkRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ala is D-enantiomeric Ala
<220> FEATURE:
<221> NAME/KEY: Variant
<222> LOCATION: (20)..(20)
<223> OTHER INFORMATION: Phe is D-enantiomeric Phe

<400> SEQUENCE: 172

Arg Lys Lys Arg Arg Gln Arg Arg Arg Pro Lys Arg Pro Ala Thr
1               5                   10                  15

Leu Asn Leu Phe
            20

<210> SEQ ID NO 173
<211> LENGTH: 20
<212> TYPE: PRT
<213> ORGANISM: Artificial
<220> FEATURE:
<223> OTHER INFORMATION: rKKrQRRrRPkRPTTLrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (18)..(18)
<223> OTHER INFORMATION: Arg is D-enantiomeric Arg
<220> FEATURE:
<221> NAME/KEY: Variant
<222> LOCATION: (20)..(20)
<223> OTHER INFORMATION: Phe is D-enantiomeric Phe

<400> SEQUENCE: 173

Arg Lys Lys Arg Arg Gln Arg Arg Arg Pro Lys Arg Pro Thr Thr
1               5                   10                  15

Leu Arg Leu Phe
```

```
                    20

<210> SEQ ID NO 174
<211> LENGTH: 17
<212> TYPE: PRT
<213> ORGANISM: Artificial
<220> FEATURE:
<223> OTHER INFORMATION: rKKRrQRRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (17)..(17)
<223> OTHER INFORMATION: Phe is D-enantiomeric Phe

<400> SEQUENCE: 174

Arg Lys Lys Arg Arg Gln Arg Arg Arg Pro Thr Thr Leu Asn Leu
1               5                   10                  15

Phe

<210> SEQ ID NO 175
<211> LENGTH: 16
<212> TYPE: PRT
<213> ORGANISM: Artificial
<220> FEATURE:
<223> OTHER INFORMATION: rKKRrQRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 175

Arg Lys Lys Arg Arg Gln Arg Arg Pro Thr Thr Leu Asn Leu Phe
1               5                   10                  15

<210> SEQ ID NO 176
<211> LENGTH: 20
<212> TYPE: PRT
<213> ORGANISM: Artificial
<220> FEATURE:
<223> OTHER INFORMATION: rKKRrQRRrRPkRPTTLNLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
```

<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Trp is D-enantiomeric Trp

<400> SEQUENCE: 176

Arg Lys Lys Arg Arg Gln Arg Arg Arg Pro Lys Arg Pro Thr Thr
1               5                   10                  15

Leu Asn Leu Trp
            20

<210> SEQ ID NO 177
<211> LENGTH: 20
<212> TYPE: PRT
<213> ORGANISM: Artificial
<220> FEATURE:
<223> OTHER INFORMATION: rKKRrQRRrRPkRPTDLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 177

Arg Lys Lys Arg Arg Gln Arg Arg Arg Pro Lys Arg Pro Thr Asp
1               5                   10                  15

Leu Asn Leu Phe
            20

<210> SEQ ID NO 178
<211> LENGTH: 17
<212> TYPE: PRT
<213> ORGANISM: Artificial
<220> FEATURE:
<223> OTHER INFORMATION: rKKRrQRRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
<220> FEATURE:

```
<221> NAME/KEY: Variant
<222> LOCATION: (17)..(17)
<223> OTHER INFORMATION: Trp is D-enantiomeric Trp

<400> SEQUENCE: 178

Arg Lys Lys Arg Arg Gln Arg Arg Arg Pro Thr Thr Leu Arg Leu
1               5                   10                  15

Trp

<210> SEQ ID NO 179
<211> LENGTH: 16
<212> TYPE: PRT
<213> ORGANISM: Artificial
<220> FEATURE:
<223> OTHER INFORMATION: rKKRrQRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 179

Arg Lys Lys Arg Arg Gln Arg Arg Arg Pro Thr Thr Leu Arg Leu Trp
1               5                   10                  15

<210> SEQ ID NO 180
<211> LENGTH: 17
<212> TYPE: PRT
<213> ORGANISM: Artificial
<220> FEATURE:
<223> OTHER INFORMATION: rKKRrQRRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
<220> FEATURE:
<221> NAME/KEY: Variant
<222> LOCATION: (17)..(17)
<223> OTHER INFORMATION: Trp is D-enantiomeric Trp

<400> SEQUENCE: 180

Arg Lys Lys Arg Arg Gln Arg Arg Arg Pro Thr Asp Leu Arg Leu
1               5                   10                  15

Trp
```

<210> SEQ ID NO 181
<211> LENGTH: 16
<212> TYPE: PRT
<213> ORGANISM: Artificial
<220> FEATURE:
<223> OTHER INFORMATION: rKKrQRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 181

Arg Lys Lys Arg Arg Gln Arg Arg Pro Thr Asp Leu Arg Leu Trp
1               5                   10                  15

<210> SEQ ID NO 182
<211> LENGTH: 17
<212> TYPE: PRT
<213> ORGANISM: Artificial
<220> FEATURE:
<223> OTHER INFORMATION: rKKrQRRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe

<400> SEQUENCE: 182

Arg Lys Lys Arg Arg Gln Arg Arg Arg Pro Ala Thr Leu Asn Leu
1               5                   10                  15

Phe

<210> SEQ ID NO 183
<211> LENGTH: 16
<212> TYPE: PRT
<213> ORGANISM: Artificial
<220> FEATURE:
<223> OTHER INFORMATION: rKKrQRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg

```
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (11)..(11)
<223> OTHER INFORMATION: Ala is D-enantiomeric Ala
<220> FEATURE:
<221> NAME/KEY: Variant
<222> LOCATION: (16)..(16)
<223> OTHER INFORMATION: Phe is D-enantiomeric Phe

<400> SEQUENCE: 183

Arg Lys Lys Arg Arg Gln Arg Arg Pro Ala Thr Leu Asn Leu Phe
1               5                   10                  15

<210> SEQ ID NO 184
<211> LENGTH: 17
<212> TYPE: PRT
<213> ORGANISM: Artificial
<220> FEATURE:
<223> OTHER INFORMATION: rKKRrQRrKRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe

<400> SEQUENCE: 184

Arg Lys Lys Arg Arg Gln Arg Arg Lys Arg Pro Ala Thr Leu Asn Leu
1               5                   10                  15

Phe

<210> SEQ ID NO 185
<211> LENGTH: 20
<212> TYPE: PRT
<213> ORGANISM: Artificial
<220> FEATURE:
<223> OTHER INFORMATION: rKKRrQRRrRPkRPsTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
```

<223> OTHER INFORMATION: Lys is D-enantiomeric Lys
<220> FEATURE:
<221> NAME/KEY: Variant
<222> LOCATION: (15)..(15)
<223> OTHER INFORMATION: Ser is D-enantiomeric Ser
<220> FEATURE:
<221> NAME/KEY: Variant
<222> LOCATION: (20)..(20)
<223> OTHER INFORMATION: Phe is D-enantiomeric Phe

<400> SEQUENCE: 185

Arg Lys Lys Arg Arg Gln Arg Arg Arg Pro Lys Arg Pro Ser Thr
1               5                   10                  15

Leu Asn Leu Phe
            20

<210> SEQ ID NO 186
<211> LENGTH: 20
<212> TYPE: PRT
<213> ORGANISM: Artificial
<220> FEATURE:
<223> OTHER INFORMATION: rKKRrQRRrRPkRPqTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Gln is D-enantiomeric Gln
<220> FEATURE:
<221> NAME/KEY: Variant
<222> LOCATION: (20)..(20)
<223> OTHER INFORMATION: Phe is D-enantiomeric Phe

<400> SEQUENCE: 186

Arg Lys Lys Arg Arg Gln Arg Arg Arg Pro Lys Arg Pro Gln Thr
1               5                   10                  15

Leu Asn Leu Phe
            20

<210> SEQ ID NO 187
<211> LENGTH: 20
<212> TYPE: PRT
<213> ORGANISM: Artificial
<220> FEATURE:
<223> OTHER INFORMATION: rKKRrQRRrRPkRPkTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant

```
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 187

Arg Lys Lys Arg Arg Gln Arg Arg Arg Pro Lys Arg Pro Lys Thr
1               5                   10                  15

Leu Asn Leu Phe
            20

<210> SEQ ID NO 188
<211> LENGTH: 18
<212> TYPE: PRT
<213> ORGANISM: Artificial
<220> FEATURE:
<223> OTHER INFORMATION: rKKRrQRRrGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe

<400> SEQUENCE: 188

Arg Lys Lys Arg Arg Gln Arg Arg Arg Gly Lys Arg Lys Ala Leu Lys
1               5                   10                  15

Leu Phe

<210> SEQ ID NO 189
<211> LENGTH: 18
<212> TYPE: PRT
<213> ORGANISM: Artificial
<220> FEATURE:
<223> OTHER INFORMATION: rKKRrQRRrGKRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (16)..(16)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe

<400> SEQUENCE: 189
```

Arg Lys Lys Arg Arg Gln Arg Arg Gly Lys Arg Lys Ala Leu Arg
1               5                   10                  15

Leu Phe

<210> SEQ ID NO 190
<211> LENGTH: 16
<212> TYPE: PRT
<213> ORGANISM: Artificial
<220> FEATURE:
<223> OTHER INFORMATION: rKKRrQRRrRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 190

Arg Lys Lys Arg Arg Gln Arg Arg Arg Lys Ala Leu Arg Leu Phe
1               5                   10                  15

<210> SEQ ID NO 191
<211> LENGTH: 8
<212> TYPE: PRT
<213> ORGANISM: Artificial
<220> FEATURE:
<223> OTHER INFORMATION: RPTTLNLF JNK inhibitor

<400> SEQUENCE: 191

Arg Pro Thr Thr Leu Asn Leu Phe
1               5

<210> SEQ ID NO 192
<211> LENGTH: 9
<212> TYPE: PRT
<213> ORGANISM: Artificial
<220> FEATURE:
<223> OTHER INFORMATION: KRPTTLNLF JNK inhibitor

<400> SEQUENCE: 192

Lys Arg Pro Thr Thr Leu Asn Leu Phe
1               5

<210> SEQ ID NO 193
<211> LENGTH: 11
<212> TYPE: PRT
<213> ORGANISM: Artificial
<220> FEATURE:
<223> OTHER INFORMATION: L-IB1(s24)

<400> SEQUENCE: 193

Arg Pro Lys Arg Pro Thr Thr Leu Asn Leu Phe
1               5                   10

-continued

<210> SEQ ID NO 194
<211> LENGTH: 29
<212> TYPE: PRT
<213> ORGANISM: Artificial
<220> FEATURE:
<223> OTHER INFORMATION: GRKKRRQRRRPPKRPTTLNLFPQVPRSQD JNK inhibitor

<400> SEQUENCE: 194

Gly Arg Lys Lys Arg Arg Gln Arg Arg Pro Pro Lys Arg Pro Thr
1               5                   10                  15

Thr Leu Asn Leu Phe Pro Gln Val Pro Arg Ser Gln Asp
            20                  25

<210> SEQ ID NO 195
<211> LENGTH: 25
<212> TYPE: PRT
<213> ORGANISM: Artificial
<220> FEATURE:
<223> OTHER INFORMATION: GRKKRRQRRRPTTLNLFPQVPRSQD JNK inhibitor

<400> SEQUENCE: 195

Gly Arg Lys Lys Arg Arg Gln Arg Arg Arg Pro Thr Thr Leu Asn Leu
1               5                   10                  15

Phe Pro Gln Val Pro Arg Ser Gln Asp
            20                  25

<210> SEQ ID NO 196
<211> LENGTH: 31
<212> TYPE: PRT
<213> ORGANISM: Artificial
<220> FEATURE:
<223> OTHER INFORMATION: L-TAT-IB1

<400> SEQUENCE: 196

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 197
<211> LENGTH: 31
<212> TYPE: PRT
<213> ORGANISM: Artificial
<220> FEATURE:
<223> OTHER INFORMATION: D-TAT-IB1
<220> FEATURE:
<221> NAME/KEY: Variant
<222> LOCATION: (1)..(31)
<223> OTHER INFORMATION: All amino acids are D-enantiomeric amino acids

<400> SEQUENCE: 197

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30

<210> SEQ ID NO 198
<211> LENGTH: 39
<212> TYPE: PRT
<213> ORGANISM: Artificial
<220> FEATURE:
<223> OTHER INFORMATION: cJun (29-67)

<400> SEQUENCE: 198

Ser Asn Pro Lys Ile Leu Lys Gln Ser Met Thr Leu Asn Leu Ala Asp
1               5                   10                  15

```
Pro Val Gly Ser Leu Lys Pro His Leu Arg Ala Lys Asn Ser Asp Leu
            20                  25                  30

Leu Thr Ser Pro Asp Val Gly
        35

<210> SEQ ID NO 199
<211> LENGTH: 20
<212> TYPE: PRT
<213> ORGANISM: Artificial
<220> FEATURE:
<223> OTHER INFORMATION: RKKRRQRRRRPKRPATLNLF antibody negative control

<400> SEQUENCE: 199

Arg Lys Lys Arg Arg Gln Arg Arg Arg Pro Lys Arg Pro Ala Thr
1               5                   10                  15

Leu Asn Leu Phe
            20

<210> SEQ ID NO 200
<211> LENGTH: 20
<212> TYPE: PRT
<213> ORGANISM: Artificial
<220> FEATURE:
<223> OTHER INFORMATION: rKKRrQRRrR PkAAaAANAf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ala is D-enantiomeric Ala
<220> FEATURE:
<221> NAME/KEY: Variant
<222> LOCATION: (20)..(20)
<223> OTHER INFORMATION: Phe is D-enantiomeric Phe

<400> SEQUENCE: 200

Arg Lys Lys Arg Arg Gln Arg Arg Arg Pro Lys Ala Ala Ala Ala
1               5                   10                  15

Ala Asn Ala Phe
            20
```

JNK INHIBITOR MOLECULES FOR TREATMENT OF VARIOUS DISEASES

SEQUENCE LISTING SUBMISSION VIA EFS-WEB

A computer readable text file, entitled "067802-5031-01-SequenceListing.txt" created on or about Jul. 22, 2016, with a file size of about 88 kb contains the sequence listing for this application and is hereby incorporated by reference in its entirety.

The present invention relates to the field of enzyme inhibition, in particular to (poly-)peptide inhibitors of c-Jun amino terminal kinase (JNK). In particular, the present invention relates to using these JNK inhibitors in the treatment of various diseases.

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well as effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease, but also in other diseases as mentioned further below. Furthermore, the mitogen-activated protein kinase (MAPK) p38alpha was shown to negatively regulate the cell proliferation by antagonizing the JNK-c-Jun-pathway. The mitogen-activated protein kinase (MAPK) p38alpha therefore appears to be active in suppression of normal and cancer cell proliferation and, as a further, demonstrates the involvement of JNK in cancer diseases (see e.g. Hui et al., Nature Genetics, Vol 39, No. 6, June 2007). It was also shown, that c-Jun N-terminal Kinase (JNK) is involved in neuropathic pain produced by spinal nerve ligation (SNL), wherein SNL induced a slow and persistent activation of JNK, in particular JNK1, whereas p38 mitogen-activated protein kinase activation was found in spinal microglia after SNL, which had fallen to near basal level by 21 days (Zhuang et al., The Journal of Neuroscience, Mar. 29, 2006, 26(13):3551-3560)). In 2007 (Biochemica et Biophysica Acta, pp. 1341-1348), Johnson et al. discussed in a review the c-Jun kinase/stress-activated pathway, the involvement of JNK signalling in diseases such as the involvement in excitotoxicity of hippocampal neurons, liver ischemia, reperfusion, neurodegenerative diseases, hearing loss, deafness, neural tube birth defects, cancer, chronic inflammatory diseases, obesity, diabetes, in particular insulin-resistant diabetes, and proposed that it is likely that selective JNK inhibitors are needed for treatment of various diseases with a high degree of specificity and lack of toxicity.

Inhibition or interruption of the JNK signalling pathway is thus a promising approach in combating disorders strongly related to JNK signalling. However, there are only a few inhibitors of the JNK signaling pathway known so far.

Inhibitors of the JNK signaling pathway as already known in the prior art include e.g. upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (see e.g. Kuan et al., Current Drug Targets—CNS & Neurological Disorders, February 2005, vol. 4, no. 1, pp. 63-67; WO 2007/031280; all incorporated herewith by reference). WO 2007/031280 discloses small cell permeable fusion peptides, comprising a so-called TAT transporter sequence derived from the basic trafficking sequence of the HIV-TAT protein and an amino acid inhibitory sequence of IB1.

WO 2007/031280 discloses in particular two specific sequences, L-TAT-IB1 (GRKKRRQRRRPPRPKRPTTLN-LFPQVPRSQD, herein SEQ ID NO: 196) and D-TAT-IB1 (dqsrpvqpflnittprkprpprrrqrrkkrg; herein SEQ ID NO: 197), the latter being the retro-inverso sequence of L-TAT-IB1. Due to the HIV TAT derived transporter sequence, these fusion peptides are more efficiently transported into the target cells, where they remain effective until proteolytic degradation.

Since ATP independent peptide inhibitors of JNK are usually more specific inhibitors, they are frequently the first choice if it comes to inhibiting JNK. However, even the peptide inhibitors disclosed in WO 2007/031280 are not optimal for all purposes. For example, compound L-TAT-IB1 (herein SEQ ID NO: 196) which consists of L amino acids only, is quickly proteolytically degraded. In order to overcome this problem the inventors of WO 2007/031280 also suggested D-TAT-IB1 (herein SEQ ID NO: 197), which comprises D amino acids. To be more precise, D-TAT-IB1 exhibits the retro-inverso sequence of L-TAT-IB1. Incorporation of D-amino acids is made difficult by the fact that the change in stereochemistry may lead to a loss of function. The retro-inverso approach may be employed to reduce said risk because the use of i) only D-amino acids ii) but in the inverse peptide sequence may more likely yield an acceptable conformational analogue to the original peptide than incorporating one or more D-amino acids into the original sequence. In the case of WO 2007/031280 this approach resulted nevertheless in a significant decrease in inhibitory capacity in comparison to L-TAT-IB1 (see FIG. 4). Additionally, the retro-inverso peptide is extremely stable towards proteolytic digestion with the consequence that controlled digestions, for example in time sensitive experiments, are hardly possible.

JNK inhibitors have been discussed, proposed and successfully tested in the art as treatment for a variety of disease states. Already in 1997, Dickens et al. described the c-Jun amino terminal kinase inhibitor JIP-1 and proposed JIP-1 as candidate compounds for therapeutic strategies for the treatment of for example chronic myeloid leukaemia, in particular, in the context of Bcr-Abl caused transformation of pre-B-cells (Science; 1997; 277(5326):693-696).

In 2001, Bonny and co-workers published that cell-permeable peptide inhibitors of JNK confirm long term protection to pancreatic β-cells from IL-1β-induced apoptosis and may, thus, preserve β-cells in the autoimmune destruction in the course of diabetes (Diabetes, 50, 2001, p. 77-82).

Bonny et al. (Reviews in Neurosciences, 2005, p. 57-67) discussed also the inhibitory action of the JNK inhibitor D-JNKI-1 and other JNK inhibitors in the context of excitotoxicity, neuronal cell death, hypoxia, ischemia, traumatic brain damage, epilepsy, neurodegenerative diseases, apoptosis of neurons and inner ear sensory auditory cells etc.

In WO 98/49188 JIP-1 derived inhibitors of JNK signalling are proposed for the treatment of neurodegenerative diseases, such as Parkinson's disease or Alzheimer's disease; stroke and associated memory loss, autoimmune diseases such as arthritis; other conditions characterized by inflammation; malignancies, such as leukemias, e.g. chronic myelogenous leukemia (CML); oxidative damage to organs such as the liver and kidney; heart diseases; and transplant rejections.

Borsello et al. (Nat Med, 2003, (9), p. 1180-1186) published that a peptide inhibitor of c-Jun-N-terminal kinase protects against excitotoxicity and cerebral ischemia.

Assi et al. have published that another specific JNK-inhibitor, SP600125, targets tumor necrosis factor-α production and epithelial cell apoptosis in acute murine colitis. The authors concluded that inhibition of JNK is of value in human inflammatory bowel disease treatment (Immunology; 2006, 118(0:112-121).

In Kennedy et al. (Cell Cycle, 2003, 2(3), p. 199-201), the role of JNK signalling in tumor development is discussed in more detail.

Lee Yong Hee et al. (J Biol Chem 2003, 278(5), P. 2896-2902) showed that c-Jun N-terminal kinase (JNK) mediates feedback inhibition of the insulin signalling cascade and have proposed that inhibition of JNK signalling is a good therapeutic approach to reduce insulin resistance in diabetic patients.

Milano et al. (Am J Physiol Heart Circ Physiol 2007; 192(4): H1828-H1835) discovered that a peptide inhibitor of c-Jun $NH_x$-terminal kinase reduces myocardial ischemia-reperfusion injury and infarct size in vivo. The authors of said study used a peptide inhibitor, D-JNKI-I, a two domain peptide containing a 20 amino acid sequence of the minimal JNK-binding domain of islet-brain-1/JNK-interacting protein-1, linked to a 10 amino acid TAT sequence of the human immuno deficiency virus TAT protein that mediates intracellular translocation. The authors have concluded that a reduction in JNK activity and phosphorylation due to the presence of said inhibitor is important in the preservation of cardiac function in rats in the phase of ischemia and apoptosis.

A further group has published that small peptide inhibitors of JNKs protect against MPTP-induced nigral dopaminergic injury via inhibiting the JNK-signalling pathway (Pan et al., Laboratory investigation, 2010, 90, 156-167). The authors concluded that a peptide comprising residues 153-163 of murine JIP-1 fused to TAT peptide offers neuroprotection against MPTP injury via inhibiting the JNK-signalling pathway and provides a therapeutic approach for Parkinson's disease.

For hearing damage, Pirvola et al. (The Journal of Neuroscience, 2000, 20(1); 43-50) described the rescue of hearing, auditory hair cells and neurons by CEP-1347/KT7515, an inhibitor of c-Jun-N-terminal kinase activation. The authors suggested in general that therapeutic intervention in the JNK signalling cascade may offer opportunities to treat inner ear injuries. Treatment of hearing loss by means of administering JNK-inhibitory peptides is also disclosed for example in WO 03/103698.

For retinal diseases and age-related macula degeneration in particular, Roduit et al. (Apoptosis, 2008, 13(3), p. 343-353) have likewise suggested to use JNK-inhibition as therapeutic approach. Similar considerations relying on JNK-inhibition are disclosed for example in WO 2010/113753 for the treatment of age-related macular degeneration, diabetic macular edema, diabetic retinopathy, central exudative chorioretinopathy, angioid streaks, retinal pigment epithelium detachment, multifocal choroiditis, neovascular maculopathy, retinopathy of prematurity, retinitis pigmentosa, Leber's disease, retinal artery occlusion, retinal vein occlusion, central serous chorioretinopathy, retinal macroaneurysm, retinal detachment, proliferative vitreoretinopathy, Stargardt's disease, choroidal sclerosis, chorioderemia, vitelliform macular dystrophy, Oguchi's disease, fundus albipunctatus, retinitis *Punctata albescens*, and gyrate atrophy of choroid and retina.

Zoukhri et al. (Journal of Neurochemistry, 2006, 96, 126-135) identified that c-Jun $NH_x$-terminal kinease mediates interleukin-1 β-induced inhibition of lacrimal gland secretion. They concluded that JNK plays a pivotal role in IL-1 β-mediated inhibition of lacrimal gland secretion and subsequent dry eye.

For uveitis, Touchard et al. (Invest Ophthalmol Vis Sci, 2010, 51(9); 4683-4693) have suggested to use D-JNKI 1 as effective treatment.

For IBD (inflammatory bowel disease) Roy et al. (World J Gastroenterol 2008, 14(2), 200-202) have highlighted the role of the JNK signal transduction pathway therein and have proposed to use peptidic JNK inhibitors for the treatment of said disease state.

Beckham et al (J Virol. 2007 July; 81(13):6984-6992) showed that the JNK inhibitor D-JNKI-1 is effective in protecting mice from viral encephalitis, and suggest thus JNK inhibition as promising and novel treatment strategy for viral encephalitis.

Palin et al. (Psychopharmacology (Berl). 2008 May; 197(4):629-635) used the same JNK inhibitor, D-JNKI-1, and found that pre-treatment with D-JNKI-1 (10 ng/mouse), but not D-TAT, significantly inhibited all three indices of sickness induced by central TNFalpha and suggested that JNK inhibition as means for treating major depressive disorders that develop on a background of cytokine-induced sickness behaviour.

In WO 2010/151638 treatment of the neurodegenerative disease spinal muscular atrophy by way of JNK inhibition was proposed.

The above passage highlights already on basis of only some selected publications the usefulness of JNK inhibitors in the treatment of various diseases. Thus, there is a constant need in the art for JNK inhibitors for use in the treatment of human (and animal) diseases.

Thus, the problem to be solved by the present invention was to provide further (peptide) inhibitors of JNK.

The object of the present invention is solved by the inventor by means of the subject-matter set out below and in the appended claims.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 1: Illustration of the inhibitory efficacy of several JNK inhibitors according to the present invention, which was investigated by in vitro AlphaScreen assay (Amplified Luminescence Proximity Homogeneous-Screen Assay).

FIG. 2: Table illustrating the inhibitory efficacy of several JNK inhibitors (SEQ ID NOs: 193, 2, 3, 5, 6, and 7) according to the present invention. Given are the IC50 values in the nM range, the respective standard error of the mean and the number of experiments performed (n).

FIG. 3: Illustration of the inhibitory efficacy of several JNK inhibitors according to the present invention, which are fusion proteins of a JNK inhibitory (poly-)peptide sequence and a transporter sequence. The inhibitory efficacy was determined by means of in vitro AlphaScreen assay (Amplified Luminescence Proximity Homogeneous-Screen Assay).

FIG. 4: Table illustrating the inhibitory efficacy of several JNK inhibitors according to the present invention, which are fusion proteins of a JNK inhibitory (poly-)peptide sequence and a transporter sequence. Given are the IC50 values in the nM range, the respective standard error of the mean (SEM) and the number of experiments performed (n).

FIG. 7A: TNF release (THP1pma 6 h 3 ng/ml LPS); FIG. 7B: TNFa release (THP1pma 6 h 10 ng/ml LPS); FIG. 7C: IL 6 release (THP1pma 6 h 10 ng/ml LPS); FIG. 7D: MCP1 release (THP1pma 6 h 3 ng/ml LPS).

JNK INHIBITORS

Figure 1A:
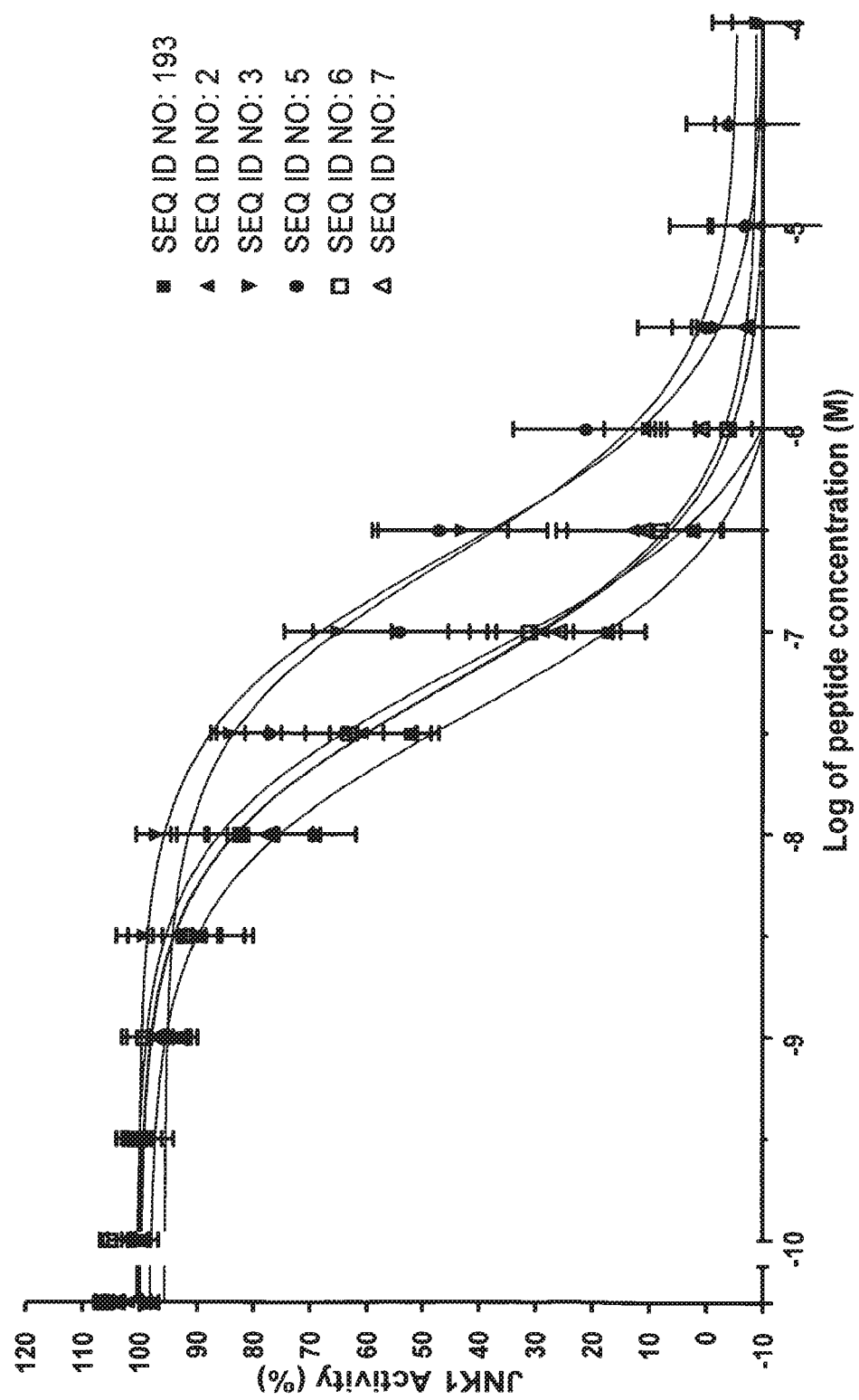
FIG. 1A: Inhibition of JNK1 by SEQ ID NOs: 193, 2, 3, 5, 6, and 7.
Figure 1B:
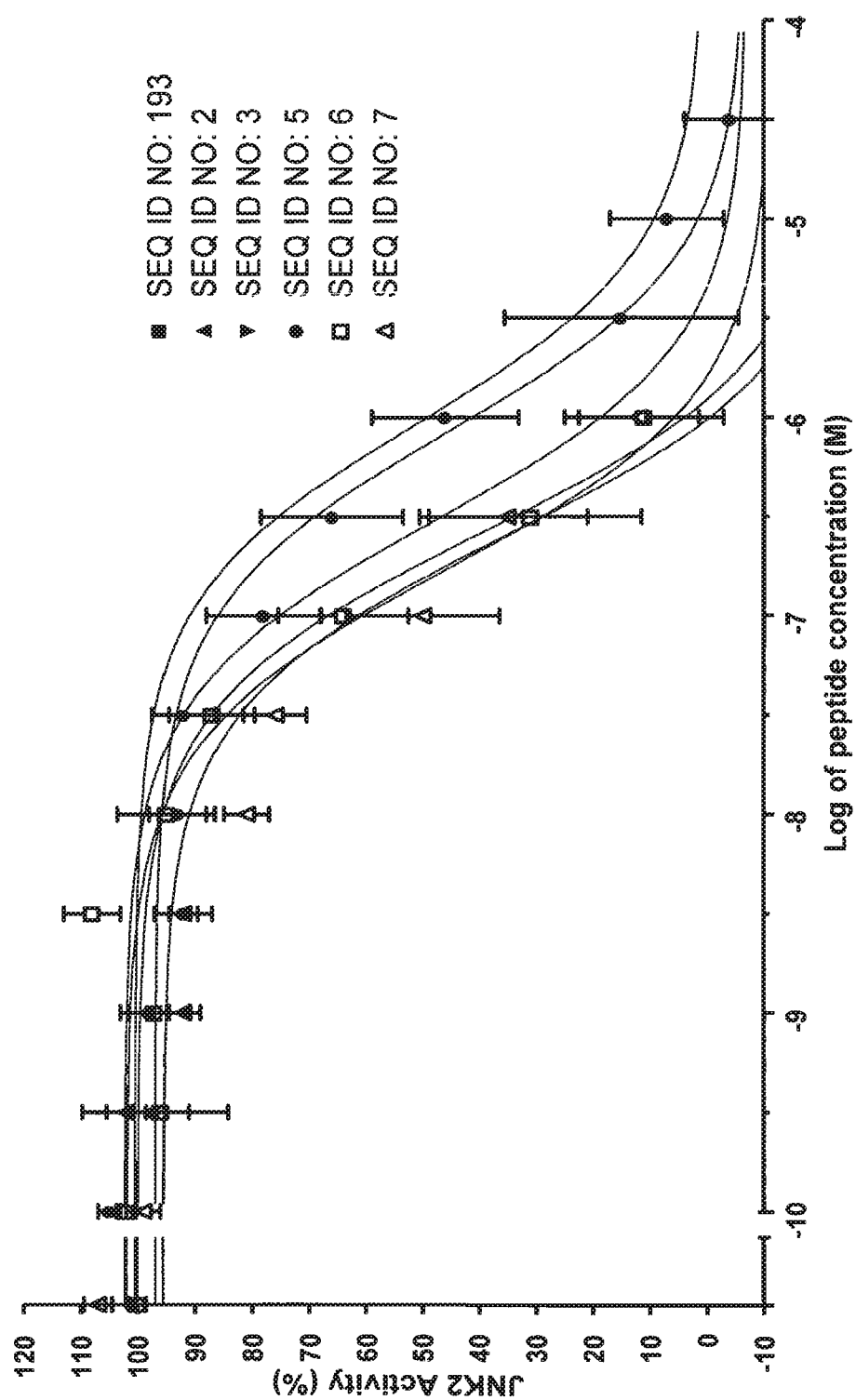
FIG. 1B: Inhibition of JNK2 by SEQ ID NOs: 193, 2, 3, 5, 6, and 7.
Figure 1C:
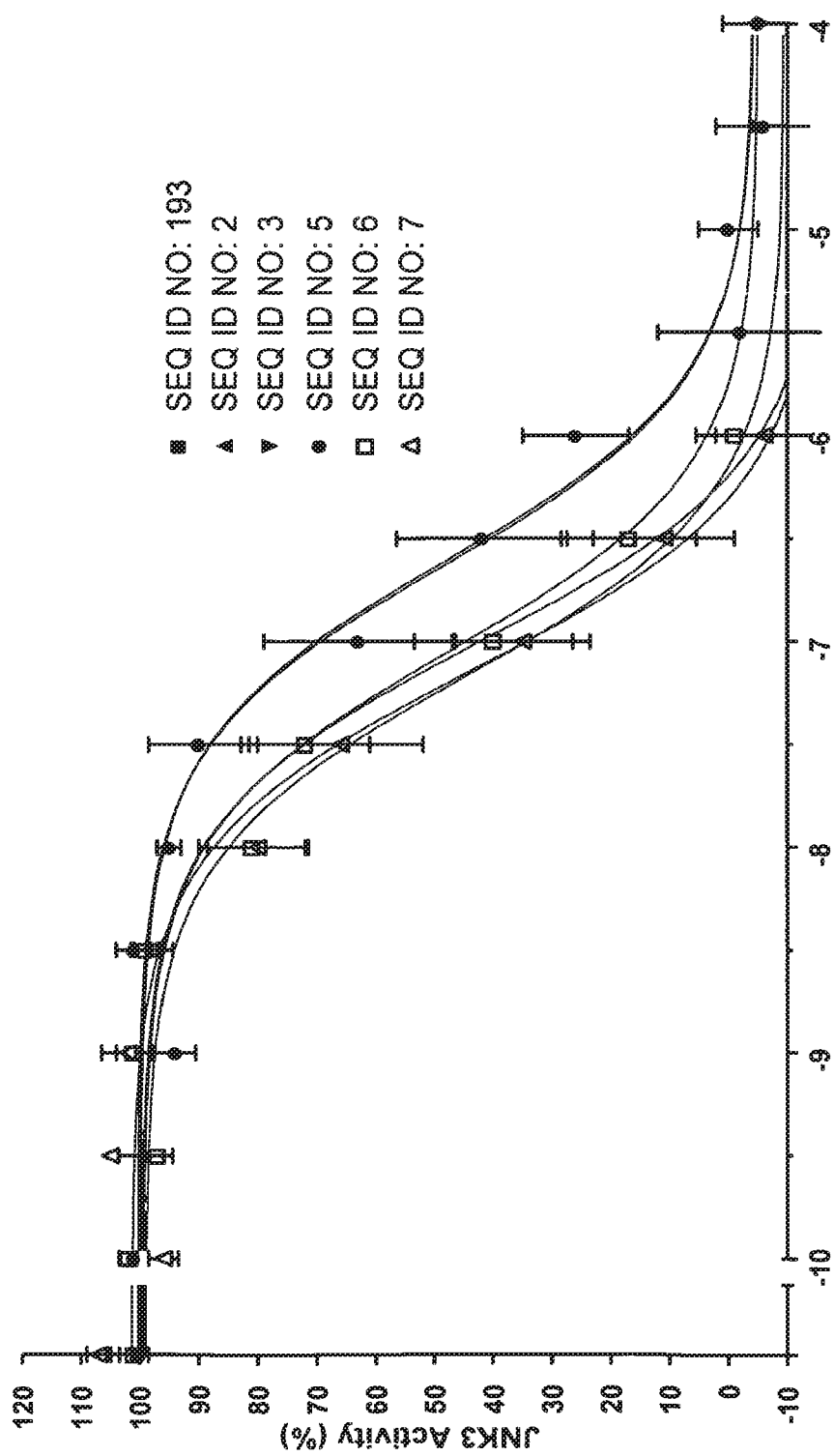
FIG. 1C: Inhibition of JNK3 by SEQ ID NOs: 193, 2, 3, 5, 6, and 7.
Figure 3A:
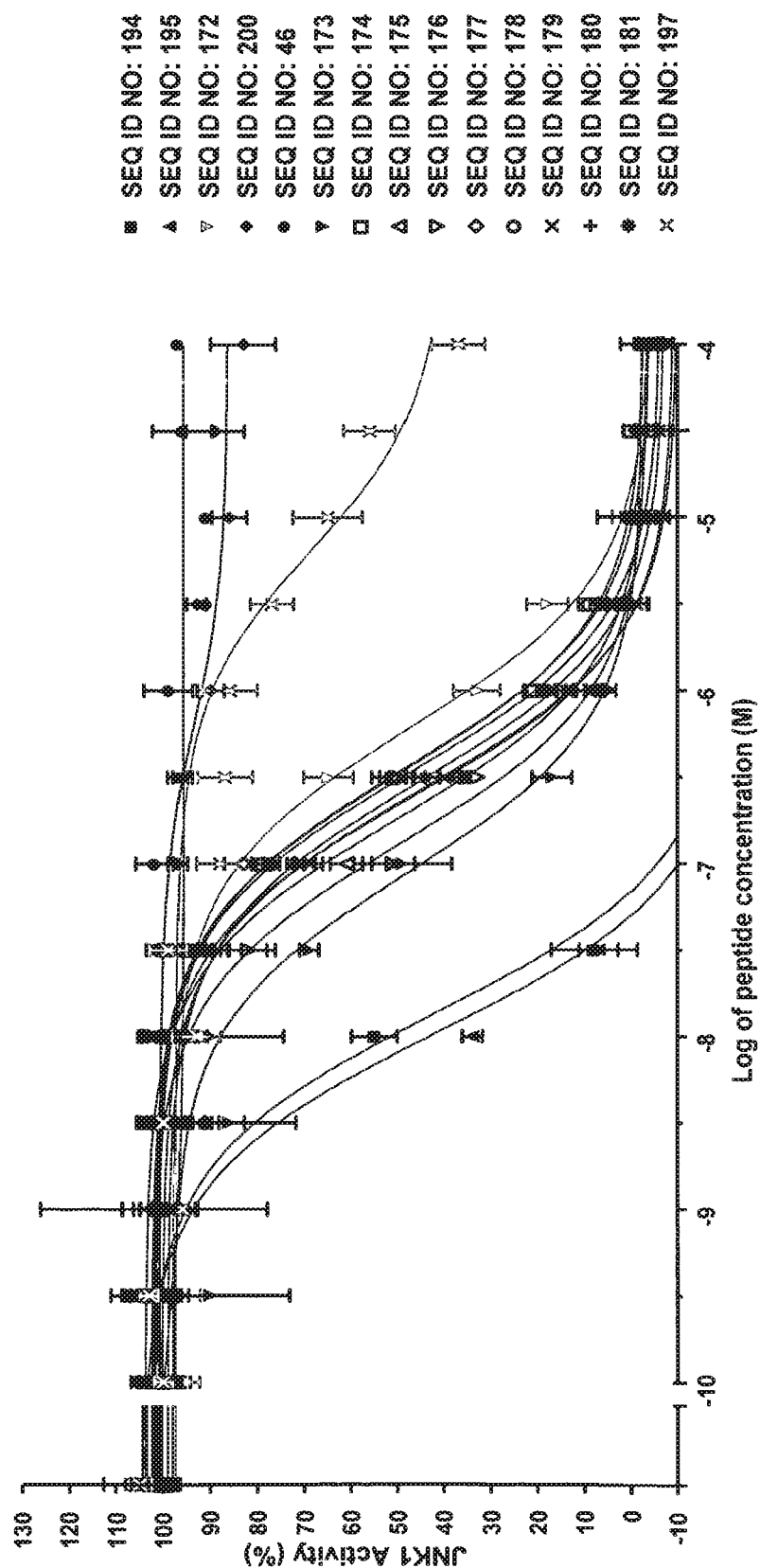
FIG. 3A: Inhibition of JNK1 by SEQ ID NOs: 194, 195, 172, 200, 46, 173, 174, 175, 176, 177, 178, 179, 180, 181 and 197.
Figure 3B:
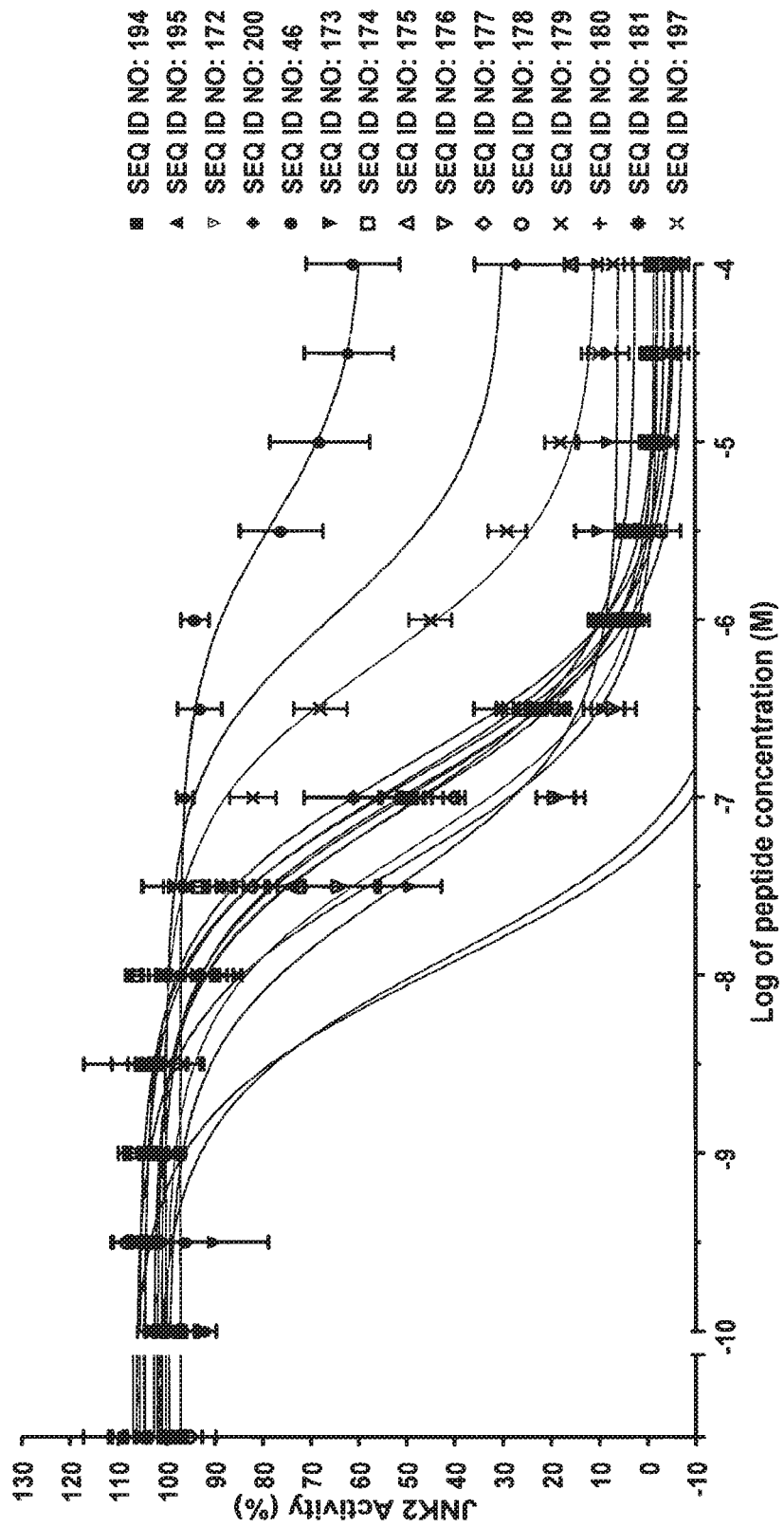
FIG. 3B: Inhibition of JNK2 by SEQ ID NOs: 194, 195, 172, 200, 46, 173, 174, 175, 176, 177, 178, 179, 180, 181 and 197.
Figure 3C:
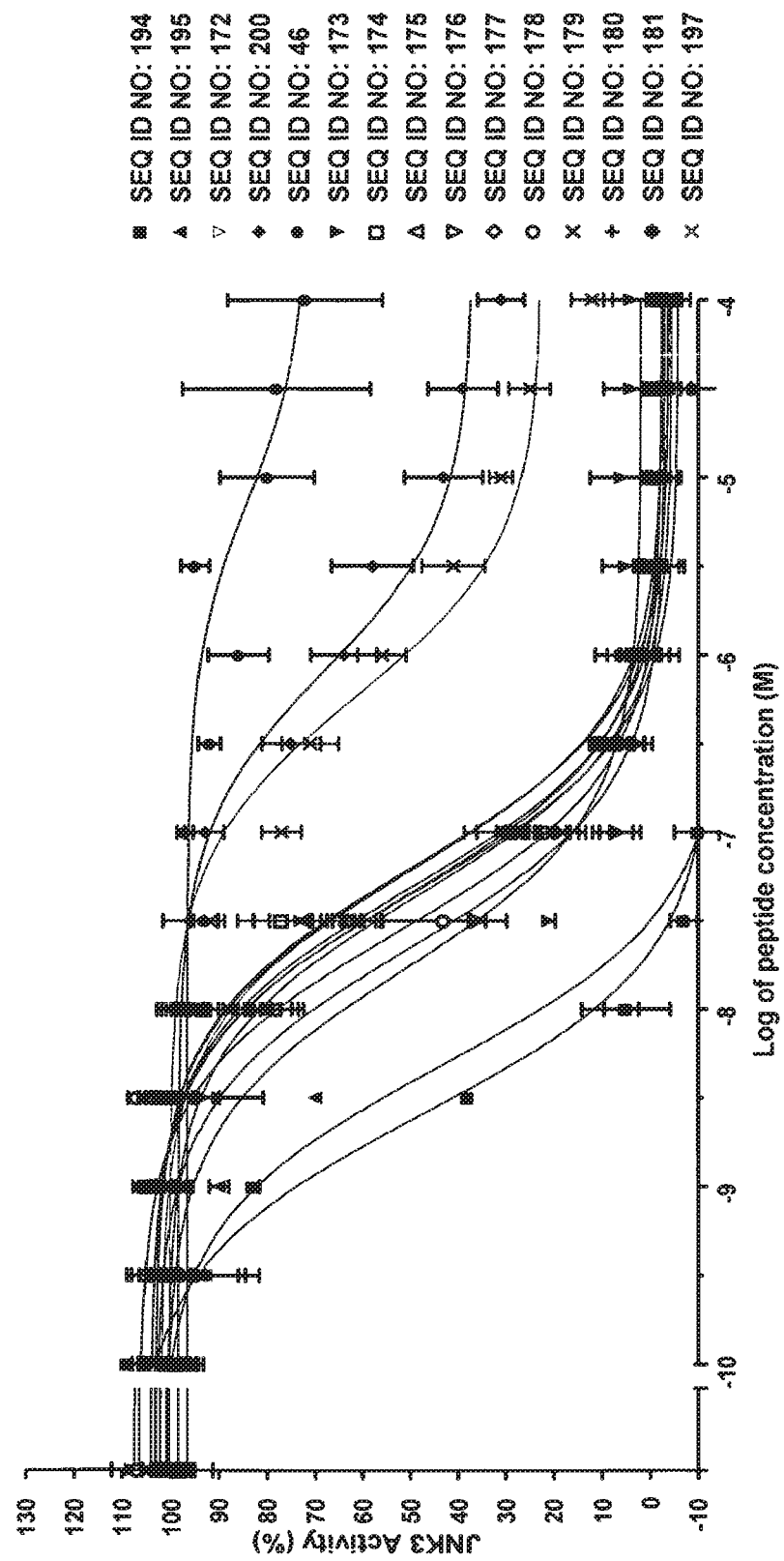
FIG. 3C: Inhibition of JNK3 by SEQ ID NOs: 194, 195, 172, 200, 46, 173, 174, 175, 176, 177, 178, 179, 180, 181 and 197.
Figure 3D:
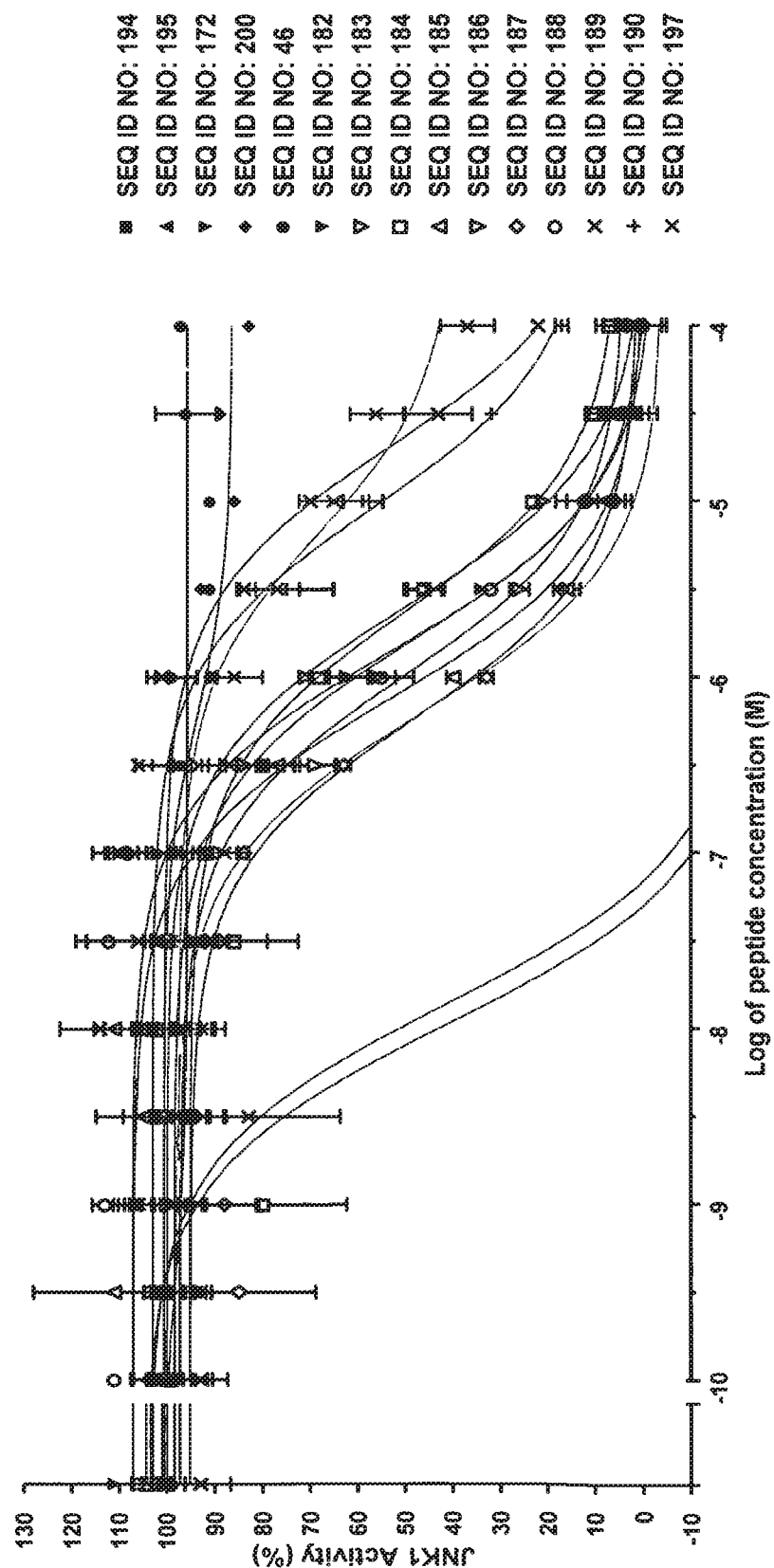
FIG. 3D: Inhibition of JNK1 by SEQ ID NOs: 194, 195, 172, 200, 46, 182, 183, 184, 185, 186, 187, 188, 189, 190 and 197.
Figure 3E:
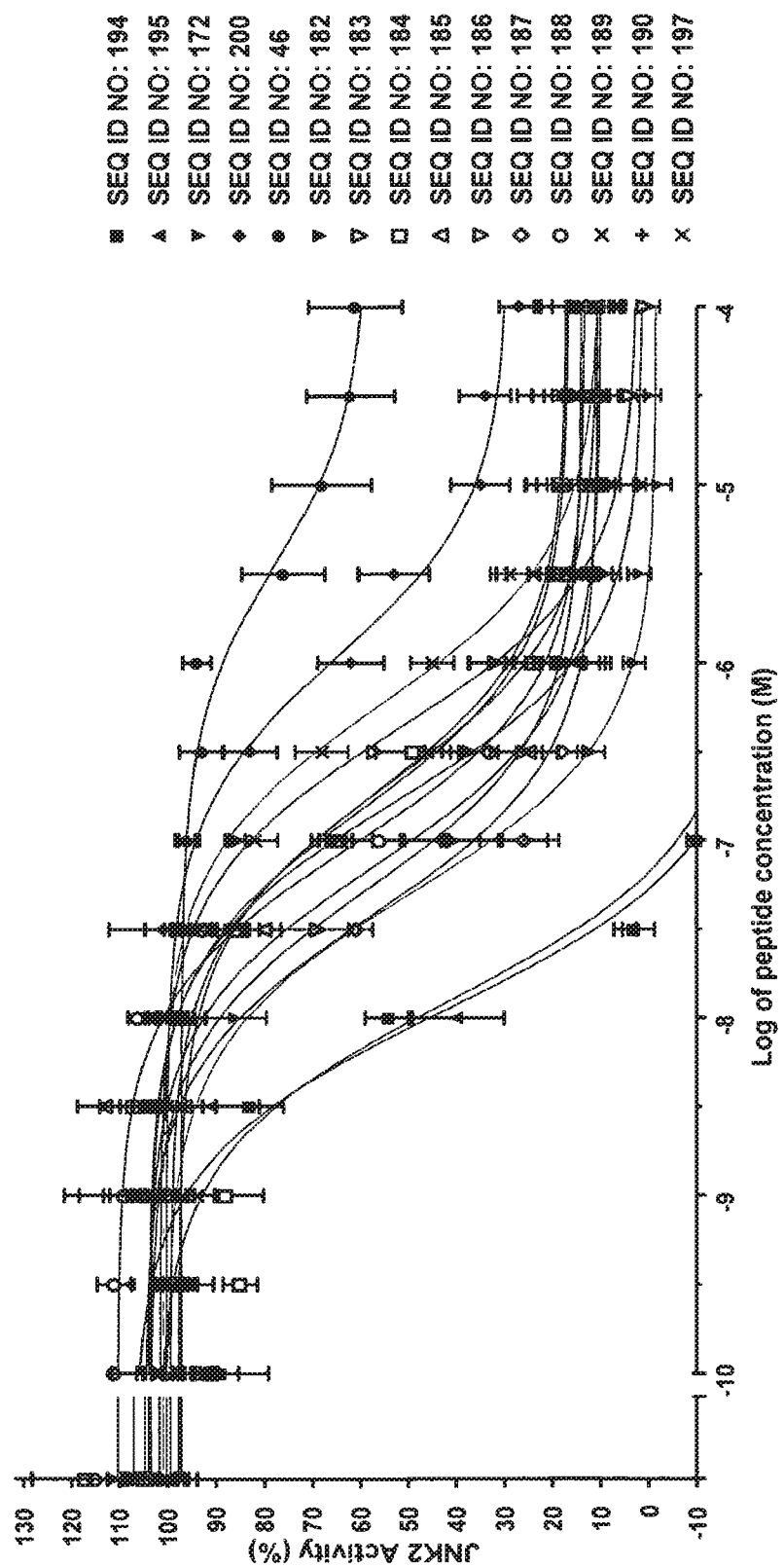
FIG. 3E: Inhibition of JNK2 by SEQ ID NOs: 194, 195, 172, 200, 46, 182, 183, 184, 185, 186, 187, 188, 189, 190 and 197.
Figure 3F:
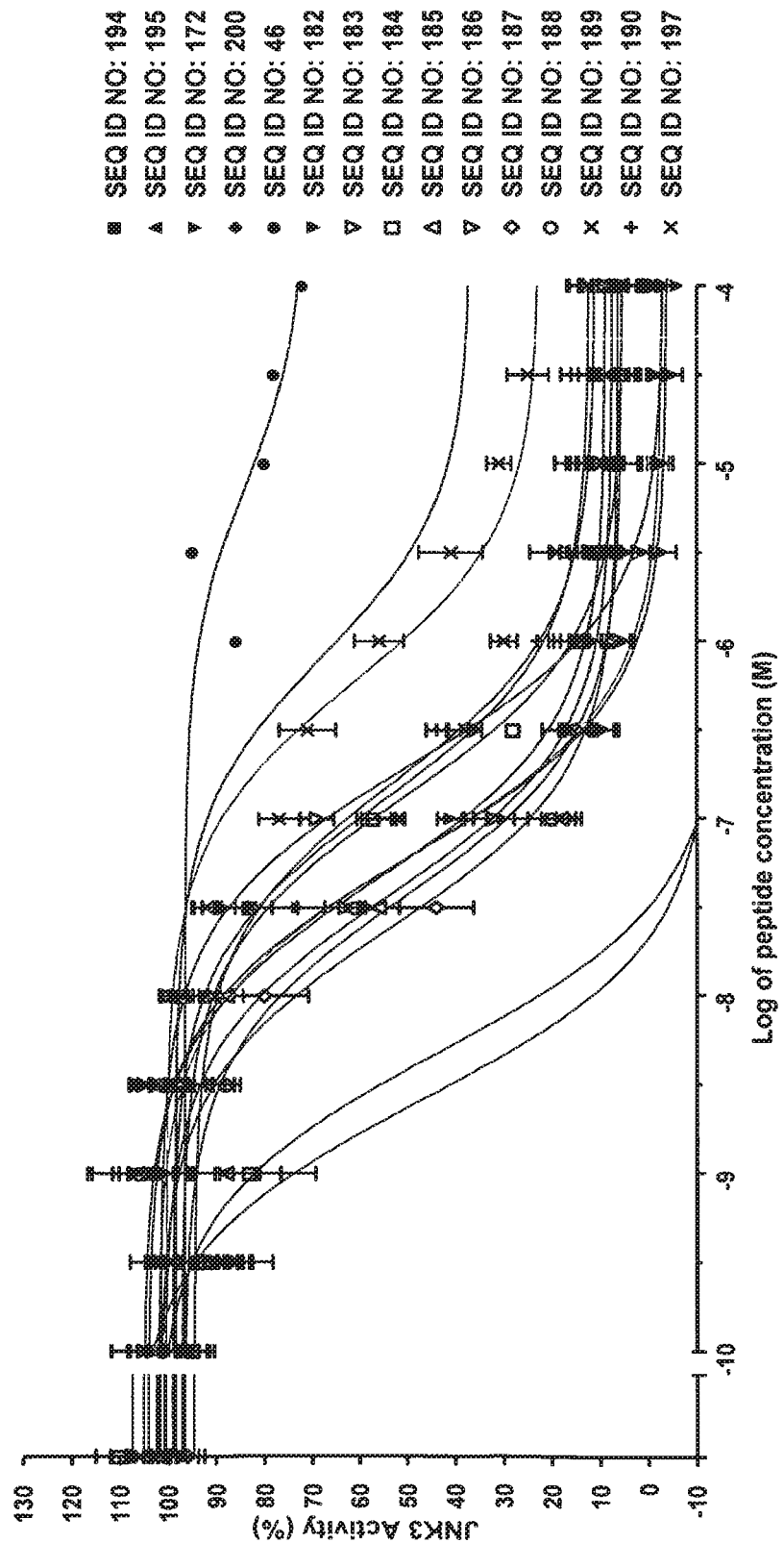
FIG. 3F: Inhibition of JNK3 by SEQ ID NOs: 194, 195, 172, 200, 46, 182, 183, 184, 185, 186, 187, 188, 189, 190 and 197.
Figure 5:
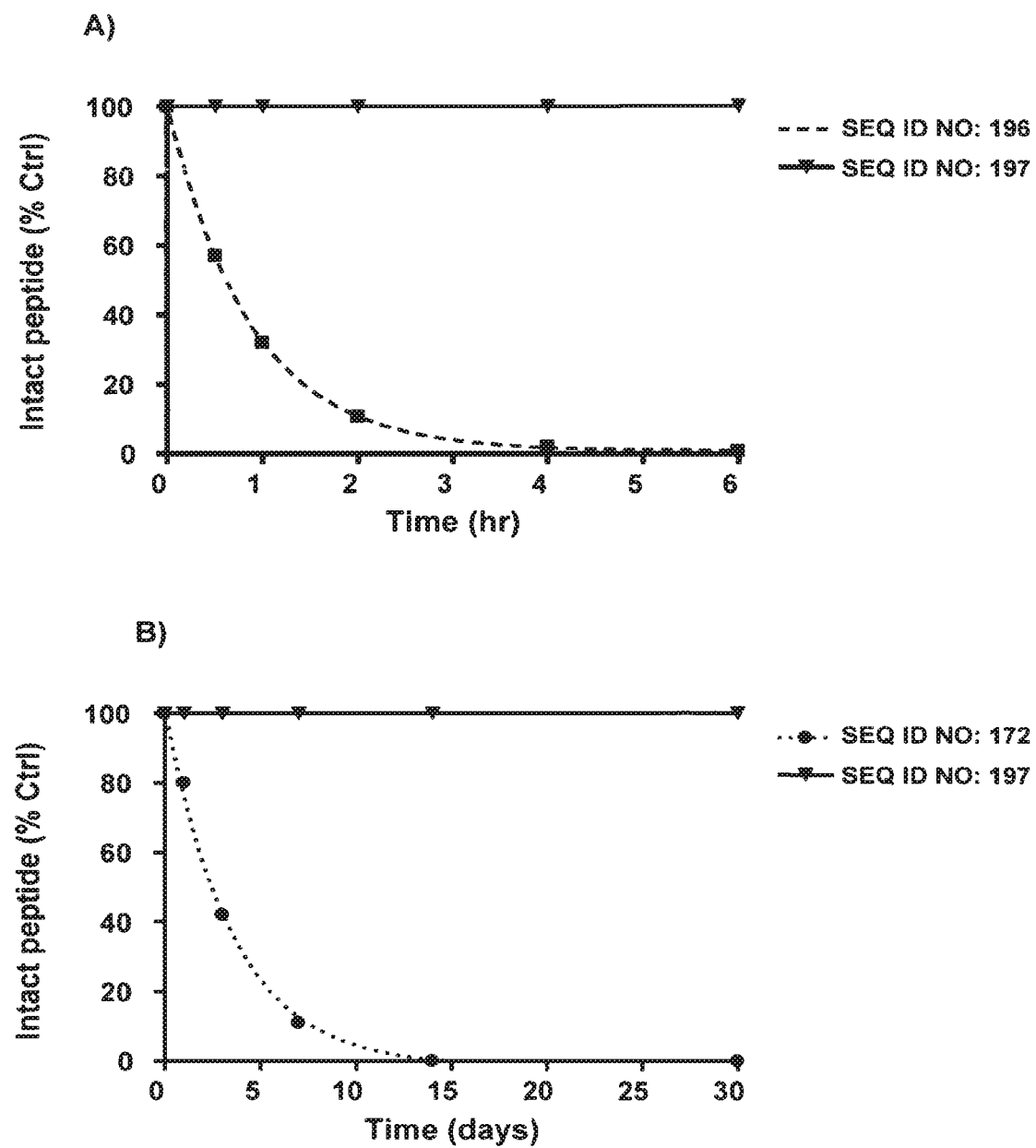
FIG. 5: Stability of JNK inhibitors with SEQ ID NOs: 172, 196 and 197 in 50% human serum. The JNK inhibitor with SEQ ID NO: 196 was totally degraded into amino acids residues within 6 hours (A). The JNK inhibitor with SEQ ID NO: 172 was completely degraded only after 14 days (B). The JNK inhibitor with SEQ ID NO: 197 was stable at least up to 30 days (B).

In a first aspect the present invention relates to a JNK inhibitor, which comprises an inhibitory (poly-) peptide sequence according to the following general formula:

$$X1\text{-}X2\text{-}X3\text{-}R\text{-}X4\text{-}X5\text{-}X6\text{-}L\text{-}X7\text{-}L\text{-}X8, \quad (\text{SEQ ID NO: 1})$$

wherein X1 is an amino acid selected from amino acids R, P, Q and r, wherein X2 is an amino acid selected from amino acids R, P, G and r, wherein X3 is an amino acid selected from amino acids K, R, k and r, wherein X4 is an amino acid selected from amino acids P and K, wherein X5 is an amino acid selected from amino acids T, a, s, q, k or is absent, wherein X6 is an amino acid selected from amino acids T, D and A, wherein X7 is an amino acid selected from amino acids N, n, r and K; and wherein X8 is an amino acid selected from F, f and w, with the proviso that at least one, at least two, at least three, at least four, at least five or six of the amino acids selected from the group consisting of X1, X2, X3, X5, X7 and X8 is/are a D-amino acid(s), preferably with the proviso that at least one, at least two, at least three or four of the amino acids selected from the group consisting of X3, X5, X7 and X8 is/are a D-amino acid(s),
for use in a method for treatment of the human or animal body by therapy.

The inhibitory (poly-)peptide sequence of the JNK inhibitor according to the present invention comprises L-amino acids and in most embodiments D-amino acids. Unless specified otherwise, L-amino acid residues are indicated herein in capital letters, while D amino acid residues are indicated in small letters. Glycine may be indicated in capital or small letters (since there is no D- or L-glycine). The amino acid sequences disclosed herein are always given from N- to C-terminus (left to right) unless specified otherwise. The given amino acid sequence may be modified or unmodified at the C- and/or N-terminus, e.g. acetylation at the C-terminus and/or amidation or modification with cysteamide at the N-terminus. For sake of clarity such possible but entirely optional modifications at the C- and/or N-terminus of the amino acid sequences disclosed herein are for sake of clarity not specifically indicated.

The JNK inhibitors of the present invention are (poly-)peptide inhibitors of the c-Jun N-terminal kinase (JNK). Said inhibitors inhibit the kinase activity of c-Jun N-terminal kinase (JNK), i.e. prevent or reduce the extent of phosphorylation of JNK substrates such as c-Jun, ATF2 and/or Elk-1. A person skilled in the art will understand that the term "inhibitor", as used herein, does not comprise compounds which irreversibly destroy the c-Jun N-terminal kinase (JNK) molecule and/or kinase activity. Furthermore, the term "inhibiting JNK activity" as used herein, refers to the inhibition of the kinase activity of c-Jun N-terminal kinase (JNK).

Furthermore, as used herein, a JNK inhibitor comprises at least one functional unit of a polymer of amino acids, i.e. a (poly-)peptide sequence. Moreover, this at least one functional polymer of amino acids provides for inhibition of JNK activity. The amino acid monomers of said inhibitory (poly-)peptide sequence are usually linked to each other via peptide bonds, but (chemical) modifications of said peptide bond(s) or of side chain residues may be tolerable, provided the inhibitory activity (inhibition of JNK activity) is not totally lost, i.e. the resulting chemical entity still qualifies as JNK inhibitor as functionally defined herein. The term "(poly-)peptide" shall not be construed as limiting the length of the (poly-)peptide unit. Preferably, the inhibitory (poly-)peptide sequence of the JNK inhibitors of the present invention is less than 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, or less than 12 amino acids long. Preferably, the inhibitory (poly-)peptide sequence does not have less than 10 amino acid residues, more preferably not less than 11 amino acid residues.

Furthermore, a "JNK inhibitor" of the present invention inhibits JNK activity, e.g. exhibits with regard to the inhibition of human JNK mediated phosphorylation of a c-Jun substrate (SEQ ID NO: 198) an IC 50 value of:

a) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK1, b) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK2, and/or c) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK3.

For some applications it is preferred that the inhibitor inhibits human JNK2 and/or human JNK3 according to the above definition, but not JNK1 according to the above definition.

Whether JNK activity is inhibited or not, may easily be assessed by a person skilled in the art. There are several methods know in the art. One example is a radioactive kinase assay or a non-radioactive kinase assay (e.g. Alpha screen test; see for example Guenat et al. J Biomol Screen, 2006; 11: pages 1015-1026).

A JNK inhibitor according to the present invention may thus for example comprise an inhibitory (poly-) peptide sequence according to any of SEQ ID NOs: 2 to 27 (see table 1).

TABLE 1

Examples for inhibitory (poly-)peptide sequences of JNK-inhibitors according to the present invention

| Amino acid sequence | SEQ ID NO: |
|---|---|
| rPKRPTTLNLF | 2 |
| RPkRPTTLNLF | 3 |
| RPKRPaTLNLF | 4 |
| RPKRPTTLnLF | 5 |
| RPKRPTTLrLF | 6 |
| RPKRPTTLNLf | 7 |
| RPkRPaTLNLf | 8 |
| RPkRPTTLNLf | 9 |
| RPkRPTTLrLf | 10 |
| RRrRPTTLNLf | 11 |
| QRrRPTTLNLf | 12 |
| RPkRPTTLNLw | 13 |
| RPkRPTDLNLf | 14 |
| RRrRPTTLrLw | 15 |
| QRrRPTTLrLw | 16 |
| RRrRPTDLrLw | 17 |
| QRrRPTDLrLw | 18 |
| RRrRPaTLNLf | 19 |
| QRrRPaTLNLf | 20 |
| RrKRPaTLNLf | 21 |
| RPkRPsTLNLf | 22 |
| RPkRPqTLNLf | 23 |
| RPkRPkTLNLf | 24 |
| rGKRKALKLf | 25 |
| rGKRKALrLf | 26 |
| RRrRKALrLf | 27 |

The JNK inhibitor according to the present invention may also be a JNK inhibitor (variant) which comprises an inhibitory (poly-)peptide sequence sharing at least 50%, more preferably at least 55%, more preferably at least 60%, more preferably at least 65%, more preferably at least 70%, more preferably at least 75%, more preferably at least 80%, more preferably at least 85%, most preferably at least 90% sequence identity with a sequence selected from SEQ ID NOs: 1-27, in particular with SEQ ID NO: 8, with the proviso that with regard to the respective sequence selected from SEQ ID NOs: 1-27, such inhibitory (poly-) peptide sequence sharing sequence identity
    a) maintains the L-arginine (R) residue on position 4,
    b) maintains the two L-leucine (L) residues at position 8 and 10 (positions 7 and 9 with regard to SEQ ID NOs: 25-27),
    c) exhibits one, two, three, four, five or six D-amino acid(s) at the respective positions corresponding to the amino acids selected from the group consisting of X1, X2, X3, X5, X7 and X8 of SEQ ID NO: 1 and respective positions in SEQ ID NOs: 2-27, more preferably exhibits one, two, three or four D-amino acid(s) at the positions corresponding to the amino acids selected from the group consisting of X3, X5, X7 and X8 of SEQ ID NO: 1 and respective positions in SEQ ID NOs: 2-27, and
    d) still inhibits JNK activity (i.e. is a JNK inhibitor as defined herein).

Certainly, variants disclosed herein (in particular JNK inhibitor variants comprising an inhibitory (poly-) peptide sequence sharing—within the above definition—a certain degree of sequence identity with a sequence selected from SEQ ID NOs: 1-27), share preferably less than 100% sequence identity with the respective reference sequence.

In view of said definition and for sake of clarity the residues which may not be changed in variants of JNK inhibitors comprising SEQ ID NOs: 1-27 (see a) and b) in the above definition) are underlined in table 1.

The non-identical amino acids are preferably the result of conservative amino acid substitutions.

Conservative amino acid substitutions, as used herein, may include amino acid residues within a group which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Ile) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art. The isomer form should preferably be maintained, e.g. K is preferably substituted for R or H, while k is preferably substituted for r and h.

Further possible substitutions within the above definition for JNK inhibitor variants are for example if:
    a) one, two or more of X1, X2, X3, X4, X5, X6, X7 and/or X8 of SEQ ID NO: 1 or the corresponding positions within the respective sequence selected from SEQ ID NOs: 2-27 are substituted for A or a,
    b) X1 or X8 of SEQ ID NO: 1 or the corresponding position within the respective sequence selected from SEQ ID NOs: 2-27 is deleted;

c) X5 of SEQ ID NO: 1 or the corresponding position within the respective sequence selected from SEQ ID NOs: 2-27 is E, Y, L, V, F or K;
d) X5 of SEQ ID NO: 1 or the corresponding position within the respective sequence selected from SEQ ID NOs: 2-27 is E, L, V, F or K; or
e) one, two or three of X1, X2, X3 of SEQ ID NO: 1 or the corresponding positions within the respective sequence selected from SEQ ID NOs: 2-27 are neutral amino acids.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. For purposes of determining sequence identity, the substitution of an L-amino acid for a D-amino acid (and vice versa) is considered to yield a non-identical residue, even if it is merely the D- (or L-isomer) of the very same amino acid.

Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U. S. A 85, 2444-2448). Sequences which are identical to other sequences to a certain extent can be identified by these programmes. Furthermore, programs available in the Wisconsin Sequence Analysis Package. version 9.1 (Devereux et al., 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences.

Certainly, the JNK inhibitor according to the present invention may comprise—aside of the inhibitory (poly-)peptide sequence mentioned above—additional sequences, domains, labels (e.g. fluorescent or radioactive labels), epitopes etc. as long as the ability to inhibit JNK activity as defined herein is not lost. For example, the JNK inhibitor according to the present invention may also comprise a transporter sequence. A "transporter sequence" as used herein, is a (poly-)peptide sequence providing for translocation of the molecule it is attached to across biological membranes. Accordingly, a JNK inhibitor according to the present invention comprising a transporter sequence is preferably capable of translocating across biological membranes. Thus, such JNK inhibitor of the present invention may more readily enter a cell, a cellular subcompartment and/or into the nucleus of a cell.

Said transporter sequence may be joined for example (e.g. directly) N-terminally or (e.g. directly) C-terminally to the inhibitory (poly-)peptide sequence of the JNK inhibitor. The transporter sequence and the inhibitory (poly-)peptide sequence may also be spaced apart, e.g. may be separated by intermediate sequences. It is also contemplated that the transporter sequence may be positioned entirely elsewhere in the JNK inhibitor molecule than the inhibitory (poly-)peptide sequence, in particular if the JNK inhibitor is a more complex molecule (e.g. comprising several domains, is a multimeric conjugate etc.). It is also contemplated that the transporter sequence and the inhibitory (poly-)peptide sequence may overlap as long as the JNK inhibitory activity is maintained. Examples for such overlap are given further below.

Transporter sequences for use with the JNK inhibitor of the present invention may be selected from, without being limited thereto, transporter sequences derived from HIV TAT (HIV), e.g. native proteins such as e.g. the TAT protein (e.g. as described in U.S. Pat. Nos. 5,804,604 and 5,674,980, each of these references being incorporated herein by reference), HSV VP22 (*Herpes simplex*) (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), transporter sequences derived from *Antennapedia*, particularly from *Drosophila antennapedia* (e.g. the *antennapedia* carrier sequence thereof), FGF, lactoferrin, etc. or derived from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine, or may be selected from e.g. arginine rich peptide sequences, such as RRRRRRRRR ($R_9$; SEQ ID NO: 152), RRRRRRRR ($R_8$; SEQ ID NO: 153), RRRRRRR ($R_7$; SEQ ID NO: 154), RRRRRR ($R_6$, SEQ ID NO: 155), RRRRR ($R_5$, SEQ ID NO: 156) etc., from VP22, from PTD-4 proteins or peptides, from RGD-$K_{16}$, from PEPT1/2 or PEPT1/2 proteins or peptides, from SynB3 or SynB3 proteins or peptides, from PC inhibitors, from P21 derived proteins or peptides, or from JNKI proteins or peptides.

Examples of transporter sequences for use in the JNK inhibitor of the present invention are in particular, without being limited thereto, basic transporter sequences derived from the HIV-1 TAT protein. Preferably, the basic transporter sequence of the HIV-1 TAT protein may include sequences from the human immunodeficiency virus HIV-1 TAT protein, e.g. as described in, e.g., U.S. Pat. Nos. 5,804,604 and 5,674,980, each incorporated herein by reference. In this context, the full-length HIV-1 TAT protein has 86 amino acid residues encoded by two exons of the HIV TAT gene. TAT amino acids 1-72 are encoded by exon 1, whereas amino acids 73-86 are encoded by exon 2. The full-length TAT protein is characterized by a basic region which contains two lysines and six arginines (amino acids 49-57) and a cysteine-rich region which contains seven cysteine residues (amino acids 22-37). The basic region (i.e., amino acids 49-57) was thought to be important for nuclear localization. Ruben, S. et al., J. Virol. 63: 1-8 (1989);

Hauber, J. et al., J. Virol. 63 1181-1187 (1989). The cysteine-rich region mediates the formation of metal-linked dimers in vitro (Frankel, A. D. et al, Science 240: 70-73 (1988); Frankel, A. D. et al., Proc. Natl. Acad. Sci USA 85: 6297-6300 (1988)) and is essential for its activity as a transactivator (Garcia, J. A. et al., EMBO J. 7: 3143 (1988); Sadaie, M. R. et al., J. Virol. 63:1 (1989)). As in other regulatory proteins, the N-terminal region may be involved in protection against intracellular proteases (Bachmair, A. et al., Cell 56: 1019-1032 (1989)). Preferred TAT transporter sequences for use in the JNK inhibitor of the present invention are preferably characterized by the presence of the TAT basic region amino acid sequence (amino acids 49-57 of naturally-occurring TAT protein); the absence of the TAT cysteine-rich region amino acid sequence (amino acids 22-36 of naturally-occurring TAT protein) and the absence of the TAT exon 2-encoded carboxy-terminal domain (amino acids 73-86 of naturally-occurring TAT protein). More preferably, the transporter sequence in the JNK inhibitor of the present invention may be selected from an amino acid sequence containing TAT residues 48-57 or 49 to 57 or variants thereof.

Preferably, the transporter sequence in a given JNK inhibitor of the present invention also exhibits D-amino acids, for example in order to improve stability towards proteases. Particularly preferred are transporter sequences which exhibit a specific order of alternating D- and L-amino acids. Such order of alternating D- and L-amino acids (the motif) may follow—without being limited thereto—the pattern of any one of SEQ ID NOs: 28-30:

d$_l$LLL$_x$d$_m$LLL$_y$d$_n$;  (SEQ ID NO: 28)

dLLLd(LLLd)$_a$;  (SEQ ID NO: 29)
and/or dLLLdLLLd;  (SEQ ID NO: 30)

wherein: d is a D-amino acid;
L is a L-amino acid;
a is 0-3, preferably 0-2, more preferably 0, 1, 2 or 3, even more preferably 0, 1, or 2 and most preferably 1;
l, m and n are independently from each other 1 or 2, preferably 1;
x and y are independently from each other 0, 1 or 2, preferably 1.

Said order of D- and L-amino acids (motif) becomes relevant when the transporter sequence is synthesized, i.e. while the amino acid sequence (i.e. the type of side chain residues) remains unaltered, the respective isomers alternate. For example, a known transporter sequence derived from HIV TAT is RKKRRQRRR (SEQ ID NO: 4.3). Applying the D-/L amino acid order of SEQ ID NO: 30 thereto would yield rKKRrQRRr (SEQ ID NO: 46).

In a particular embodiment the transporter sequence of the JNK inhibitor of the present invention may comprise at least one sequence according to rXXXrXXXr (SEQ ID NO: 31), wherein:
r represents an D-enantiomeric arginine;
X is any L-amino acid (including glycine);
and wherein each X may be selected individually and independently of any other X within SEQ ID NO: 31. Preferably at least 4 out of said 6 X L-amino acids within SEQ ID NO: 31 are K or R. In another embodiment the JNK inhibitor according to the present invention comprises the transporter sequence rX$_1$X$_2$X$_3$rX$_4$X$_5$X$_6$r (SEQ ID NO: 32), wherein X$_1$ is K, X$_2$ is K, X$_3$ is R and X$_4$, X$_5$, and X$_6$ are any L-amino acid (including glycine) selected independently from each other. Similarly, the transporter sequence of the JNK inhibitor according to the present invention may comprise the sequence rX$_1$X$_2$X$_3$rX$_4$X$_5$X$_6$r (SEQ ID NO: 33), wherein X$_4$ is Q, X$_5$ is R, X$_6$ is R and X$_1$, X$_2$, and X$_3$ are any L-amino acid (including glycine) selected independently from each other. The inventive JNK inhibitor may also comprise the sequence rX$_1$X$_2$X$_3$rX$_4$X$_5$X$_6$r (SEQ ID NO: 34), wherein one, two, three, four, five or six X amino acid residues are chosen from the group consisting of X$_1$ is K, X$_2$ is K, X$_3$ is R, X$_4$ is Q, X$_5$ is R, X$_6$ is R, while the remaining X amino acid residues not selected from above group may be any L-amino acid (including glycine) and are selected independently from each other. X$_1$ is then preferably Y and/or X$_4$ is preferably K or R.

Examples of transporter sequences for use in the inventive JNK inhibitor molecule may be selected, without being limited thereto, from sequences as given in table 2 below, (SEQ ID NOs: 31-170) or from any fragment or variant or chemically modified derivative thereof (preferably it retains the function of translocating across a biological membrane).

TABLE 2

Examples for transporter (poly-)peptide sequences for use in the JNK-inhibitors according to the present invention

| SEQUENCE/PEPTIDE NAME | SEQ ID NO | AA | SEQUENCE |
| --- | --- | --- | --- |
| r3 (generic) | 31 | 9 | rXXXrXXXr |
| r3 (generic; right half) | 32 | 9 | rKKRrX4X5X6r |
| r3 (generic; left half) | 33 | 9 | rXiX2X3rQRRr |
| r3 (generic; individual) | 34 | 9 | rX1X2X3rX4X5X6r |
| TAT (1-86) | 35 | 86 | MEPVDPRLEP WKHPGSQPKT ACTNCYCKKC CFHCQVCFIT KALGISYGRK KRRQRRRPPQ GSQTHQVSLS KQPTSQSRGD PTGPKE |
| TAT (37-72) | 36 | 36 | CFITKALGIS YGRKKRRQRR RPPQGSQTHQ VSLSKQ |
| TAT (37-58) | 37 | 22 | CFITKALGIS YGRKKRRQRR RP |

TABLE 2-continued

Examples for transporter (poly-)peptide sequences for use in the
JNK-inhibitors according to the present invention

| SEQUENCE/PEPTIDE NAME | SEQ ID NO | AA | SEQUENCE |
|---|---|---|---|
| TAT (38-58)GGC | 38 | 24 | FITKALGISY GRKKRRQRRR PGGC |
| TAT CGG(47-58) | 39 | 15 | CGGYGRKKRR QRRRP |
| TAT (47-58)GGC | 40 | 15 | YGRKKRRQRR RPGGC |
| TAT (1-72) Mut Cys/Ala 72 | 41 | 56 | MEPVDPRLEP WKHPGSQPKT AFITKALGIS YGRKKRRQRR RPPQGSQTHQ VSLSKQ |
| L-TAT (s1a) | 42 | 10 | GRKKRRQRRR (NH$_2$-GRKKRRQRRR-COOH) |
| L-TAT (s1b) | 43 | 9 | RKKRRQRRR (NH$_2$-GRKKRRQRRR-COOH) |
| L-TAT (s1c) | 44 | 11 | YDRKKRRQRRR |
| D-TAT | 45 | 9 | rrrqrrkkr |
| r$_s$-L-TAT | 46 | 9 | rKKRrQRRr |
| r$_s$-L-TATi | 47 | 9 | rRRQrRKKr |
| βA-r3-L-TAT | 48 | 9 | βA-rKKRrQRRr (βA: beta alanine) |
| βA-r3-L-TATi | 49 | 9 | βA-rRRQrRKKr (βA: beta alanine) |
| FITC-βA-r$_s$-L-TAT | 50 | 9 | FITC-βA-rKKRrQRRr (βA: beta alanine) |
| FITC-βA-r$_s$-L-TATi | 51 | 9 | FITC-βA-rRRQrRKKr (βA: beta alanine) |
| TAT(s2-1) | 52 | 9 | rAKRrQRRr |
| TAT(s2-2) | 53 | 9 | rKARrQRRr |
| TAT(s2-3) | 54 | 9 | rKKArQRRr |
| TAT(s2-4) | 55 | 9 | rKKRrARRr |
| TAT(s2-5) | 56 | 9 | rKKRrQARr |
| TAT(s2-6) | 57 | 9 | rKKRrQRAr |
| TAT(s2-7) | 58 | 9 | rDKRrQRRr |
| TAT(s2-8) | 59 | 9 | rKDRrQRRr |
| TAT(s2-9) | 60 | 9 | rKKDrQRRr |
| TAT(s2-10) | 61 | 9 | rKKRrDRRr |
| TAT(s2-11) | 62 | 9 | rKKRrQDRr |
| TAT(s2-12) | 63 | 9 | rKKRrQRDr |
| TAT(s2-13) | 64 | 9 | rEKRrQRRr |
| TAT(s2-14) | 65 | 9 | rKERrQRRr |
| TAT(s2-15) | 66 | 9 | rKKErQRRr |
| TAT(s2-16) | 67 | 9 | rKKRrERRr |
| TAT(s2-17) | 68 | 9 | rKKRrQERr |
| TAT(s2-18) | 69 | 9 | rKKRrQREr |
| TAT(s2-19) | 70 | 9 | rFKRrQRRr |
| TAT(s2-20) | 71 | 9 | rKFRrQRRr |
| TAT(s2-21) | 72 | 9 | rKKFrQRRr |
| TAT(s2-22) | 73 | 9 | rKKRrFRRr |

TABLE 2-continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT(s2-23) | 74 | 9 | rKKRrQFRr |
| TAT(s2-24) | 75 | 9 | rKKRrQRFr |
| TAT(s2-25) | 76 | 9 | rRKRrQRRr |
| TAT(s2-26) | 77 | 9 | rKRRrQRRr |
| TAT(s2-27) | 78 | 9 | rKKKrQRRr |
| TAT(s2-28) | 79 | 9 | rKKRrRRRr |
| TAT(s2-29) | 80 | 9 | rKKRrQKRr |
| TAT(s2-30) | 81 | 9 | rKKRrQRKr |
| TAT(s2-31) | 82 | 9 | rHKRrQRRr |
| TAT(s2-32) | 83 | 9 | rKHRrQRRr |
| TAT(s2-33) | 84 | 9 | rKKHrQRRr |
| TAT(s2-34) | 85 | 9 | rKKRrHRRr |
| TAT(s2-35) | 86 | 9 | rKKRrQHRr |
| TAT(s2-36) | 87 | 9 | rKKRrQRHr |
| TAT(s2-37) | 88 | 9 | rIKRrQRRr |
| TAT(s2-38) | 89 | 9 | rKIRrQRRr |
| TAT(s2-39) | 90 | 9 | rKKIrQRRr |
| TAT(s2-40) | 91 | 9 | rKKRrIRRr |
| TAT(s2-41) | 92 | 9 | rKKRrQIRr |
| TAT(s2-42) | 93 | 9 | rKKRrQRIr |
| TAT(s2-43) | 94 | 9 | rLKRrQRRr |
| TAT(s2-44) | 95 | 9 | rKLRrQRRr |
| TAT(s2-45) | 96 | 9 | rKKLrQRRr |
| TAT(s2-46) | 97 | 9 | rKKRrLRRr |
| TAT(s2-47) | 98 | 9 | rKKRrQLRr |
| TAT(s2-48) | 99 | 9 | rKKRrQRLr |
| TAT(s2-49) | 100 | 9 | rMKRrQRRr |
| TAT(s2-50) | 101 | 9 | rKMRrQRRr |
| TAT(s2-51) | 102 | 9 | rKKMrQRRr |
| TAT(s2-52) | 103 | 9 | rKKRrMRRr |
| TAT(s2-53) | 104 | 9 | rKKRrQMRr |
| TAT(s2-54) | 105 | 9 | rKKrTQRMr |
| TAT(s2-55) | 106 | 9 | rNKRrQRRr |
| TAT(s2-56) | 107 | 9 | rKNRrQRRr |
| TAT(s2-57) | 108 | 9 | rKKNrQRRr |
| TAT(s2-58) | 109 | 9 | rKKRrNRRr |
| TAT(s2-59) | 110 | 9 | rKKRrQNRr |

TABLE 2-continued

Examples for transporter (poly-)peptide sequences for use in the
JNK-inhibitors according to the present invention

| SEQUENCE/PEPTIDE NAME | SEQ ID NO | AA | SEQUENCE |
|---|---|---|---|
| TAT(s2-60) | 111 | 9 | rKKRrQRNr |
| TAT(s2-61) | 112 | 9 | rQKRrQRRr |
| TAT(s2-62) | 113 | 9 | rKQRrQRRr |
| TAT(s2-63) | 114 | 9 | rKKQrQRRr |
| TAT(s2-64) | 115 | 9 | rKKRrKRRr |
| TAT(s2-65) | 116 | 9 | rKKRrQQRr |
| TAT(s2-66) | 117 | 9 | rKKRrQRQr |
| TAT(s2-67) | 118 | 9 | rSKRrQRRr |
| TAT(s2-68) | 119 | 9 | rKSRrQRRr |
| TAT(s2-69) | 120 | 9 | rKKSrQRRr |
| TAT(s2-70) | 121 | 9 | rKKRrSRRr |
| TAT(s2-71) | 122 | 9 | rKKRrQSRr |
| TAT(s2-72) | 123 | 9 | rKKRrQRSr |
| TAT(s2-73) | 124 | 9 | rTKRrQRRr |
| TAT(s2-74) | 125 | 9 | rKTRrQRRr |
| TAT(s2-75) | 126 | 9 | rKKTrQRRr |
| TAT(s2-76) | 127 | 9 | rKKRrTRRr |
| TAT(s2-77) | 128 | 9 | rKKRrQTRr |
| TAT(s2-78) | 129 | 9 | rKKRrQRTr |
| TAT(s2-79) | 130 | 9 | rVKRrQRRr |
| TAT(s2-80) | 131 | 9 | rKVRrQRRr |
| TAT(s2-81) | 132 | 9 | rKKVrQRRr |
| TAT(s2-82) | 133 | 9 | rKKRrVRRr |
| TAT(s2-83) | 134 | 9 | rKKRrQVRr |
| TAT(s2-84) | 135 | 9 | rKKRrQRVr |
| TAT(s2-85) | 136 | 9 | rWKRrQRRr |
| TAT(s2-86) | 137 | 9 | rKWRrQRRr |
| TAT(s2-87) | 138 | 9 | rKKWrQRRr |
| TAT(s2-88) | 139 | 9 | rKKRrWRRr |
| TAT(s2-89) | 140 | 9 | rKKRrQWRr |
| TAT(s2-90) | 141 | 9 | rKKRrQRWr |
| TAT(s2-91) | 142 | 9 | rYKRrQRRr |
| TAT(s2-92) | 143 | 9 | rKYRrQRRr |
| TAT(s2-93) | 144 | 9 | rKKYrQRRr |
| TAT(s2-94) | 145 | 9 | rKKRrYRRr |
| TAT(s2-95) | 146 | 9 | rKKRrQYRr |
| TAT(s2-96) | 147 | 9 | rKKRrQRYr |

TABLE 2-continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| TAT(s2-97) | 148 | 8 | rKKrQRr |
| TAT(s2-98) | 149 | 9 | rKKrQRrK |
| TAT(s2-99) | 150 | 9 | rKKrQRrR |
| $r_sR_6$ | 151 | 9 | rRRRrRRRr |
| L-$R_9$ | 152 | 9 | RRRRRRRRR |
| L-$R_8$ | 153 | 8 | RRRRRRRR |
| L-$R_7$ | 154 | 7 | RRRRRRR |
| L-$R_6$ | 155 | 6 | RRRRRR |
| L-$R_5$ | 156 | 5 | RRRRR |
| $r_9$ | 157 | 9 | rrrrrrrrr |
| $r_sR_4$(D/L) | 158 | 9 | rRrRrRrRr |
| $r_sR_4$(DD/LL) | 159 | 9 | rrRRrrRRr |
| PTD-4 | 160 | 11 | YARAAARQARA |
| PTD-4 (variant 1) | 161 | 11 | WARAAARQARA |
| PTD-4 (variant 2) | 162 | 11 | WARAQRAAARA |
| L-P1 Penetratin | 163 | 16 | RQVKVWFQNRRMKWKK |
| D-P1 Penetratin | 164 | 16 | KKWKMRRNQFWVKVQR |
| JNKI, bestfit | 165 | 17 | WKRAAARKARAMSLNLF |
| JNKI, bestfit (variant 1) | 166 | 17 | WKRAAARAARAMSLNLF |
| MDCK transcytose sequence | 167 | 9 | RYRGDLGRR |
| YKGL | 168 | 4 | YKGL |
| P1 | 169 | 4 | RRTK |
| P66 | 170 | 4 | RRPK |

As mentioned above, transporter sequences may also be selected from fragments or variants of the above sequences of table 2 (with the proviso that such fragment or variant retain preferably the function to provide for translocation across biological membranes). In this specific context, variants and/or fragments of those transporter sequences preferably comprise a peptide sequence sharing at least 10%, at least 20%, at least 30%, at least 40%, at least 50%, at least 60%, at least 70%, at least 80% or at least 85%, preferably at least 90%, more preferably at least 95% and most preferably at least 99% sequence identity over the whole length of the sequence of such a transporter sequence as defined in Table 2. In this specific context, a "fragment" of a transporter sequence as defined in Table 2, is preferably to be understood as a truncated sequence thereof, i.e. an amino acid sequence, which is N-terminally, C-terminally and/or intrasequentially truncated compared to the amino acid sequence of the original sequence.

Furthermore, a "variant" of a transporter sequence or its fragment as defined above, is preferably to be understood as a sequence wherein the amino acid sequence of the variant differs from the original transporter sequence or a fragment thereof as defined herein in one or more mutation(s), such as one or more substituted, (or, if necessary, inserted and/or deleted) amino acid(s). Preferably, variants of such a transporter sequence as defined above have the same biological function or specific activity compared to the respective original sequence, i.e. provide for transport, e.g. into cells or the nucleus. In this context, a variant of such a transporter sequence as defined above may for example comprise about 1 to 50, 1 to 20, more preferably 1 to 10 and most preferably 1 to 5, 4, 3, 2 or 1 amino acid alterations. Variants of such a transporter sequence as defined above may preferably comprise conservative amino acid substitutions. The concept of conservative amino acid substitutions is known in the art and has already been set out above for the JNK inhibitory (poly-)peptide sequence and applies here accordingly.

The length of a transporter sequence incorporated in the JNK inhibitor of the present invention may vary. It is contemplated that in some embodiments the transporter sequence of the JNK inhibitor according to the present invention is less than 150, less than 140, less than 130, less than 120, less than 110, less than 100, less than 90, less than 80, less than 70, less than 60, less than 50, less than 40, less than 30, less than 20, and/or less than 10 amino acids in length.

Whether a specific transporter sequence is still functional in the context of the JNK inhibitor according to the present invention may easily be determined by a person skilled in the art. For instance, the JNK inhibitor comprising a transporter domain may be fused to a label, e.g. a fluorescent protein such as GFP, a radioactive label, an enzyme, a fluorophore, an epitope etc. which can be readily detected in a cell. Then, the JNK inhibitor comprising the transporter sequence and the label is transfected into a cell or added to a culture supernatant and permeation of cell membranes can be monitored by using biophysical and biochemical standard methods (for example flow cytometry, (immuno)fluorescence microscopy etc.).

Specific examples of JNK inhibitors according to the present invention comprising a transporter sequence are given in table 3:

TABLE 3

Examples for JNK inhibitors comprising an inhibitory (poly-)peptide sequence and a transporter sequence

| Amino acid sequence | AA | SEQ ID NO: |
|---|---|---|
| rKKRrQRRrRPkRPTTLNLf | 20 | 171 |
| rKKRrQRRrRPkRPaTLNLf | 20 | 172 |
| rKKRrQRRrRPkRPTTLrLf | 20 | 173 |
| rKKRrQRRrRPTTLNLf | 17 | 174 |
| rKKRrQRrRPTTLNLf | 16 | 175 |
| rKKRrQRRrRPkRPTTLNLw | 20 | 176 |
| rKKRrQRRrRPkRPTDLNLf | 20 | 177 |
| rKKRrQRRrRPTTLrLw | 17 | 178 |
| rKKRrQRrRPTTLrLw | 16 | 179 |
| rKKRrQRRrRPTDLrLw | 17 | 180 |
| rKKRrQRrRPTDLrLw | 16 | 181 |
| rKKRrQRRrRPaTLNLf | 17 | 182 |
| rKKRrQRrRPaTLNLf | 16 | 183 |
| rKKRrQRrKRPaTLNLf | 17 | 184 |
| rKKRrQRRrRPkRPsTLNLf | 20 | 185 |
| rKKRrQRRrRPkRPqTLNLf | 20 | 186 |
| rKKRrQRRrRPkRPkTLNLf | 20 | 187 |
| rKKRrQRRrGKRKALKLf | 18 | 188 |
| rKKRrQRRrGKRKALrLf | 18 | 189 |
| rKKRrQRRrRKALrLf | 16 | 190 |

As mentioned above, in a particular embodiment of the present invention the transporter sequence and the inhibitory (poly-)peptide sequence may overlap. In other words, the N-terminus of the transporter sequence may overlap with the C-terminus of the inhibitory (poly-)peptide sequence or the C-terminus of the transporter sequence may overlap with the N-terminus of the inhibitory (poly-)peptide sequence. The latter embodiment is particularly preferred. Preferably, the transporter sequence overlaps by one, two or three amino acid residues with the inhibitory (poly-)peptide sequence. In such scenario a given transporter sequence may overlap with SEQ ID NO:1 or the respective variants thereof at position 1 (X1), position 1 and 2 (X1, X2), positions 1, 2 and 3 (X1, X2, X3).

SEQ ID NOs: 174, 175, 178, 179, 180, 181, 182, 183, 184, 188, 189 and 190 are good examples for JNK inhibitors according to the present invention, wherein transporter sequence and the inhibitory (poly-) peptide sequence overlap, e.g.

(SEQ ID NO: 174)
rKKRrQRRrRPTTLNLf is an overlap of SEQ ID NO: 46 (underlined) and SEQ ID NO: 11 (italics).

Certainly the JNK inhibitor according to the present invention may also be selected from JNK inhibitors, which are a variant of any one of the JNK inhibitors according to SEQ ID NOs: 171-190. Preferably, such variant shares at least 50%, more preferably at least 55%, more preferably at least 60%, more preferably at least 65%, more preferably at least 70%, more preferably at least 75%, more preferably at least 80%, more preferably at least 85%, more preferably at least 90%, most preferably at least 95% sequence identity with the sequence of SEQ ID NOs: 171-190, in particular with SEQ ID NO: 172, with the proviso that with respect to the inhibitory (poly-) peptide sequence within said sequences of SEQ ID NOs: 171-190 (see for reference inhibitory (poly-)peptide sequence of SEQ ID NO: 1 and specific examples of SEQ ID NOs: 2-27)) such sequence sharing sequence identity a) maintains the L-arginine (R) residue on position 4 within the inhibitory (poly-)peptide sequence,
b) maintains the two L-leucine (L) residues at position 8 and 10 (positions 7 and 9 with regard to SEQ ID NOs: 25-27) within the inhibitory (poly-)peptide sequence,
c) exhibits at least one, at least two, at least three, at least four, at least five or six D-amino acid(s) at the respective positions corresponding to the amino acids selected from the group consisting of X1, X2, X3, X5, X7 and or X8 of SEQ ID NO: 1 and respective positions in SEQ ID NOs: 2-27, more preferably exhibits at least one, at least two, at least three or four D-amino acid(s) at the positions corresponding to the amino acids selected from the group consisting of X3, X5, X7 and X8 of SEQ ID NO: 1 and respective positions in SEQ ID NOs: 2-27, and
d) still inhibits JNK activity (i.e. is a JNK inhibitor as defined herein).

In view of said definition and for sake of clarity the residues which may not be changed in variants of JNK inhibitors comprising SEQ ID NOs: 171-190 (see a) and b) in the above definition) are underlined in table 3.

The non-identical amino acids in the variants of JNK inhibitors comprising SEQ ID NOs: 171-190 are preferably the result of conservative amino acid substitutions (see above). Certainly, the further possible substitutions mentioned above are also contemplated for variants of JNK inhibitors comprising SEQ ID NOs: 171-190. Likewise, the present invention certainly also contemplates variants of any one of the JNK inhibitors according to SEQ ID NOs: 171-190, which deviate from the original sequence not or not exclusively in the inhibitory (poly-)peptide sequence, but exhibits variant residues in the transporter sequence. For variants and fragments of transporter sequences see in particular respective disclosure above.

As mentioned previously, the transporter sequence and the JNK inhibitory (poly)-peptide sequence of the JNK inhibitors according to the present invention need not necessarily be directly joined to each other. They may also be spaced apart, e.g. by intermediate (poly-)peptide sequences. Preferred intermediate sequences separating the inhibitory (poly-)peptide sequences and other (functional) sequences such as transporter sequences consist of short peptide sequences less than 10 amino acids in length like a hexaamer, a pentamer, a tetramer, a tripeptide or even only a dipeptide or a single amino acid residue. Particularly preferred intermediate sequence are one, two or more copies of di-proline, di-glycine, di-arginine and/or di-lysine, all either in L-amino acid form only, or in D-amino acid form only, or with mixed D- and L-amino acids. Certainly, other known peptide spacer sequences may be employed as well.

A particularly preferred JNK inhibitor according to the present invention comprises SEQ ID NO: 8 (or a sequence sharing sequence identity with SEQ ID NO: 8 with the scope and limitations defined further above) and a transporter sequence. The transporter sequence is preferably selected from any one of SEQ ID Nos: 31-170 or variants thereof as defined herein, even more preferably from any one of SEQ ID NOs: 31-34 and 46-151. A particularly preferred embodiment of a JNK inhibitor according to the present invention is a JNK inhibitor comprising SEQ ID NO: 8 and SEQ ID NO: 46 (or sequences sharing respective sequence identity thereto within the scope and limitations defined further above). A preferred example is a JNK inhibitor comprising the sequence of SEQ ID NO: 172 or respective variants thereof varying in the transporter sequence and/or the inhibitory (poly-)peptide sequence as defined herein.

In a further aspect the present invention relates to a JNK inhibitor comprising
a) an inhibitory (poly-)peptide comprising a sequence from the group of sequences consisting of RPTTLNLF (SEQ ID NO: 191), KRPTTLNLF (SEQ ID NO: 192), RRPTTLNLF and/or RPKRPTTLNLF (SEQ ID NO: 193), and
b) a transporter sequence, preferably a transporter sequence selected from the transporter sequences disclosed in table 2 or variants/fragments thereof, even more preferably selected from SEQ ID NOs: 31-34 and 46-151 or respective variants or fragments thereof.

The transporter sequence and the inhibitory (poly-)peptide sequence may overlap. Preferred transporter sequences for said embodiment of the invention are particularly the transporter sequence of SEQ ID NO: 46, preferably joined (e.g. directly) to the N-Terminus of the inhibitory (poly-)peptide sequence. A JNK inhibitor of the present invention may also be a JNK inhibitor comprising or consisting of the sequence GRKKRRQRRRPPKRPTTLNLFPQVPRSQD (SEQ ID NO: 194), or the sequence GRKKRRQRRRPTTLNLFPQVPRSQD (SEQ ID NO: 195).

In a further aspect the present invention relates to a (poly-)peptide comprising a transporter sequence selected from the group of sequences consisting of rKKRrQRr (SEQ ID NO: 148), rKKRrQRrK (SEQ ID NO: 149), and/or rKKRrQRrR (SEQ ID NO: 150).

As used herein, comprising a certain sequence or a certain SEQ ID NO: usually implies that (at least) one copy of said sequence is present, e g. in the JNK inhibitor molecule. For example, one inhibitory (poly-)peptide sequence will usually suffice to achieve sufficient inhibition of JNK activity. However, the inventor certainly contemplate that the use of two or more copies of the respective sequence (e.g. two or more copies of an inhibitory (poly-)peptide sequence of different or same type and/or two or more copies of a transporter sequence of different or the same type) may also employed as long as the overall ability of the resulting molecule to inhibit JNK activity is not abolished (i.e. the respective molecule is still a JNK inhibitor as defined herein).

The inventive JNK inhibitors may be obtained or produced by methods well-known in the art, e.g. by chemical synthesis via solid-phase peptide synthesis using Fmoc (9-fluorenylmethyloxycarbonyl) strategy, i.e. by successive rounds of Fmoc deprotection and Fmoc-amino acid coupling cycles. A commercial service offering such peptide synthesis is provided by many companies, for example the company PolyPeptide (Straßbourg, France).

The JNK inhibitors for use according to the present invention may optionally be further modified, in particular at the amino acid residues of the inhibitory (poly-peptide) sequence. Possible modifications may for example be selected from the group consisting of:
(i) radioactive labels, i.e. radioactive phosphorylation or a radioactive label with sulphur, hydrogen, carbon, nitrogen, etc.;
(ii) colored dyes (e.g. digoxygenin, etc.);
(iii) fluorescent groups (e.g. fluorescein, etc.);
(iv) chemoluminescent groups;
(v) groups for immobilization on a solid phase (e.g. His-tag, biotin, strep-tag, flag-tag, antibodies, epitopes, etc.);
(vi) pegylation,
(vii) glycosylation,
(viii) hesylation,
(ix) protease cleavage sites (e.g. for controlled release of the JNK inhibitor)
(x) peptide backbone modifications (e.g. ($\Psi CH_2$—NH) bonds)
(xi) protection of amino acid side chain residues,
(xii) protection of N- and/or C-terminus (e.g. N-terminal amidation or C-terminal acetylation)
(xiii) a combination of elements of two or more of the elements mentioned under (i) to (xii).

Particularly preferred are modifications selected from (i) to (xi) and combinations of elements of two or more of the elements mentioned under (i) to (xi). In this context the present invention relates in a further aspect to a JNK inhibitor as disclosed herein modified with modifications selected from (i) to (xi) or modified with a combination of two or more of the elements mentioned under (i) to (xi), and a pharmaceutical composition (see below) comprising such modified JNK inhibitor.

Pharmaceutical Compositions

The JNK inhibitors as defined according to the invention can be formulated in a pharmaceutical composition, which may be applied in the prevention or treatment of any of the diseases as defined herein. Typically, such a pharmaceutical composition used according to the present invention includes as an active component a JNK inhibitor as defined herein, in particular a JNK inhibitor comprising or consisting of an inhibitory (poly-)peptide sequence according to SEQ ID NO: 1, as defined herein. Preferably, the active compound is a JNK inhibitor comprising or consisting of an inhibitory (poly-) peptide sequence according to any one of SEQ ID NOs: 2-27; or, if a transporter sequence is attached, according to any one of SEQ ID NOs: 171-190.

The inventors of the present invention additionally found, that the JNK-inhibitors as defined herein, in particular if fused to a transporter sequence; exhibit a particular well uptake rate into cells involved in the diseases of the present invention. Therefore, the amount of a JNK-inhibitor inhibitor in the pharmaceutical composition to be administered to a subject, may—without being limited thereto—have a very low dose. Thus, the dose may be much lower than for peptide drugs known in the art, such as DTS-108 (Florence Meyer-Losic et al., Clin Cancer Res., 2008, 2145-53). This has several positive aspects, for example a reduction of potential side reactions and a reduction in costs.

Preferably, the dose (per kg bodyweight) is in the range of up to about 10 mmol/kg, preferably up to about 1 mmol/kg, more preferably up to about 100 µmol/kg, even more preferably up to about 10 µmol/kg, even more preferably up to about 1 µmol/kg, even more preferably up to about 100 nmol/kg, most preferably up to about 50 nmol/kg.

Thus, the dose range may preferably be from about 1 pmol/kg to about 1 mmol/kg, from about 10 pmol/kg to about 0.1 mmol/kg, from about 10 pmol/kg to about 0.01 mmol/kg, from about 50 pmol/kg to about 1 µmol/kg, from about 100 pmol/kg to about 500 nmol/kg, from about 200 pmol/kg to about 300 nmol/kg, from about 300 pmol/kg to about 100 nmol/kg, from about 500 pmol/kg to about 50 nmol/kg, from about 750 pmol/kg to about 30 nmol/kg, from about 250 pmol/kg to about 5 nmol/kg, from about 1 nmol/kg to about 10 nmol/kg, or a combination of any two of said values.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, a "safe and effective amount" for components of the pharmaceutical compositions as used according to the present invention means an amount of each or all of these components, that is sufficient to significantly induce a positive modification of diseases or disorders strongly related to JNK signalling as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of such a component will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

The pharmaceutical composition as used according to the present invention may furthermore comprise, in addition to one or more of the JNK inhibitors, a (compatible) pharmaceutically acceptable carrier, excipient, buffer, stabilizer or other materials well known to those skilled in the art.

In this context, the expression "(compatible) pharmaceutically acceptable carrier" preferably includes the liquid or non-liquid basis of the composition. The term "compatible" means that the constituents of the pharmaceutical composition as used herein are capable of being mixed with the pharmaceutically active component as defined above and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the pharmaceutical composition as used herein is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline or buffered (aqueous) solutions, e.g. phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection of the pharmaceutical composition as used herein, a buffer, preferably an aqueous buffer, may be used.

If the pharmaceutical composition as used herein is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The precise nature of the (compatible) pharmaceutically acceptable carrier or other material may depend on the route of administration. The choice of a (compatible) pharmaceutically acceptable carrier may thus be determined in principle by the manner in which the pharmaceutical composition as used according to the invention is administered. The pharmaceutical composition as used according to the invention can be administered, for example, systemically. Routes for administration include, for example, parenteral routes (e.g. via injection), such as intravenous, intramuscular, subcutaneous, intradermal, or transdermal routes, etc., enteral routes, such as oral, or rectal routes, etc., topical routes, such as nasal, or intranasal routes, etc., or other routes, such as epidermal routes or patch delivery. Also contemplated (in particular for eye related diseases) are instillation, intravitreal, and subconjunctival administration. Likewise administration may occur intratympanical, for example if ear related diseases are treated.

The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the compound is to be administered per orally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

Pharmaceutical compositions for oral administration may be in tablet, capsule, powder or liquid form. A tablet may include a solid carrier as defined above, such as gelatin, and optionally an adjuvant. Liquid pharmaceutical compositions for oral administration generally may include a liquid carrier as defined above, such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Treatment of a disease as defined herein typically includes administration of a pharmaceutical composition as defined above. The JNK inhibitors of the present invention will modulate the JNK activity in the subject. The term "modulate" includes in particular the suppression of phosphorylation of c-jun, ATF2 or NFAT4 in any of the above diseases, for example, by using at least one JNK inhibitor comprising or consisting of an inhibitory (poly)peptide sequence according to any of sequences of SEQ ID NOs: 2 to 27, potentially comprising an additional transporter sequence, as a competitive inhibitor of the natural c-jun, ATF2 and NFAT4 binding site in a cell. The term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos.

Treatment of a subject with the pharmaceutical composition as disclosed above may be typically accomplished by administering (in vivo) an ("therapeutically effective") amount of said pharmaceutical composition to a subject, wherein the subject may be e.g. a human subject or an animal. The animal is preferably a non-human mammal, e.g., a non-human primate, mouse, rat, dog, cat, cow, horse or pig. The term "therapeutically effective" means that the active component of the pharmaceutical composition is of sufficient quantity to ameliorate the diseases and disorders as discussed herein.

Diseases and Disorders

The gist of the present invention is to use the above disclosed JNK inhibitors and pharmaceutical compositions in a method for treatment of the human or animal body by therapy, in particular of the human body. As mentioned above JNK signalling is involved in a multitude of diverse disease states and disorder and inhibition of said signalling has proposed and successfully tested for many of these. The inventors of the present invention found that the JNK inhibitors disclosed herein are effective JNK inhibitors and are thus equally suitable for the treatment of the diseases as disclosed in the art.

Treatment of a human or animal body by therapy, as used herein, refers to any kind of therapeutic treatment of a respective subject. It includes for example prevention of onset of the disease or symptoms (prophylaxis), i.e. typically prior to manifestation of the disease in the patient. The term also includes the "mere" treatment of symptoms of a given disease, i.e. the treatment will ameliorate pathogenesis by reducing disease associated symptoms, without necessarily curing the underlying cause of the disease and symptoms. Certainly, curing the underlying cause of the disease is also encompassed by the term. The term also encompasses a treatment which delays or even stops progression of the respective disease.

In one embodiment the JNK inhibitors according to the present invention may be administered for example prophylactically prior to potential onset of a foreseeable disorder, e.g. prior to a planned surgical intervention or planned exposure to stressful stimuli. A surgical intervention could for example bear the risk of inflammation of the respective wound or neighbouring tissue (e.g. dry eye syndrome after surgical eye treatment, peri-implantitis after dental implantation treatment, rejection of the graft after transplantation, etc.). Exposure to stressful stimuli like radiation could lead to apoptosis of affected tissue and cells. In such scenario the JNK inhibitors according to the present invention may for example be administered at least once up to about 4 weeks in advance. The JNK inhibitors may for example be administered at least 24 hours, at least 48 hours, at least 1 week, at least 2 weeks or 4 weeks in advance.

The diseases and disorders to be treated with the JNK inhibitors as disclosed herein may be acute or chronic.

Due to the involvement of JNK signalling in a vast diversity of pathological conditions, the JNK inhibitors of the present invention may for example be used for the treatment of diseases of various organs, such as diseases of the eye, diseases of the bone, neural diseases, neuronal diseases, neurodegenerative diseases, diseases of the skin, immune and/or autoimmune diseases, diseases of the eye, diseases of the mouth, inflammatory diseases, metabolic diseases, cardiovascular diseases, proliferative diseases (in particular cancers and tumors), diseases of the ear, diseases of the intestine. diseases of the respiratory system (e.g. lung diseases), infectious diseases, and various other diseases.

The JNK inhibitors of the present invention may be used for example for the treatment of inflammatory diseases including for example acute inflammation as well as chronic inflammation. The JNK inhibitors of the present invention may be used to treat any type of tissue inflammation, e.g. inflammation in the eye, inflammation in the mouth, inflammation of the respiratory system including in particular the lung, inflammation of the skin, inflammation within the cardiovascular system, inflammation of the brain, inflammation in the ear, etc. Some non-limiting examples for such inflammatory disease states are mucositis, stomatitis, peri-implantitis, retinitis, chorioiditis, keratoconjunctivitis sicca, inflammatory bowel diseases (IBD), uveitis (e.g. anterior uveitis, intermediate uveitis, posterior uveitis), periodontitis, COPD, asthma, pulpitis, rheumatoid arthritis, osteoarthritis, Crohn's disease, psoriatic arthritis, vasculitis, interstitial cystitis; acute inflammation at a site of infection or wound, meningitis, encephalitis, pneumonia, pharyngitis, tonsillitis, otitis (including otitis media), vasculitis, synovitis, enteritis, Crohn's disease, ulcerative colitis, graft rejection etc.

The JNK inhibitors as disclosed herein may for example be used in methods of treatment of ear diseases (in particular diseases of the inner ear), hearing loss (in particular acute hearing loss), damaged hair cell stereocilia, hair cell apoptosis, noise trauma, otitis, otitis media etc. Hearing loss and associated hair cell apoptosis are non-limiting examples for disorders resulting from stress situations for cells in which JNK inhibition can modulate the stress response and for example block apoptosis.

The JNK inhibitors of the present invention may also be used for the treatment of metabolic disorders, for example for the treatment of diabetes (type 1 or type 2, in particular type 1), Fabry disease, Gaucher disease, hypothermia, hyperthermia hypoxia, lipid histiocytosis, lipidoses, metachromatic leukodystrophy, mucopolysaccharidosis, Niemann Pick disease, obesity, and Wolman's disease. Hypothermia, hyperthermia and hypoxia are again non-limiting examples for stress situations for cells in which JNK inhibition can modulate the stress response and for example block apoptosis.

Likewise, the JNK inhibitors of the present invention may be used for the treatment of neural, neuronal and/or neurodegenerative diseases, respectively. Examples for such diseases are for example Alexander disease, Alzheimer's disease, amyotrophic lateral sclerosis (ALS), apoplexy, Ataxia Telangiectasia, cut or otherwise disrupted axons, axotomy, brain lesions, CMT (Charcot-Marie-Tooth), corticobasal degeneration, dementia, diseases or disorders of the nervous system, dystonia, epilepsy, Farber's disease, Friedreich ataxia (SCA), gangliosidoses, Guillain-Barré syndrome, hereditary spastic paraplegia, Hirschsprung's disease, human immunodeficiency virus dementia, Huntington's disease, infarct of the brain, ischemic stroke, Krabbe disease, Lennox Gastaut Syndrome, lissencephaly, multiple sclerosis, myelodysplastic syndromes, myelopathy, AIDS-related neurodegenerative diseases, neurofibromatosis type 2 (NF-2), neurolatyerism, neuronal apoptosis, neuronal death, neuropathic pain, neuropathy, chemotherapy induced neuropathy, diabetes induced neuropathy, NMDA-induced neurotoxicity, pain, Parkinson's disease, parkinsonism, Pick's Disease, polyneuropathy, progressive supranuclear palsy, Sandhoff disease, spina bifida, stroke, Tay Sachs, TBI (diffuse axonal injury), treatment of dark neurone induced for example by an inflammatory pain, West Syndrome, spinal muscular atrophy etc.

With respect to autoimmune disorders, the JNK inhibitor peptides of the present invention may for example be used in a method of treatment of autoimmune diseases of the CNS, auto-inflammatory diseases, Celiac disease; Sjogren's syndrome, systemic lupus erythematosus etc.

Examples for bone diseases which may be treated with the JNK inhibitors of the present invention are for example arthritis, disc herniation, fibrodysplasia ossificans progressiva (FOP), osteoarthritis, osteopetrosis, osteoporosis, in particular diabetes induced osteoporosis, Paget's Disease, rheumatoid arthritis, etc.

Examples for skin diseases which may be treated with the JNK inhibitors of the present invention are for example psoriasis and lupus erythematosus.

Diseases of the eye, which may be treated with the JNK inhibitors of the present invention involve for example age-related macular degeneration (AMD); angioid streaks; anterior ischemic optic neuropathy; anterior uveitis; cataract, in particular age related cataract; central exudative chorioretinopathy; central serous chorioretinopathy; chalazion; chorioderemia; chorioiditis; choroidal sclerosis; conjunctivitis; cyclitis; diabetic retinopathy; dry eye syndrome; endophthalmitis; episcleritis; eye infection; fundus albipunctatus; gyrate atrophy of choroid and retina; hordeolum; inflammatory diseases of the blephara; inflammatory diseases of the choroid; inflammatory diseases of the ciliary body; inflammatory diseases of the conjunctiva; inflammatory diseases of the cornea; inflammatory diseases of the iris; inflammatory diseases of the lacrimal gland; inflammatory diseases of the orbital bone; inflammatory diseases of the sclera; inflammatory diseases of the vitreous body; inflammatory diseases of the uvea; inflammatory diseases of the retina; intermediate uveitis; irititis; keratitis; Leber's disease; multifocal choroiditis; myositis of the eye muscle; neovascular maculopathy (e.g. caused by high myopia, tilted disc syndrome, choroidal osteoma or the like); NMDA induced retinotoxicity; non-chronic or chronic inflammatory eye diseases; Oguchi's disease; optic nerve disease; orbital phlegmon; panophtalmitis; panuveitis; post caspule opacification; posterior capsule opacification (PCO) (a cataract after-surgery complication); posterior uveitis; proliferative vitreoretinopathy; retinal artery occlusion; retinal detachment, retinal diseases; retinal injuries; retinal macroaneurysm; retinal pigment epithelium detachment; retinal vein occlusion; retinitis; retinitis pigmentosa; retinitis *punctata albescens*; retinopathy, in particular retinopathy of prematurity and diabetic retinopathy; scleritis; Stargardt's disease; treatment of inflamed ocular wounds and/or ocular wound edges; treatment of intraocular inflammation after eye surgery or trauma; uveitis; vitelliform macular dystrophy; etc.

Exemplary diseases of the mouth which may be treated with the JNK inhibitors as disclosed herein are periodontitis, in particular chronic periodontitis; mucositis, oral desquamative disorders, oral liquen planus, pemphigus vulgaris, pulpitis; stomatitis; temporomandibular joint disorder, peri-implantitis etc.

Likewise the JNK inhibitors of the present invention may—as already previously proposed for other JNK inhibitors—be used for the treatment of proliferative diseases like cancer and tumor diseases, such as acusticus neurinoma lung carcinomas; acute lymphocytic leukemia (L1, L2, L3); acute lymphoid leukaemia (ALL); acute myelogenous leukemia (AML); adenocarcinomas; anal carcinoma; bronchial carcinoma; cervix carcinoma; cervical cancer; astrocytoma; basalioma; cancer with Bcr-Abl transformation; bladder cancer; blastomas; bone cancer; brain metastases; brain tumours; breast cancer; Burkitt's lymphoma; carcinoids; cervical cancer; chronic lymphocytic leukaemia (CLL); chronic myeloid leukaemia (CML); colon cancer; colon carcinoma; corpus carcinoma; craniopharyngeomas; CUP syndrome; virus-induced tumours; EBV-induced B cell lymphoma; endometrium carcinoma; erytholeukemia (M6); esophagus cancer; gallbladder cancer; gastrointestinal cancer; gastrointestinal stromal tumors; gastrointestinal tumours; genitourinary cancer; glaucoma; glioblastoma; gliomas; head/neck tumours; hepatitis B-induced tumours; hepatocell carcinomas; hepatomas; herpes virus-induced tumours; Hodgkin's syndrome; HTLV-1-induced lymphomas; HTLV-2-induced lymphomas; insulinomas; intestinal cancer; Kaposi's sarcoma; kidney cancer; kidney carcinomas; laryngeal cancer; leukemia; lid tumour; liver cancer; liver metastases; lung cancer; lymphoid cancer; lymphomas; malignant melanomas; mammary carcinomas; mantle cell lymphoma; medulloblastoma; megakaryoblastic leukemia (M7); melanoma, in particular malignant melanoma; meningioma; mesothelioma; monocytic leukemia (MS); multiple myeloma; mycosis fungoides; myeloblastic leukemia (M1); myeloblastic leukemia (M2); myelomonocytic leukemia (M4); neurinoma; non-Hodgkin's lymphomas; non-small cell carcinoma; non-small cell carcinoma of the lung; oesophageal cancer; oesophageal carcinoma; oligodendroglioma; ovarian cancer; ovarian carcinoma; pancreatic cancer; pancreatic carcinoma; papilloma virus-induced carcinomas; penis cancer; pituitary tumour; plasmocytoma; promyelocytic leukemia (M3); prostate cancer; prostate tumours; rectal tumours; rectum carcinoma; renal-cell carcinoma; retinoblastoma; sarcomas; Schneeberger's disease; small cell lung carcinomas; small intestine cancer; small intestine tumours; soft tissue tumours; spinalioma; squamous cell carcinoma; stomach cancer; testicular cancer; throat cancer; thymoma; thyroid cancer; thyroid carcinoma; tongue cancer; undifferentiated AML (MO); urethral cancer; uterine cancer; vaginal cancer; Von Hippel Lindau disease; vulval cancer; Wilms' Tumor; Xeroderma pigmentosum; etc.

Since JNK signalling is also involved in many cardiovascular diseases and disorders, the use of JNK inhibitors in the treatment of such diseases has already been suggested in the past. The inhibitors of the present invention may be used accordingly, e.g. for the treatment of cardiovascular diseases such as arterial hypertension; arteriosclerosis; arteriosclerotic lesions; Behcet's syndrome; bifurcations of blood vessels; cardiac hypertrophy; cardiavascular hypertrophy; cardiomyopathies, in particular chemotherapy induced cardiomyopathies; cerebral ischemia; coronary heart diseases; dilatation of the abdominal aorta: focal cerebral ischemia; global cerebral ischemia; heart hypertrophy; infrarenal aneurism hypertension; ischemia; myocardial infarct, in particular acute myocardial infarction; myocarditis; reperfusion; restenosis; vasculitis; Wegener's granulomatosis; etc.

The JNK inhibitors of the present invention may in the context of cardiovascular diseases also be used complementary to coronary artery bypass graft surgery (CABG surgery); percutaneous transluminal coronary angioplasty (PTCA); and/or stent treatment, for example to prevent or treat intimal hyperplasia resulting from said (surgical) treatment.

Diseases of the respiratory system and in particular lung diseases which may be treated effectively with the JNK inhibitors of the present invention are for example acute respiratory distress syndrome (ARDS); asthma; chronic illnesses involving the respiratory system; chronic obstructive pulmonary disease (COPD); cystic fibrosis; inflammatory lung diseases; pneumonia; pulmonary fibrosis; etc.

Like the inhibitors in the prior art the inhibitors of the present invention may also be used to treat disease of the intestinal tract, e.g. colitis (e.g. atypical colitis, chemical colitis; collagenous colitis, distal colitis, diversion colitis; fulminant colitis, indeterminate colitis, infectious colitis, ischemic colitis, lymphocytic colitis, or microscopic colitis), Crohn's disease, gastroenteritis, Hirschsprung's disease, inflammatory digestive diseases; inflammatory bowel disease (IBD), Morbus Crohn, non-chronic or chronic digestive diseases, non-chronic or chronic inflammatory digestive diseases; regional enteritis; ulcerative colitis etc.

The JNK inhibitors of the present invention may also serve as therapeutic agent for the treatment of infectious diseases resulting from e.g. bacterial or viral infection. The JNK inhibitors as disclosed herein may for example prevent or ameliorate inflammatory reactions caused by said infections. Examples for such diseases states, which are not considered to be limiting, are viral encephalitis; viral induced cancers (e.g. as mentioned above), human immunodeficiency virus dementia, meningitis, meningoencephalitis, encephalomyelitis, tonsillitis, etc.

There are many other diseases, disease states and disorders for which the JNK inhibitors of the present invention can be used as treatment, for example Aarskog syndrome, acetaminophen hepatotoxicity; Alder-Reilly anomaly; alopecia areata; alpha-1-antitrypsin deficiency; anaphylaxis; apoptosis; apoptotic cell death; atypical hemolytic uremic syndrome; basopenia; basophilia; bipolar disorders; burns; cellular shear stress; Chedial-Higashi syndrome; DNA damage due to chemotherapeutic drugs; cholestasis; chromosome 11, Partial Monosomy 11q; chromosome 22, Trisomy Mosaic; chronic granulomatous disease; hepatitis, such as chronic or fulminant hepatitis; clinical depression; common variable hypogammaglobulinemia; congenital C3 deficiency; CTL protection from activation-induced cell death (AICD); deafness; depression and depressive disorders (in particular prevention of depressive disorders develop on a background of cytokine-induced sickness behaviour), DiGeorge's syndrome; diseases caused by defective apoptosis; diseases of the liver; diseases of the spine; diseases of the uterus; diseases states and symptoms due to exposure to DNA damaging agents and/or ionizing radiation and resulting cellular stress; Down Syndrome; Duchenne muscular dystrophy; ectodermal dysplasias; endometriosis; eosinopenia; eosinophilia; exocitoxic cell death; fetal alcohol syndrome; fibrosis; fibrotic disease; formation of fibrous tissue; free radicals (leading to cellular stress); graft rejection; Graft versus host Disease; hair loss; hemolytic uremic syndrome; hepatotoxicity; hyperalgesia, such as diabetes induced hyperalgesia; hyperthermia; hypoglycemia; hypothyroidism; idiopathic hypereosinophilic syndrome; IgA nephropathy; infantile sex-linked agammaglobulinemia; inflammatory pain; infrarenal aneyrism; islet regeneration; islet transplantation; Job's syndrome (hyper-IgE); lazy leukocyte syndrome; leukocyte glucose-6-phosphate dehydrogenase deficiency; leukodystrophy; leukopenia; lymphocytic leukocytosis; lymphocytopenia; lymphocytosis; major depression; mania; maniac depression; Marfan syndrome; mastocytosis; May Hegglin Anomaly; membranoproliferative glomerulonephritis Type II; monocytopenia; monocytosis; myeloperoxidase deficiency-benign; myopathies; neutropenia; neutrophilia; Nezelofs syndrome; organ transplantation; oxidative stress injuries; Pelger-Huet anomaly; polycystic kidney diseases; post-dialysis syndrome; radiation syndromes; radiotherapy; renal diseases; renal failure; rescuing CTL from activation induced cell death; severe combined immunodeficiency disease; transplant rejection; transplantation; trisomy; unipolar depression; UV-induced injuries; Wiskott Aldrich syndrome; wound healing; etc.

The inventors of the present invention consider temporomandibular joint disorder, mucositis, stomatitis, oral liquen planus (desquamative disorder), Pemphigus vulgaris (desquamative disorder), periodontitis, chronic periodontitis, pulpitis, peri-implantitis, uveitis (anterior uveitis, intermediate uveitis, posterior uveitis), keratoconjunctivitis sicca (dry eye syndrome), coronary artery bypass graft surgery (CABG surgery), acute myocardial infarction, prevention of intimal hyperplasia following percutaneous transluminal coronary angioplasty (PTCA), prevention of intimal hyperplasia following stent placement, atherosclerosis, COPD, asthma, rheumatoid arthritis, osteoarthritis, Crohn's disease, inflammatory bowel disease (IBD), psoriasis, diabetes, stroke, Parkinson's disease, Alzheimer's disease, systemic lupus erythematosus, and vasculitis, in particular Wegener's granulomatosis, to be particularly useful for treatment with the JNK inhibitors of the present invention.

A person skilled in the art will readily realize that the above mentioned disease states and disorders may belong to more than one of the above mentioned disease classes. For example, bronchial carcinoma is certainly not only a proliferative disease but would also belong in the group of diseases of the respiratory system including lung diseases. Thus, the above mentioned classification of individual diseases is not considered to be limiting or concluding but is considered to of exemplary nature only. It does not preclude that individual disease states recited in one class are factually also suitable examples for the application of the JNK inhibitors of the present invention as treatment in another class of disease states. A person skilled in the art will readily be capable of assigning the different disease states and disorders to matching classifications.

Finally, as mentioned above, the present invention contemplates the use of a JNK inhibitor as defined herein for the treatment of various diseases states and disorders. The present invention does not contemplate to use the JNK inhibitors as defined herein for immunizing non-human animals, e.g. for the production of monoclonal antibodies. Such methods are herein not considered to be methods for treatment of the animal body by therapy.

All references cited herein are herewith incorporated by reference.

EXAMPLES

In the following, particular examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Synthesis of JNK Inhibitor SEQ ID NO: 172

As illustrative example, synthesis of the JNK inhibitor with SEQ ID NO: 172 is set out below. A person skilled in the art will know that said synthesis may also be used for and easily adapted to the synthesis of any other JNK inhibitor according to the present invention.

The JNK inhibitor with SEQ ID NO: 172 was manufactured by solid-phase peptide synthesis using the Fmoc (9-fluorenylmethyloxycarbonyl) strategy. The linker between the peptide and the resin was the Rink amide linker (p-[Fmoc-2,3-dimethoxybenzyl]-phenoxyacetic acid). The peptide was synthesized by successive Fmoc deprotection and Fmoc-amino acid coupling cycles. At the end of the synthesis, the completed peptide was cleaved by trifluoroacetic acid (TFA) directly to yield the crude C-terminal amide, which was then purified by preparative reverse phase HPLC. The purified fractions were pooled in a homogeneous batch that is treated by ion exchange chromatography to obtain its acetate salt. The peptide was then freeze-dried.

1.1 Solid Phase Synthesis of the Peptide

Except when noted, the manufacturing took place at room temperature (22° C.±7° C.) in an air-filtered environment. The scale of synthesis was 0.7 mmoles of the starting amino acid on the resin, for an expected yield of about 1 g of purified peptide. Synthesis was performed manually in a 30-50 mL reactor equipped with a fritted disk with mechanical stirring and/or nitrogen bubbling.

1.2 Preparation of the Resin

The p-methylbenzhydrylamide resin (MBHA-resin) was first washed with dichloromethane/dimethylformamide/diisoproplyethylamine under nitrogen. The washed resin was then coupled to the Rink amide linker (p-[Fmox-2,4-dimethoxybenzyl]-phenoxyacetic acid) in PyBOB (benzotriazole-1-yl-oxy-tris-pyrrolidino-phosphonium hexafluorophosphate)/diisopropyl-ethylamine/1-hydroxybenzotriazole to yield Fmoc-Rink amide-MBHA resin.

1.3 Coupling of Amino Acids

Amino acids were coupled to the resin using the following cycle:

The Fmoc-Rink amide-MBHA resin was deprotected by washing it in 35% (v/v) piperidine/dimethylformamide, followed by dimethylformamide. The deprotection reaction took approximately 16 minutes. Fmoc-protected amino acids (e.g., 2 eq of amino acid and HOBt (1-hydroxybenzotriazole) in dimethylformamide/dichloromethane (50/50) were added to the resin followed by addition of 2 eq of the coupling agent diisopropylcarbodiimide (DIC). The coupling reaction took from one hour to overnight depending upon the respective amino acid being added. Volumes were calculated on a basis of 0.5 mL/100 mg of peptide-resin and adjusted after each cycle. After coupling, the resin was washed 3 times with DMF. Completeness of coupling was tested by the ninhydrin test (or Kaiser test 1) on primary amines and the chloranyl test 2 on secondary amines. On some occasions, the chloranyl test may be associated with a ninhydrin test as a security control. In case the coupling test indicated incompleteness of reaction, coupling was repeated with a lower excess (0.5-1 eq) of amino acid, PYBOP, HOBT in dimethylformamide/dichloromethane and diisopropylethylamine. Functionality of the resin was measured and generally 0.6-0.2 meq/g, depending on the original loading of the resin. After the last amino acid has been coupled, the peptide-resin was deprotected as usual and then washed 5 times with DCM before drying in an oven under vacuum at 30° C. After the peptide-resin had dried, the yield of the solid-phase synthesis was calculated as the ratio of the weight increase of the peptide resin compared to the theoretical weight increase calculated from the initial loading of the resin. The yield may be close to 100%.

1.4 Cleavage And Deprotection

The peptide was cleaved from the resin in a mixture of trifluoroacetic acid/1,2-ethanedthiol/thioanisole/water/phenol (88/2.2/4.4/4.4/7 v/v), also called TFA/K reagent, for 4 hours at room temperature. The reaction volume was 1 mL/100 mg of peptide resin. During addition of the resin to the reagent, the mixture temperature was regulated to stay below 30° C.

1.5 Extraction of the Peptide from the Resin:

The peptide was extracted from the resin by filtration through a fritted disc. After concentration on a rotavapor to ⅓ of its volume, the peptide was precipitated by cold t-butyl methyl ether and filtered. The crude peptide was then dried under vacuum at 30° C.

1.6 Preparative HPLC Purification:

The crude peptide was then purified by reverse-phase HPLC to a purity of ≥95%. The purified fractions were concentrated on a rotavaporator and freeze-dried.

1.7 Ion Exchange Chromatography

The concentrated freeze-dried pools of purified peptide with the sequence of SEQ ID NO: 172 was dissolved in water and purified by ion exchange chromatography on Dowex acetate, 50-100 mesh resin.

The required starting reagents for the synthesis were:

|  | CAS Registry Number | Chemical Name | Molecular Weight |
|---|---|---|---|
| Fmoc-Rink amide linker | 145069-56-3 | p-[Fmoc-2,4-dimethoxybenzyl]-phenoxyacetic acid | 539.6 |
| Fmoc-D-Ala-OH, H$_2$O | 79990-15-1 | N-alpha-Fmoc-D-alanine | 311.3 |
| Fmoc-Arg(Pbf)-OH | 154445-77-9 | N$_\alpha$-Fmoc-N$_\omega$-(2,2,4,6,7-pentamethyldihydro-benzofuran-5-sulfonyl)-arginine | 648.8 |
| Fmoc-D-Arg(Pbf)-OH | 187618-60-6 | N$_\alpha$-Fmoc-N$_\omega$-(2,2,4,6,7-pentamethyldihydro-benzofuran-5-sulfonyl])D-arginine | 648.8 |
| Fmoc-Asn(Trt)-OH | 132388-59-1 | N-α-Fmoc-N-β-trityl-L-asparagine | 596.7 |
| Fmoc-Gln(Trt)-OH | 132327-80-1 | N$_\alpha$-Fmoc-N$_\delta$-trityl-L-glutamine | 610.7 |
| Fmoc-Leu-OH | 35661-60-0 | N-alpha-Fmoc-leucine | 353.4 |
| Fmoc-Lys(Boc)-OH | 71989-26-9 | N$_\alpha$-Fmoc-N$_\epsilon$-Boc-L-lysine | 468.5 |
| Fmoc-D-Lys(Boc)-OH | 92122-45-7 | N$_\alpha$-Fmoc-N$_\epsilon$-Boc-D-lysine | 468.5 |
| Fmoc-D-Phe-OH | 86123-10-6 | N-alpha-Fmoc-D-phenylalanine | 387.4 |
| Fmoc-Pro-OH | 71989-31-6 | N-alpha-Fmoc-proline | 337.4 |
| Fmoc-Thr(tBu)-OH | 71989-35-0 | N-alpha-Fmoc-O-t-butyl-threonine | 397.5 |

Other JNK inhibitors of the present invention may be prepared in similar manner.

Example 2: Inhibitory Efficacy of Selected JNK Inhibitors According to the Present Invention In the following a standard operating procedure will be set forth describing how the Inhibitory efficacy of JNK inhibitors according to the present invention was measured. The method allows to measure in vitro, in a non radioactive standardized assay, the ability of a candidate compound to decrease the phosphorylation of the c-Jun specific substrate by JNK. Moreover, it will be illustrated how to determine the inhibitory effect (IC50) and the Ki of a chosen compound for JNK. The method is suitable to verify whether a candidate compound does or does not inhibit JNK activity and a person skilled in the art will certainly understand how to adapt the below methods for his specific purposes and needs.

2.1 Material

AlphaScreen Reagent and Plate:

His-JNK1 (ref 14-327, Upstate, 10 μg in 100 μl: concentration: 2.2 μM) 5 nM final His-JNK2 (ref 14-329, Upstate, 10 μg in 100 μl: concentration: 2 μM) 5 nM final His-JNK3 (ref 14-501, Upstate, 10 μg in 100 μl: concentration: 1.88 μM) 5 nM final Anti-Phospho-cJun (ref 06-828, Upstate, lot DAM1503356, concentration: 44.5 μM) 10 nM final Biotin-cJun (29-67):

sequence: Biotin—SNPKILKQSMTLNLADPVGSLK-PHLRAKNSDLLTSPDVG (SEQ ID NO: 198), lot 100509 (mw 4382.11, P 99.28%) dissolved in H$_2$O, concentration: 10 mM) 30 nM final ATP (ref AS001A, Invitrogen, lot 50860B, concentration 100 mM)) 5 μM final SAD beads (ref 6760617M, PerkinElmer, lot 540-460-A, concentration 5 mg/ml) 20 μg/ml final AprotA beads (ref 6760617M, PerkinElmer, lot 540-460-A, concentration 5 mg/ml) 20 μg/ml final Optiplate 384 well white plate (ref 6007299, PerkinElmer, lot 654280/2008)

96 well plate for peptide dilution (ref 82.1581, Sarstedt)

TopSeals-A (ref 6005185, Perkin Elmer, Lot 65673)

Bioluminescent energy transfer reading

The bioluminescent energy transfer was read on the Fusion Alpha Plate reader (Perkin Elmer).

Pipette:

An electronic EDP3 pipette 20-300 (Ref 17007243; Rainin) was used to fill in the plate with the Enzme-Antibody mix, the Subtrate-ATP mix and the Beads.

A PIPETMAN® Ultra multichannel 8X20 (Ref 21040; Gilson) was used to fill in the plate with the inhibitory compounds.

Buffer and Solutions

Kinase Buffer: 20 mM Tris-base pH 7.4, 10 mM MgCl$_2$, 1 mM DTT, 100 μM Na$_3$VO$_4$, 0.01% Tween, (1% DMSO)

Stop Buffer: 20 mM Tris-base pH 7.4, 200 mM NaCl, 80 mM EDTA-K (pH de 8 with KOH instead of NaOH), 0.3% BSA JNK dilution Kinase buffer: 50 mM Tris-base pH 7.4, 150 mM NaCl, 0.1 mM EGTA, 0.03% Brij-35, 270 mM sucrose, 0.1% β-mercaptoethanol.

2.2 Method

To assess inhibitory effect of the peptides, a standard AlphaScreen assay (see for example Guenat et al. J Biomol Screen, 2006; 11: pages 1015-1026) was performed. The different components were prepared and subsequently mixed as indicated. The plates were sealed and incubated as following:

| 5 μl | JNK + Antibody | |
|---|---|---|
| 5 μl | TP kinase +/− inhibitor | Pre-incubation 30 min |
| 5 μl | Biotin-cJun + ATP | Incubation 60 min at 24° C. |
| 10 μl | Beads SAD + A protA | Incubation 60 min in the dark at 24° C. |

To avoid contamination, the mixes were added with the pipette in different corner of the well. After the filling in of the plate with each mix, the plate was tapped (Keep one side fix and let the opposite side tap the table) to let the mix go down the walls of the wells.

The bioluminescent energy transfer was read on the Fusion Alpha Plate reader (Perkin Elmer).

All compounds should at least be tested in triplicate in 3 independent experiments for each isoform of JNK. Possibly concentrations of the compounds to be tested were 0, 0.03 nM, 0.1 nM, 0.3 nM, 1 nM, 3 nM, 10 nM, 30 nM, 100 nM, 300 nM, 1 μM, 3 μM, 10 μM, 30 μM, and 100 μM. Controls were samples either without JNK or without substrate (c-Jun).

Mix Preparation
JNK1, JNK2 and JNK3 5 nM
Biotin-cJun 30 nM
ATP 5 µM; Anti phospho-cJun (S63) 10 nM
Bile SAD/AprotA 20 µg/ml
Antibody [final]=10 nM (anti Phospho cJun (S63))
Detection part: [Mix]×5 (5 µl in final volume of 25 µl)
[Stock]=44.5 µM (ref 06-828, Upstate, Lot DAM1503356)
  10 nM→50 nM in Kinase Buffer
JNK1, JNK2 and JNK3 [final]=5 nM
Reaction part: [Mix]×3 (5 µl in final volume of 15 µl)

[Stock] = 2.2 µM for $JNK_1$(ref 14-327, Upstate, lot D7KN022CU)

2.0 µM for $JNK_2$(ref 14-329, Upstate, lot 33221CU)

1.88 µM for $JNK_3$(ref 14-501, Upstate, lot D7CN041CU)

5 nM → 15 nM in Antibody Buffer

Inhibitor:
Reaction part: [Mix]×3 (5 µl in final volume of 15 µl)
[Stock]=10 mM
100 µM→300 µM in Kinase Buffer
30 µM→90 µM in Kinase Buffer
10 µM→30 µM in Kinase Buffer
. . .
0.03 nM→0.09 nM in Kinase Buffer
And 0 nM→Kinase Buffer
Two series of 10 times serial dilutions were performed in a 96 well plate, one beginning with 300 µM to 0 nM, the second with 90 µM to 0.03 nM. The peptides are added in the 384 plates with an 8 channels multipipette (ref F14401, Gilson, 8X20).
ATP [final]=5 µM
Reaction part: [Mix]×3 (5 µl in final volume of 15 µl)
[Stock]=100 mM (ref AS001A, Invitrogen, lot 50860B)
5 µM→15 µM in Kinase Buffer
Biotin c-Jun [final]=30 nM
Reaction part: [Mix]×3 (5 µl in final volume of 15 µl)
[Stock]=10 mM
30 nM→30 nM in ATP Buffer
Beads SAD/A ProtA [final]=20 µg/ml (Light sensitive)
Detection part: [Mix]×2.5 (10 µl in final volume of 25 µl)
[Stock]=5 mg/ml→20 µg/ml 50 µg/ml in STOP Buffer
Mix in the dark room (green Light) or in the darkness.
Analysis of the IC50 curves:
The analysis was performed by the GraphPad Prism4 software with the following equation: Sigmoidal dose-response (No constraint).

$$Y=\text{Bottom}+(\text{Top}-\text{Bottom})/(1+10^{\wedge}((\text{Log EC50}-X)))$$

The outliers data were avoided using Grugg's test.
Comparison of the IC50:
The analysis was performed by the GraphPad Prism4 software with the following test: One way ANOVA test followed by a Tukey's Multiple Comparison Test. P<0.05 was considerate as significant.
The Km of the ATP for JNK and the Km of biotin-cJun specific peptide were determined in the report AlphaScreen standardization assay
The mathematical relation between Ki and IC50 (Ki=IC50/(1+([Substrate]/Km of the substrate)) may be used to calculate the Ki values.

Example 3: Internalization Experiments and Analysis 3.1 Materials and Methods for Uptake Experiments
a) Cell line:
  The cell line used for this experiment was HL-60 (Ref CCL-240, ATCC, Lot 116523)
b) Culture medium and plates
  RPMI (Ref 21875-091, Invitrogen, Lot 8296) or DMEM (Ref 41965, Invitrogen, Lot 13481) complemented on May 5, 2008 with:
    10% FBS (Ref A64906-0098, PAA, Lot A15-151): decomplemented at 56° C., 30 min, on Apr. 4, 2008.
    1 mM Sodium Pyruvate (Ref 58636, Sigma, Lot 56K2386)
    Penicillin (100 unit/ml)/Streptomycin (100 µg/ml) (Ref P4333, Sigma, Lot 106K2321)
  PBS 10× (Ref 70011, Invitrogen, Lot 8277): diluted to 1× with sterile $H_2O$
  Trypsine-0.05% EDTA (Ref L-11660, PAA, Lot L66007-1194)
  6 well culture plates (Ref 140675, Nunc, Lot 102613)
  24 well culture plates (Ref 142475, Nunc, Lot 095849)
  96 well culture plates (Ref 167008, Nunc, Lot 083310)
  96 well plates for protein dosing (Ref 82.1581, Sarstedt)
  96 well plates for fluorescence measurement (Ref 6005279, Perkin Elmer)
c) Solutions
  Poly-D-lysine coating solution (Sigma P9011 Lot 095K5104): 25 µg/ml final diluted in PBS 1×
  Acidic wash buffer: 0.2M Glycin, 0.15M NaCl, pH 3.0
  Ripa lysis buffer: 10 mM $NaH_2PO_4$ pH 7.2, 150 mM NaCl, 1% Triton X-100, 1 mM EDTA pH 8.0, 200 µM $Na_3VO_2$, 0.1% SDS, 1× protease inhibitor cocktail (Ref 11873580001, Roche, Lot 13732700)
d) Microscopy and fluorescence plate reader
  Cells were observed and counted using an inverted microscope (Axiovert 40 CFL; Zeiss; 20×).
  The fluorescence was read with the Fusion Alpha Plate reader (Perkin Elmer).
e) Method
  FITC marked peptide internalization was studied on suspension cells. Cells were plated into poly-DL-lysine coated dishes at a concentration of 1×10$^6$ cells/ml. Plates were then incubated for 24 h at 37° C., 5% $CO_2$ and 100% relative humidity prior to the addition of a known concentration of peptide. After peptide addition, the cells were incubated 30 min, 1, 6 or 24 h at 37° C., 5% $CO_2$ and 100% relative humidity. Cells were then washed twice with an acidic buffer (Glycin 0.2 M, NaCl 0.15 M, pH 3.0) in order to remove the cell-surface adsorbed peptide (see Kameyama et al., (2007), *Biopolymers*, 88, 98-107). The acidic buffer was used as peptides rich in basic amino acids adsorb strongly on the cell surfaces, which often results in overestimation of internalized peptide. The cell wash using an acidic buffer was thus employed to remove the cell-surface adsorbed peptides. The acid wash was carried out in determining cellular uptake of Fab/cell-permeating peptide conjugates, followed by two PBS washes. Cells were broken by the addition of the RIPA lysis buffer. The relative amount of internalized peptide was then determined by fluorescence after background subtraction and protein content normalization.

The steps are thus: 1. Cell culture
2. Acidic wash and cellular extracts
3. Analysis of peptide internalization with a fluorescence plate reader f) Cell culture and peptide treatment The 6 well culture plates are coated with 3 ml of Poly-D-Lys (Sigma P9011; 25 µg/ml in PBS), the 24 well plates with 600 µl and the 96 well plates with 125 µl and incubated for 4 h at 37° C., $CO_2$ 5% and 100% relative humidity.

After 4 hours the dishes were washed twice with 3.5 ml PBS, 700 µl or 150 µl PBS for the 6, 24 or 96 well plates, respectively.

The cells were plated into the dishes in 2.4 ml medium (RPMI) at plating densities of 1,000,000 cells/ml for suspension cells. After inoculation, the plates were incubated at 37° C., 5% $CO_2$ and 100% relative humidity for 24 hours prior to the addition of the peptide. Adherent cells should be at a density of 90-95% the day of treatment and were plated in DMEM:

| well | Surface of culture ($cm^2$) | Medium | Nb adherent cells | Nb suspension cells |
|---|---|---|---|---|
| 96 well | 0.3 | 100-200 µl | 8,000-30,000 | 100,000 |
| 24 well | 2 | 500-1000 µl | 100,000-200,000 | 500,000-1,000,000 |
| 35 mm (P35)/ 6 well | 10 | 2.4 ml | 250,000-2,100,000 | 2,400,000 |
| 60 mm (P60) | 20 | 3.5 ml | 15 * $10^5$ | 1,000,000/ml |
| 10 cm (P100) | 60 | 10 ml | 15-60 * $10^5$ | |

The cells were treated with the desired concentration of FITC labeled peptide (stock solution at a concentration of 10 mM in $H_2O$).

Following peptide addition, the cells were incubated 0 to 24 hours (e.g. 30 min, 1, 6 or 24 hours) at 37° C., $CO_2$ 5% and 100% relative humidity.

Acidic Wash and Cellular Extracts:

The extracts were cooled on ice.

Suspension cells (or cells, which don attach well to the dish):

Transfer the cells in «Falcon 15 ml». To recover the maximum of cells, wash the dish with 1 ml of PBS.

Harvest the cells 2 min at 2400 rpm max.

Suspend the cells in 1 ml cold PBS.

Transfer the cells into a coated "Eppendorf tube" (coated with 1 ml of poly D-Lys for 4 hours and washed twice with 1 ml PBS).

Wash three times with 1 ml of cold acidic wash buffer and centrifuge 2 min at 2400 rpm max. Beware of the spreading of the cells in the "eppendorf".

Wash twice with 1 ml cold PBS to neutralize.

Add 50 µl of lysis RIPA Buffer.

Incubate 30 min-1 h on ice with agitation.

Adherent cells:

Wash three times with 3 ml, 1 ml or 200 µl (for 6, 24 or 96 well plates, respectively) of cold acidic wash buffer. Beware of the cells who detach from the dish.

Wash twice with 1 ml cold PBS (for 6, 24 or 96 well plates, respectively) to neutralize. Add 50 µl of lysis RIPA buffer.

Incubate 30 min-1 h on ice with agitation.

Scrap the cells with a cold scrapper. The 24 and 96 well plates were directly centrifuged at 4000 rpm at 4° for 15 min to remove the cellular debris. Then the supernatants (100 or 50 ml respectively for the 24 or 96 well plates) were directly transferred in a dark 96 well plated. The plates were read by a fluorescence plate reader (Fusion Alpha, Perkin Elmer).

Transfer the lysate in a coated "eppendorf" (coated with 1 ml of poly D-Lys for 4 hours and wash twice with 1 ml PBS).

The lysed cells were then centrifuged 30 min at 10000 g at 4° C. to remove the cellular debris.

Remove the supernatant and store it at −80° C. in a coated "Eppendorf tube" (coated with 1 ml of poly D-Lys for 4 hours and washed twice with 1 ml PBS).

Analysis of Peptide Internalization with a Fluorescence Plate Reader:

The content of each protein extract was determined by a standard BCA assay (Kit N° 23225, Pierce), following the instructions of the manufacturer.

The relative fluorescence of each sample is determined after reading 10 µl of each sample in a fluorescence plate reader (Fusion Alpha, Perkin Elmer), background subtraction and normalization by protein concentration.

3.2 Uptake Experiments

The time dependant internalization (uptake) of FITC-labeled TAT derived transporter constructs into cells of the HL-60 cell line was carried out as described above using sequences transporter peptides of SEQ ID NOs: 52-96, 43, and 45-47. These sequences are listed below in Table 4.

TABLE 4

Transporter sequence tested in uptake experiments

Figure 6A:
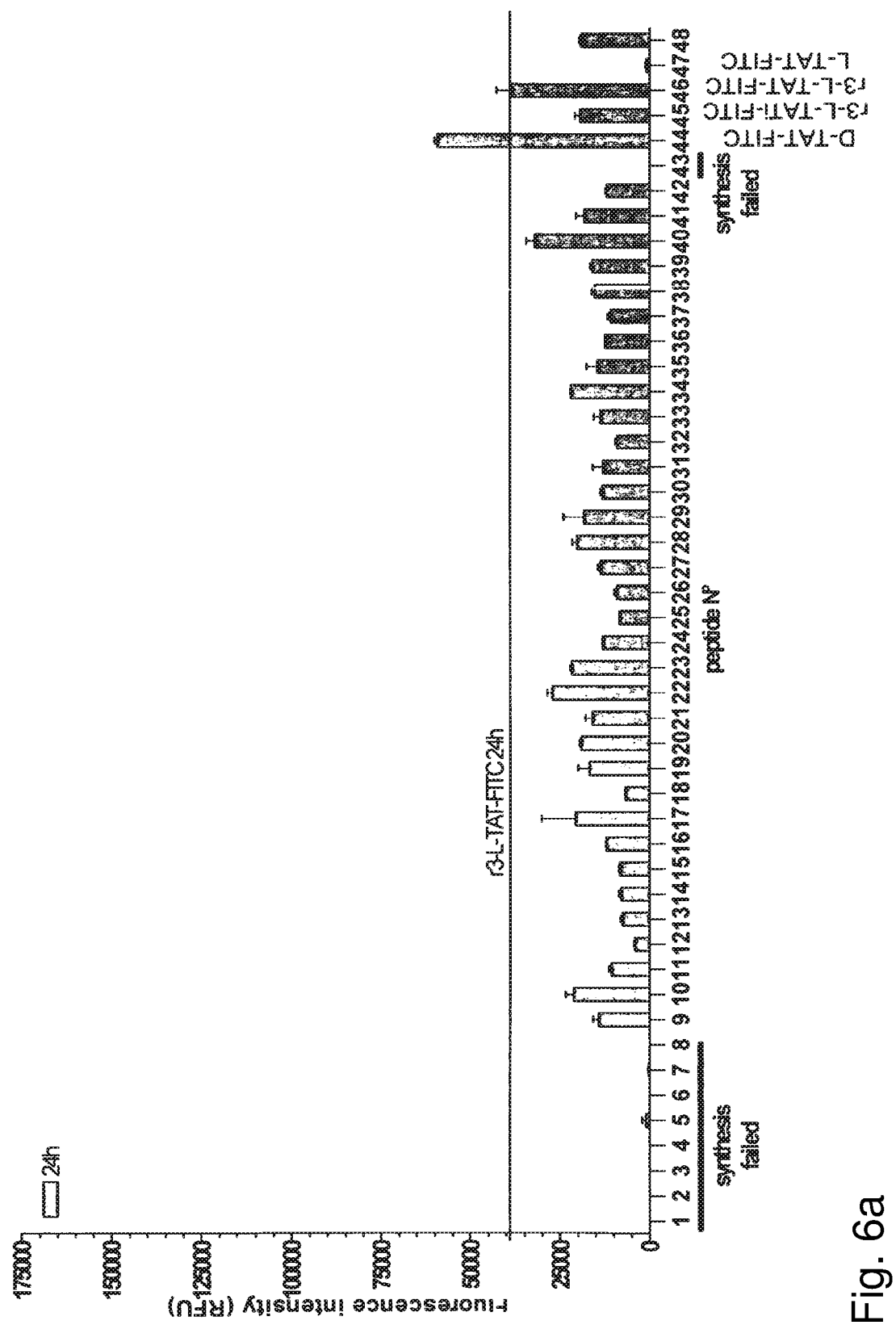
FIG. 6: shows internalizations experiments using TAT derived transporter constructs with D-amino acid/L-amino acid pattern as denoted in SEQ ID NO: 30. The transporter sequences analyzed correspond to SEQ ID NOs: 52-94 plus SEQ ID NOs: 45, 47, 46, 43 and 99 (FIG. 6a) and SEQ ID NOs: 100-147 (FIG. 6b). As can be seen, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the respective transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction.
Figure 6B:
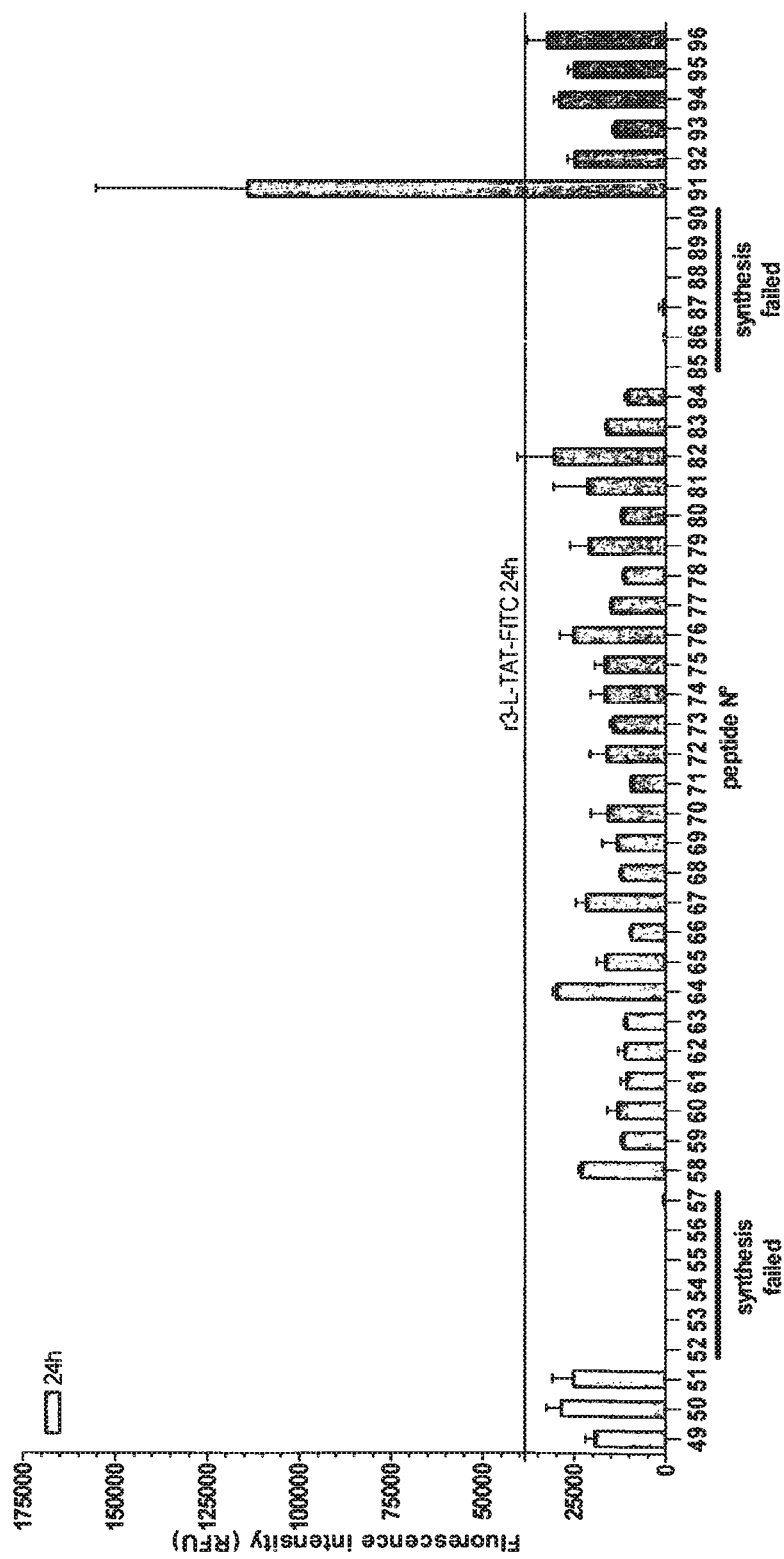
Figure 7:
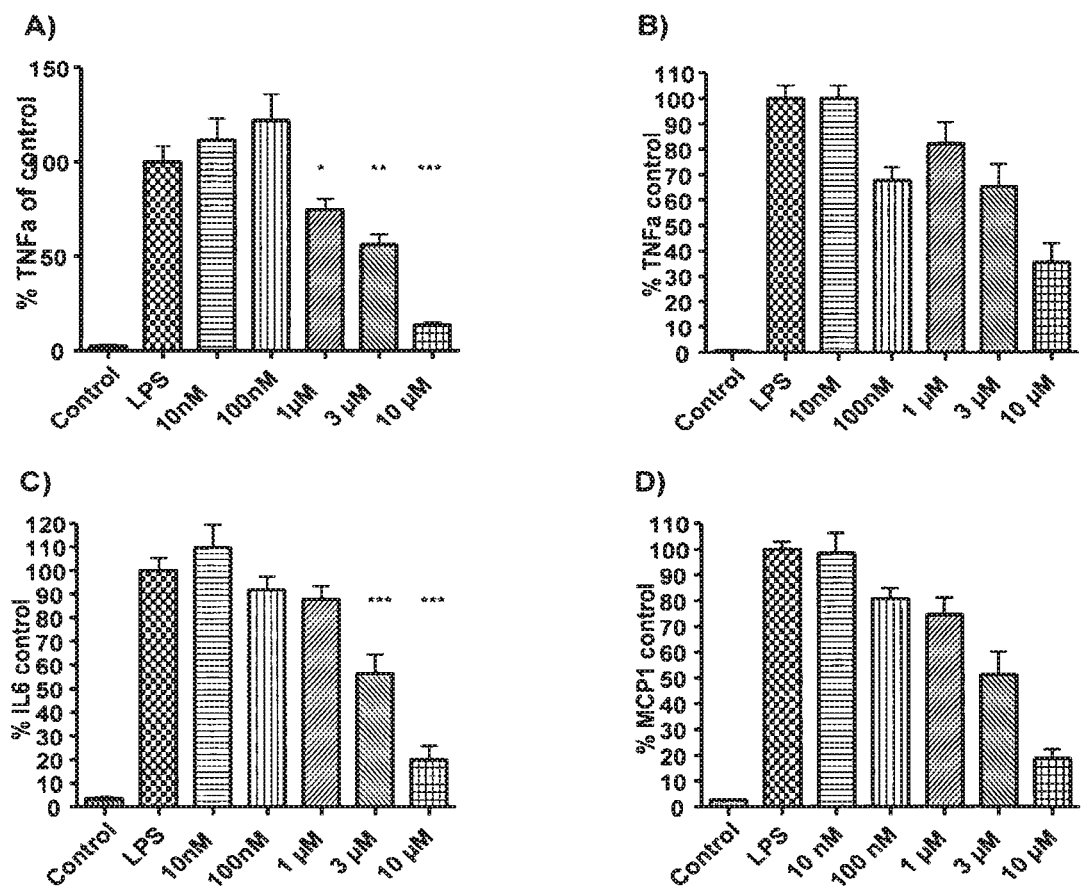
FIG. 7 The JNK inhibitor with the sequence of SEQ ID NO: 172 blocks LPS-induced cytokine and chemokine release in THP1-PMA-differentiated macrophages.
Figure 8:
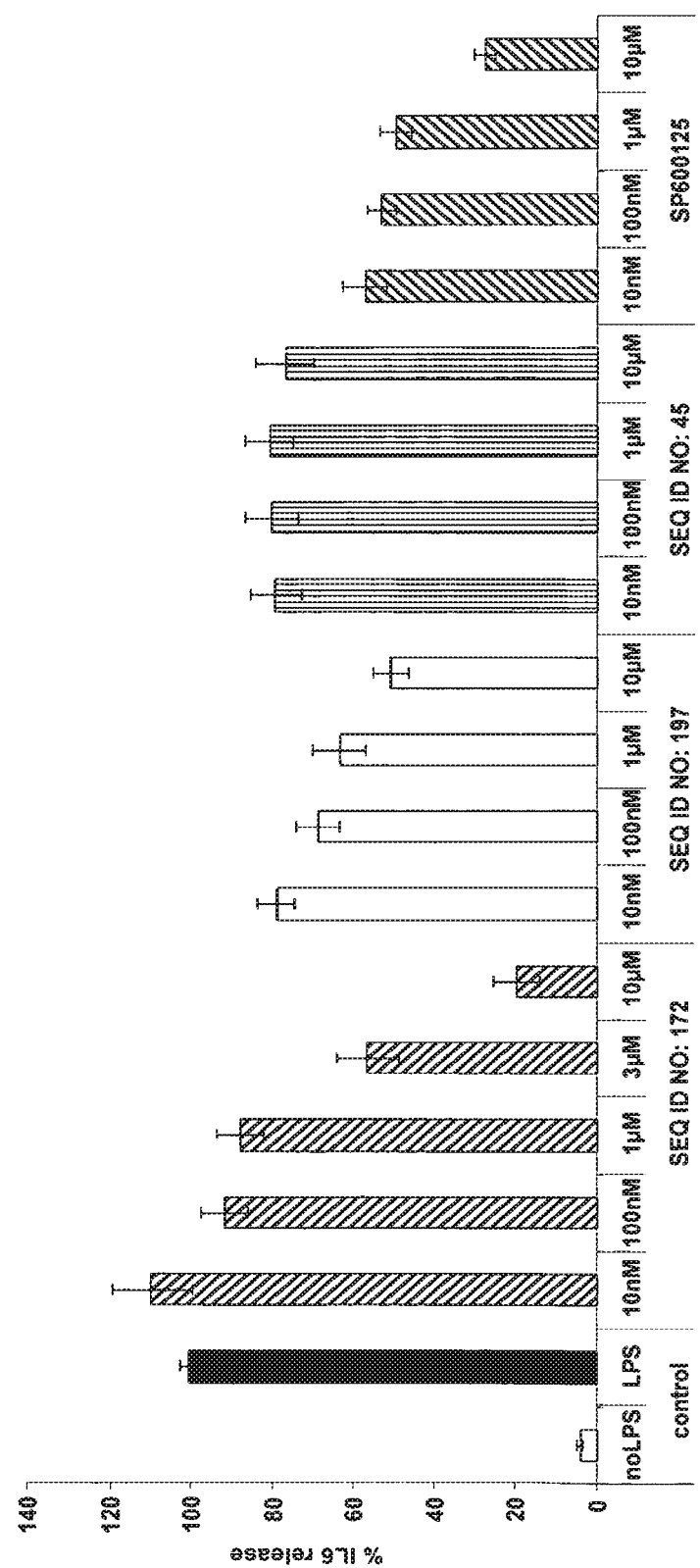
FIG. 8 The JNK inhibitor of SEQ ID NO: 172 blocks LPS-induced IL6 release in THP1 differentiated macrophages with higher potency than D-TAT-IB1 (SEQ ID NO: 197), dTAT (SEQ ID NO: 45) and SP 600125. LPS was added for 6 h (10 ng/ml).
Figure 9:
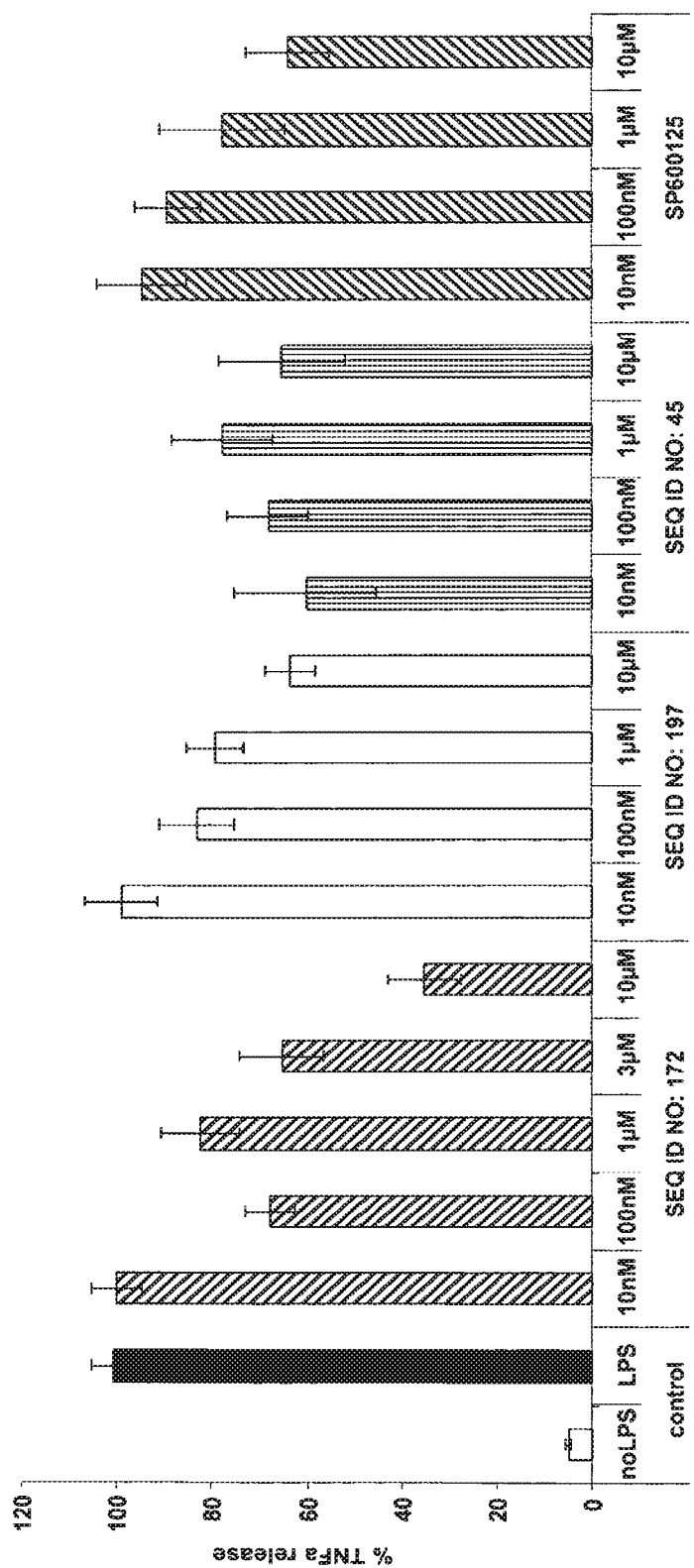
FIG. 9 The JNK inhibitor of SEQ ID NO: 172 blocks LPS-induced TNFα release in THP1 differentiated macrophages with higher potency than D-TAT-IB1 (SEQ ID NO: 197), dTAT (SEQ ID NO: 4.5) and SP 600125. LPS was added for 6 h (10 ng/ml).
Figure 10:
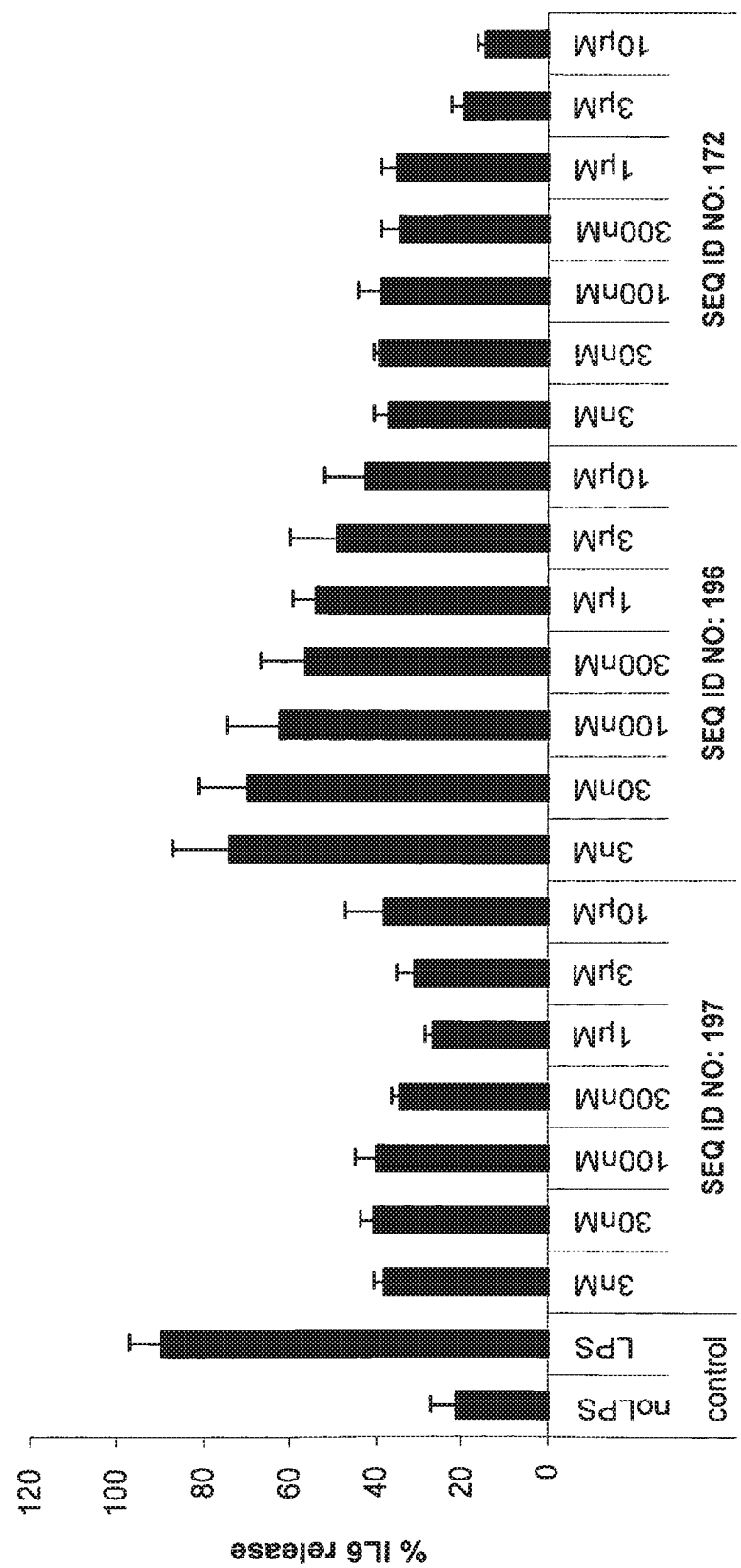
FIG. 10 The JNK inhibitor of SEQ ID NO: 172 blocks LPS-induced IL-6 release in PMA differentiated macrophages with higher potency than D-TAT-IB1 (SEQ ID NO: 197) and L-TAT-IB1 (SEQ ID NO: 196). LPS was added for 6 h.
Figure 11:
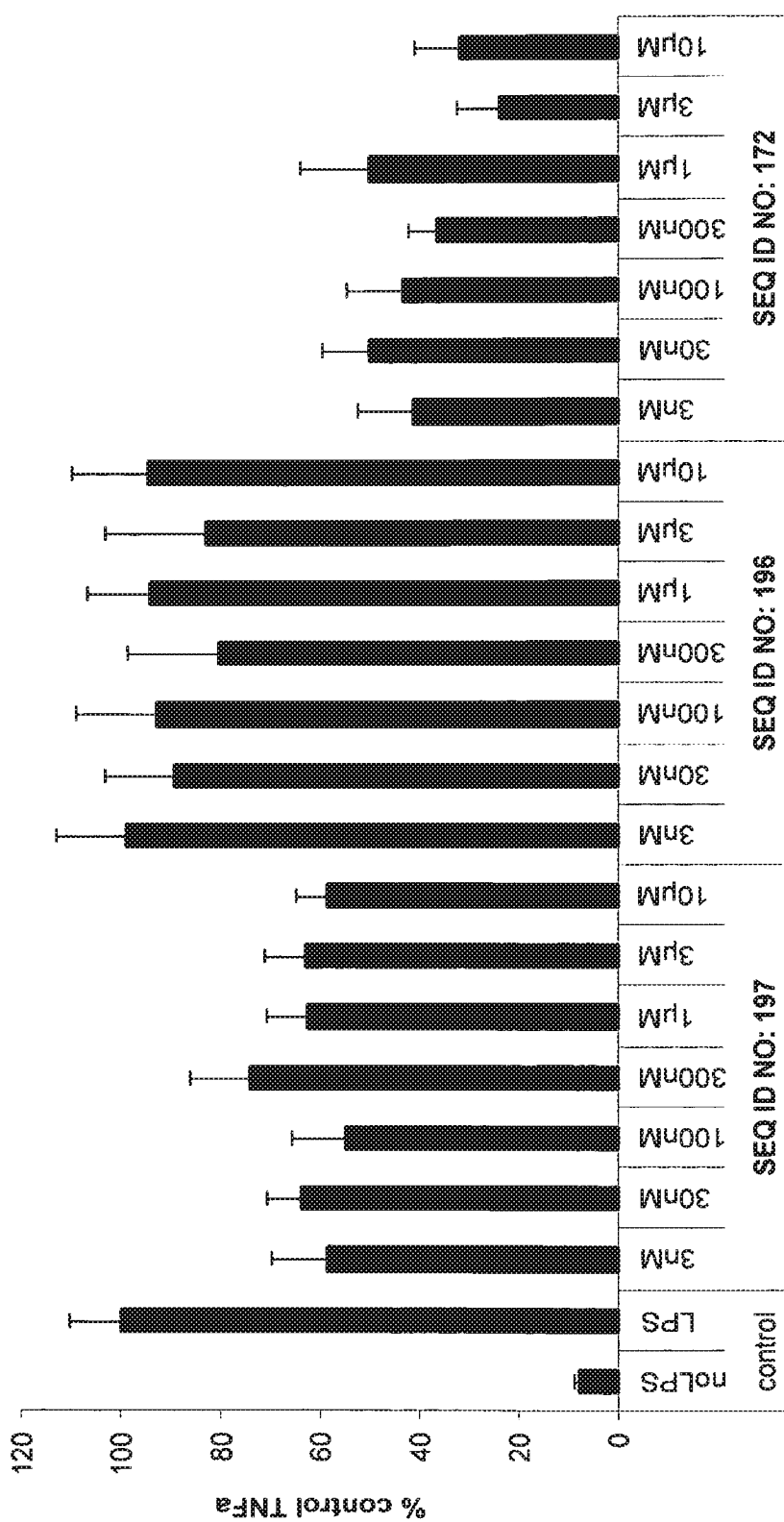
FIG. 11 The JNK inhibitor of SEQ ID NO: 172 blocks LPS-induced TNFα release in PMA differentiated macrophages with higher potency than D-TAT-IB1 (SEQ ID NO: 197) and L-TAT-IB1 (SEQ ID NO: 196).
Figure 12:
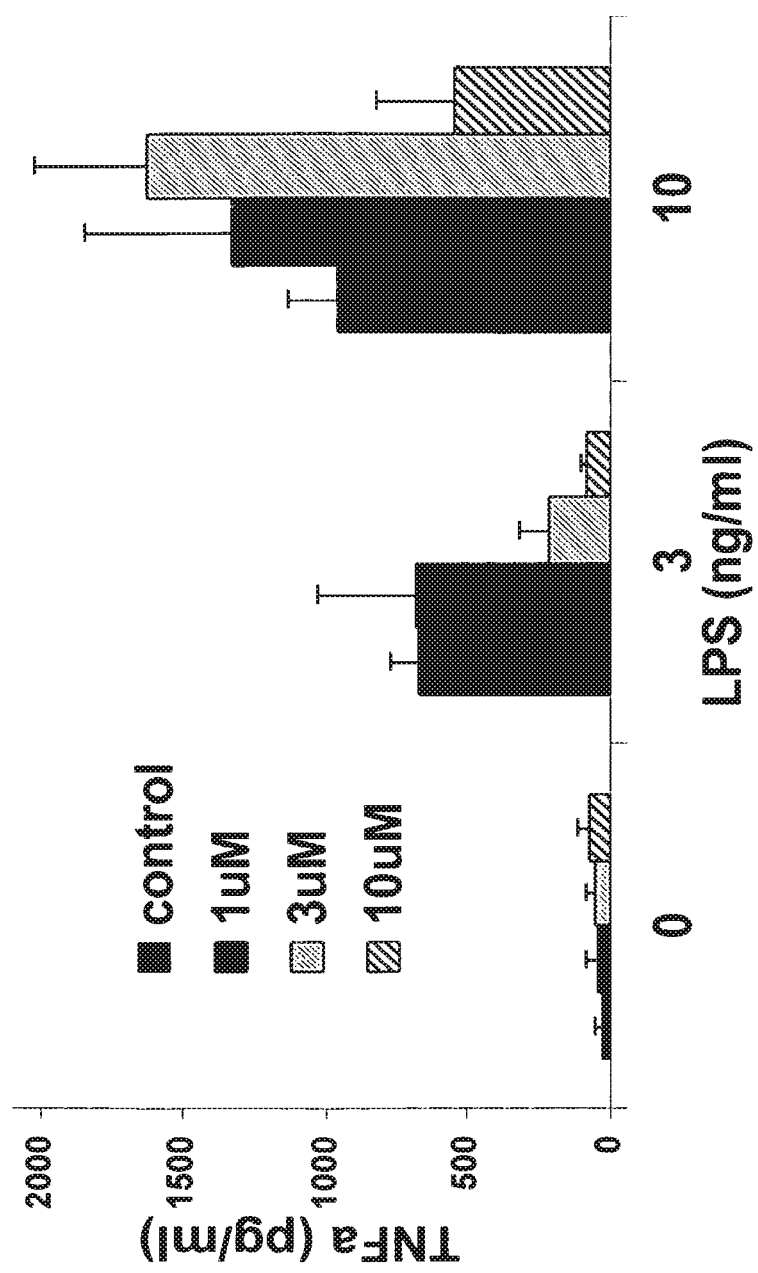
FIG. 12 The JNK inhibitor of SEQ ID NO: 172 blocks LPS-induced TNFα release in Primary Rat Whole Blood Cells at 3 ng/ml. Given are the results for the control, 1 µM of SEQ ID NO: 172, 3 µM of SEQ ID NO: 172, and 10 µM of SEQ ID NO: 172 at different levels of LPS (ng/ml).
Figure 13:
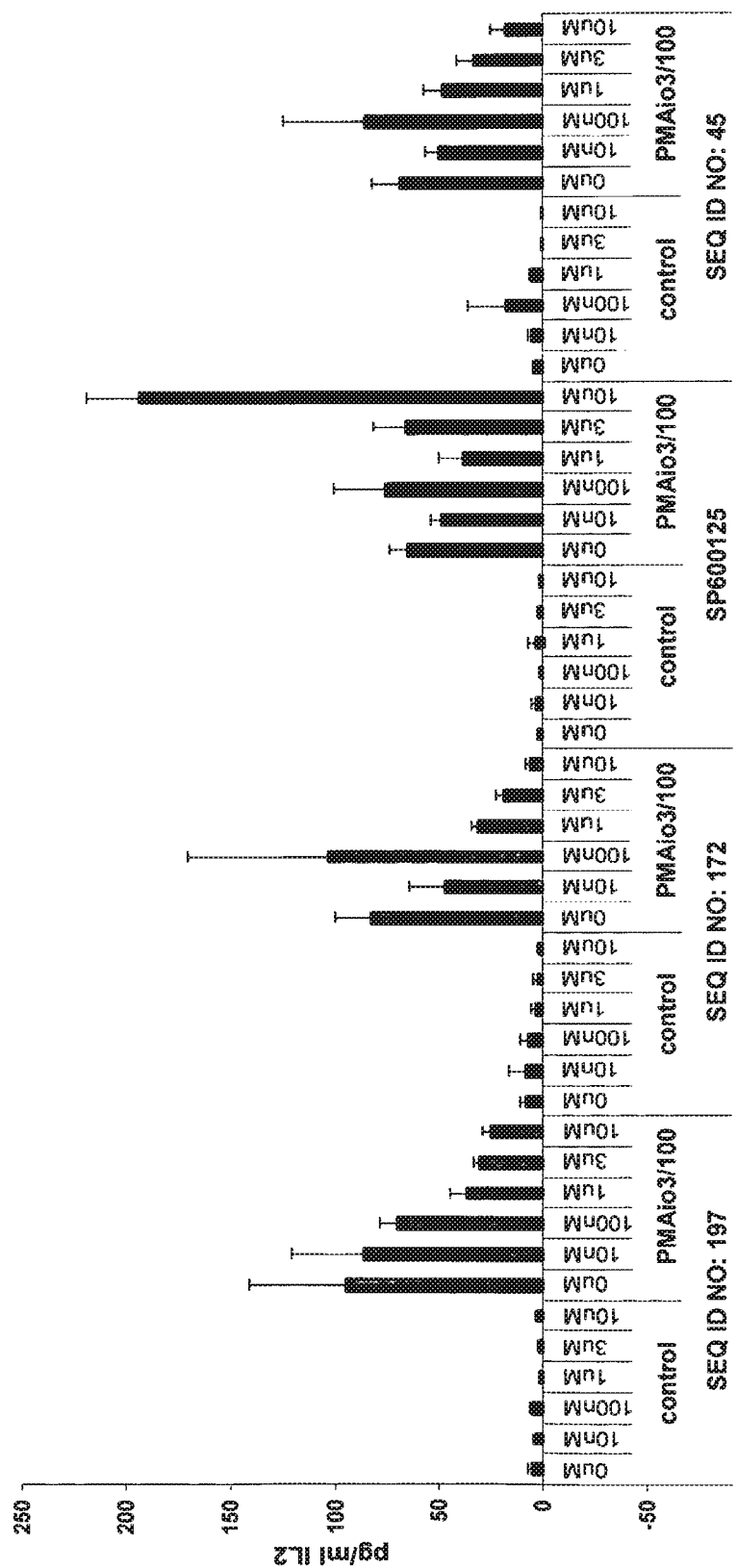
FIG. 13 The JNK inhibitor of SEQ ID NO: 172 blocks IL2 secretion by primary human T-cells in response to PMA/Ionomycin.
Figure 14:
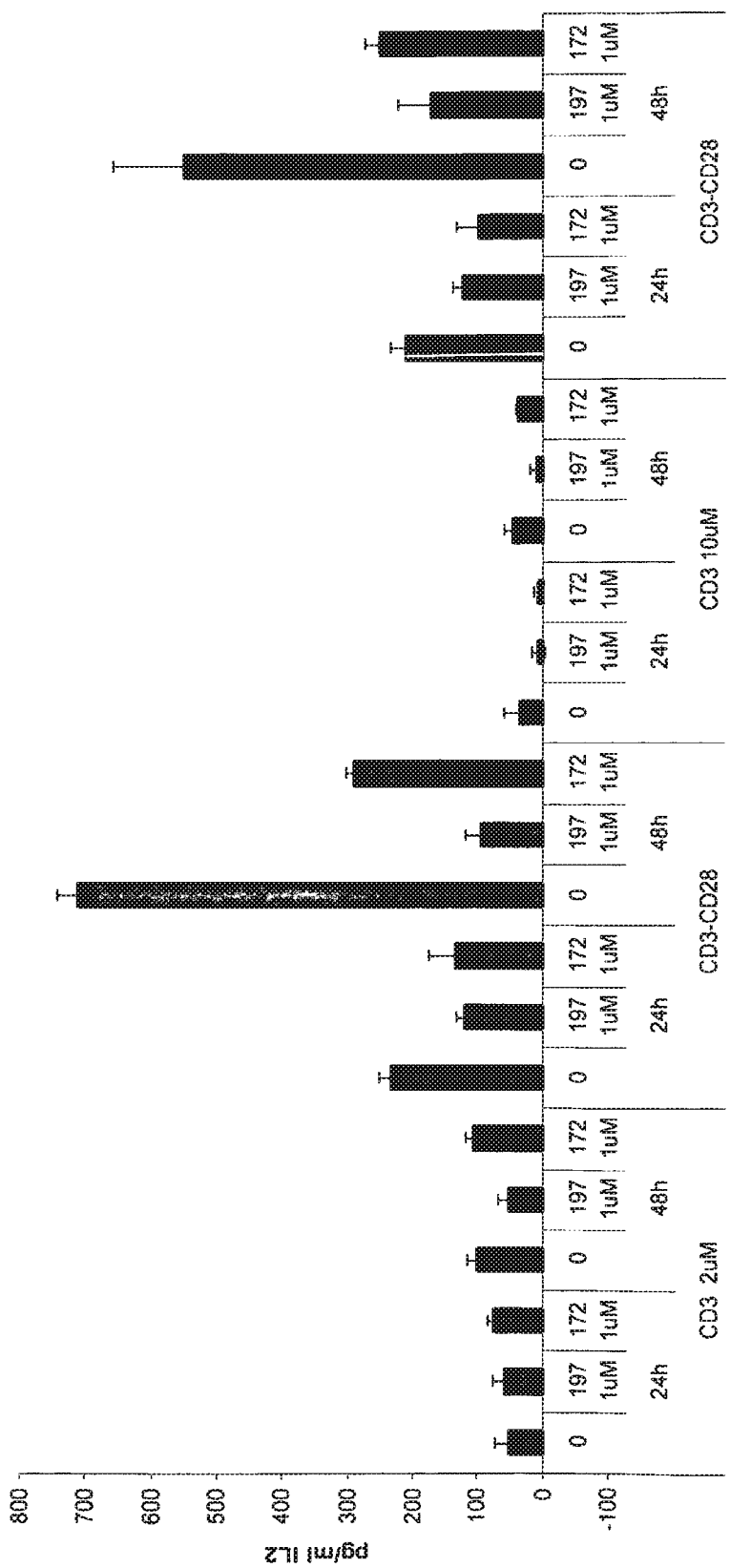
FIG. 14 The JNK inhibitor of SEQ ID NO: 172 blocks IL2 secretion by primary human T-cells in response to CD3/CD28 stimulation. The JNK inhibitors used are indicated by their SEQ ID NO: 172 and 197.
Figure 15:
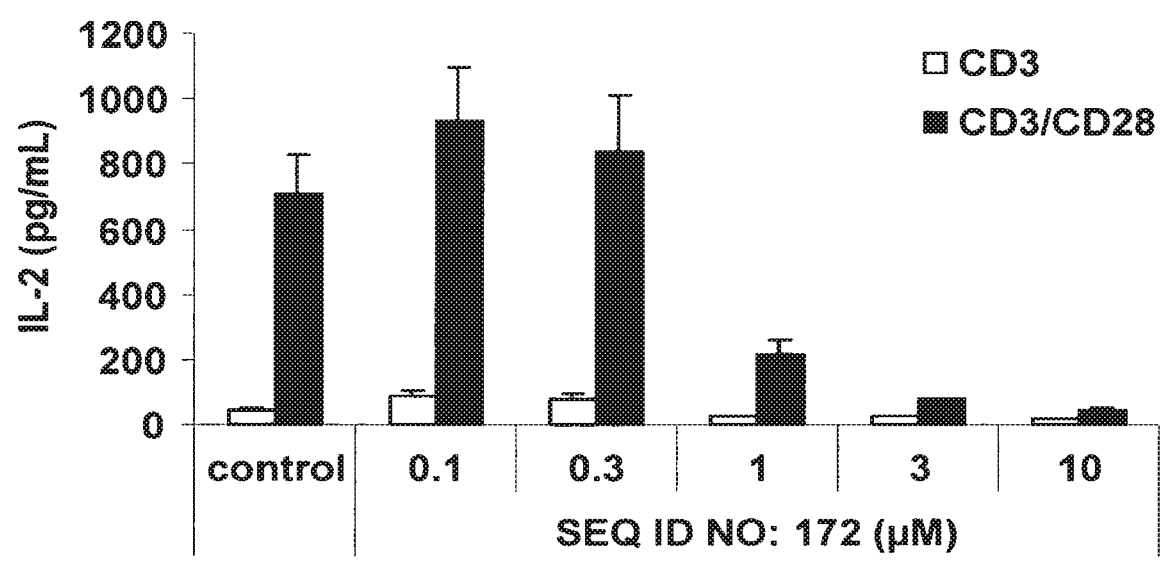
FIG. 15 Dose-dependent inhibition by JNK inhibitor with SEQ ID NO: 172 of CD3/CD28-induced IL-2 release in primary rat lymph-nodes purified T cells. Control rat were sacrificed and lymph-nodes were harvested. T cells further were purified (using magnetic negative selection) and plated into 96-well plates at 200.000 cells/well. Cells were treated with anti-rat CD3 and anti-rat CD28 antibodies (2 µg/mL). JNK inhibitor with SEQ ID NO: 172 was added to the cultures 1 h before CD3/CD28 treatment and IL-2 release was assessed in supernatant 24 h after treatment.
Figure 16:
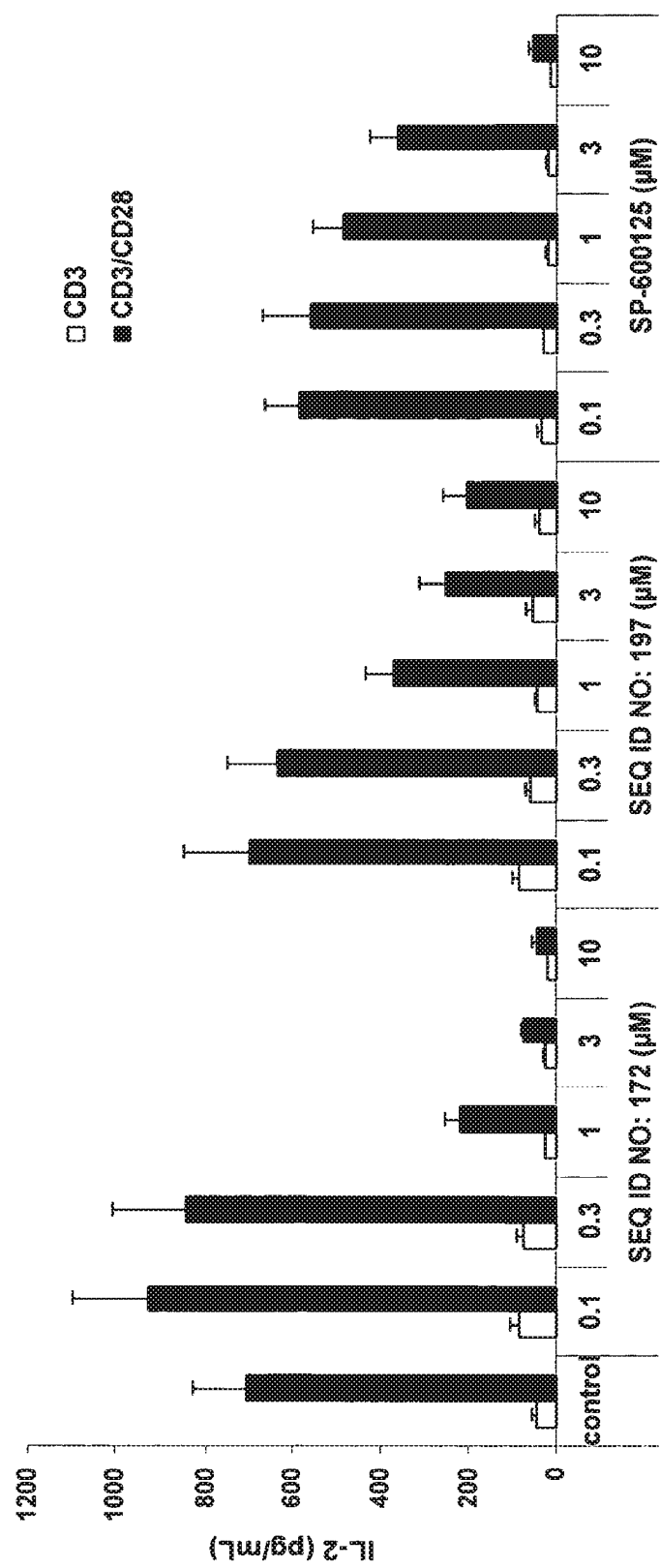
FIG. 16 Dose-dependent inhibition of CD3/CD28-induced IL-2 release in primary rat lymph-nodes purified T cells: Comparison of several JNK inhibitors, namely SEQ ID NOs: 172, 197 and SP600125.
Figure 17:
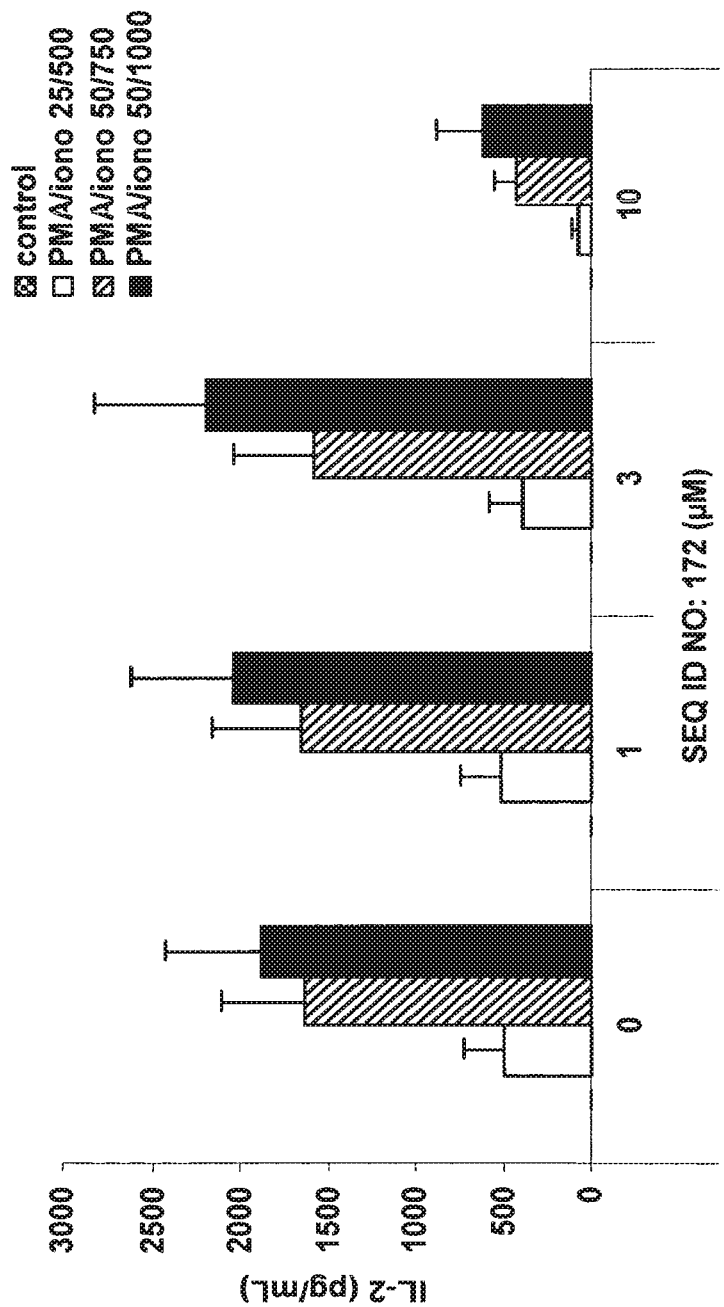
FIG. 17 Dose dependent inhibition of IL-2 release in rat whole blood stimulated with PMA+ionomycin. JNK inhibitor with SEQ ID NO: 172 was added at three different concentrations, namely 1, 3 and 10 µM 1 h before stimulation with PMA+ionomycin. Three doses of activators were added (25/500 ng/mL, 50/750 ng/mL and 50/1000 ng/mL) for 4 h. IL-2 release was assessed in supernatant. JNK inhibitor with SEQ ID NO: 172 at 10 µM did efficiently reduce PMA-iono-induced IL-2 release at the three tested activator concentrations.
Figure 18:
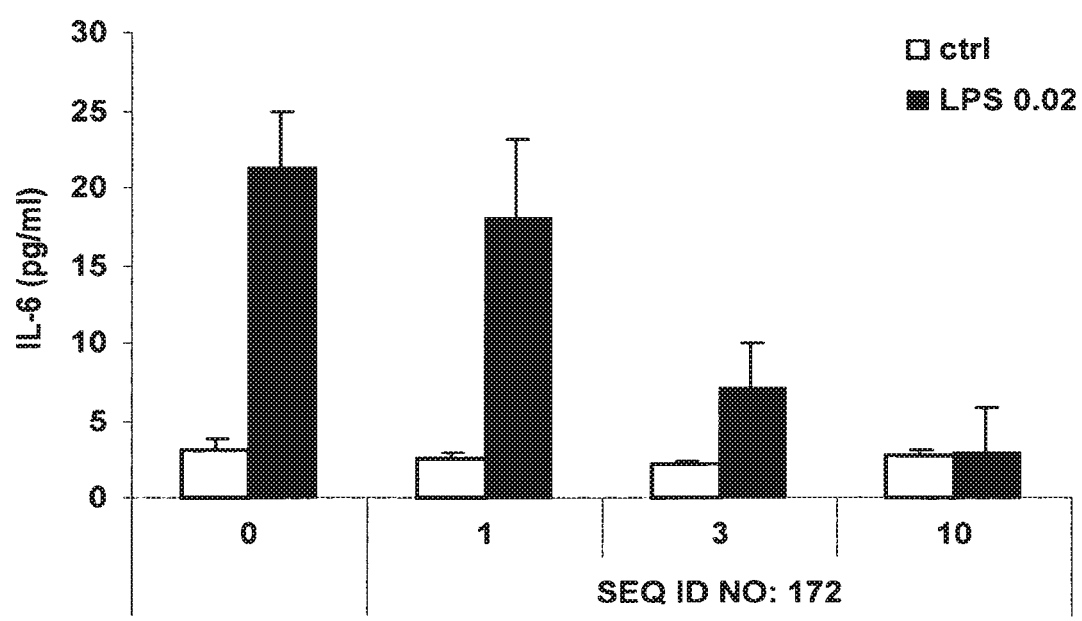
FIG. 18 JNK inhibition and IL-6 release in human whole blood. The JNK inhibitor with SEQ ID NO: 172 was added at three different concentrations, namely 1, 3 and 10 µM 1 h before whole blood stimulation with LPS (0.02 ng/mL) for 4 hours. The JNK inhibitor with SEQ ID NO: 172 did reduce the LPS-induced IL-6 release in a dose-dependent manner.
Figure 19:
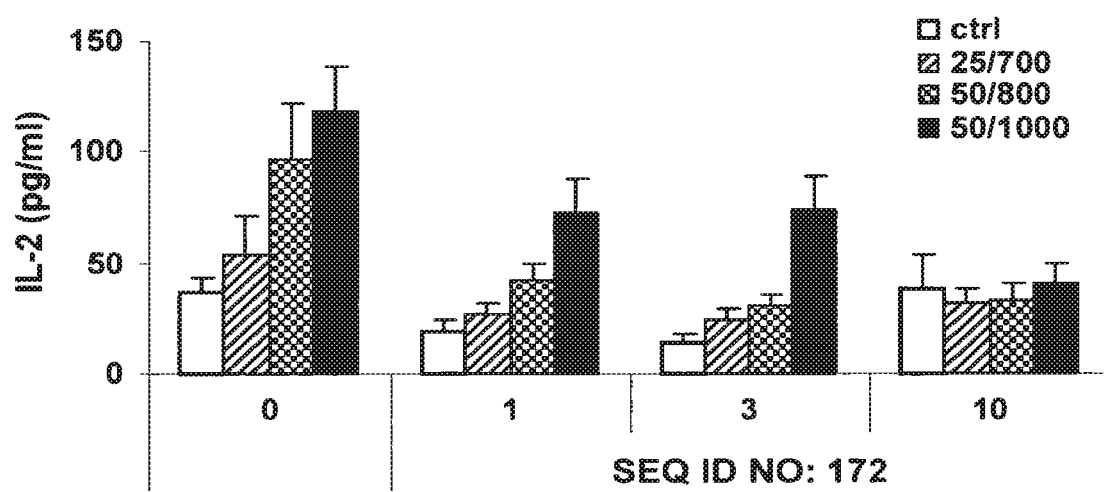
FIG. 19 JNK inhibition and IL-2 release in human whole blood. The JNK inhibitor with SEQ ID NO: 172 was added at three different concentrations, namely 1, 3 and 10 µM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced IL-2 release in a dose-dependent manner.
Figure 20:
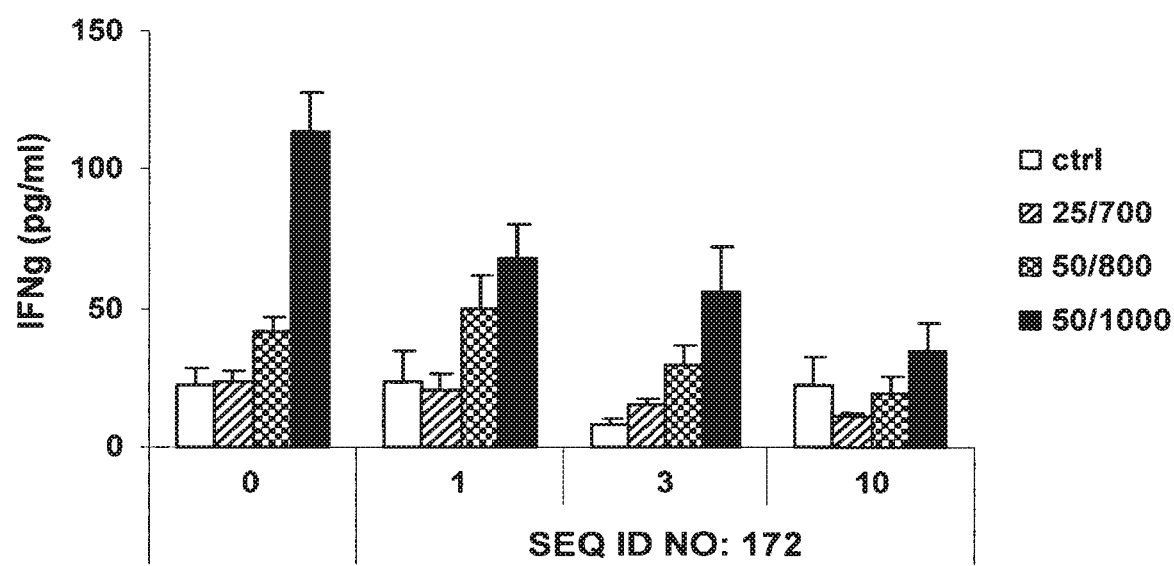
FIG. 20 JNK inhibition and IFN-γ release in human whole blood. The JNK inhibitor with SEQ ID NO: 172 was added at three different concentrations, namely 1, 3 and 10 μM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced IFN-γ release in a dose-dependent manner.
Figure 21:
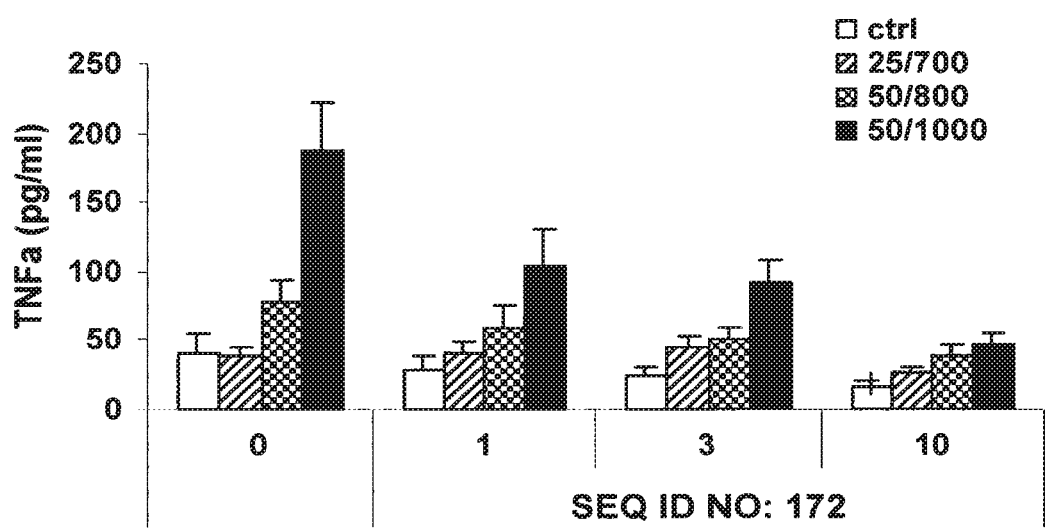
FIG. 21 JNK inhibition and TNF-α release in human whole blood. The JNK inhibitor with SEQ ID NO: 172 was added at three different concentrations, namely 1, 3 and 10 μM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced TNF-α release in a dose-dependent manner.
Figure 22:
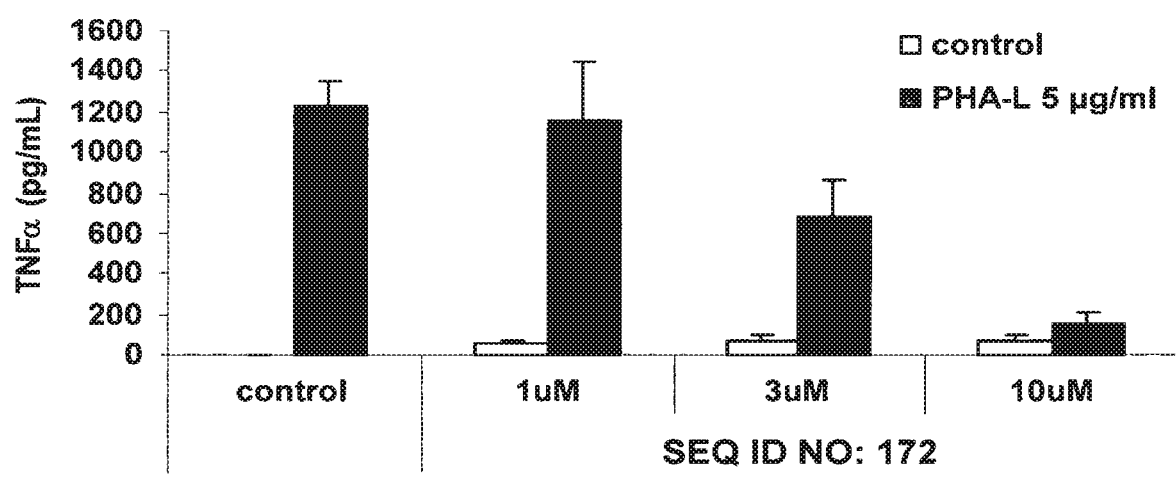
FIG. 22 JNK inhibition and TNF-α release in human whole blood. The JNK inhibitor with SEQ ID NO: 172 was added at three different concentrations, namely 1, 3 and 10 μM 1 h before whole blood stimulation with PHA-L (5 μg/mL) for 3 days. The JNK inhibitor with SEQ ID NO: 172 did reduce the PHA-L-induced TNF-α release in a dose-dependent manner.
Figure 23:
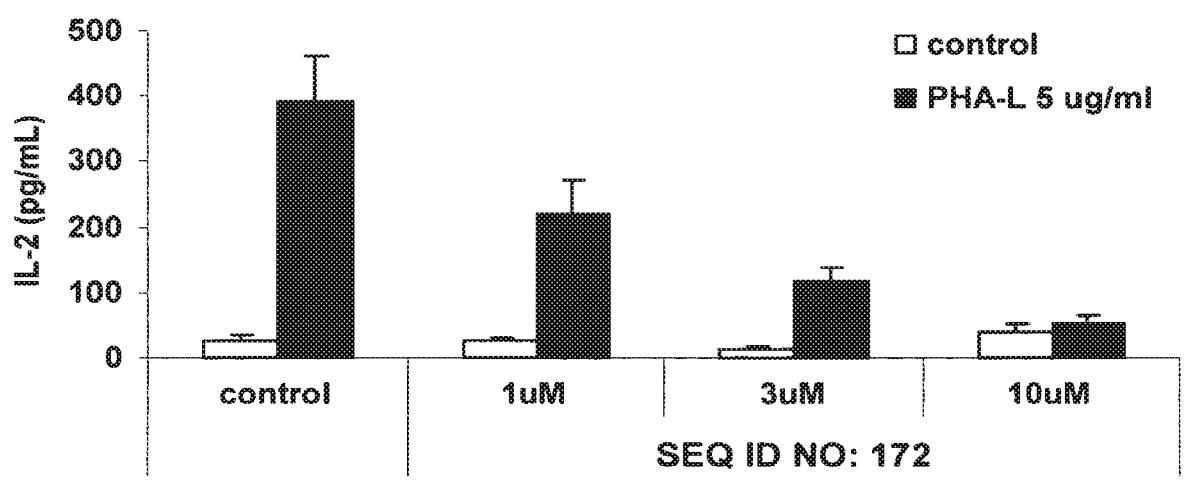
FIG. 23 JNK inhibition and IL-2 release in human whole blood. The JNK inhibitor with SEQ ID NO: 172 was added at three different concentrations, namely 1, 3 and 10 μM 1 h before whole blood stimulation with PHA-L (5 μg/mL) for 3 days. The JNK inhibitor with SEQ ID NO: 172 did reduce the PHA-L-induced IL-2 release in a dose-dependent manner.
Figure 24:
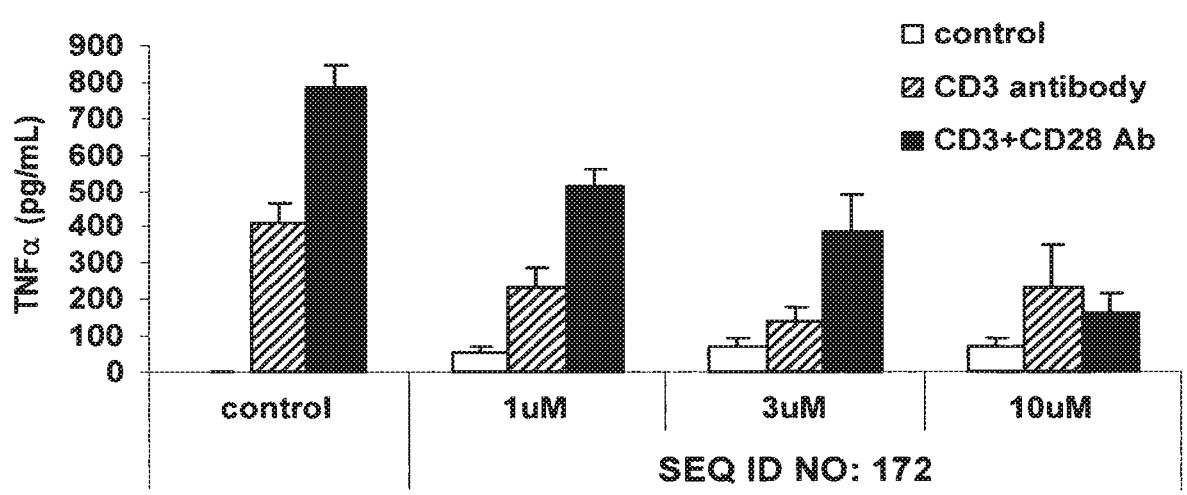
FIG. 24 JNK inhibition and TNF-α release in human whole blood. The JNK inhibitor with SEQ ID NO: 172 was added at three different concentrations, namely 1, 3 and 10 μM 1 h before whole blood stimulation with CD3+/−CD28 antibodies (2 μg/mL) for 3 days. The JNK inhibitor with SEQ ID NO: 172 did reduce the CD3/CD28-induced TNF-α release in a dose-dependent manner.
Figure 25:
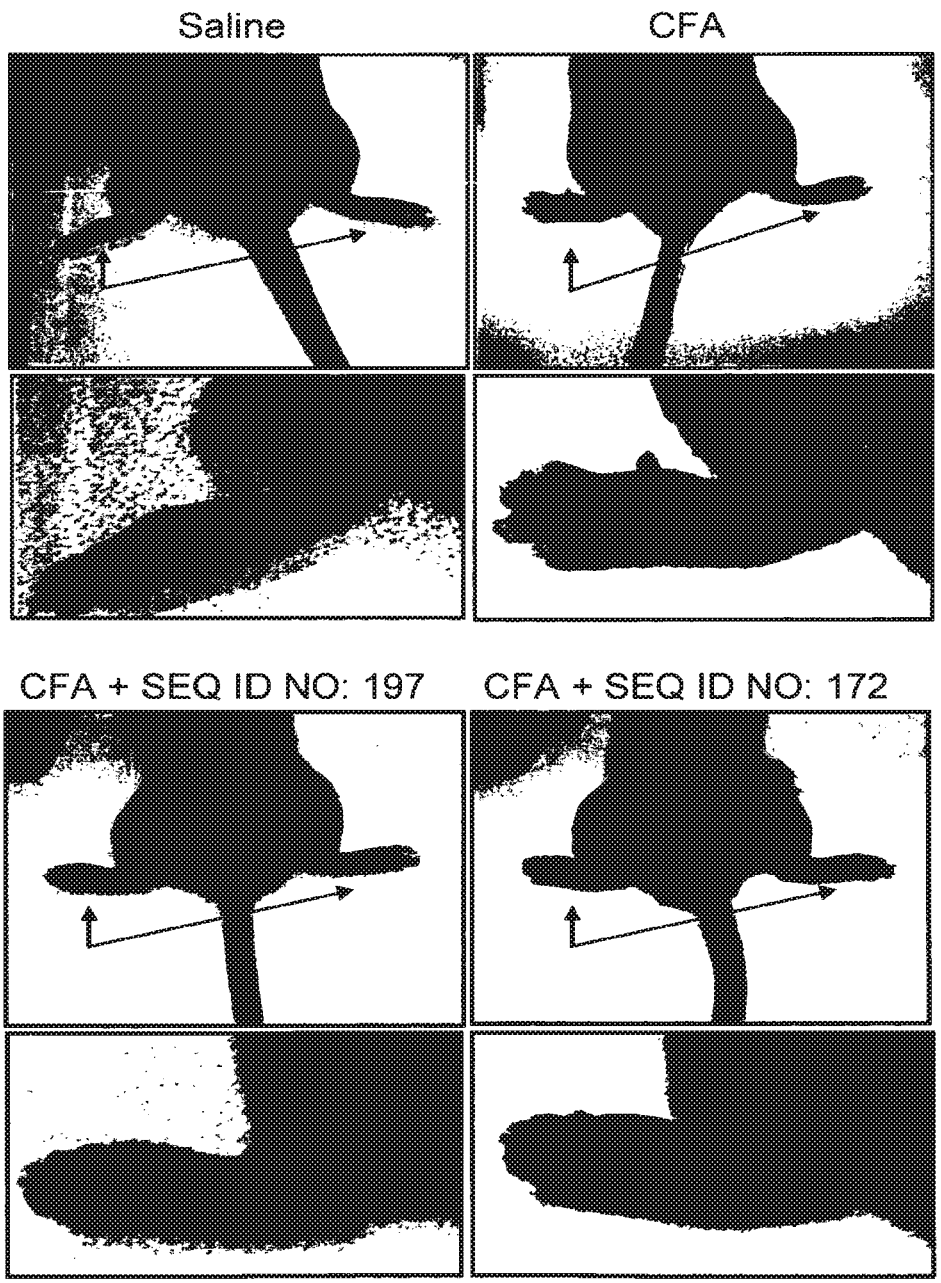
FIG. 25 Photographic illustration of in vivo anti-inflammatory properties of the JNK inhibitors with SEQ ID NO: 197 (10 μg/kg) and SEQ ID NO: 172 (10 μg/kg) after CFA (complete Freund's adjuvant) induced paw swelling. Paw swelling was induced in the left hind paw, the right hind paw was not treated.
Figure 26:
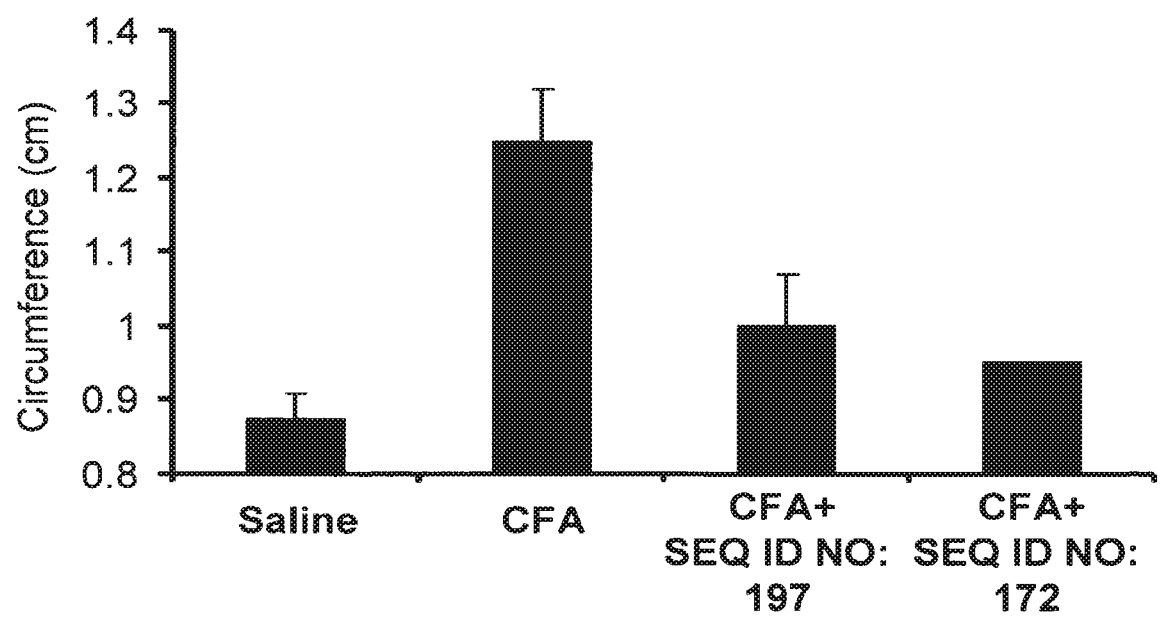
FIG. 26 Graphical representation of in vivo anti-inflammatory properties of the JNK inhibitors with SEQ ID NO: 197 (10 μg/kg, n=4) and SEQ ID NO: 172 (10 μg/kg, n=3) after CFA (complete Freund's adjuvant) induced paw swelling. Indicated is the measured circumference of the left hind paw after treatment.
Figure 27:
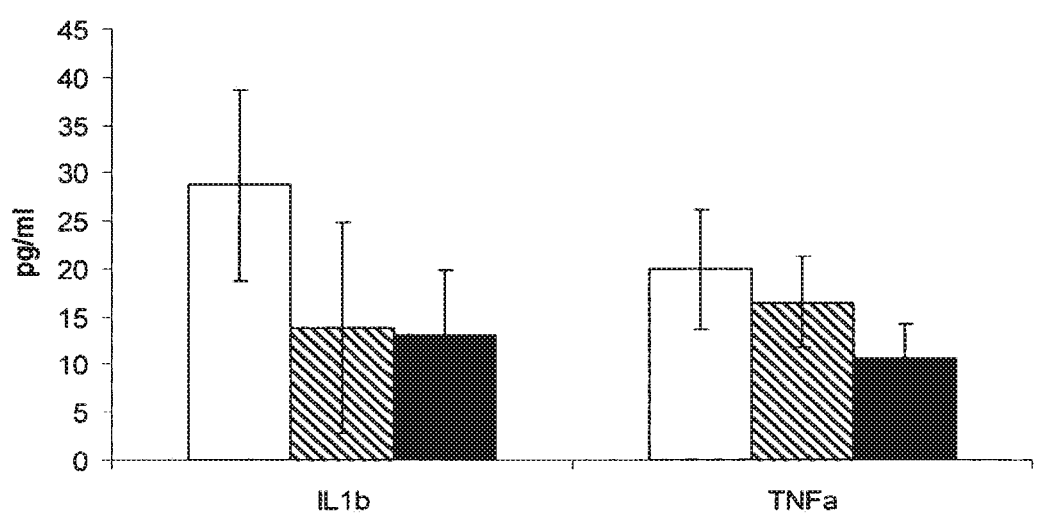
FIG. 27 Graphical representation of in vivo anti-inflammatory properties of the JNK inhibitors with SEQ ID NO: 197 (10 μg/kg) and SEQ ID NO: 172 (10 μg/kg) after CFA (complete Freund's adjuvant) induced paw swelling. Indicated is the measured in vivo cytokine release one hour after CFA induced paw swelling.
Figure 28:
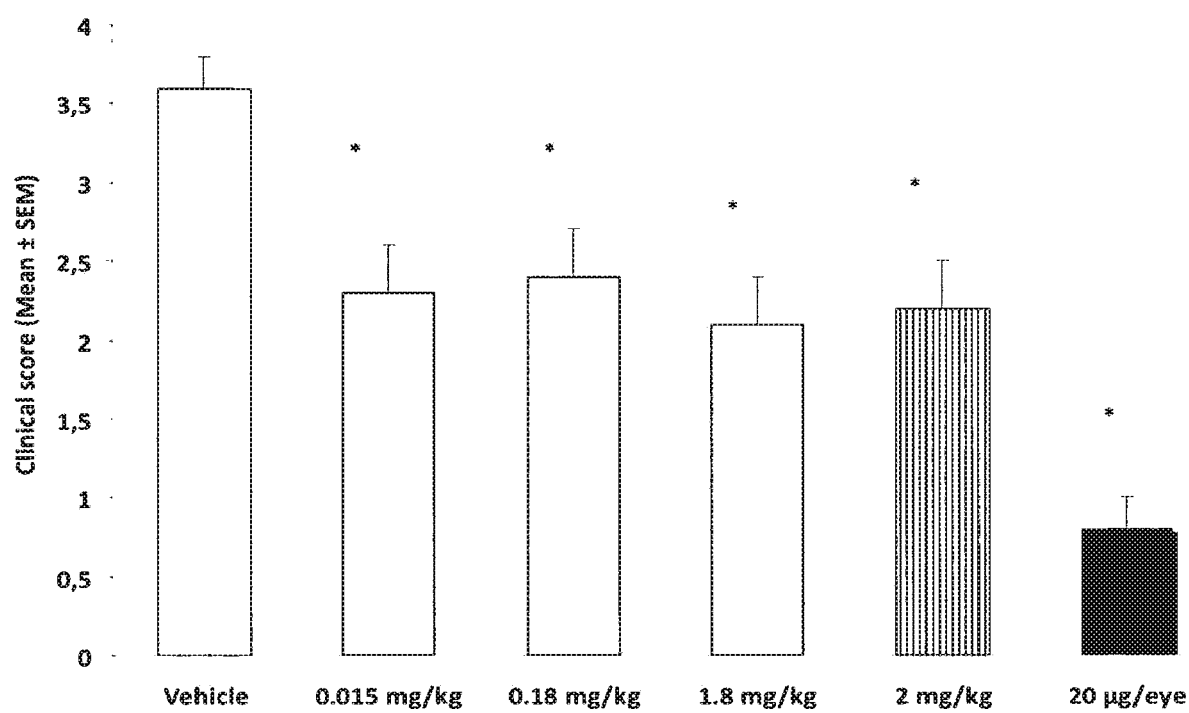
FIG. 28 Clinical evaluation of administration of different amounts of the JNK inhibitor according to SEQ ID NO: 172 in albino rats after intravenous administration (endotoxins induced uveitis model). Form left to right: Vehicle, 0.015 mg/kg (i.v.) of SEQ ID NO: 172; 0.18 mg/kg (i.v.) of SEQ ID NO: 172; 1.8 mg/kg (i.v.) of SEQ ID NO: 172, 2 mg/kg (i.v.) of SEQ ID NO: 197 and 20 μg dexamethasone (administered directly by subconjuctival injection to the eye). Indicated is the clinical score (mean and the SEM).
Figure 29:
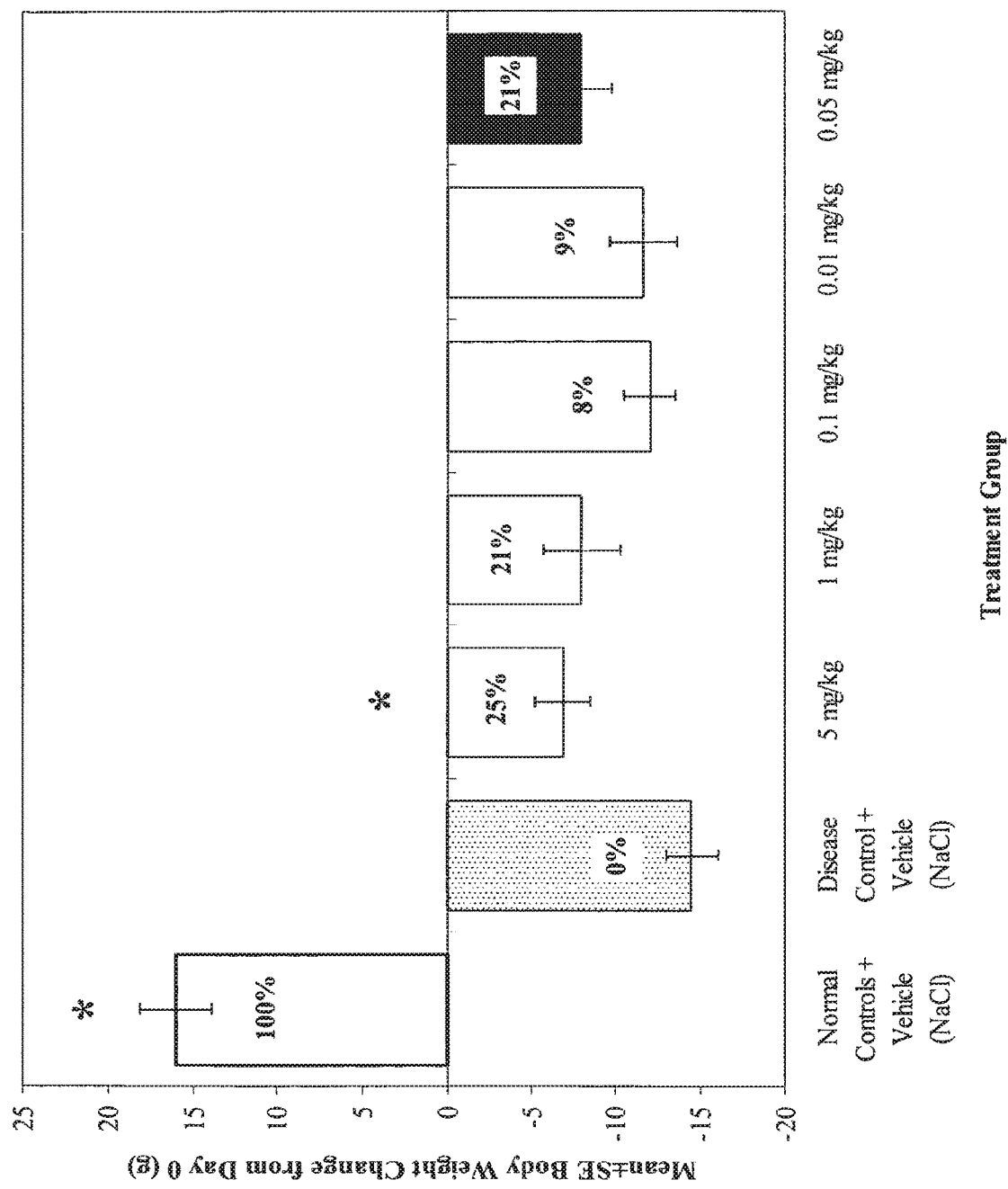
FIG. 29 Responsive effects of the JNK inhibitor of SEQ ID NO: 172 after daily intravenous administration in 14 day rat chronic established Type II collagen arthritis (RTTC/SOL-1). Shown is the body weight change from day 0 to day 14. From left to right: Normal contrail+Vehicle (NaCl), Disease Control+Vehicle (NaCl), 5 mg/kg (i.v.) of SEQ ID NO: 172; 1 mg/kg (i.v.) of SEQ ID NO: 172; 0.1 mg/kg (i.v.) of SEQ ID NO: 172, 0.01 mg/kg (i.v.) of SEQ ID NO: 172, 0.05 mg/kg (i.v.) of dexamethasone. Indicated is the clinical score (mean and the SEM). n=4/normal group, n=8/treatment group; *p≤0.05 1-way ANOVA to disease control+Vehicle (NaCl)
Figure 30:
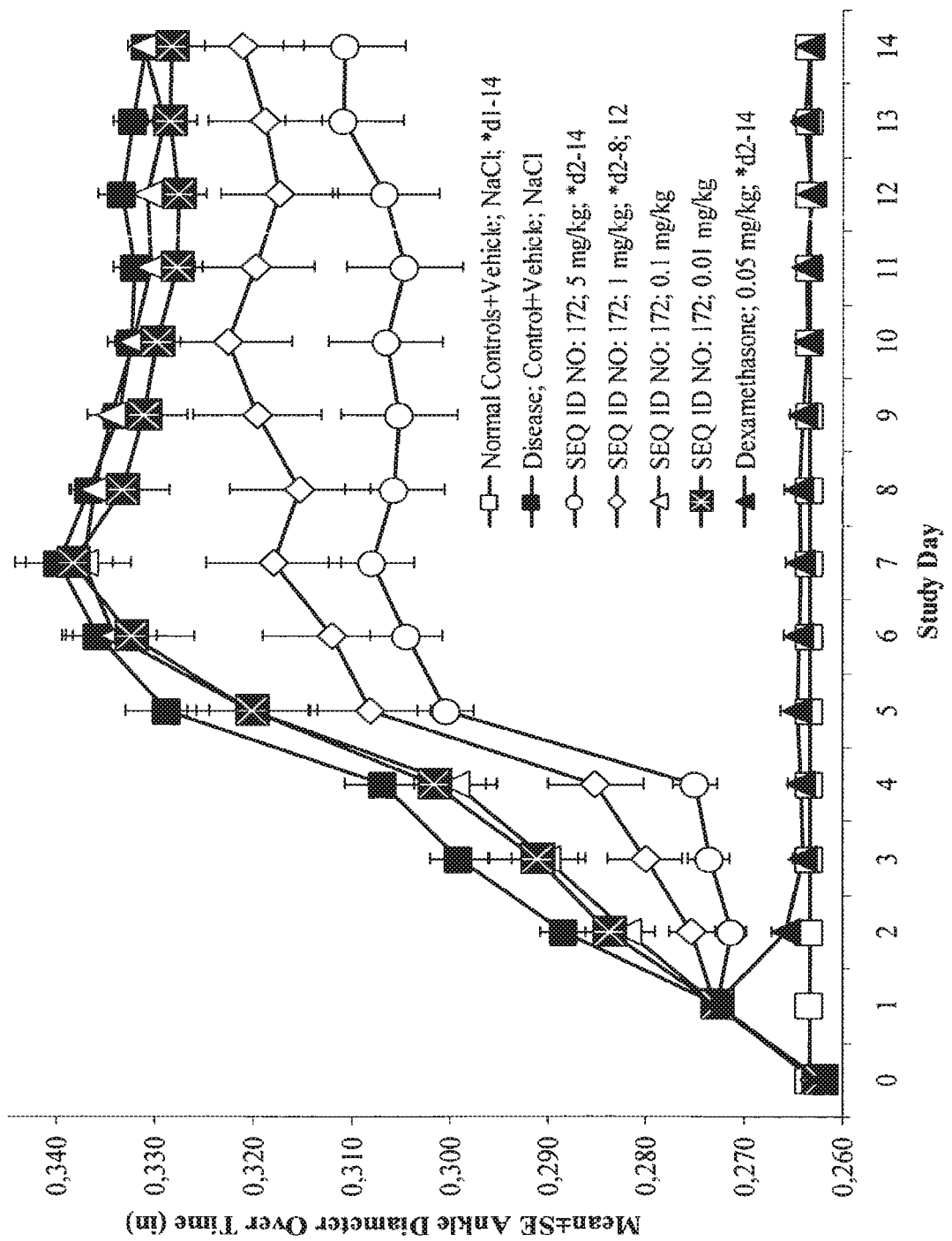
FIG. 30 Responsive effects of the JNK inhibitor of SEQ ID NO: 172 after daily intravenous administration in 14 day rat chronic established Type II collagen arthritis (RTTC/SOL-1). Shown is the ankle diameter (in) over time. n=4/normal group, n=8/treatment group; *p≤0.05 2-way RM ANOVA to disease control+Vehicle (NaCl).
Figure 31:
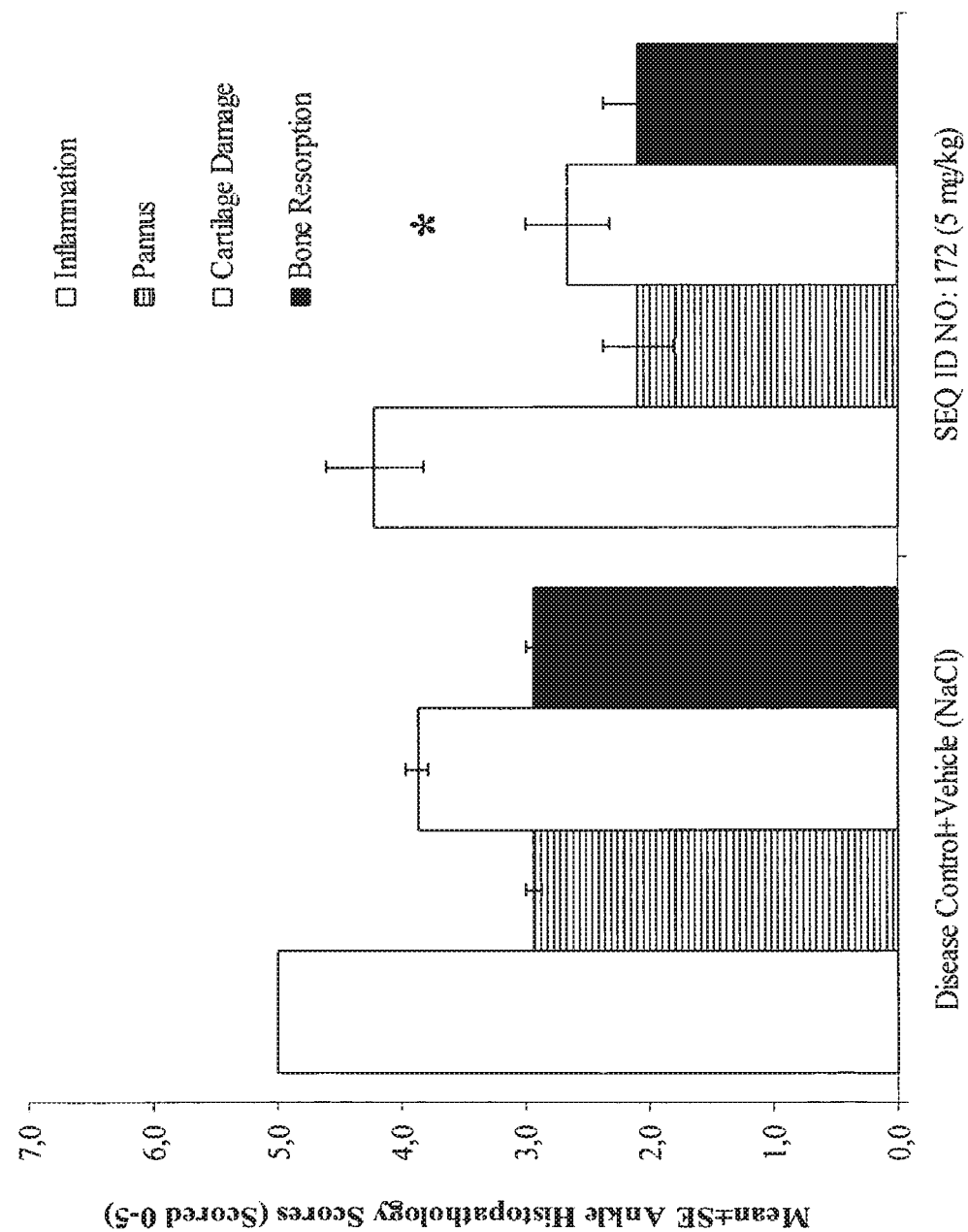
FIG. 31 Responsive effects of the JNK inhibitor of SEQ ID NO: 172 after daily intravenous administration in 14 day rat chronic established Type II collagen arthritis (RTTC/SOL-1). Illustrated are the ankle histopathology scores regarding inflammation, pannus, cartilage damage and bone resorption. n=8 in the treatment group. *p≤0.05 Mann-Whitney U test to disease control+Vehicle (NaCl).
Figure 32:
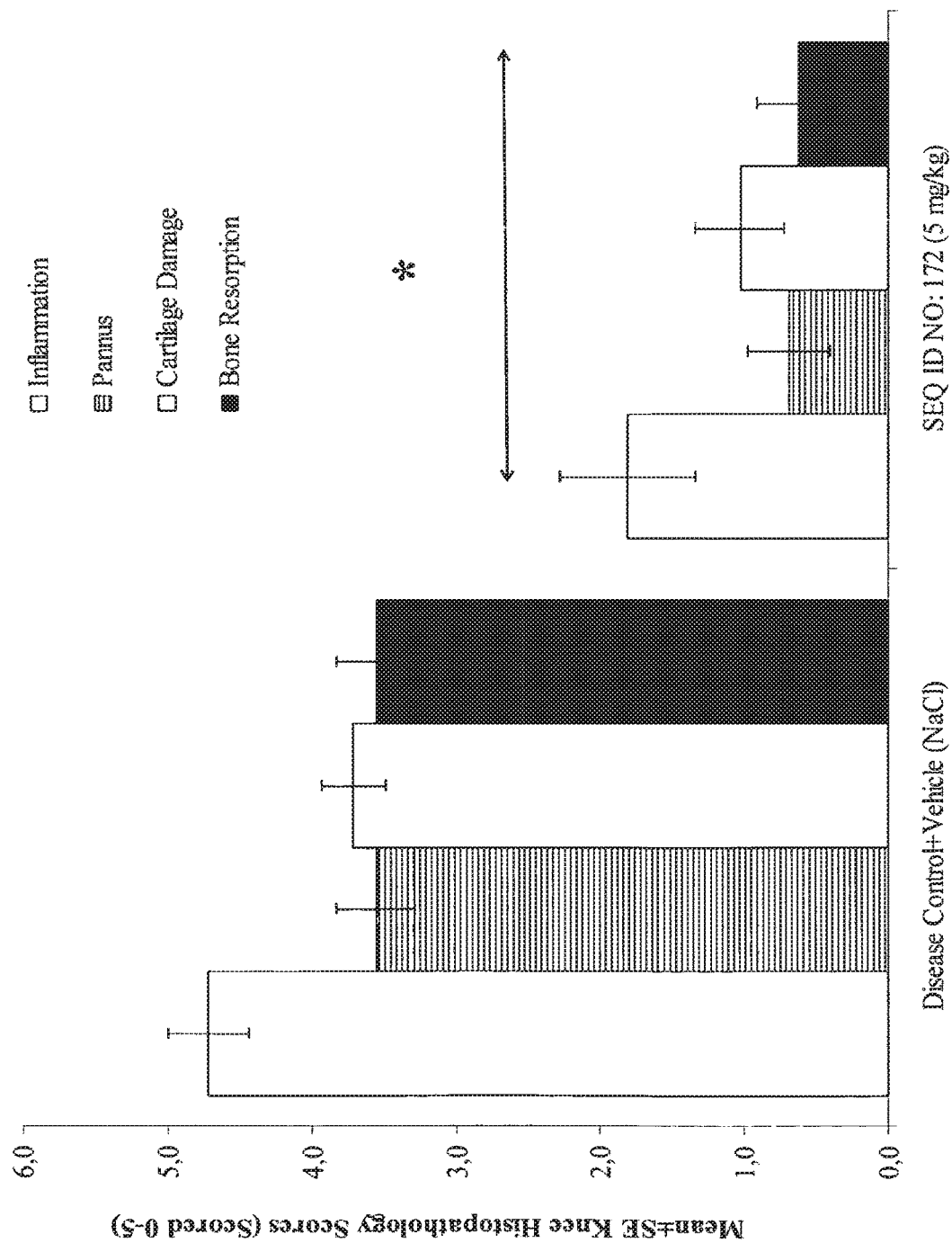
FIG. 32 Responsive effects of the JNK inhibitor of SEQ ID NO: 172 after daily intravenous administration in 14 day rat chronic established Type II collagen arthritis (RTTC/SOL-1). Illustrated are the knee histopathology scores regarding inflammation, pannus, cartilage damage and bone resorption. n=8 in the treatment group. *p≤0.05 Mann-Whitney U test to disease control+Vehicle (NaCl).
Figure 33:
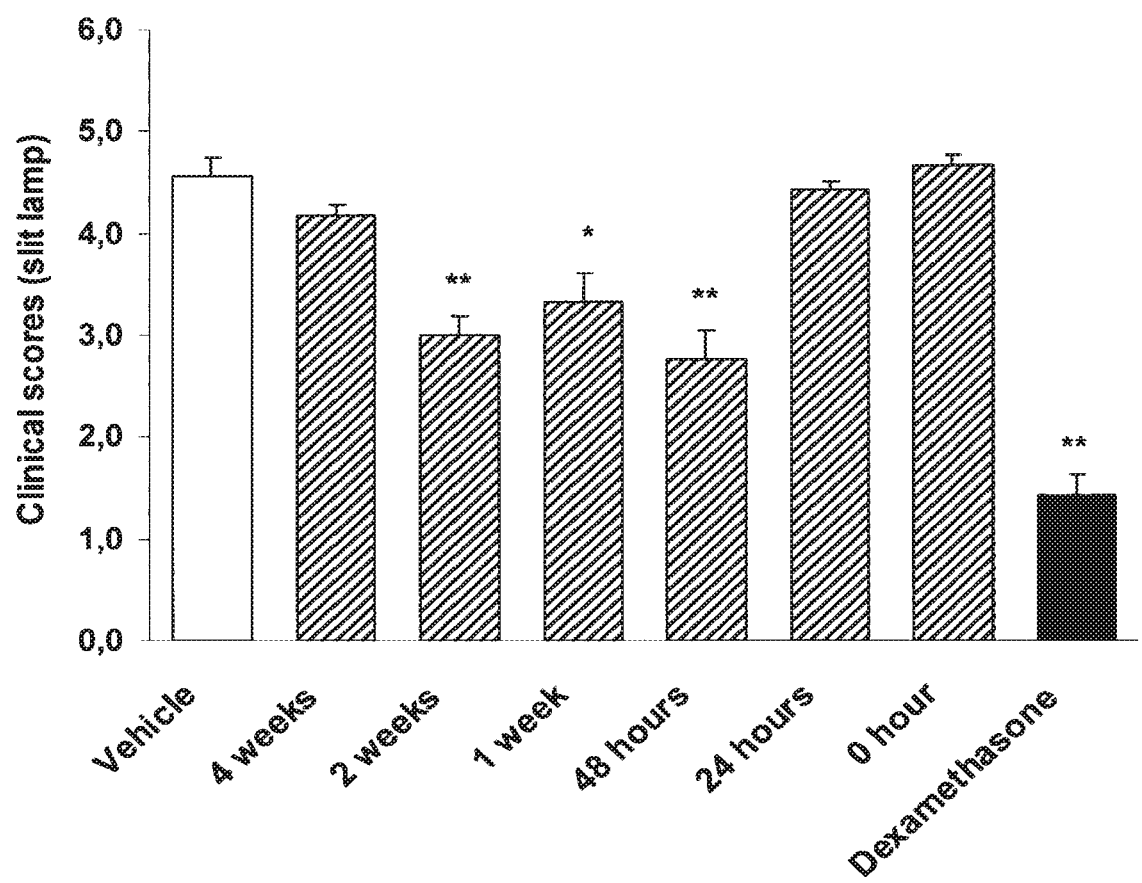
FIG. 33 Clinical scoring by slit lamp 24 hours after EIU induction and administration of JNK inhibitor according to SEQ ID NO: 172 (1 mg/kg i.v.) at different times prior to EIU induction. From left to right: Vehicle (0 hours); SEQ ID NO: 172 4 weeks prior to EIU induction; SEQ ID NO: 172 2 weeks prior to EIU induction; SEQ ID NO: 172 1 week prior to EIU induction; SEQ ID NO: 172 48 hours prior to EIU induction; SEQ ID NO: 172 24 hours prior to EIU induction; SEQ ID NO: 172 0 hours prior to EIU induction; Dexamethasone (2 mg/kg i.v.) 0 hours prior to EIU induction. Mean±SEM. *p<0.05 versus vehicle, **p<0.01 versus vehicle.
Figure 34:
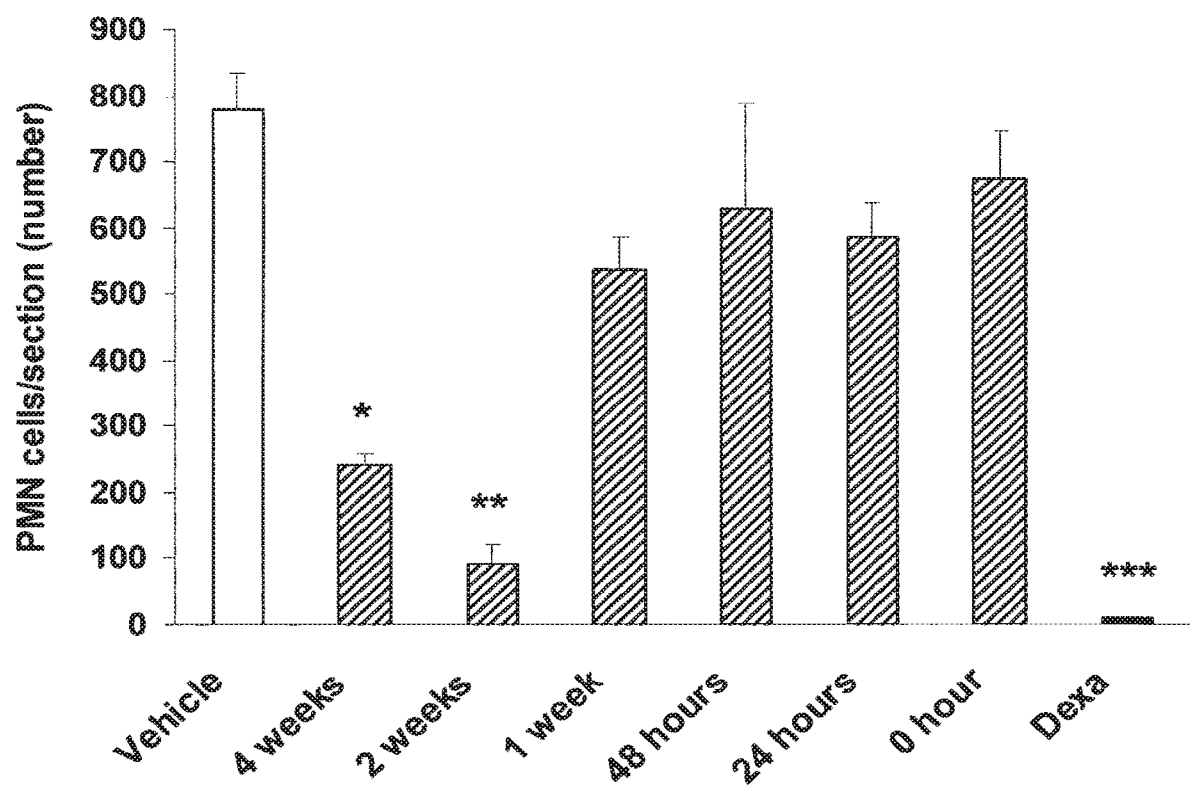
FIG. 34 Number of PMN cells per section quantified 24 hours after EIU induction and administration of JNK inhibitor according to SEQ ID NO: 172 (1 mg/kg i.v.) at different times prior to EIU induction. From left to right: Vehicle (0 hours); SEQ ID NO: 172 4 weeks prior to EIU induction; SEQ ID NO: 172 2 weeks prior to EIU induction; SEQ ID NO: 172 1 week prior to EIU induction; SEQ ID NO: 172 48 hours prior to EIU induction; SEQ ID NO: 172 24 hours prior to EIU induction; SEQ ID NO: 172 0 hours prior to EIU induction; Dexamethasone (2 mg/kg i.v.) 0 hours prior to EIU induction. Mean±SEM. *p<0.05 versus vehicle, **p<0.01 versus vehicle.
Figure 35:
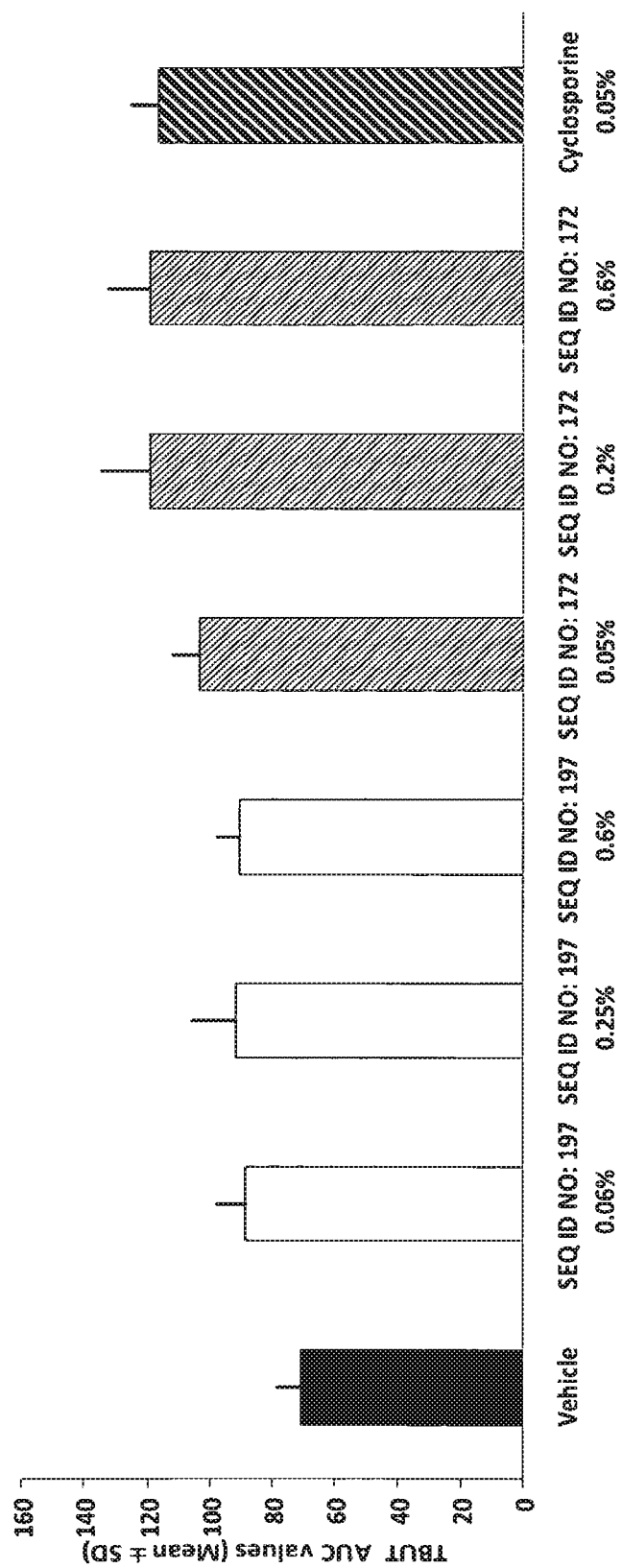
FIG. 35 shows the mean calculated TBUT AUC values for animals with scopolamine induced dry eye syndrome. Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.
Figure 36:
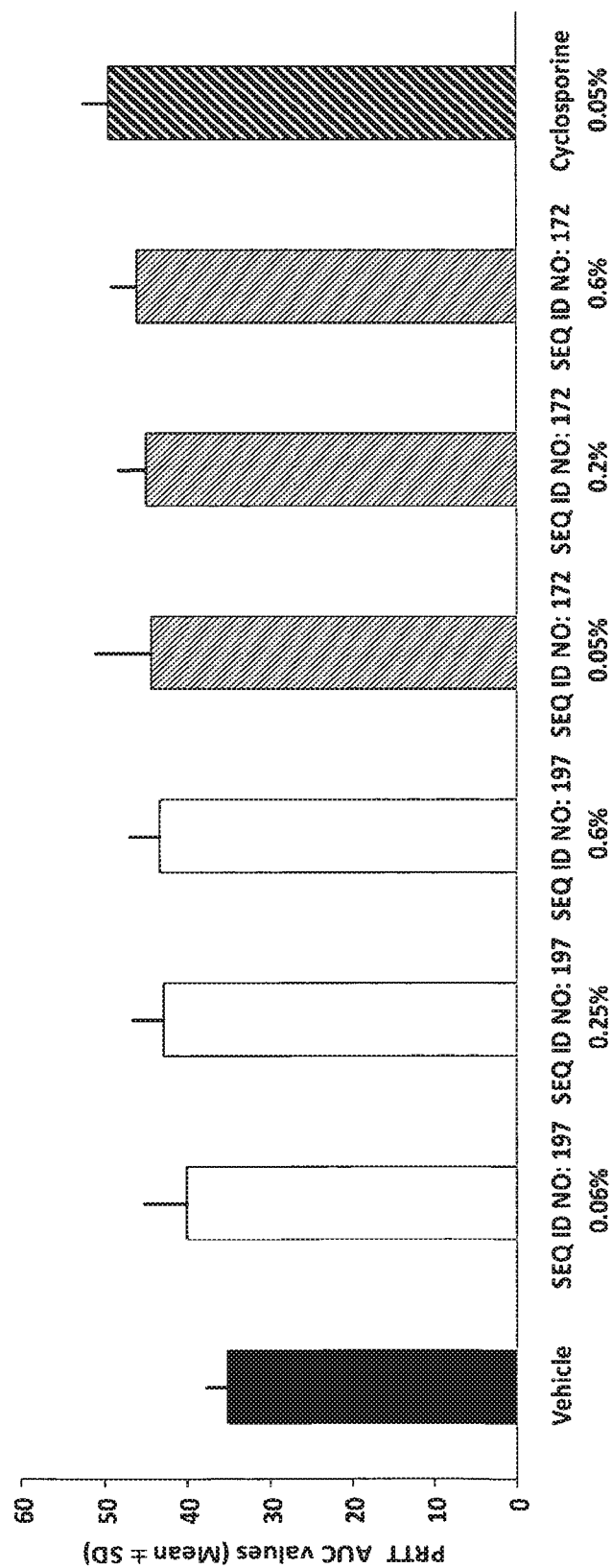
FIG. 36 shows the mean calculated PRTT AUCs for animals with scopolamine induced Dry Eye (Day 7-21). Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.
Figure 37:
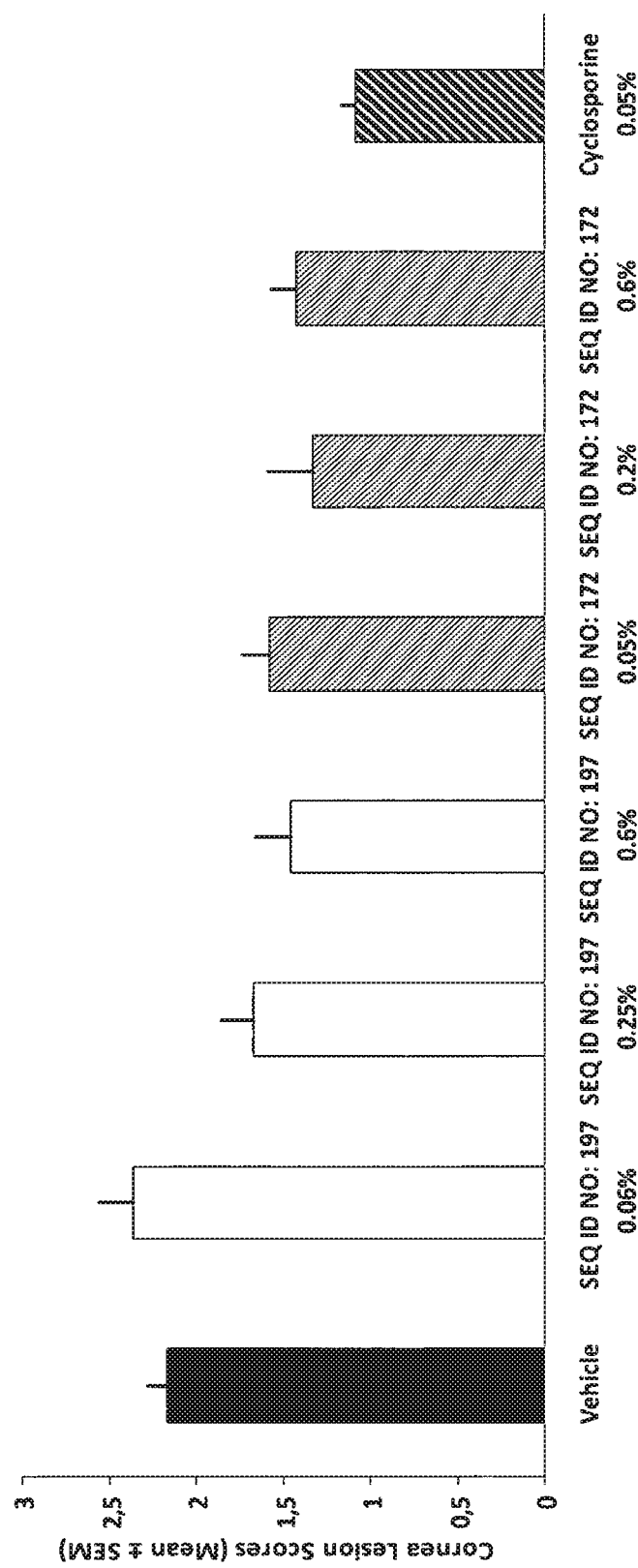
FIG. 37 shows the mean histological Cornea Lesion Scores for animals with scopolamine induced dry eye syndrome. Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.

| SEQ ID NO: | peptide No: abbreviation in FIG. 6 | | | | | | | | | | |
|---|---|---|---|---|---|---|---|---|---|---|---|
| 46 | rs-L-TAT | $H_2N$ | dR | K | K | R | dR | Q | R | R | dR $CONH_2$ |
| 52 | 1 | $H_2N$ | dR | A | K | R | dR | Q | R | R | dR $CONH_2$ |
| 53 | 2 | $H_2N$ | dR | K | A | R | dR | Q | R | R | dR $CONH_2$ |
| 54 | 3 | $H_2N$ | dR | K | K | A | dR | Q | R | R | dR $CONH_2$ |
| 55 | 4 | $H_2N$ | dR | K | K | R | dR | A | R | R | dR $CONH_2$ |
| 56 | 5 | $H_2N$ | dR | K | K | R | dR | Q | A | R | dR $CONH_2$ |
| 57 | 6 | $H_2N$ | dR | K | K | R | dR | Q | R | A | dR $CONH_2$ |
| 58 | 7 | $H_2N$ | dR | D | K | R | dR | Q | R | R | dR $CONH_2$ |
| 59 | 8 | $H_2N$ | dR | K | D | R | dR | Q | R | R | dR $CONH_2$ |
| 60 | 9 | $H_2N$ | dR | K | K | D | dR | Q | R | R | dR $CONH_2$ |
| 61 | 10 | $H_2N$ | dR | K | K | R | dR | D | R | R | dR $CONH_2$ |
| 62 | 11 | $H_2N$ | dR | K | K | R | dR | Q | D | R | dR $CONH_2$ |
| 63 | 12 | $H_2N$ | dR | K | K | R | dR | Q | R | D | dR $CONH_2$ |
| 64 | 13 | $H_2N$ | dR | E | K | R | dR | Q | R | R | dR $CONH_2$ |
| 65 | 14 | $H_2N$ | dR | K | E | R | dR | Q | R | R | dR $CONH_2$ |
| 66 | 15 | $H_2N$ | dR | K | K | E | dR | Q | R | R | dR $CONH_2$ |
| 67 | 16 | $H_2N$ | dR | K | K | R | dR | E | R | R | dR $CONH_2$ |
| 68 | 17 | $H_2N$ | dR | K | K | R | dR | Q | E | R | dR $CONH_2$ |
| 69 | 18 | $H_2N$ | dR | K | K | R | dR | Q | R | E | dR $CONH_2$ |
| 70 | 19 | $H_2N$ | dR | F | K | R | dR | Q | R | R | dR $CONH_2$ |
| 71 | 20 | $H_2N$ | dR | K | F | R | dR | Q | R | R | dR $CONH_2$ |
| 72 | 21 | $H_2N$ | dR | K | K | F | dR | Q | R | R | dR $CONH_2$ |
| 73 | 22 | $H_2N$ | dR | K | K | R | dR | F | R | R | dR $CONH_2$ |
| 74 | 23 | $H_2N$ | dR | K | K | R | dR | Q | F | R | dR $CONH_2$ |
| 75 | 24 | $H_2N$ | dR | K | K | R | dR | Q | R | F | dR $CONH_2$ |
| 76 | 25 | $H_2N$ | dR | R | K | R | dR | Q | R | R | dR $CONH_2$ |
| 77 | 26 | $H_2N$ | dR | K | R | R | dR | Q | R | R | dR $CONH_2$ |
| 78 | 27 | $H_2N$ | dR | K | K | K | dR | Q | R | R | dR $CONH_2$ |

TABLE 4-continued

Transporter sequence tested in uptake experiments

| SEQ ID NO: | peptide No: abbreviation in FIG. 6 | | | | | | | | | |
|---|---|---|---|---|---|---|---|---|---|---|
| 79 | 28 | H₂N | dR | K | K | R | dR | R | R | R | dR CONH₂ |
| 80 | 29 | H₂N | dR | K | K | R | dR | Q | K | R | dR CONH₂ |
| 81 | 30 | H₂N | dR | K | K | R | dR | Q | R | K | dR C0NH₂ |
| 82 | 31 | H₂N | dR | H | K | R | dR | Q | R | R | dR CONH₂ |
| 83 | 32 | H₂N | dR | K | H | R | dR | Q | R | R | dR CONH₂ |
| 84 | 33 | H₂N | dR | K | K | H | dR | Q | R | R | dR CONH₂ |
| 85 | 34 | H₂N | dR | K | K | R | dR | H | R | R | dR CONH₂ |
| 86 | 35 | H₂N | dR | K | K | R | dR | Q | H | R | dR CONH₂ |
| 87 | 36 | H₂N | dR | K | K | R | dR | Q | R | H | dR CONH₂ |
| 88 | 37 | H₂N | dR | I | K | R | dR | Q | R | R | dR CONH₂ |
| 89 | 38 | H₂N | dR | K | I | R | dR | Q | R | R | dR CONH₂ |
| 90 | 39 | H₂N | dR | K | K | I | dR | Q | R | R | dR CONH₂ |
| 91 | 40 | H₂N | dR | K | K | R | dR | I | R | R | dR CONH₂ |
| 92 | 41 | H₂N | dR | K | K | R | dR | Q | I | R | dR CONH₂ |
| 93 | 42 | H₂N | dR | K | K | R | dR | Q | R | I | dR CONH₂ |
| 94 | 43 | H₂N | dR | L | K | R | dR | Q | R | R | dR CONH₂ |
| 45 | 44 (D-TAT) | H₂N | dR | dR | dR | dQ | dR | dR | dK | dK | dR CONH₂ |
| 47 | 45 (r3-L-TATi) | H₂N | dR | R | R | Q | dR | R | K | K | dR CONH₂ |
| 46 | 46 (r3-L-TAT) | H₂N | dR | K | K | R | dR | Q | R | R | dR CONH₂ |
| 43 | 47 (L-TAT) | H₂N | R | K | K | R | Q | R | R | R | CONH₂ |
| 99 | 48 | H₂N | dR | K | K | R | dR | Q | R | L | dR CONH₂ |
| 100 | 49 | H₂N | dR | M | K | R | dR | Q | R | R | dR CONH₂ |
| 101 | 50 | H₂N | dR | K | M | R | dR | Q | R | R | dR CONH₂ |
| 102 | 51 | H₂N | dR | K | K | M | dR | Q | R | R | dR CONH₂ |
| 103 | 52 | H₂N | dR | K | K | R | dR | M | R | R | dR CONH₂ |
| 104 | 53 | H₂N | dR | K | K | R | dR | Q | M | R | dR CONH₂ |
| 105 | 54 | H₂N | dR | K | K | R | dR | Q | R | M | dR CONH₂ |
| 106 | 55 | H₂N | dR | N | K | R | dR | Q | R | R | dR CONH₂ |
| 107 | 56 | H₂N | dR | K | N | R | dR | Q | R | R | dR CONH₂ |
| 108 | 57 | H₂N | dR | K | K | N | dR | Q | R | R | dR CONH₂ |
| 109 | 58 | H₂N | dR | K | K | R | dR | N | R | R | dR CONH₂ |
| 110 | 59 | H₂N | dR | K | K | R | dR | Q | N | R | dR CONH₂ |
| 111 | 60 | H₂N | dR | K | K | R | dR | Q | R | N | dR CONH₂ |
| 112 | 61 | H₂N | dR | Q | K | R | dR | Q | R | R | dR CONH₂ |
| 113 | 62 | H₂N | dR | K | Q | R | dR | Q | R | R | dR CONH₂ |
| 114 | 63 | H₂N | dR | K | K | Q | dR | Q | R | R | dR CONH₂ |
| 115 | 64 | H₂N | dR | K | K | R | dR | K | R | R | dR CONH₂ |
| 116 | 65 | H₂N | dR | K | K | R | dR | Q | Q | R | dR CONH₂ |
| 117 | 66 | H₂N | dR | K | K | R | dR | Q | R | Q | dR CONH₂ |
| 118 | 67 | H₂N | dR | S | K | R | dR | Q | R | R | dR CONH₂ |
| 119 | 68 | H₂N | dR | K | S | R | dR | Q | R | R | dR CONH₂ |
| 120 | 69 | H₂N | dR | K | K | S | dR | Q | R | R | dR CONH₂ |
| 121 | 70 | H₂N | dR | K | K | R | dR | S | R | R | dR CONH₂ |
| 122 | 71 | H₂N | dR | K | K | R | dR | Q | S | R | dR CONH₂ |
| 123 | 72 | H₂N | dR | K | K | R | dR | Q | R | S | dR CONH₂ |
| 124 | 73 | H₂N | dR | T | K | R | dR | Q | R | R | dR CONH₂ |
| 125 | 74 | H₂N | dR | K | T | R | dR | Q | R | R | dR CONH₂ |
| 126 | 75 | H₂N | dR | K | K | T | dR | Q | R | R | dR CONH₂ |
| 127 | 76 | H₂N | dR | K | K | R | dR | T | R | R | dR CONH₂ |
| 128 | 77 | H₂N | dR | K | K | R | dR | Q | T | R | dR CONH₂ |
| 129 | 78 | H₂N | dR | K | K | R | dR | Q | R | T | dR CONH₂ |
| 130 | 79 | H₂N | dR | V | K | R | dR | Q | R | R | dR CONH₂ |
| 131 | 80 | H₂N | dR | K | V | R | dR | Q | R | R | dR CONH₂ |
| 132 | 81 | H₂N | dR | K | K | V | dR | Q | R | R | dR CONH₂ |
| 133 | 82 | H₂N | dR | K | K | R | dR | V | R | R | dR CONH₂ |
| 134 | 83 | H₂N | dR | K | K | R | dR | Q | V | R | dR CONH₂ |
| 135 | 84 | H₂N | dR | K | K | R | dR | Q | R | V | dR CONH₂ |
| 136 | 85 | H₂N | dR | W | K | R | dR | Q | R | R | dR CONH₂ |
| 137 | 86 | H₂N | dR | K | W | R | dR | Q | R | R | dR CONH₂ |
| 138 | 87 | H₂N | dR | K | K | W | dR | Q | R | R | dR CONH₂ |
| 139 | 88 | H₂N | dR | K | K | R | dR | W | R | R | dR CONH₂ |
| 140 | 89 | H₂N | dR | K | K | R | dR | Q | W | R | dR CONH₂ |
| 141 | 90 | H₂N | dR | K | K | R | dR | Q | R | W | dR CONH₂ |
| 142 | 91 | H₂N | dR | Y | K | R | dR | Q | R | R | dR CONH₂ |
| 143 | 92 | H₂N | dR | K | Y | R | dR | Q | R | R | dR CONH₂ |
| 144 | 93 | H₂N | dR | K | K | Y | dR | Q | R | R | dR CONH₂ |
| 145 | 94 | H₂N | dR | K | K | R | dR | Y | R | R | dR CONH₂ |
| 146 | 95 | H₂N | dR | K | K | R | dR | Q | Y | R | dR CONH₂ |
| 147 | 96 | H₂N | dR | K | K | R | dR | Q | R | Y | dR CONH₂ |

In the above table D amino acids are indicated by a small "d" prior to the respective amino acid residue (e.g. dR=D-Arg).

For a few sequences synthesis failed in the first approach unfortunately due to technical reasons. These sequences are abbreviated in FIG. 6 as 1, 2, 3, 4, 5, 6, 7, 8, 43, 52, 53, 54, 55, 56, 57, 85, 86, 87, 88, 89, and 90. However, the remaining sequences were used in the internalization experiments.

The results are shown in FIG. 6.

As can be seen in FIG. 6, after 24 hours incubation, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the r3-L-TAT-derived transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction As can be seen in FIG. 6, one positions appears to be critical for highest transporter activity and for improved kinetics of transport activity: Y in position 2 (peptide N° 91 corresponding to SEQ ID NO: 142).

The conclusion of this experiment is as follows:

After 24 hours incubation, all transporters with the consensus sequence rXXXrXXXr (SEQ ID NO: 31) (see Table 2 for a selection of possible sequences) showed a higher internalization capability than the L-TAT transporter (SEQ ID NO: 43) (FIG. 6). Those results fully validate the consensus sequence rXXXrXXXr (SEQ ID NO: 31).

One position is critical for highest transporter activity and (FIG. 6): Y in position 2 (sequence 91 corresponding to SEQ ID NO: 142).

Accordingly, such TAT derived sequences as shown in Table 4 are preferred, which exhibit a Y in position 2, particularly when the sequence exhibits 9 aa and has the consensus sequence rXXXrXXXr (SEQ ID NO: 31).

Example 4: Measurement of Cytokine and Chemokine Release

In the following the procedure will be set forth describing how the released amount of several human cytokines after ligand induced secretion from human cells (Blood, WBC, PBMC, purified primary lymphocytes, cell lines, . . . ) was measured.

The technique used is a Sandwich ELISA, which allows measuring the amount of antigen between two layers of antibodies (i.e. capture and detection antibody). The antigen to be measured must contain at least two antigenic sites capable of binding to antibody, since at least two antibodies act in the sandwich. Either monoclonal or polyclonal antibodies can be used as the capture and detection antibodies in Sandwich ELISA systems. Monoclonal antibodies recognize a single epitope that allows fine detection and quantification of small differences in antigen. A polyclonal is often used as the capture antibody to pull down as much of the antigen as possible. The advantage of Sandwich ELISA is that the sample does not have to be purified before analysis, and the assay can be very sensitive (up to 2 to 5 times more sensitive than direct or indirect).

The method may be used to determine the effect of the JNK inhibitors of the present invention in vitro/cell culture. At non toxic doses, compound efficacy is indicated by the decrease of the cytokine levels (the variation of optical density (absorbance at 450 nm)) as compared to non-treated samples and is monitored by ELISA. Results are express in ng/ml.

4.1 Material 96 well plate:
  for collecting the supernatants (Ref 82.1581, Sarstedt)
  for ELISA (F96 maxisorp, Ref 442404, Nunc)
TopSeal-A: 96 well microplate seals (Ref 600585, PerkinElmer).
ELISA reagent
  Coating buffer ELISA: 0.1M NaCarbonate pH 9.5 (=7.13 g $NaHCO_3$ (ref 71627, Fluka)+1.59 g $Na_2CO_3$ (ref 71345, Fluka) in 1 litre H2O, pH to 9.5 with NaOH concentrated)
  Wash buffer ELISA: PBS 1×+0.01% Tween20. Prepare 1 litre PBS 1×(PBS10×: ref 70011, GIBCO) and add 100 ul of Tween20 (ref P1379, Sigma) slowly while mixing with magnetic agitator)
  Assay diluent: PBS 1X+10% FBS (Ref A15-151, PAA, decomplemented at 56° C., 30 min).
  DAKO TMB (ref S1599, DAKO): commercial substrate solution
  Stop Solution: 1M $H_3PO_4$ (→for 200 ml=177 ml $H_2O$+ 23 ml $H_3PO_4$ 85% (ref 345245, Aldrich).
ELISA Kit (reagent for 20 plates)
  IFN-γ: Human IFN-☐ ELISA set, BD OptEIA™ (ref 555142, DB).
  IL-1β: Human IL-1☐ ELISA set II, BD OptEIA™ (ref 557953, BD)
  IL-10: Human IL-10 ELISA set II, BD OptEIA™ (ref 555157, DB).
  IL-12: Human IL-12 (p70) ELISA set, BD OptEIA™ (ref 555183, DB).
  IL-15: Human IL-15 ELISA Set, BD OptEIA™ (ref 559268, DB).
  IL-2: Human IL-2 ELISA set, BD OptEIA™ (ref 555190, DB).
  IL-4: Human IL-4 ELISA set, BD OptEIA™ (ref 555194, DB).
  IL-5: Human IL-5 ELISA set, BD OptEIA™ (ref 555202, DB).
  IL-6: Human IL-6 ELISA setI, BD OptEIA™ (ref 555220, DB).
  IL-8: Human IL-8 ELISA set, BD OptEIA™ (ref 555244, DB).
  MCP-1: Human MCP-1 ELISA set, BD OptEIA™ (ref 555179, BD)
  TNF-α: Kit human TNF ELISA set, BD OptEIA™ (ref 555212, DB).
Absorbance reading: The absorbance was read on the Fusion Alpha Plate reader (Perkin Elmer).
Repeating pipettes, digital pipettes or multichannel pipettes.

4.2 Method

Preparation of the Samples

The samples are culture medium supernatant from cultured human cells (typically whole blood, WBC, PBMC, Purified subtype of WBC, cancerous cell lines). Remove any particulate material by centrifugation (400 g 5 min 4° C.) and assay immediately or store samples at ≤−20° C. Avoid repeated freeze-thaw cycles.

One hour before using, defrost the samples on ice and centrifuge them. At step 11, dilute the samples in assay diluent directly into the plate (add first assay diluent, then the samples and pipette up and down):

Preparation of Standard

After warming lyophilized standard to room temperature, carefully open vial to avoid loss of material. Reconstitute lyophilized standard with the proposed volume of deionized water to yield a stock standard. Allow the standard to equilibrate for at least 15 minutes before making dilutions. Vortex gently to mix. After reconstitution, immediately aliquot standard stock in polypropylene vials at 50 ☐l per vial and freeze at −20° C. for up to 6 months. If necessary, store at 2-8° C. for up to 8 hours prior to aliquotting/freezing. Do not leave reconstituted standard at room temperature. Immediately before use, prepare a ten point standard curve using 2-fold serial dilutions in reagent Diluent. A high standard of 4000 pg/ml is recommended.

Preparation of Detector Mix

One-step incubation of Biotin/SAv reagents. Add required volume of Detection Antibody to Assay Diluent. Within 15 minutes prior to use, add required quantity of Enzyme Reagent, vortex or mix well. For recommended dilutions, see lot-specific Instruction/Analysis Certificate. Discard any remaining Working Detector after use.

Coating with Capture Antibody

1. Coat the wells of a PVC microtiter plate with 100 ☐L per well of Capture Antibody diluted in Coating Buffer. For recommended antibody coating dilution, see lot-specific Instruction/Analysis Certificate.
2. Cover the plate with an adhesive plastic and incubate overnight at 4° C.
3. Remove the coating solution and wash the plate by filling the wells with 150 ☐l wash buffer.
4. The solutions or washes are removed by flicking the plate over a sink.
5. Repeat the process two times for a total of three washes.
6. After the last wash, remove any remaining wash buffer by patting the plate on a paper towel.

Blocking

7. Block the remaining protein-binding sites in the coated wells by adding 100 ☐l reagent Diluent per well.
8. Cover the plate with an adhesive plastic and incubate for 1 h at room temperature.
9. During the incubation, start preparing the standard.

Adding Samples

10. Do one wash as in step 3 with 150 ☐l of wash buffer. The plates are now ready for sample addition.
11. Add 50 ☐l of appropriately diluted samples in assay diluent to each well. For accurate quantitative results, always compare signal of unknown samples against those of a standard curve. Standards (triplicates) and blank must be run with each cytokine to ensure accuracy.

12. Cover the plate with an adhesive plastic and incubate for 2 h at room temperature.

Incubation with Detection Antibody and Secondary Antibody

13. Wash the plate four times with 150 µl wash buffer like step 3.
14. Add 50 □l of detector MIX (detection antibody+ Secondary Streptavidin-HRP antibody in assay diluent) to each well at recommended dilutions (see lot-specific Instruction/Analysis Certificate).
15. Cover the plate with an adhesive plastic and incubate for 1 h at room temperature light protect.
16. Wash the plate six times with 150 µl wash buffer as in step 3.
17. Add 50 □l DAKO TMB solution to each well, incubate for 15-20 min at room temperature, in the dark, not sealed.
18. Add 50 □l of stop solution to each well. Gently tap the plate to ensure thorough mixing.
19. Mix the plate 5 min at 500 rpm on a plate mixer.
20. Read the optical density at 450 nm. (Program: Cytokine_ELISA on Fusion Alpha Plate reader).

Data Analysis

Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoided using Grugg's test. Then the data which weren't in the interval of two times the SD, were discard. The independent experiments are taken into account if the positive control showed data as previously observed. The independent experiments are pooled (N>3).

The data are presented in pg/ml of cytokine release or in %, compared to the induced condition without inhibitor treatment.

Example 5: THP1 Differentiation—Stimulation for Cytokine Release

In the following the procedure will be set forth describing how cytokine production from human PMA differentiated THP1 cells challenged by LPS for 6 h was induced in order to test the ability of JNK inhibitors of the present invention, in particular of a JNK inhibitor with SEQ ID NO: 172, to reduce stimulation-induced cytokine release. THP1 cells were stimulated ex-vivo by different ligands for the readout of cytokine release. At non toxic doses, JNK inhibitor efficacy is indicated by the decrease of the cytokine levels as compared to non-treated samples and is monitored by ELISA. The toxicity of the compound are evaluated by the reduction of a tretazolium salt (MTS) to formazan, giving a purple colour.

Procedure:

a. Material

Cell Line: THP-1 (Ref TIB-202, ATCC, lot 57731475)
Culture medium, reagent and plates
RPMI (Ref 21875-091, Invitrogen) complemented with:
10% FBS (Ref A15-151, PAA): decomplemented at 56° C., 30 min.
10 mM Hepes (Ref H0887, Sigma)
50 µM β-mercaptoethanol (Ref 63690, Fluka: stock at 14.3M): add 560 µl of 50 mM aliquots in PBS stocked at −20° C.)
1 mM Sodium Pyruvate (Ref 58636, Sigma)
Penicilline (100 unit/ml)/Streptomycine (100 µg/ml) (Ref P4333, Sigma)
The RPMI medium is then filtrated with a 0.22 µM filter (Ref SCGPU05RE, Millipore).
PBS 10× (Ref 70011, Invitrogen): diluted to 1× with sterile $H_2O$
DMSO: Ref 41444, Fluka
PMA (phorbol 12-myristate 13-acetate, Ref P1585, Sigma, concentration 1 mM=616.8 ug/ml in DMSO at −20° C.). Use directly at a final concentration of 100 nM in RPMI (1 ul in 10 ml of medium).
LPS ultrapure (Lipopolysaccharide, Ref tlrl-eklps, Invivogen, concentration 5 mg/ml): Stock solution of LPS: 3 µg/ml in PBS at 4° C. Use directly to prepare a 4× concentrated solution of 40 ng/ml in RPMI medium (min 1800 µl/plate; for 5 plates: 125 µl of LPS 3 µg/ml+9250 µl RPMI).
96 well plate:
for adherent cell culture (Ref 167008, Nunc)
for collecting the supernatants (Ref 82.1581, Sarstedt)
for ELISA (F96 maxisorp, Ref 442404, Nunc)
Coating solutions: poly-D-lysine (Ref P9011, Sigma): 25 µg/ml final diluted in PBS 1×
ELISA reagent and kits
Coating buffer ELISA: 0.1M NaCarbonate pH 9.5 (=7.13 g $NaHCO_2$ (ref 71627, Fluka)+1.59 g $Na_2CO_3$ (ref 71345, Fluka) in 1 liter H2O, pH to 9.5 with NaOH concentrated)
Wash buffer ELISA: PBS 1X+0.01% Tween20 (ref P1379, Sigma, lot 094K0052)(=prepare 1 liter PBS 1× and add 100 ul of Tween20 slowly while mixing with magnetic agitator)
Assay diluent: PBS 1X+10% FBS (Ref A15-151, PAA, decomplemented at 56° C., 30 min).
DAKO TMB (ref S1599, DAKO): commercial substrate solution
Stop Solution: 1M $H_3PO_4$ (→for 200 ml=177 ml $H_2O$+23 ml $H_3PO_4$85% (ref 345245, Aldrich).
TNF-α: Kit human TNF ELISA set, BD OptEIA (ref 555212, DB).
Cytotoxicity measurement: CellTiter 96 reagent (ref G3581, Promega)
Control compound: SP600125 (ref ALX-270-339-M025, Alexis, concentration: 20 mM DMSO)
Absorbance reading: The absorbance was read on the Fusion Alpha Plate reader (Perkin Elmer).
Repeating pipettes, digital pipettes or multichannel pipettes.
TopSeal-A: 96 well microplate seals (Ref 600585, PerkinElmer).

b. Method

Well Coating

The plates had been coated with 200 µl of poly D-Lysine (1×) and incubated 2 hours at 37° C., $CO_2$ 5% and 100% relative humidity.

Cell Plating

After 2 hours the wells were washed twice with 200 µl PBS 1× (use immediately or leave with 200 □l of PBS 1× at 37° C. till use, but no more than 3 days).

The cells were counted. The desired number of cells was taken and resuspended in the amount of media necessary to get a dilution of 1,000,000 cells/ml. 100 nM of PMA was added to induce the differentiation of the THP1 from suspension monocytes to adherent macrophages. The cells were plated into the wells in 100 µl medium at plating densities of 100,000 cells/well. After inoculation, the plates were incubated at 37° C., 5% CO2 and 100% relative humidity 3 days to let them differentiate, prior to the addition of experimental drugs.

Cell Treatment

After 3 days, the adherent cells were observed with the microscope. The media containing PMA was aspirated and replaced by 100 µl of fresh RPMI media without PMA (no washing step with PBS 1×). Experimental drug were prepared at the concentration of 10 mM in $H_2O$ or DMSO and stored at −80° C. Prior to each daily use, one aliquot of JNK inhibitor was defrosted and diluted to reach a 4× concentrated solution (120 µM) in RPMI medium and then to the desired concentration in RPMI. The SP600125 was diluted to reach a 4× concentrated solution (40 µM) in RPMI medium and then to the desired concentration in RPMI containing 0.8% DMSO.

The plates were treated with 50 µl of medium or a solution of 4× the final desired drug concentration (0, 100 nM, 1, 3, 10 or 30 µM final for JNK compound or at 0, 10, 100 nM, 1, 3 or 10 µM final for the SP600125 positive control). Following drug addition, the plates were incubated for an additional 1 h at 37° C., 5% $CO_2$ and 100% relative humidity.

After 1 hour, the secretion of TNFα was induced by the addition of 50 µl of a 4× concentrated dilution of LPS ultrapure (3 ng/ml final).

Assay

After 6 hours, 100 µl of the supernatant were transferred to new 96 well plates. Those plates were sealed and stored at −20° till the analysis by ELISA (e.g. see example 4) of the secretion of the cytokines.

The cytotoxic effect of the compounds was evaluated by MTS absorbance (e.g. see example 4) and cells were observed using an inverted microscope (Axiovert 40 CFL; Zeiss; 10×).

Data Analysis

Analyses of the data are performed as indicated in the ELISA (see example 4). Briefly, for ELISA: Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoid using Grugg's test. Then the data which weren't in the interval of two times the SD, were discard. The independent experiments are taken into account if the positive control showed data as previously observed. The independent experiments are pooled (N>3).

For the Cytotoxicity effect evaluation: on each plate of each independent experiment taken into account for the cytokine release experiment analysis, the average of the absorbance of the medium alone was considerate as the background and subtracted to each absorbance value. The average of triplicate of the non treated cells of each compound was considerate as the 100% viability. The average of triplicate of each compound was normalized by its 100%. The outliers data were avoid using Grugg's test. Then the data which weren't in the interval of two times the SD, were discard. The independent experiments are pooled (N>3).

All statistical comparisons of conditions were performed by the GraphPad Prism4 software with the following test:

One way ANOVA test followed by a Tukey's Multiple Comparison Test. P<0.05 was considerate as significant.

Example 6: JNK Inhibitor of SEQ ID NO: 172 and TNFα Release in Primary Rat or Human Whole Blood Cells Whole blood is collected from anesthetized rat or human healthy volunteers using a venipuncture connected to a pre-labeled vacuum tube containing sodium citrate. Tubes are gently mixed by inversion 7-8 times; and are then kept at RT until stimulation. JNK inhibitor of SEQ ID NO: 172_is prepared 6 times concentrated in PBS, and 30 µl/well of mix is added into 96-well plate. Whole blood is diluted by 1:2 in PBS and 120 µl of diluted blood is added in each well where either PBS alone or JNK inhibitor of SEQ ID NO: 172 has been previously added. Whole blood is incubated at 37° C.; 85 rpm (Stuart Orbital incubator S1500) for 60 min. Activators (LPS) are the prepared, 30 µl/well of LPS, 6 times concentrated. After 60 min incubation, LPS is added to the blood, blood is mixed by pipetting up and down, and then kept for 4 h under agitation (85 rpm), at 37° C. After the 4 h incubation, the plates are centrifuged at about 770 g, 4° C. for 15 min in a pre-cooled centrifuge. Supernatants are finally collected and kept at −20° C. until cytokine measurement. Cytokine (IL-6, IL-2, IFNγ and TNFα) were then measured using standard Elisa kits (e.g. from R&D Systems: DuoSet Elisas; or from BD Biosciences: BD Opteia Set Elisa). Results are expressed as pg/ml of supernatant of the measured cytokine.

A similar experiment was conducted with PMA+ionomycin instead of LPS as activator/stimulant.

Example 7: Half-Life of Specific JNK Inhibitors Disclosed Herein

The JNK inhibitors with the sequence of SEQ ID NOs: 196, 197, and 172 (0.1 mM final concentration) were digested in human serum (10 and 50% in PBS 1×). The experiment was performed as described by Tugyi et al. (Proc Natl Acad Sci USA, 2005, 413-418). The remaining intact peptide was quantified by UPLC-MS. Stability was assessed for SEQ ID NOs: 196, 197, and 172 identically but in two separate assays. While the JNK inhibitor with SEQ ID NO: 196 was totally degraded into amino acids residues within 6 hours, the JNK inhibitor with SEQ ID NO: 172 was completely degraded only after 14 days. The JNK inhibitor with SEQ ID NO: 197 was still stable after 30 days.

Example 8: Dose-Dependent Inhibition by JNK Inhibitor with Sequence of SEQ ID NO: 172 of CD3/CD28-Induced IL-2 Release in Rat Primary T-Cells Control animal were sacrificed, lymph nodes (LN) were harvested and kept in complete RPMI medium. LN were smashed with complete RPMI on 70 µm filter using a 5 ml piston. A few drops of media were added to keep strainer wet. Cells were centrifuged for 7 min at 450 g and 4° C. Pellet was resuspended in 5 ml fresh medium. Cells were passed again through cell strainer. An aliquot of cells was counted, while cells were centrifuged again 10 min at 1400 rpm and 4° C. Cells were resuspended in MACS buffer (80 µl of MACS buffer per $10^7$ cells). 10 µl of anti-rat MHC microbeads were added per 10 million cells, cells were incubated for 15 min at 4°-8° C. Cells were washed with 15 ml MACS buffer and centrifuge for 7 min at 700 g and 4°

C. Pellet was resuspended in 500 µl MACS buffer per $10^8$ cells. One LS column was placed in the magnetic field of the MACS separator per animal. Column was first rinsed with 3 ml of MACS buffer. One tube was placed below the column in ice to collect cells=T cells (negative selection so we collect what is eluted). Cell suspension was added and elute was collected on ice. Column was washed 3 times with 3 mL MACS buffer. Eluted T cells were centrifuges for 7 min at 700 g and 4° C. Resuspended cells were counted and plated at density of 200000 cells/well in 100 µl of complete medium. Plates were pre-coated the day before experiment with 2 µg/mL of CD3 antibody, and the day of experiment plates were washed three times with PBS. Cells were treated with 100 µl of (poly-)peptide JNK inhibitor (SEQ ID NO: 172), two times concentrated for 1 h before ligand activation. After 1 h of pretreatment with (poly-)peptide JNK inhibitor (SEQ ID NO: 172), cells were then stimulated with 2 µg/mL of anti CD28 antibody for 24 h. After 24 h of stimulation, supernatant were collected and stored at −20° C. until analysis. Cytokines were then measured using standard Elisa kits. Results are expressed as pg/ml of supernatant of the measured cytokine.

In a further experiment, essentially the same protocol as set forth above was used, but in addition to the (poly-)peptide JNK inhibitors with SEQ ID NO: 172, JNK inhibitors with the sequence of SEQ ID NO: 197 and the drug molecule SP600125 were also tested thus allowing to compare the effects of these inhibitors on the inhibition of CD3/CD28-induced IL-2 release.

Example 9: JNK Inhibitor and TNFα/IL-2 Release in Human Whole Blood

Whole blood from human healthy volunteers was collected using a venipuncture connected to a pre-labeled vacuum tube containing sodium citrate. Tubes are gently mixed by inversion 7-8 times; and are then kept at RT until stimulation. 350 µl of RPMI+P/S were added into 1.2 ml-96-well plate. 10 times concentrated of SEQ ID NO: 172 was prepared in RPMI+P/S (50 µl per well). 50 µl was added into 1.2 ml-96 well plates. 50 µl of whole blood was then added in each well where either medium alone or JNK inhibitor has been previously added. Whole blood was incubated at 37° C., 5% CO2 for 60 min. 50 µl/well of ligands diluted in RPMI+P/S was prepared, corresponding to the final dilution 10 times concentrated. After 60 min of incubation, ligand was added; wells were then mixed by pipetting up and down the blood. Whole blood was incubated for 3 days at 37° C. (wells were mixed by pipetting each well up and down once per day). At the end of incubation, plates were mixed and then centrifuged at 2500 rpm, 4° C. for 15 min in a pre-cooled centrifuge. Cytokine were then measured using standard Elisa kits. Results are expressed as pg/ml of supernatant of the measured cytokine.

A similar experiment was carried out with slight modifications. In the case of CD3/CD8 stimulation, CD3 antibody was coated at 2 µg/mL in PBS overnight at 4° C. The day of experiment, wells were washed three times with PBS and left in PBS until use at 37° C. CD28 antibody was added 1 h after SEQ ID NO: 172 at final concentration of 2 µg/mL; supernatants were collected after 3 days of stimulation.

Example 10: Anti-Inflammatory Potency in a Rat Model of Endotoxins Induced Uveitis (EIU)

The anti-inflammatory potency of the JNK inhibitor of SEQ ID NO: 172 was tested in albino rats following intravenous administration (EIU/LPS model). The aim of this study was to determine the effects of single intravenous injections of SEQ ID NO: 172 (0.015, 0.18, and 1.80 mg/kg) on the inflammatory response in an endotoxins-induced uveitis albino rat model and to compare these affects to those obtained with prior art JNK inhibitor of SEQ ID NO: 197 (2 mg/kg). As a further control served phosphate sodic dexamethasone.

Sixty (60) male Lewis rats were randomly divided into six (6) groups of ten (10) animals each. EIU was induced by footpad injection of lipopolysaccharide (LPS, 1 mg/kg). NaCl (0.9%), SEQ ID NO: 197 at 2 mg/kg and SEQ ID NO: 172 at three concentrations (1.80 mg/kg, 0.18 mg/kg and 0.015 mg/kg) were administered by intravenous injection. Phosphate sodic dexamethasone (20=g/eye) was administered by sub-conjunctival injection in both eyes. 24 hours after LPS injection, inflammatory response was evaluated by clinical scoring.

The intensity of clinical ocular inflammation was scored on a scale from 0 to 4 for each eye:
Grade 0 no inflammation
Grade 1 slight iris and conjunctival vasodilation
Grade 2 moderate iris and conjunctival vasodilation with flare
Grade 3 intense iris and conjunctival vasodilation with flare
Grade 4 intense inflammatory reaction
(+1) fibrin formation and seclusion of pupils Twenty-four hours after LPS induction, clinical scores for the vehicle-treated rats were 3.6±0.2 (mean±SEM, n=20) with a median of 4 (range, 2-5). A significant reduction (p<0.001) in the severity of the ocular inflammation was detected 24 hours after induction and intravenous treatment with SEQ ID NO: 197 (2 mg/kg) (mean score: 2.2±0.3, median: 2), corresponding to a 40% decrease of EIU scores compared with the score observed in vehicle group. Intravenous treatment with SEQ ID NO: 172, at approximately the same dose (1.80 mg/kg) reduced also significantly the severity of the ocular inflammation by 42% (mean score: 2.1±0.3, median: 2, p=0.001). The lower doses (0.18 and 0.015 mg/kg) reduced by 33% (mean score: 2.4±0.3, median: 2) and 36% (mean score: 2.3±0.3, median: 2) the inflammation, respectively. The reduction was significant with p<0.001.

A sub-conjunctival treatment with dexamethasone (20 □g/eye), used as positive control drug also significantly reduced the clinical scores by 79% (mean score: 0.8±0.2, median: 0.5, p<0.001).

Under these experimental conditions, it can be stated that a single intravenous injection of SEQ ID NO: 197 at 2 mg/kg partially prevented the endotoxin-induced inflammation observed in the anterior chamber. In comparison, SEQ ID NO: 172 intravenously injected at 0.015, 0.18, 1.80 mg/kg also reduced the endotoxin-induced inflammation in the anterior chamber.

Example 11: Dose-Responsive Effects after Intravenous Administration of JNK Inhibitor after 14 Days in a Rat Model of Chronic Established Type II Collagen Arthritis Rat collagen arthritis is an experimental model of polyarthritis that has been widely used for preclinical testing of numerous anti-arthritic agents that are either under preclinical or clinical investigation or are currently used as therapeutics in this disease. The hallmarks of this model are reliable onset and progression of robust, easily measurable polyarticular inflammation, marked cartilage destruction in association with pannus formation, and mild to moderate bone resorption and periosteal bone proliferation.

Intravenous (IV) efficacy of the JNK inhibitor of SEQ ID NO: 172 administered daily (QD) for 14 days (arthritis d1-14) for inhibition of the inflammation (paw swelling), cartilage destruction, and bone resorption that occurs in established type II collagen arthritis in rats was determined in said experimental model.

Animals (8/group for arthritis) were anesthetized with Isoflurane and injected with 300 □l of Freund's Incomplete Adjuvant (Difco, Detroit, Mich.) containing 2 mg/ml bovine type II collagen (Elastin Products, Owensville, Miss.) at the base of the tail and 2 sites on the back on days 0 and 6. On day 10 of the study (arthritis do), onset of arthritis occurred and rats were randomized into treatment groups. Randomization into each group was done after ankle joint swelling was obviously established in at least one hind paw.

Female Lewis rats with established type II collagen arthritis were treated daily (QD) on arthritis days 1-14 by the intravenous (IV) route with vehicle (NaCl), SEQ ID NO: 172 (0.01, 0.1, 1, or 5 mg/kg), or the reference compound dexamethasone (Dex, 0.05 mg/kg). Animals were terminated on arthritis day 14. Efficacy evaluation was based on animal body weights, daily ankle caliper measurements, ankle diameter expressed as area under the curve (AUC), terminal hind paw weights, and histopathologic evaluation of ankles and knees of selected groups.

Scoring of Joints Collagen arthritic ankles and knees are given scores of 0-5 for inflammation, pannus formation and bone resorption according to the following criteria:

Knee and/or Ankle Inflammation
0 Normal
0.5 Minimal focal inflammation
1 Minimal infiltration of inflammatory cells in synovium/periarticular tissue
2 Mild infiltration
3 Moderate infiltration with moderate edema
4 Marked infiltration with marked edema
5 Severe infiltration with severe edema
Ankle Pannus
0 Normal
0.5 Minimal infiltration of pannus in cartilage and subchondral bone, affects only marginal zones and affects only a few joints
1 Minimal infiltration of pannus in cartilage and subchondral bone, primarily affects marginal zones
2 Mild infiltration (<¼ of tibia or tarsals at marginal zones)
3 Moderate infiltration (¼ to ⅓ of tibia or small tarsals affected at marginal zones)
4 Marked infiltration (½ to ¾ of tibia or tarsals affected at marginal zones)
5 Severe infiltration (>¾ of tibia or tarsals affected at marginal zones, severe distortion of overall architecture)
Knee Pannus
0 Normal
0.5 Minimal infiltration of pannus in cartilage and subchondral bone, affects only marginal zones and affects only a few joints
1 Minimal infiltration of pannus in cartilage and subchondral bone, approximately 1-10% of cartilage surface or subchondral bone affected
2 Mild infiltration (extends over up to ¼ of surface or subchondral area of tibia or femur), approximately 11-25% of cartilage surface or subchondral bone affected
3 Moderate infiltration (extends over >¼ but <½ of surface or subchondral area of tibia or femur) approximately 26-50% of cartilage surface or subchondral bone affected
4 Marked infiltration (extends over ½ to ¾ of tibial or femoral surface) approximately 51-75% of cartilage surface or subchondral bone affected
5 Severe infiltration approximately 76-100% of cartilage surface or subchondral bone affected
Ankle Cartilage Damage (Emphasis on Small Tarsals)
0 Normal
0.5 Minimal decrease in T blue staining, affects only marginal zones and affects only a few joints
1 Minimal=minimal to mild loss of toluidine blue staining with no obvious chondrocyte loss or collagen disruption
2 Mild=mild loss of toluidine blue staining with focal mild (superficial) chondrocyte loss and/or collagen disruption
3 Moderate=moderate loss of toluidine blue staining with multifocal moderate (depth to middle zone) chondrocyte loss and/or collagen disruption, smaller tarsals affected to ½ to ¾ depth with rare areas of full thickness loss
4 Marked=marked loss of toluidine blue staining with multifocal marked (depth to deep zone) chondrocyte loss and/or collagen disruption, 1 or 2 small tarsals surfaces have full thickness loss of cartilage
5 Severe=severe diffuse loss of toluidine blue staining with multifocal severe (depth to tide mark) chondrocyte loss and/or collagen disruption affecting more than 2 cartilage surfaces
Knee Cartilage Damage
0 Normal
0.5 Minimal decrease in T blue staining, affects only marginal zones
1 Minimal=minimal to mild loss of toluidine blue staining with no obvious chondrocyte loss or collagen disruption
2 Mild=mild loss of toluidine blue staining with focal mild (superficial) chondrocyte loss and/or collagen disruption, may have few small areas of 50% depth of cartilage affected
3 Moderate=moderate loss of toluidine blue staining with multifocal to diffuse moderate (depth to middle zone) chondrocyte loss and/or collagen disruption, may have 1-2 small areas of full thickness loss affecting less than ¼ of the total width of a surface and not more than 25% of the total width of all surfaces
4 Marked=marked loss of toluidine blue staining with multifocal to diffuse marked (depth to deep zone) chondrocyte loss and/or collagen disruption or 1 surface with near total loss and partial loss on others, total overall loss less than 50% of width of all surfaces combined
5 Severe=severe diffuse loss of toluidine blue staining with multifocal severe (depth to tide mark) chondrocyte loss and/or collagen disruption on both femurs and/or tibias, total overall loss greater than 50% of width of all surfaces combined Ankle Bone Resorption
0 Normal
0.5 Minimal resorption affects only marginal zones and affects only a few joints
1 Minimal=small areas of resorption, not readily apparent on low magnification, rare osteoclasts
2 Mild=more numerous areas of resorption, not readily apparent on low magnification, osteoclasts more numerous, <¼ of tibia or tarsals at marginal zones resorbed ☐
3 Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4 Marked=Full thickness defects in cortical bone, often with distortion of profile of remaining cortical surface, marked loss of medullary bone, numerous osteoclasts, ½ to ¾ of tibia or tarsals affected at marginal zones
5 Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture Knee Bone Resorption
0 Normal
0.5 Minimal resorption affects only marginal zones
1 Minimal=small areas of resorption, not readily apparent on low magnification, approximately 1-10% of total joint width of subchondral bone affected
2 Mild=more numerous areas of resorption, definite loss of subchondral bone, approximately 11-25% of total joint width of subchondral bone affected
3 Moderate=obvious resorption of subchondral bone approximately 26-50% of total joint width of subchondral bone affected
4 Marked=obvious resorption of subchondral bone approximately 51-75% of total joint width of subchondral bone affected
5 Severe=distortion of entire joint due to destruction approximately 76-100% of total joint width of subchondral bone affected Results:

Disease severity in the disease control group increased from days 1 to 5 with day 4-5 having the greatest daily increase. Then the incremental increases were smaller to the peak at day 7. From that point forward, acute swelling generally decreased and calliper measures were decreased. The treatment groups followed this general pattern as well.

Body weight loss was observed in all disease groups whereas the normal control group had a weight increase. Body weight loss was significantly (25%, $p<0.05$ by ANOVA) inhibited for rats treated with 5 mg/kg SEQ ID NO: 172 as compared to vehicle treated disease controls. When compared to disease controls using a Student's t-test, inhibition of body weight loss was also significant for rats treated with 1 mg/kg SEQ ID NO: 172 (21%, $p<0.05$) or Dex (21%, $p<0.05$). Results of treatment with SEQ ID NO: 172 were dose responsive for this parameter.

Daily ankle diameter measurements were significantly ($p<0.05$ by 2-way RM ANOVA) reduced toward normal for rats treated with 5 mg/kg SEQ ID NO: 172 ($p<0.05$ days 4-12) or Dex ($p<0.05$ d3-14) as compared to disease controls.

Ankle diameter AUC was significantly ($p<0.05$ by ANOVA) reduced toward normal for rats treated with 5 mg/kg SEQ ID NO: 172 (43% reduction), 1 mg/kg SEQ ID NO: 172 (27%), or Dex (97%) as compared to disease controls. Results of treatment with SEQ ID NO: 172 were dose responsive for this parameter.

Final paw weights were significantly ($p<0.05$ by ANOVA) reduced toward normal for rats treated with 5 mg/kg SEQ ID NO: 172 (26% reduction) or Dex (114%) as compared to disease controls. Results of treatment with SEQ ID NO: 172 were dose responsive for this parameter.

Relative liver weights were not significantly (by ANOVA) affected for rats in any treatment group as compared to disease controls.

Spleen weights relative to body weight were significantly ($p<0.05$ by ANOVA) reduced for rats treated with Dex as compared to disease controls. Relative spleen weights for Dex treated rats were also significantly reduced as compared to normal controls. Relative spleen weights were not significantly affected for rats treated with SEQ ID NO: 172.

Thymus weights relative to body weight were significantly ($p<0.05$ by ANOVA) reduced for rats treated with Dex as compared to disease controls. Relative thymus weights for Dex treated rats were also significantly reduced as compared to normal controls. Relative thymus weights were not significantly affected for rats treated with SEQ ID NO: 172.

All ankle histopathology parameters were significantly (by Mann-Whitney U test) reduced toward normal for rats treated with 5 mg/kg SEQ ID NO: 172 (25% reduction of summed scores) as compared to disease controls.

All knee histopathology parameters were significantly (by Mann-Whitney U test) reduced toward normal for rats treated with 5 mg/kg SEQ ID NO: 172 (73% reduction of summed scores) as compared to disease controls.

Results of this study indicated that daily intravenous treatment with SEQ ID NO: 172 (5 mg/kg) had significant beneficial effect on the clinical and histopathology parameters associated with established type II collagen arthritis in rats. Treatment with SEQ ID NO: 172 (1 mg/kg) resulted in significantly reduced ankle diameter AUC. The beneficial effect on ankle diameter was observed up to day 12 despite the reduction of swelling after day 7 in disease control animals. Results of treatment with SEQ ID NO: 172 were dose responsive.

Treatment with SEQ ID NO: 172 had no adverse effect on organ weights unlike dexamethasone.

Example 12: Effect of the all-D-Retro-Inverso JNK-Inhibitor (Poly-)Peptide of SEQ ID NO: 197 and the JNK Inhibitor (Poly-)Peptide of SEQ ID NO: 172 at Three Doses in a Scopolamine-Induced Model of Dry Eye in Mice Study Concept The objective of this study was to assess the effects of two different compounds, the all-D-retro-inverso JNK-inhibitor (poly-)peptide of SEQ ID NO: 197 and the JNK inhibitor (poly-)peptide of SEQ ID NO: 172, at three dose levels in a mouse model of scopolamine-induced dry eye.

The peptides of SEQ ID NO: 197 and SEQ ID NO: 172 were tested for efficacy in this murine model of dry eye. The peptides were both tested at a low, medium and a high dose. For the peptide of SEQ ID NO: 197 the concentrations measured in the formulation samples for low, medium and high dose levels were 0.06% (w/v), 0.25% (w/v) and 0.6% (w/v), respectively, and for SEQ ID NO: 172 the concentrations measured in the formulation samples for the low, medium and high dose levels, were 0.05% (w/v), 0.2% (w/v)

and 0.6% (w/v), respectively. The vehicle, which also served as the negative control, was 0.9% Sodium Chloride for Injection USP.

The study consisted of a total of 9 groups of female C57BL/6 mice, comprising 8 groups of 12 mice each and an additional group of 4 mice. Bilateral short-term dry eye was induced by a combination of scopolamine hydrobromide (Sigma-Aldrich Corp., St. Louis, Mo.) injection (subcutaneous (SC), four times daily, 0.5 mg/dose, Days 0-21) and by exposing mice to the drying environment of constant air draft. Starting on Day 1, mice of Groups 1-8 were treated three times daily (TID) for 21 days with bilateral topical ocular (oculus uterque; OU) administration (5 µL/eye/dose) of vehicle (0.9% sterile saline; negative control article); the peptide of SEQ ID NO: 197 (0.06%, 0.25% and 0.6%), the peptide of SEQ ID NO: 172 (0.05%, 0.2% and 0.6%); or cyclosporine (0.05%; positive control, an immunosuppressant drug used to reduce the activity of the immune system). Mice of Group 9 were maintained as un-induced, (no dry eye) untreated controls.

During the in-life (treatment) period, clinical observations were recorded once daily; slit-lamp examination (SLE) with corneal fluorescein staining, tear break-up time test (TBUT), and phenol red thread test (PRTT) were performed three times per week. Necropsies were performed on Day 22; eyes, eye lids, conjunctivae, and lacrimal glands were collected from both eyes of each animal. Tissues from the right eyes (oculus dexter, OD) were fixed and then evaluated microscopically. Tissues from the left eyes (oculus sinister; OS) were flash-frozen in liquid nitrogen and stored frozen at −80° C. for possible subsequent analyses.

TABLE 5

Experimental Design

| Group | Number of animals (females) | Induction of Dry Eye (QID, SC) Days 0 to 21 | Treatment (TID, OU, 5 (µL/eye) Days 1 to 21 |
|---|---|---|---|
| 1 | 12 | Scopolamine (200 µL of 2.5 mg/mL sol., 0.5 mg/dose) | Vehicle |
| 2 | 12 | | SEQ ID NO: 197 (0.06%) |
| 3 | 12 | | SEQ ID NO: 197 (0.25%) |
| 4 | 12 | | SEQ ID NO: 197 (0.6%) |
| 5 | 12 | | SEQ ID NO: 172 (0.05%) |
| 6 | 12 | | SEQ ID NO: 172 (0.2%) |
| 7 | 12 | | SEQ ID NO: 172 (0.6%) |
| 8 | 12 | | Restasis ®* (0.05%) |
| 9 | 4 | No dry eye induction | No treatment |

*Cyclosporine

Methods

1. Dose Preparation

The (poly-)peptide of SEQ ID NO: 197 was obtained from Polypeptide Laboratories (France) as a 1.5-mL clear plastic microfuge vial containing 300.65 mg of dry powder.

The (poly-)peptide of SEQ ID NO: 172 was obtained from Polypeptide Laboratories (France) as a 1.5-mL clear plastic microfuge vial containing 302.7 mg of dry powder.

Prior to the start of the study, the (poly-)peptides of SEQ ID NO: 172 and of SEQ ID NO: 197 were formulated in sterile saline (vehicle). Dosing solutions at each concentration were sterilized using 0.2-µm filters, aliquoted to multiple pre-labeled vials, and frozen at −20° C. The concentrations measured in the formulation samples for the peptide of SEQ ID NO: 197 were 0.058%, 0.25% and 0.624%, rounded to 0.06%, 0.25% and 0.6%. The concentrations measured in the formulation samples for the peptide of SEQ ID NO: 172 were 0.053%, 0.217% and 0.562%, rounded to 0.05, 0.2% and 0.6%.

On each day of dosing, one set of dosing solutions was thawed and used for that day's dose administrations. The controls (vehicle, cyclosporine) were provided ready to dose; no dose preparation was necessary.

2. Slit-Lamp Examinations (SLE)

Prior to entry into the study, each animal underwent a SLE and indirect ophthalmic examination using topically-applied fluorescein. Ocular findings were recorded using the Draize scale ocular scoring. SLE and Draize scoring were repeated three times a week during the in-life period.

3. Tear Break-Up Time (TBUT) Test and Subsequent Corneal Examination

The TBUT test was conducted three times weekly by measuring the time elapsed in seconds between a complete blink after application of fluorescein to the cornea and the appearance of the first random dry spot in the tear film. To perform the TBUT, 0.1% liquid sodium fluorescein was dropped into the conjunctival sac, the eyelids were manually closed three times and then held open revealing a continuous fluorescein-containing tear film covering the cornea, and the time (in seconds) required for the film to break (appearance of a dry spot or streak) was recorded. At least ninety seconds later, corneal epithelial damage was graded using a slit-lamp with a cobalt blue filter after another drop of 0.1% fluorescein was reapplied to the cornea; the cornea then was scored per the Draize ocular scale.

4. Phenol Red Thread Tear Test (PRTT)

Tear production was measured three times a week in both eyes using PRTT test strips (Zone-Quick; Menicon, Nagoya, Japan). Prior to the first treatment of the day, a thread was applied to the lateral canthus of the conjunctival fornix of each eye for 30 seconds under slit-lamp biomicroscopy. Tear migration up the tread (i.e., the length of the wetted cotton thread) was measured using a millimeter scale.

5. Necropsy and Pathology

At necropsy on Day 22, both eyes from each animal, including the globes, lacrimal glands, eyelids, and conjunctivae, were excised. The right eye and associated tissues were fixed by overnight submersion in modified Davidson's solution followed by transfer to 10% neutral buffered formalin (NBF). The fixed tissues of the right eye were dehydrated, embedded in paraffin, sectioned at 3 to 5-µm thicknesses, and slide-mounted tissues were stained with hematoxylin and eosin (H & E). Stained slides were evaluated via light microscopy. Detailed and complete histopathologic assessment was conducted on all parts of the eye, with at least two section levels being examined histopathologically for each right eye. Special attention was paid to the cornea, epithelia (including goblet cells) of the conjunctiva and cornea, as well as the lacrimal gland. These tissues were scored for injury based upon a 0-4 scale, with 0 being normal, 1 being minimal, 2 being mild, 3 being moderate, and 4 being severe. For each cornea, scores were based on corneal epithelium thickness, and corneal inflammation. Conjunctivae were scored for erosion and inflammation as well as presence or absence of goblet cells.

Results

Four-times daily SC administration of scopolamine (0.5 mg/dose) induced a dry eye syndrome in female C57BL/6 mice characterized by a decrease in the volume of aqueous tear production and changes in the physiochemical properties of the tears rendering them less capable of maintaining a stable tear film able to effectively lubricate and protect the eye.

1. Tear Break-Up Time (TBUT) Teat and Corneal Examination

The tear break-up time tests (TBUTs) were performed prior to the induction of dry eye, and again on Days 2, 4, 7, 9, 11, 14, 16, 18 and 21 after dry eye induction. After initiation of dosing with scopolamine (dry eye induction) TBUT mean values began to decrease in all animals, but appeared to decrease more slowly in Group 6 (mid-dose of SEQ ID NO: 172). The TBUT mean nadir for Groups 5, 6, 7 (low, mid and high-dose of the peptide of SEQ ID NO: 172), and Group 8 (cyclosporine) occurred on Day 7, reaching similar values (6.6±0.4, 6.7±0.4, 6.7±0.3, and 6.4±0.4 s, respectively). Subsequently, the TBUT means of these groups increased to a peak on Day 9. Groups 6 and 7 (SEQ ID NO: 172 mid and high-dose groups) TBUT means rose to higher values (10.0±0.7 s and 9.9±0.8 s, respectively) than Group 8, the cyclosporine group (8.5±0.3 s), while the peak TBUT mean of Group 5, the low-dose of SEQ ID NO: 172 (8.0±0.4 s) was slightly below that of Group 8 (cyclosporine). TBUT means for the mid and high-dose of SEQ ID NO: 197-treated animals, Groups 3 and 4, continued to decline after onset of dosing, reaching a nadir on Day 9, while the low-dose Group 2 increased on Day 9. The low, medium and high-dose TBUT means of SEQ ID NO: 172-treated animals (Groups 2, 3 and 4, respectively) were above the vehicle group and generally below the low, mid and high-dose group means of SEQ ID NO: 172-treated animals.

When the area under the curve (AUC) for TBUT values from Day 7 to Day 21 was used to compare the various treatments with the vehicle control, treatment with mid, low and high-dose of the peptide of SEQ ID NO: 172 (0.05%, 0.2% and 0.6%, respectively), Groups 5, 6, and 7, as well as animals treated with cyclosporine (0.05%), Group 8, showed significant increases in the TBUT AUC (Kruskal-Wallis nonparametric ANOVA). The peptide of SEQ ID NO: 172 appeared to produce a dose-dependent increase in TBUT, with the mid and high-doses often producing similar effects. Furthermore, there were no significant differences in TBUT AUC between the cyclosporine-treated group, the groups treated with three dose levels of SEQ ID NO: 172 and the un-induced group (Groups 5, 6, 7, 8, and 9). This finding suggests that all three doses of the peptide of SEQ ID NO: 172 and cyclosporine were approximately equally effective in improving or reversing the ophthalmological changes that underlie the TBUT changes in this dry eye model.

Groups treated with low, mid and high dose levels of the peptide of SEQ ID NO: 197 (Groups 2-4) showed slight generally dose-dependent increases in TBUT which started to increase approximately two days later than animals treated with SEQ ID NO: 172 or cyclosporine.

TABLE 6

| Mean Calculated TBUT AUC Values: | |
| --- | --- |
| Group | TBUT AUC |
| Group 1 | 71.19 |
| Group 2 | 88.54 |
| Group 3 | 91.19 |
| Group 4 | 89.98 |
| Group 5 | 102.98 |

TABLE 6-continued

| Mean Calculated TBUT AUC Values: | |
| --- | --- |
| Group | TBUT AUC |
| Group 6 | 119.08 |
| Group 7 | 119.31 |
| Group 8 | 116.1 |
| Group 9 | 124.54 |

2. Phenol Red Thread Tear Test (PRTT)

PRTT tests were performed prior to the induction of dry eye, and again on Days 2, 4, 7, 9, 11, 14, 16, 18 and 21. PRTT values from Day 0 to Day 4 decreased in all mice that had dry eye induced, indicating a decrease in tear production after the administration of scopolamine and exposure to a drying environment of increased air draft created by the blowers. The nadir in PRTT in most groups occurred at approximately Day 7. PRTT kept decreasing in the vehicle control group (Group 1) reaching a nadir on Day 14. After the nadir, there was an increase in all dry eye groups. These findings indicate that initiation of scopolamine treatment one day earlier than initiation of compound treatment was sufficient to initiate physiological changes in the eye associated with dry eye syndrome. Even the cyclosporine-treated group showed a decrease in PRTT similar to other groups through approximately Day 7, then increased to a peak on Days 11-14, followed by a slight decrease. In the last PRTT test (Day 21) cyclosporine (Group 8), and Groups 6 and 7 all had similar PRTT values suggesting that both the mid and high-dose of the peptide of SEQ ID NO: 172 treatments have therapeutic effects similar to cyclosporine in increasing the aqueous tear production in this murine dry eye model.

Animals treated with the low, mid or high-dose of the peptide of SEQ ID NO: 172 produced significantly more aqueous tears compared to vehicle-treated animals. Thus, similar to TBUT, the peptide of SEQ ID NO: 172 produced generally dose-related significant increases in the production of aqueous tears in this model.

Groups treated with low, mid and high dose levels of the peptide of SEQ ID NO: 197 (0.06%, 0.25% and 0.6%, Groups 2, 3 and 4, respectively) showed generally dose-dependent increases in PRTT.

TABLE 7

| Mean PRTT AUC Values | |
| --- | --- |
| Group | PRTT AUC |
| Group 1 | 35.02 |
| Group 2 | 39.96 |
| Group 3 | 42.79 |
| Group 4 | 43.17 |
| Group 5 | 44.38 |
| Group 6 | 44.85 |
| Group 7 | 46.10 |
| Group 8 | 49.44 |
| Group 9 | 113.63 |

3. Histopathology

In this study histologic changes were generally confined to the cornea. Findings in the cornea consisted of increased keratinization of the corneal epithelial surface, increased thickness of the corneal epithelium, increased cellularity of the corneal epithelium, mildly increased incidence of mitosis of the basal epithelial layer consistent with increased epithelial cell turnover. These findings are indicative of a physiologic adaptive response to corneal drying and corneal surface irritation. Surface ulceration, corneal stromal edema and inflammatory infiltrate into the cornea were not seen in this study. The eyes in Group 9, the untreated group (normal mice, no scopolamine treatment), were within normal limits. There was some minimal nonsuppurative inflammation of the eye lids scattered throughout all groups, but the conjunctiva, retina, lacrimal glands and other parts of the eye were within normal limits. Goblet cells appeared to be within limits in all groups. Goblet cells are a primary producer of mucin which helps the tears form a stronger more adhesive film.

Mild to moderate corneal changes were noted in all groups except the untreated normal eye group (Group 9) and were slightly more severe in Group 1, the vehicle-treated group and Group 2, the low dose of the peptide of SEQ ID NO: 197, in comparison to the other treatment groups. These findings were consistent with the positive beneficial effects of increased tear production on the cornea.

When histological scores of the various treatment groups were compared to the histological scores in the cyclosporine group to determine if any other treatments produced "similar score reductions" to cyclosporine, Groups 4, 6, and 7 were found to be not significantly different than the cyclosporine group scores. Thus, these three treatments, mid and high-dose of the peptide of SEQ ID NO: 172 and the high-dose of the peptide of SEQ ID NO: 197, were the most effective, after cyclosporine, in reducing/ameliorating the corneal changes associated with this murine dry eye model.

The invention claimed is:

1. A method of treating interstitial cystitis in a subject in need of treatment thereof, the method comprising administering to the subject a fusion peptide comprising a c-Jun amino terminal kinase (JNK) inhibitor peptide and a transporter peptide, wherein the fusion peptide comprises the amino acid sequence of rKKRrQRRrRPkRPaTLNLf (SEQ ID NO: 172), wherein an amino acid residue given in capital letters indicates an L-amino acid and an amino acid residue given in small letters indicates a D amino acid residue.

2. The method of claim 1, wherein said subject is human.

3. The method of claim 1, wherein said fusion peptide is administered intravenously, intramuscularly, subcutaneously, intradermally, transdermally, enterally, orally, rectally, topically, nasally, locally, intranasally, epidermally, by patch delivery, by instillation, intravitreally, subconjunctivally and/or intratympanically.

4. The method of claim 1, wherein the fusion peptide consists of the sequence of SEQ ID NO: 172.

5. The method of claim 1, wherein the fusion peptide is comprised in a pharmaceutical composition, which further comprises a pharmaceutically acceptable carrier.

* * * * *